(12) United States Patent
Terrett et al.

(10) Patent No.: US 11,254,912 B2
(45) Date of Patent: *Feb. 22, 2022

(54) METHODS AND COMPOSITIONS FOR TREATING CANCER

(71) Applicant: CRISPR Therapeutics AG, Zug (CH)

(72) Inventors: Jonathan Alexander Terrett, Cambridge, MA (US); Demetrios Kalaitzidis, Cambridge, MA (US); Mary-Lee Dequéant, Cambridge, MA (US); Zinkal Samir Padalia, Cambridge, MA (US)

(73) Assignee: CRISPR Therapeutics AG, Zug (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/238,729

(22) Filed: Apr. 23, 2021

(65) Prior Publication Data

US 2021/0246425 A1 Aug. 12, 2021

Related U.S. Application Data

(63) Continuation of application No. 16/409,737, filed on May 10, 2019.
(Continued)

(51) Int. Cl.
*C12N 5/0783* (2010.01)
*A61P 35/00* (2006.01)
(Continued)

(52) U.S. Cl.
CPC ............ *C12N 5/0636* (2013.01); *A61K 35/17* (2013.01); *A61K 47/6849* (2017.08);
(Continued)

(58) Field of Classification Search
None
See application file for complete search history.

(56) References Cited

U.S. PATENT DOCUMENTS 7,083,785 B2 8/2006 Browning et al.
7,435,596 B2 10/2008 Campana et al.
(Continued)

FOREIGN PATENT DOCUMENTS

WO WO 2004/073656 A2 9/2004
WO WO 2006/060878 A1 6/2006
(Continued)

OTHER PUBLICATIONS

Eyquem et al., Targeting a CAR to the TRAC locus with CRISPR/Cas9 enhances tumour rejection. Nature. Mar. 2, 2017;543(7643):113-117. Epub Feb. 22, 2017.
(Continued)

*Primary Examiner* — Kevin K Hill
*Assistant Examiner* — Anjeanette Roberts
(74) *Attorney, Agent, or Firm* — McDermott Will & Emery LLP

(57) ABSTRACT

Provided herein, in some embodiments, are methods and compositions (e.g., cell compositions) for the treatment of cancer. The methods and compositions involve genetically engineered immune cells (e.g., T cells), in which the endogenous CD70 gene is disrupted by genetic editing, for example, the CRISPR/Cas9 gene editing technology.

14 Claims, 68 Drawing Sheets

Specification includes a Sequence Listing.

Related U.S. Application Data

(60) Provisional application No. 62/826,600, filed on Mar. 29, 2019, provisional application No. 62/773,658, filed on Nov. 30, 2018, provisional application No. 62/756,643, filed on Nov. 7, 2018, provisional application No. 62/701,340, filed on Jul. 20, 2018, provisional application No. 62/670,417, filed on May 11, 2018.

(51) Int. Cl.
| | |
|---|---|
| A61K 35/17 | (2015.01) |
| C07K 14/725 | (2006.01) |
| C07K 16/28 | (2006.01) |
| C12N 15/11 | (2006.01) |
| C07K 14/705 | (2006.01) |
| C07K 14/74 | (2006.01) |
| C12N 9/22 | (2006.01) |
| C12N 15/86 | (2006.01) |
| A61K 47/68 | (2017.01) |
| A61K 51/10 | (2006.01) |
| A61K 38/00 | (2006.01) |
| A61K 39/00 | (2006.01) |

(52) U.S. Cl.
CPC .......... *A61K 51/1027* (2013.01); *A61P 35/00* (2018.01); *C07K 14/7051* (2013.01); *C07K 14/70517* (2013.01); *C07K 14/70521* (2013.01); *C07K 14/70539* (2013.01); *C07K 14/70578* (2013.01); *C07K 16/2803* (2013.01); *C07K 16/2875* (2013.01); *C07K 16/2878* (2013.01); *C12N 9/22* (2013.01); *C12N 15/11* (2013.01); *C12N 15/86* (2013.01); *A61K 38/00* (2013.01); *A61K 2039/505* (2013.01); *A61K 2039/5156* (2013.01); *C07K 2317/565* (2013.01); *C07K 2317/622* (2013.01); *C07K 2317/74* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2310/20* (2017.05); *C12N 2510/00* (2013.01); *C12N 2750/14143* (2013.01); *C12N 2800/80* (2013.01)

(56) References Cited

U.S. PATENT DOCUMENTS

| | | | |
|---|---|---|---|
| 7,446,179 B2 | 11/2008 | Jensen et al. | |
| 7,446,190 B2 | 11/2008 | Sadelain et al. | |
| 7,452,981 B2 | 11/2008 | Wijdenes et al. | |
| 7,491,390 B2 | 2/2009 | Law et al. | |
| 7,641,903 B2 | 1/2010 | Law et al. | |
| 7,662,387 B2 | 2/2010 | Law et al. | |
| 7,700,739 B2 | 4/2010 | Lacy et al. | |
| 7,741,465 B1 | 6/2010 | Eshhar et al. | |
| 7,771,720 B2 | 8/2010 | Staunton et al. | |
| 7,888,121 B2 | 2/2011 | Umov et al. | |
| 8,067,546 B2 | 11/2011 | McDonagh et al. | |
| 8,124,738 B2 | 2/2012 | Terret et al. | |
| 8,337,838 B2 | 12/2012 | Law et al. | |
| 8,440,806 B2 | 5/2013 | Wijdenes et al. | |
| 8,535,678 B2 | 9/2013 | Law et al. | |
| 8,562,987 B2 | 10/2013 | McDonagh et al. | |
| 8,609,104 B2 | 12/2013 | Law et al. | |
| 8,629,257 B2 | 1/2014 | Lacy et al. | |
| 8,647,624 B2 | 2/2014 | Law et al. | |
| 8,663,642 B2 | 3/2014 | Law et al. | |
| 8,673,304 B2 | 3/2014 | Wijdenes et al. | |
| 8,834,882 B2 | 9/2014 | Silence et al. | |
| 8,871,908 B2 | 10/2014 | Liu et al. | |
| 8,956,828 B2 | 2/2015 | Bonini et al. | |
| 9,023,999 B2 | 5/2015 | Mori et al. | |
| 9,051,372 B2 | 6/2015 | Law et al. | |
| 9,102,737 B2 | 8/2015 | Chen et al. | |
| 9,120,854 B2 | 9/2015 | Ryan et al. | |
| 9,169,325 B2 | 10/2015 | Keler et al. | |
| 9,382,319 B2 | 7/2016 | Tso et al. | |
| 9,399,074 B2 | 7/2016 | Liu et al. | |
| 9,403,914 B2 | 8/2016 | Kubota | |
| 9,428,585 B2 | 8/2016 | McDonagh et al. | |
| 9,701,752 B2 | 7/2017 | McDonagh et al. | |
| 9,758,581 B2 | 9/2017 | Wijdenes et al. | |
| 9,765,148 B2 | 9/2017 | Silence et al. | |
| 9,765,149 B2 | 9/2017 | Silence et al. | |
| 9,855,297 B2* | 1/2018 | Duchateau | C12N 5/0637 |
| 9,889,160 B2 | 2/2018 | Jantz et al. | |
| 9,937,207 B2 | 4/2018 | Gregory et al. | |
| 10,166,255 B2 | 1/2019 | Moriarity et al. | |
| 10,442,849 B2 | 10/2019 | Baeuerle et al. | |
| 10,584,352 B2 | 3/2020 | Duchateau et al. | |
| 2006/0051346 A1 | 3/2006 | Wijdenes | |
| 2008/0138343 A1 | 6/2008 | Law et al. | |
| 2009/0081239 A1 | 3/2009 | Staunton et al. | |
| 2009/0148942 A1 | 6/2009 | McDonagh et al. | |
| 2009/0208496 A1 | 8/2009 | Wijdenes et al. | |
| 2010/0129362 A1 | 5/2010 | Law et al. | |
| 2012/0034159 A1 | 2/2012 | Kindsvogel | |
| 2012/0045436 A1 | 2/2012 | McDonagh et al. | |
| 2012/0213771 A1 | 8/2012 | Keler et al. | |
| 2012/0294863 A1 | 11/2012 | Law et al. | |
| 2013/0039911 A1 | 2/2013 | Bedi et al. | |
| 2013/0122020 A1 | 5/2013 | Liu et al. | |
| 2013/0138586 A1 | 5/2013 | Jung et al. | |
| 2013/0287748 A1 | 10/2013 | June et al. | |
| 2014/0105915 A1 | 4/2014 | Algate et al. | |
| 2014/0112942 A1 | 4/2014 | Van Eenennaam et al. | |
| 2014/0178936 A1 | 6/2014 | McDonagh et al. | |
| 2014/0220008 A1 | 8/2014 | Wijdenes et al. | |
| 2014/0349402 A1 | 11/2014 | Cooper et al. | |
| 2014/0357844 A1 | 12/2014 | Liu et al. | |
| 2015/0176013 A1 | 6/2015 | Musunuru et al. | |
| 2015/0266963 A1 | 9/2015 | Silence et al. | |
| 2015/0284467 A1 | 10/2015 | Lipp et al. | |
| 2015/0337047 A1 | 11/2015 | Keler et al. | |
| 2015/0368351 A1 | 12/2015 | Vu et al. | |
| 2016/0046724 A1 | 2/2016 | Brogdon et al. | |
| 2016/0289675 A1 | 10/2016 | Ryan et al. | |
| 2017/0022282 A1 | 1/2017 | McDonagh et al. | |
| 2017/0157176 A1 | 6/2017 | Wang et al. | |
| 2017/0173080 A1 | 6/2017 | Lee et al. | |
| 2017/0183418 A1 | 6/2017 | Galetto | |
| 2017/0226216 A1 | 8/2017 | Morgan et al. | |
| 2017/0233484 A1 | 8/2017 | Sussman et al. | |
| 2017/0267771 A1 | 9/2017 | Van Eenennaam et al. | |
| 2017/0281766 A1 | 10/2017 | Wiltzius | |
| 2017/0313759 A1 | 11/2017 | Batuwangala | |
| 2017/0320957 A1 | 11/2017 | Chen et al. | |
| 2017/0335281 A1 | 11/2017 | Loew et al. | |
| 2017/0342157 A1 | 11/2017 | McDonagh et al. | |
| 2017/0355776 A1 | 12/2017 | Xiao et al. | |
| 2017/0362297 A1 | 12/2017 | Marasco | |
| 2017/0369581 A9 | 12/2017 | Silence et al. | |
| 2018/0002435 A1 | 1/2018 | Sasu et al. | |
| 2018/0186878 A1 | 7/2018 | Rosenthal | |
| 2018/0318435 A1 | 11/2018 | Pastan et al. | |

FOREIGN PATENT DOCUMENTS

| | | |
|---|---|---|
| WO | WO 2006/113909 A2 | 10/2006 |
| WO | WO 2008/121420 A1 | 10/2008 |
| WO | WO 2011/059836 A2 | 5/2011 |
| WO | WO 2011/130434 A2 | 10/2011 |
| WO | WO 2012/004367 A1 | 1/2012 |
| WO | WO 2012/058460 A2 | 5/2012 |
| WO | WO 2012/079000 A1 | 6/2012 |
| WO | WO 2013/074916 A1 | 5/2013 |
| WO | WO 2013/138586 A1 | 9/2013 |
| WO | WO 2013/154760 A1 | 10/2013 |
| WO | WO 2013/176915 A1 | 11/2013 |
| WO | WO 2014/068079 A1 | 5/2014 |
| WO | WO 2014/122143 A1 | 8/2014 |

(56) References Cited

FOREIGN PATENT DOCUMENTS

| | | | | |
|---|---|---|---|---|
| WO | WO 2014/140374 A2 | 9/2014 | | |
| WO | WO 2014/165119 A1 | 10/2014 | | |
| WO | WO 2014/165825 A2 | 10/2014 | | |
| WO | WO-2014158821 A1 * | 10/2014 | .......... | A61K 51/109 |
| WO | WO 2014/191128 A1 | 12/2014 | | |
| WO | WO 2015/120096 A2 | 8/2015 | | |
| WO | WO 2015/121454 A1 | 8/2015 | | |
| WO | WO 2015/134877 A1 | 9/2015 | | |
| WO | WO 2015/136001 A1 | 9/2015 | | |
| WO | WO 2015/158671 A1 | 10/2015 | | |
| WO | WO 2015/161276 A2 | 10/2015 | | |
| WO | WO 2015/164594 A1 | 10/2015 | | |
| WO | WO 2015/187528 A1 | 12/2015 | | |
| WO | WO 2015/188056 A1 | 12/2015 | | |
| WO | WO 2016/014789 A2 | 1/2016 | | |
| WO | WO 2016/025454 A2 | 2/2016 | | |
| WO | WO-2016016341 A1 * | 2/2016 | ....... | C07K 14/70517 |
| WO | WO 2016/063264 A1 | 4/2016 | | |
| WO | WO 2016/069282 A1 | 5/2016 | | |
| WO | WO 2016/069283 A1 | 5/2016 | | |
| WO | WO 2016/073955 A2 | 5/2016 | | |
| WO | WO 2016/090320 A1 | 6/2016 | | |
| WO | WO 2016/094304 A2 | 6/2016 | | |
| WO | WO 2016/100985 A2 | 6/2016 | | |
| WO | WO 2016/120216 A1 | 8/2016 | | |
| WO | WO 2016/151315 A1 | 9/2016 | | |
| WO | WO 2016/160721 A1 | 10/2016 | | |
| WO | WO 2016/164356 A1 | 10/2016 | | |
| WO | WO 2016/174652 A1 | 11/2016 | | |
| WO | WO 2016/183041 A2 | 11/2016 | | |
| WO | WO 2017/058850 A1 | 4/2017 | | |
| WO | WO 2017/062451 A1 | 4/2017 | | |
| WO | WO 2017/070429 A1 | 4/2017 | | |
| WO | WO 2017/075537 A1 | 5/2017 | | |
| WO | WO 2017/083511 A1 | 5/2017 | | |
| WO | WO 2017/093969 A1 | 6/2017 | | |
| WO | WO 2017/100176 A1 | 6/2017 | | |
| WO | WO 2017/106528 A1 | 6/2017 | | |
| WO | WO 2017/112859 A2 | 6/2017 | | |
| WO | WO 2017/130233 A1 | 8/2017 | | |
| WO | WO 2017/143069 A1 | 8/2017 | | |
| WO | WO 2017/149515 A1 | 9/2017 | | |
| WO | WO 2017/156484 A1 | 9/2017 | | |
| WO | WO 2017/177137 A1 | 10/2017 | | |
| WO | WO 2017/180993 A1 | 10/2017 | | |
| WO | WO 2017/186928 A1 | 11/2017 | | |
| WO | WO 2017/189959 A1 | 11/2017 | | |
| WO | WO 2017/210617 A2 | 12/2017 | | |
| WO | WO 2017/211900 A1 | 12/2017 | | |
| WO | WO 2017/222593 A1 | 12/2017 | | |
| WO | WO 2018/068257 A1 | 4/2018 | | |
| WO | WO 2018/073391 A2 | 4/2018 | | |
| WO | WO-2018073393 A2 * | 4/2018 | ..... | A61K 39/001129 |
| WO | WO 2018/132479 A1 | 7/2018 | | |

OTHER PUBLICATIONS

Fraiietta et al., Determinants of response and resistance to CD19 chimeric antigen receptor (CAR) T cell therapy of chronic lymphocytic leukemia. Nat Med. 2018;24(5):563-71.

Jaspers et al., Development of CAR T cells designed to improve antitumor efficacy and safety. Pharmacol Ther. Oct. 2017;178:83-91. Epub Mar. 22, 2017.

Liu et al., CRISPR-Cas9-mediated multiplex gene editing in CAR-T cells. Cell Res. Jan. 2017;27(1):154-157. Epub Dec. 2, 2016.

MacLeod et al., Integration of a CD19 CAR into the TCR alpha chain locus streamlines production of alleogenic gene-edited CAR T cells. Mol Ther. 2017;25(4):949-61.

Maude et al., Chimeric antigen receptor T cells for sustained remissions in leukemia. N Engl J Med. 2014;371:1507-17.

Mirzaei et al., Chimeric Antigen Receptors T Cell Therapy in Solid Tumor: Challenges and Clinical Applications. Front Immunol. Dec. 22, 2017;8:1850(1-13). doi: 10.3389/fimmu.2017.01850. Erratum in: Front Immunol. Apr. 17, 2019;10:780.

Mollanoori et al., CRISPR/Cas9 and CAR-T cell, collaboration of two revolutionary technologies in cancer immunotherapy, an instruction for successful cancer treatment. Hum Immunol. Dec. 2018;79(12):876-882. Epub Sep. 24, 2018.

Newick et al., Chimeric antigen receptor T-cell therapy for solid tumors. Mol Ther Oncolytics. Apr. 13, 2016;3:16006(1-7).

Osborn et al., Evaluation of TCR gene editing achieved by TALENs, CRISPR/Cas9, and megaTAL nucleases. Mol Ther. 2016;24(3):570-81.

Poirot et al., Multiplex genome-edited T-cell manufacturing platform for "off-the-shelf" adoptive T-cell immunotherapies. Cancer Res. 2015;75(18):3853-64.

Ren et al., A versatile system for rapid multiplex genome-edited CAR T cell generation. Oncotarget. 2017;8(10):17002-11.

Ren et al., Advancing chimeric antigen receptor T cell therapy with CRISPR/Cas9. Protein Cell. Sep. 2017;8(9):634-643. Epub Apr. 22, 2017.

Ren et al., Multiplex Genome Editing to Generate Universal CAR T Cells Resistant to PD1 Inhibition. Clin Cancer Res. May 1, 2017;23(9):2255-2266. Epub Nov. 4, 2016.

Rupp et al., CRISPR/Cas9-mediated PD-1 disruption enhances anti-tumor efficacy of human chimeric antigen receptor T cells. Sci Rep. Apr. 7, 2017;7(1):737.

Torikai et al., A foundation for universal T-cell based immunotherapy: T cells engineered to express a CD19-specific chimeric-antigen-receptor and eliminate expression of endogenous TCR. Blood. Jun. 14, 2012;119(24):5697-705. Epub Apr. 24, 2012. Erratum in: Blood. Nov. 26, 2015;126(22):2527. Rabinovitch, Brian [corrected to Rabinovich, Brian].

Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016.

U.S. Appl. No. 16/409,737, filed May 10, 2019, Terrett et al.
U.S. Appl. No. 17/054,483, filed Nov. 10, 2020, Terrett et al.
U.S. Appl. No. 17/238,741, filed Apr. 23, 2021, Terrett et al.

* cited by examiner

METHODS AND COMPOSITIONS FOR TREATING CANCER

RELATED APPLICATIONS

This application is a continuation of, and priority the benefit of and priority to, U.S. patent application Ser. No. 16/409,737 filed on May 10, 2019, which claims the benefit of U.S. Provisional Patent Application Ser. No. 62/670,417, filed May 11, 2018; U.S. Provisional Patent Application Ser. No. 62/701,340, filed Jul. 20, 2018; U.S. Provisional Patent Application Ser. No. 62/756,643, filed Nov. 7, 2018; U.S. Provisional Patent Application Ser. No. 62/773,658, filed Nov. 30, 2018; and U.S. Provisional Patent Application Ser. No. 62/826,600, filed Mar. 29, 2019. The entire contents of each of the above-referenced patent applications are incorporated by reference herein.

SEQUENCE LISTING

The application contains a Sequence Listing that has been filed electronically in the form of a text file, created Oct. 18, 2019, and named "CRTN_106_Sequence_Listing.TXT" (143,436 bytes), the contents of which are incorporated by reference herein in their entirety.

BACKGROUND

Chimeric antigen receptor (CAR) T-cell therapy uses genetically-modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

SUMMARY

In some aspects, the present disclosure provides engineered immune cells (e.g., T cells) and methods of producing immune cells that have been edited using CRISPR/Cas9 gene editing technology to disrupt endogenous CD70 expression (knockout CD70).

In some aspects of the present disclosure provide an engineered immune cell (e.g., T cell) comprising a disruption in the CD70 gene. In some embodiments, the engineered immune cells are allogeneic T cells comprising a disrupted CD70 gene and a nucleic acid encoding a CAR. In some embodiments, the engineered immune cells are allogeneic T cells comprising a TRAC gene disrupted by insertion of a nucleic acid encoding a CAR, a disrupted β2M gene, and a disrupted CD70 gene. In some embodiments, the T cells are human T cells. In some embodiments, the engineered immune cells (e.g., T cells) comprise a disrupted TRAC gene, a disrupted B2M gene, a disrupted CD70 gene, and a nucleic acid encoding a CAR. In some embodiments, the disrupted TRAC gene comprises the nucleic acid encoding the CAR. In some embodiments the engineered immune cell (e.g., T cell) further comprises a disrupted PD-1 gene. In some embodiments the nucleic acid encoding a CAR target a tumor antigen (e.g., BCMA, CD19, CD33 or CD70).

In some aspects the engineered immune cell (e.g., T cell) provided exhibits improved T cell function including the prevention of premature exhaustion, enhanced CAR T cell expansion, and increased efficiency of cancer cell killing. In some aspects the engineered immune cell (e.g., T cell) provided exhibit continued, steady cell growth, relative to unedited T cells or relative to edited T cells that express CD70, as well as showing increased cytotoxicity and cytokine (e.g., IL-2 and/or IFN-gamma) secretion.

In some aspects, the disclosure provides an engineered T cell comprising a disrupted CD70 gene and a nucleic acid encoding a CAR that does not bind CD70. In some aspects, the engineered T cell comprises a disrupted T cell receptor alpha constant region (TRAC) gene. In some aspects, the disrupted TRAC gene comprises the nucleic acid encoding the CAR that does not bind CD70. In some aspects, the engineered T cell comprises a disrupted beta-2-microglobulin (β2M) gene.

In some aspects, the disclosure provides an engineered T cell comprising: (i) a disrupted TRAC gene; (ii) a disrupted B2M gene; (iii) a disrupted CD70 gene; and (iv) a nucleic acid encoding a CAR that does not bind CD70.

In some aspects, the disclosure provides a population of cells comprising engineered T cells, wherein the engineered T cells comprise a disrupted CD70 gene and a nucleic acid encoding a CAR that does not bind CD70.

In some aspects, the engineered T cell in the population of cells comprises a disrupted T cell receptor alpha constant region (TRAC) gene. In some aspects, the disrupted TRAC gene comprises the nucleic acid encoding the CAR that does not bind CD70. In some aspects, the engineered T cell in the population of cells comprises a disrupted beta-2-microglobulin (β2M) gene.

In some aspects, the disclosure provides a population of cells comprising engineered T cells, wherein the engineered T cells comprise: (i) a disrupted TRAC gene; (ii) a disrupted B2M gene; (iii) a disrupted CD70 gene; and (iv) a nucleic acid encoding a CAR that does not bind CD70.

In any of the foregoing or related aspects, the CAR comprises an ectodomain that binds i-B cell maturation antigen (BCMA). In some aspects, the ectodomain comprises an anti-BCMA antibody. In some aspects, the ectodomain comprises an anti-BCMA single-chain variable fragment (scFv). In some aspects, the anti-BCMA scFv comprises variable heavy (VH) chain complementarity determining regions (CDRs) and the same variable light (VL) chain CDRs as a reference antibody, wherein the reference antibody comprises a VH set forth as SEQ ID NO: 60 and a VL set forth as SEQ ID NO: 61. In some aspects, the anti-BCMA scFv comprises VH and VL chains comprising the amino acid sequences set forth in SEQ ID NOs: 60 and 61, respectively. In some aspects, the anti-BCMA scFv comprises the amino acid sequence of SEQ ID NO: 59. In some aspects, the anti-BCMA scFv is encoded by a nucleotide sequence having at least 80%, 85%, 90%, 95%, 96%, 97%, 98% or 99% identity to SEQ ID NO: 57.

In any of the foregoing or related aspects, the anti-BCMA scFv comprises the amino acid sequence of SEQ ID NO: 59. In some embodiments, the anti-BCMA scFv comprises a VH comprising the amino acid sequence of SEQ ID NO: 60. In some embodiments, the anti-BCMA scFv comprises a VL comprising the amino acid sequence of SEQ ID NO: 61. In some embodiments, the anti-BCMA scFv comprises a VH comprising CDR amino acid sequences of (i) SEQ ID NO: 80, SEQ ID NO: 82, and/or SEQ ID NO: 84 or (ii) SEQ ID NO: 81, SEQ ID NO: 83, or SEQ ID NO: 85; and/or the anti-BCMA scFv comprises a VL sequence comprising CDR amino acid sequences of (i) SEQ ID NO: 74, SEQ ID NO: 76, and/or SEQ ID NO: 78.

In any of the foregoing or related aspects, the CAR comprises an ectodomain that binds CD33. In some the ectodomain comprises an anti-CD33 antibody. In some aspects, the ectodomain comprises an anti-CD33 scFv. In some aspects, the anti-CD33 scFv comprises the same VH CDRs and the same VL chain CDRs as a reference antibody, wherein the reference antibody comprises a VH set forth as SEQ ID NO: 140 and a VL set forth as SEQ ID NO: 141. In some aspects, the anti-CD33 scFv comprises VH and VL chains comprising the amino acid sequences set forth in SEQ ID NOs: 140 and 141, respectively. In some aspects, the anti-CD33 scFv comprises the amino acid sequence of SEQ ID NO: 137.

In any of the foregoing or related aspects, the CAR comprises an ectodomain that binds CD19. In some aspects, wherein the ectodomain comprises an anti-CD19 antibody. In some aspects, the ectodomain comprises an anti-CD19 scFv. In some aspects, the anti-CD19 scFv comprises the same VH CDRs and the same VL chain CDRs as a reference antibody, wherein the reference antibody comprises a VH set forth as SEQ ID NO: 152 and a VL set forth as SEQ ID NO: 153. In some aspects, the anti-CD19 scFv comprises VH and VL chains comprising the amino acid sequences set forth in SEQ ID NOs: 152 and 153, respectively. In some aspects, the anti-CD19 scFv comprises the amino acid sequence of SEQ ID NO: 151.

In some aspects, the disclosure provides an engineered T cell comprising: (i) a disrupted TRAC gene; (ii) a disrupted B2M gene; (iii) a disrupted CD70 gene; and (iv) a nucleic acid encoding a CAR that binds CD70. In some aspects, the disrupted TRAC gene comprises the nucleic acid encoding the CAR.

In some aspects, the disclosure provides a population of cells comprising engineered T cells, wherein the engineered T cells comprise: (i) a disrupted TRAC gene; (ii) a disrupted B2M gene; (iii) a disrupted CD70 gene; and (iv) a nucleic acid encoding a CAR that binds CD70.

In some aspects, the disclosure provides a population of cells comprising engineered T cells, wherein the engineered T cells comprise:
  (i) a disrupted TRAC gene;
  (ii) a disrupted β2M gene;
  (iii) a disrupted CD70 gene
  (iv) a nucleic acid encoding a CAR comprising (a) an ectodomain that comprises an anti-CD70 scFv, (b) a CD8 transmembrane domain, and (c) an endodomain that comprises a 41BB co-stimulatory domain and a CD3z signaling domain.

In any of the foregoing or related aspects, the CAR that binds CD70 comprises an ectodomain comprising an anti-CD70 antibody. In some aspects, CAR comprises an ectodomain comprising an anti-CD70 scFv. In some aspects, the anti-CD70 scFv comprises the same VH CDRs and the same VL CDRs as a reference antibody, wherein the reference antibody comprises a VH set forth as SEQ ID NO: 51 and a VL set forth as SEQ ID NO: 52. In some aspects, the anti-CD70 scFv comprises VH and VL chains comprising the amino acid sequences set forth in SEQ ID NOs: 51 and 52, respectively. In some aspects, the anti-CD70 scFv comprises the amino acid sequence of SEQ ID NO: 48 or 50. In some aspects, the anti-CD70 scFv comprises the amino acid sequence of SEQ ID NO: 50.

In any of the foregoing or related aspects, the anti-CD70 scFv comprises a VH comprising the amino acid sequence of SEQ ID NO: 51. In some embodiments, the anti-CD70 scFv comprises a VL comprising the amino acid sequence of SEQ ID NO: 52. In some embodiments, the anti-CD70 scFv comprises a VH comprising CDR amino acid sequences of (i) SEQ ID NO: 68, SEQ ID NO: 70, and/or SEQ ID NO: 72 or (ii) SEQ ID NO: 69, SEQ ID NO: 71, and/or SEQ ID NO: 73; and/or the anti-CD70 scFv comprises a VL sequence comprising CDR amino acid sequences of (i) SEQ ID NO: 62, SEQ ID NO: 64, and/or SEQ ID NO: 66 or (ii) SEQ ID NO: SEQ ID NO: 63, SEQ ID NO: 65, and/or SEQ ID NO: 67.

In any of the foregoing or related aspects, the CAR comprises a CD28 or 41BB co-stimulatory domain. In any of the foregoing or related aspects, the CAR comprises a CD3ζ signaling domain. In any of the foregoing or related aspects, the CAR comprises a CD8 transmembrane domain.

In any of the foregoing or related aspects, there is a deletion in the TRAC gene relative to unmodified T cells. In some aspects, the deletion is 15-30 base pairs. In some aspects, the deletion is 20 base pairs. In some aspects, the deletion comprises SEQ ID NO: 86. In some aspects, the deletion is of SEQ ID NO: 86.

In some aspects, the disclosure provides an engineered T cell comprising a disrupted CD70 gene and a nucleic acid encoding a CAR that binds CD70, wherein the CAR comprises the amino acid sequence set forth in SEQ ID NO: 46. In some aspects, the disclosure provides an engineered T cell comprising a disrupted CD70 gene, and a nucleic acid encoding a CAR that binds CD70, wherein the nucleic acid sequence is at least 90% identical to SEQ ID NO: 45. In some aspects, the disclosure provides an engineered T cell comprising a disrupted CD70 gene, and a nucleic acid encoding a CAR that binds CD70, wherein the nucleic acid sequence is SEQ ID NO: 45.

In some embodiments, the CD70 gene is disrupted by CRISPR/Cas9 gene editing. In some embodiments, the TRAC gene is disrupted by CRISPR/Cas9 gene editing. In some embodiments, the B2M gene is disrupted by CRISPR/Cas9 gene editing. In some embodiments, the PD-1 gene is disrupted by CRISPR/Cas9 gene editing.

In some aspects, the disclosure provides an engineered T cell comprising:
  (i) a disrupted TRAC gene, wherein the disrupted TRAC gene comprises a nucleic acid encoding a CAR comprising the amino acid sequence set forth in SEQ ID NO: 46;
  (ii) a disrupted B2M gene; and
  (iii) a disrupted CD70 gene. In some embodiments, the nucleic acid encoding the CAR comprises a sequence at least 80%, at least 90%, at least 95%, at least 96%, at least 97%, at least 98% or at least 99% identical to SEQ ID NO: 45.

In other aspects, the disclosure provides an engineered T cell comprising:
  (i) a disrupted TRAC gene, wherein the disrupted TRAC gene comprises a nucleic acid encoding a CAR, wherein the nucleic acid sequence is at least 90% identical to SEQ ID NO: 45;
  (ii) a disrupted B2M gene; and
  (iii) a disrupted CD70 gene. In some embodiments, the disrupted TRAC gene comprises a donor sequence comprising the nucleotide sequence set forth in SEQ ID NO: 45 or SEQ ID NO: 44.

In some aspects, the disclosure provides an engineered T cell comprising:
  (i) a disrupted TRAC gene comprising a nucleic acid sequence at least 90% identical to SEQ ID NO: 44;
  (ii) a disrupted B2M gene; and
  (iii) a disrupted CD70 gene.

In some aspects, the disclosure provides an engineered T cell comprising:
  (i) a disrupted TRAC gene comprising the nucleic acid sequence of SEQ ID NO: 44;
  (ii) a disrupted B2M gene; and
  (iii) a disrupted CD70 gene.

In any of the foregoing or related aspects, the engineered T cell comprises a disrupted PD-1 gene.

In any of the foregoing or related aspects, the engineered T cell maintains cytotoxicity following 5 rechallenges with a target cell, wherein the target cell expresses an antigen specific for the CAR. In some aspects, the engineered T cell maintains cytotoxicity following 10 rechallenges with the target cell. In some aspects, the target cell is a cancer cell. In some aspects, the target cell is a cancer cell of a hematological cancer or solid tumor.

In any of the foregoing or related aspects, the engineered T cell or population of cells comprises a CAR comprising the amino acid sequence of SEQ ID NO: 57. In some aspects, the CAR is encoded by a nucleic acid sequence having at least 90% identity to SEQ ID NO: 56.

In any of the foregoing or related aspects, the engineered T cell or population of cells comprises a CAR comprising the amino acid sequence of SEQ ID NO: 139. In some aspects, the CAR is encoded by a nucleic acid sequence having at least 90% identity to SEQ ID NO: 136.

In any of the foregoing or related aspects, the engineered T cell or population of cells comprises a CAR comprising the amino acid sequence of SEQ ID NO: 149. In some aspects, the CAR is encoded by a nucleic acid sequence having at least 90% identity to SEQ ID NO: 148.

In any of the foregoing or related aspects, the engineered T cell or population of cells comprises a CAR comprising the amino acid sequence of SEQ ID NO: 46. In some aspects, the CAR is encoded by a nucleic acid sequence having at least 90% identity to SEQ ID NO: 45.

Other aspects of the present disclosure provide a population of cells comprising any of the engineered immune cells (e.g., T cells) described herein. In some embodiments, a population of cells comprise T cells that comprise a TRAC gene disrupted by insertion of a nucleic acid encoding a CAR, a disrupted β2M gene, and a disrupted CD70 gene. In some embodiments, a population of cells comprise T cells that comprise a disrupted TRAC gene, a disrupted B2M gene, a disrupted CD70 gene, and a nucleic acid encoding a CAR. In some aspects, a population of cells comprise T cells that comprise a disrupted TRAC gene, wherein the disrupted TRAC gene comprises a nucleic acid encoding a CAR, a disrupted B2M gene, and a disrupted CD70 gene.

In some aspects, the disclosure provides a population of cells comprising engineered T cells, wherein the engineered T cells comprise:
(i) a disrupted TRAC gene, wherein the disrupted TRAC gene comprises a nucleic acid encoding a CAR comprising (a) an ectodomain that comprises an anti-CD70 antigen-binding fragment, (b) a CD8 transmembrane domain, and (c) an endodomain that comprises a 41BB co-stimulatory domain and a CD3z signaling domain;
(ii) a disrupted beta-2-microglobulin (B2M) gene; and
(iii) a disrupted CD70 gene.

In some aspects, the disclosure provides a population of cells comprising engineered T cells, wherein the engineered T cells comprise:
(i) a disrupted TRAC gene, wherein the disrupted TRAC gene comprises a nucleic acid encoding a CAR comprising the amino acid sequence set forth in SEQ ID NO: 46;
(ii) a disrupted β2M gene; and
(iii) a disrupted CD70 gene.

In other aspects, the disclosure provides a population of cells comprising engineered T cells, wherein the engineered T cells comprise:

(i) a disrupted TRAC gene, wherein the disrupted TRAC gene comprises a nucleic acid encoding a CAR, wherein the nucleic acid sequence is at least 90% identical to SEQ ID NO: 45;
(ii) a disrupted β2M gene; and
(iii) a disrupted CD70 gene. In some aspects, the disrupted TRAC gene comprises the nucleic acid sequence set forth in SEQ ID NO: 45.

In some aspects, the disclosure provides a population of cells comprising engineered T cells, wherein the engineered T cells comprise:
(i) a disrupted TRAC gene comprising a nucleic acid sequence at least 90% identical to SEQ ID NO: 44;
(ii) a disrupted β2M gene; and
(iii) a disrupted CD70 gene. In some aspects, the disrupted TRAC gene comprises the nucleic acid sequence set forth in SEQ ID NO: 44.

In some embodiments, the CAR comprises a CD3z signaling domain. In some embodiments, the CAR comprises a CD8 transmembrane domain. In some embodiments, the CAR comprises a CD28 or 41BB co-stimulatory domain.

In any of the foregoing or related aspects of the population of cells, the disrupted β2M gene comprises at least one nucleotide sequence selected from any one of SEQ ID NOS: 9-14. In any of the foregoing or related aspects of the population of cells, the disrupted CD70 gene comprises at least one nucleotide sequence selected from any one of SEQ ID NOS: 129-134.

In some embodiments, the TRAC gene comprises the nucleotide sequence of SEQ ID NO: 45 and/or the nucleic acid encoding the anti-CD70 CAR comprises the nucleotide sequence of SEQ ID NO: 45. In some embodiments, the TRAC gene comprises the nucleotide sequence of SEQ ID NO: 45. In some embodiments, the TRAC gene comprises the nucleotide sequence of SEQ ID NO: 44. In some embodiments, the TRAC gene comprises the nucleotide sequence of SEQ ID NO: 56 and/or the nucleic acid encoding the anti-BCMA CAR comprises the nucleotide sequence of SEQ ID NO: 56. In some embodiments, the TRAC gene comprises the nucleotide sequence of SEQ ID NO: 56. In some embodiments, the TRAC gene comprises the nucleotide sequence of SEQ ID NO: 55.

In some embodiments, the TRAC gene comprises the nucleotide sequence of SEQ ID NO: 156 and/or the nucleic acid encoding the anti-CD19 CAR comprises the nucleotide sequence of SEQ ID NO: 148. In some embodiments, the TRAC gene comprises the nucleotide sequence of SEQ ID NO: 148. In some embodiments, the TRAC gene comprises the nucleotide sequence of SEQ ID NO: 156. In some embodiments, the TRAC gene comprises the nucleotide sequence of SEQ ID NO: 135 and/or the nucleic acid encoding the anti-CD33 CAR comprises the nucleotide sequence of SEQ ID NO: 136. In some embodiments, the TRAC gene comprises the nucleotide sequence of SEQ ID NO: 136. In some embodiments, the TRAC gene comprises the nucleotide sequence of SEQ ID NO: 135.

In any of the foregoing aspects, the engineered T cells:(a) exhibit increased cellular proliferative capacity;
(b) exhibit increased cell lysis;
(c) exhibit reduced cellular exhaustion;
(d) maintain cytokine-dependent proliferation;
(e) exhibit increased cytokine secretion; or
(f) any combination of (a)-(e),
relative to control T cells, wherein control T cells express endogenous CD70 protein.

In some embodiments, at least 50%, optionally 50%-65%, of the engineered T cells do not express a detectable level of TCR surface protein, do not express a detectable level of β2M surface protein, do not express a detectable level of CD70 surface protein, and/or express a detectable level of the CAR.

In some embodiments, at least 90%, optionally 90%-100%, of the engineered T cells do not express a detectable level of TCR surface protein. In some embodiments, greater than 99.5% of the engineered T cells do not express a detectable level of TCR surface protein.

In some embodiments, at least 60%, optionally 60%-75%, of the engineered immune cells (e.g., T cells) do not express a detectable level of β2M surface protein.

In some embodiments, at least 80%, optionally 80%-100%, of the engineered immune cells (e.g., T cells) do not express a detectable level of CD70 surface protein.

In some embodiments, at least 80%, optionally 80%-95%, of the engineered immune cells (e.g., T cells) express a detectable level of the CAR (e.g., an anti-CD70 CAR or an anti-BCMA CAR).

In some embodiments, the engineered immune cells (e.g., T cells) further comprise a disrupted PD-1 gene.

In some embodiments, at least 50%, optionally 50%-70%, of the engineered T cells do not express a detectable level of TCR surface protein, do not express a detectable level of β2M surface protein, do not express a detectable level of PD-1 surface protein, do not express a detectable level of CD70 surface protein, and/or express a detectable level of the CAR.

In some aspects, the disclosure provides a method for producing an engineered T cell, the method comprising:
(a) delivering to a T cell
an RNA-guided nuclease,
a gRNA targeting a CD70 gene, and
a vector comprising a donor template that comprises a nucleic acid encoding a CAR; and
(b) producing an engineered T cell comprising a disrupted CD70 gene and expressing the CAR.

In some aspects, the method further comprises delivering to the T cell a gRNA targeting a TRAC gene; wherein the engineered T cell further comprises a disrupted TRAC gene. In some aspects, the nucleic acid encoding the CAR is flanked by left and right homology arms to the TRAC gene; and wherein the engineered T cell comprises the nucleic acid encoding the CAR in the TRAC gene. In some aspects, the method further comprises delivering to the T cell a gRNA targeting a β2M gene; wherein the engineered T cell of further comprises a disrupted β2M gene.

Also provided herein are methods for producing an engineered T cell, the method comprising (a) delivering to a T cell an RNA-guided nuclease, a gRNA targeting a TRAC gene, a gRNA targeting a β2M gene, a gRNA targeting a CD70 gene, and a vector comprising a donor template that comprises a nucleic acid encoding a CAR, optionally wherein the nucleic acid encoding the CAR is flanked by left and right homology arms to the TRAC gene locus, and (b) producing an engineered T cell.

In some embodiments, the RNA-guided nuclease is a Cas9 nuclease, optionally a *Streptococcus pyogenes* Cas9 nuclease. Other RNA-guided nucleases may be used and are described below.

In some embodiments, wherein the gRNA targeting the TRAC gene comprises the nucleotide sequence of SEQ ID NO: 98 or targets the nucleotide sequence of SEQ ID NO: 118, and optionally wherein the gRNA targeting the TRAC gene comprises the nucleotide sequence of SEQ ID NO: 30. In some embodiments, the gRNA targeting the β2M gene comprises the nucleotide sequence of SEQ ID NO: 99 or targets the nucleotide sequence of SEQ ID NO: 119, and optionally wherein the gRNA targeting the β2M gene comprises the nucleotide sequence of SEQ ID NO: 31. In some embodiments, the gRNA targeting the CD70 gene comprises the nucleotide sequence of SEQ ID NOS: 94 or 95 or targets the nucleotide sequence of SEQ ID NO: 114 or 115, and optionally wherein the gRNA targeting the CD70 gene comprises the nucleotide sequence of SEQ ID NOS: 26 or 27.

In any of the foregoing aspects, the RNA-guided nuclease and gRNA are complexed in a ribonucleorotein particle (RNP).

In some embodiments, the methods further comprise delivering to the T cell a gRNA targeting a PD-1 gene. In some aspects, the engineered immune cells are allogeneic T cells comprising a TRAC gene disrupted by insertion of a nucleic acid encoding a CAR, a disrupted β2M gene, and a disrupted PD-1 gene. In some embodiments the engineered immune cell (e.g., T cell) further comprises a disrupted CD70 gene.

In some embodiments, the gRNA targeting the PD-1 gene comprises the nucleotide sequence of SEQ ID NO: 100 or targets the nucleotide sequence of SEQ ID NO: 120, and optionally wherein the gRNA targeting the PD-1 gene comprises the nucleotide sequence of SEQ ID NO: 32.

In some aspects, the disclosure provides a method for producing an engineered T cell for immunotherapy against a target cell, comprising:
(a) disrupting a CD70 gene in a T cell, and
(b) expressing a CAR that binds to an antigen expressed on the target cell, wherein the antigen is not CD70. In some aspects, the target cell is a cancer cell. In some aspects, the method is ex vivo. In some aspects, the method further comprises comprising disrupting a TRAC gene in the T cell. In some aspects, the method further comprises disrupting a β2M gene in the T cell. In some aspects, the CAR is encoded by a nucleic acid in the disrupted TRAC gene. In some aspects, the CAR is any one of the CARs described herein.

In some aspects, the disclosure provides a population of engineered T cells produced by any one of the methods described herein.

In some aspects, the disclosure provides a method of increasing proliferation of T cells, comprising disrupting the CD70 gene in the T cells. In some aspects, the disclosure provides a method of reducing exhaustion of T cells, comprising disrupting the CD70 gene in the T cells. In any of the foregoing aspects, the CD70 gene is disrupted by CRISPR/Cas gene editing. In some aspects, the method further comprises disrupting the TRAC gene, the β2M gene, or both the TRAC and β2M genes in the T cells. In some aspects, the TRAC gene, β2M gene or both TRAC and β2M gene is disrupted by CRISPR/Cas gene editing.

In some embodiments, the vector comprises a nucleic acid encoding a CAR that comprises the amino acid sequence of SEQ ID NO: 46. In some embodiments, the vector comprises a nucleic acid encoding a CAR that comprises the amino acid sequence of SEQ ID NO: 57. In some embodiments, the vector comprises a nucleic acid encoding a CAR that comprises the amino acid sequence of SEQ ID NO: 149. In some embodiments, the vector comprises a nucleic acid encoding a CAR that comprises the amino acid sequence of SEQ ID NO: 139.

In some aspects, the disclosure provides methods for administering the population of cells or an engineered T cells described herein to a subject. In some aspects, the engineered T cells are engineered human T cells. In some aspects, the subject has cancer. In some aspects, the cancer expresses CD70, BMCA, CD19, CD33 or combinations thereof. In some aspects, the population of cells is administered to the subject in an amount effective to treat the cancer. In some aspects, the cancer is a solid tumor malignancy or a hematological malignancy. In some aspects, the solid tumor malignancy is selected from the group consisting of: ovarian tumor, pancreatic tumor, kidney tumor, lung tumor, and intestinal tumor. In some aspects, the population of cells is administered to the subject in an amount effective to reduce the volume of a tumor in the subject.

In some aspects, the disclosure provides a method for treating cancer in a subject, comprising administering the population of cells or an engineered T cells described herein to a subject.

In some aspects, the disclosure provides a method for treating cancer in a subject, comprising administering to the patient a population of cells comprising engineered T cells, wherein the engineered T cells comprise a disrupted CD70 gene and a nucleic acid encoding a CAR, thereby treating cancer in the subject. In some embodiments, the CAR binds CD70. In some embodiments, the CAR does not bind CD70.

In other aspects, the disclosure provides a method for treating cancer in a subject, comprising administering to the patient a population of cells comprising engineered T cells, wherein the engineered T cells comprise:
  (i) a disrupted TRAC gene;
  (ii) a disrupted B2M gene;
  (iii) a disrupted CD70 gene; and
  (iv) a nucleic acid encoding a CAR;
thereby treating the cancer in the subject.

In yet other aspects, the disclosure provides a method for treating cancer in a subject, comprising administering to the patient a population of cells comprising engineered T cells, wherein the engineered T cells comprise:
  (i) a disrupted TRAC gene;
  (ii) a disrupted B2M gene;
  (iii) a disrupted CD70 gene; and
  (iv) a nucleic acid encoding a CAR comprising (a) an ectodomain that comprises an anti-CD70 antigen-binding fragment, (b) a CD8 transmembrane domain, and (c) an endodomain that comprises a 41BB co-stimulatory domain and a CD3z signaling domain,
thereby treating the cancer in the subject. In some embodiments, the CAR comprises the amino acid sequence of SEQ ID NO: 46. In some embodiments, the nucleic acid encoding the CAR comprises the nucleotide sequence of SEQ ID NO: 45. In some embodiments, the disrupted TRAC gene comprises the nucleotide sequence of SEQ ID NO: 45 or SEQ ID NO: 44.

In some aspects, the disclosure provides a method of treating cancer in a subject, comprising administering to the subject a population of cells comprising engineered T cells, wherein the engineered T cells comprise:
  (i) a disrupted TRAC gene, wherein the disrupted TRAC gene comprises a nucleic acid encoding a CAR comprising the amino acid sequence set forth in SEQ ID NO: 46;
  (ii) a disrupted β2M gene; and
  (iii) a disrupted CD70 gene, thereby treating the cancer in the subject.

In some aspects, the disclosure provides a method of treating cancer in a subject, comprising administering to the subject a population of cells comprising engineered T cells, wherein the engineered T cells comprise:
  (i) a disrupted TRAC gene, wherein the disrupted TRAC gene comprises a nucleic acid encoding a CAR, wherein the nucleic acid sequence is at least 90% identical to SEQ ID NO: 45;
  (ii) a disrupted β2M gene; and
  (iii) a disrupted CD70 gene,
thereby treating the cancer in the subject. In some aspects, the disrupted TRAC gene comprises the nucleic acid sequence set forth in SEQ ID NO: 45.

In some aspects, the disclosure provides a method of treating cancer in a subject, comprising administering to the subject a population of cells comprising engineered T cells, wherein the engineered T cells comprise:
  (i) a disrupted TRAC gene comprising a nucleic acid sequence at least 90% identical to SEQ ID NO: 44;
  (ii) a disrupted β2M gene; and
  (iii) a disrupted CD70 gene,
thereby treating the cancer in the subject. In some aspects, the disrupted TRAC gene comprises the nucleic acid sequence set forth in SEQ ID NO: 44.

In any of the foregoing or related aspects, the engineered T cells are engineered human T cells. In some embodiments, the engineered T cells are engineered allogeneic T cells.

DETAILED DESCRIPTION

Figure 1:
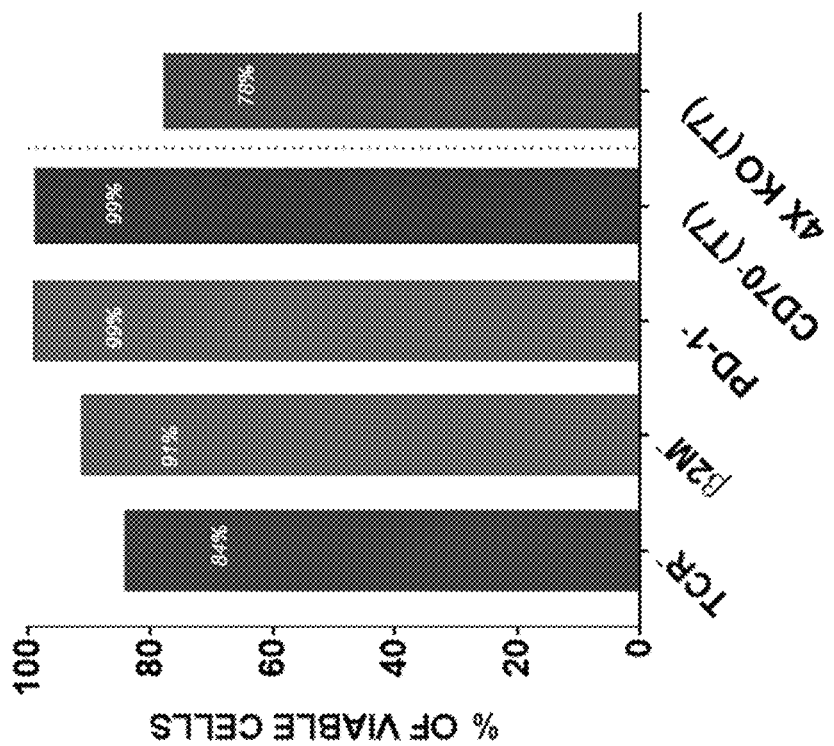
FIG. 1 includes a graph showing highly efficient multiple gene editing in TRAC-/β2M-/PD-1-/CD70- (quadruple knockout) T cells.

The present disclosure is based, at least in part, on the discovery that disrupting the CD70 gene in immune cells engineered to express an antigen targeting moiety (e.g., a CAR) enhances several characteristics important for cell-based immunotherapy, including anti-tumor efficacy. Specifically, such engineered immune cells showed unexpected superior features, including extended proliferation and in vivo persistence resulting in long-term, enhanced anti-tumor efficacy. Notably, these unexpected features have been demonstrated with targeting moieties specific for various antigens, including BCMA, CD19, CD33 and CD70.

As demonstrated herein, disrupting the CD70 gene resulted in maintenance of cytotoxicity of immune cells engineered to express an antigen targeting moiety after multiple rounds of challenges by cancer cells in vitro. Without wishing to be bound by theory, this maintenance of cytotoxicity indicates disrupting the CD70 gene makes the engineered immune cells resistant to exhaustion and may result in cells that live longer.

It was also found that disrupting the CD70 gene in immune cells engineered to express an antigen targeting moiety enhanced anti-tumor efficacy against large tumors and induced a durable anti-cancer memory response. Specifically, the anti-cancer memory response prevented tumor growth upon re-challenge. Further, it has been demonstrated disrupting the CD70 gene results in enhanced cytotoxicity of immune cells engineered to express an antigen targeting moiety at lower ratios of engineered immune cells to target cells, indicating the potential efficacy of low doses of engineered immune cells.

It has also been shown disruption of the CD70 gene enhances cell proliferation and in vivo persistence of engineered immune cells. Without wishing to be bound by theory, it is believed the superior features of the engineered immune cells described herein allow for more consistent cell populations, larger scale production due to the cells' ability to survive more cell division, and fewer starting cells required to produce the engineered cells. Such features may also prove beneficial in a clinical setting. For example, increased expansion and decreased exhaustion indicates increased efficacy per dose and the ability to obtain efficacy with lower doses.

It has also been demonstrated that disrupting the CD70 gene in immune cells engineered to express an antigen targeting moiety maintains cytotoxicity against cancer cells expressing highly immune suppressive molecules, i.e., PD-L1. Without wishing to be bound by theory, it is believed the internal negative signal of PD-1 expressed on immune cells when bound to PD-L1 expressed on cancer cells, is overcome by disrupting CD70.

Accordingly, provided herein are methods and compositions (e.g., cell compositions) for the treatment of cancer, such as BCMA$^+$, CD19$^+$, CD33$^+$, and CD70$^+$ malignancies, involving the use of the engineered immune cells with increased efficacy and persistence.

CD70 Gene Edit

Cluster of Differentiation 70 (CD70) is a member of the tumor necrosis factor superfamily and its expression is restricted to activated T and B lymphocytes and mature dendritic cells. CD70 is implicated in tumor cell and regulatory T cell survival through interaction with its ligand, CD27. CD70 and its receptor CD27 have multiple roles in immune function in multiple cell types including T cells (activated and T regs), and B cells. It is unclear exactly how CD70 functions in all of these cell types to control functions such as apoptosis, with publications indicating contradicting roles. For example, it has been reported that CD70 induces apoptosis or survival of T cells depending on the antigenic load (Wensveen, F., et al J. Immunol, Vol 188: 4256-4267, 2012).

While CAR T cells have proved to be an effective immunotherapeutic, various challenges remain. For example, over time CAR T cells become exhausted and become ineffective in vivo. With regards to manufacturing, it takes significant time to produce enough cells to dose a patient. To address these limitations, the present disclosure provides CAR T cells that have been engineered to disrupt endogenous CD70 expression while at the same time expressing an antigen targeting moiety (e.g., an scFv).

Surprisingly, the present disclosure shows disrupting the CD70 gene enables increased CAR T health and function (e.g., extended proliferation, reduced exhaustion) regardless of the antigen being targeted by the scFv in the CAR T. This applies even to antigens expressed on T cells such as CD33 and CD70 where the effects of the disrupted CD70 gene retain CAR T function even where fratricide may be expected. That is, these CD70 knockout cells (e.g., in which the CD70 gene has been edited using CRISPR/Cas9 gene editing technology), independent of the CAR insertion, exhibit continued, steady cell growth, relative to unmodified T cells (or edited T cells that express CD70) and express lower levels of exhaustion markers, such as LAG5. The CAR T cells of the present disclosure, may include any antibody (including whole antibodies and antibody fragments) or other molecule (e.g., receptor or ligand) that specifically binds to a cancer antigen to guide the CAR T cell to a cancer cell. In some embodiments, the antibody is an anti-CD70 antibody (e.g., an anti-CD70 scFv). In other embodiments, the antibody is an anti-CD19 antibody (e.g., an anti-CD19 scFv). In yet other embodiments, the antibody is an anti-BCMA antibody (e.g., an anti-BCMA scFv). In other embodiments, the antibody is an anti-CD33 antibody (e.g., an anti-CD33 scFv). Other cancer antigens are encompassed by the present disclosure.

It should be understood that gene disruption encompasses gene modification through gene editing (e.g., using CRISPR/Cas gene editing to insert or delete one or more nucleotides). In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a CD70 gene edit may be considered a CD70 knockout cell if CD70 protein cannot be detected at the cell surface using an antibody that specifically binds CD70 protein.

Provided herein, in some embodiments, are populations of cells in which a certain percentage of the cells has been edited (e.g., CD70 gene edited), resulting in a certain percentage of cells not expressing a particular gene and/or protein. In some embodiments, at least 50% (e.g., 50%, 55%, 60%, 65%, 70%, 75%, 80%, 85%, 90%, or 85%) of the cells of a gene-edited population of cells are CD70 knockout cells. In some embodiments, at least 50% of the cells (e.g. T cells) of the population do not express detectable levels of CD70 protein. In some embodiments, at least 55%, at least 60%, at least 65%, at least 70%, at least 75%, at least 80%, at least 85%, at least 90%, or at least 95% of the cells of a gene-edited population of cells may be CD70 knockout cells.

In some embodiments, 10%, 15%, 20%, 25%, 30%, 35% or 40% of the engineered T cells of a population do not express a detectable level of CD70 surface protein. In some embodiments, the percent of engineered T cells that do not express a detectable level of CD70 surface protein increases over time. Thus, in some embodiments, at least 50% of the engineered T cells of a population of engineered T cells does not express a detectable level of CD70 surface protein. For example, at least 55%, at least 60%, at least 70%, at least 75%, at least 80%, at least 85%, at least 90%, or at least 95% of the engineered T cells of a population may not express a detectable level of CD70 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of CD70 surface protein.

Non-limiting examples of modified and unmodified CD70 gRNA sequences that may be used as provided herein to create a genomic alteration (e.g., disruption, e.g., deletion, insertion, substitution) in the CD70 gene are listed in Table 5 (e.g., SEQ ID NOS: 23-29 and 33-39). Other gRNA sequences may be designed using the CD70 gene sequence located on Chromosome 19 (GRCh38 coordinates: Chromosome 19: 6,583,183-6,604,103; Ensembl: ENSG00000125726). In certain embodiments, gRNAs targeting the CD70 genomic region create Indels (e.g.: insertions, deletions or substitutions) in, or around, the CD70 gene disrupting expression of the CD70 mRNA and/or protein.

In some embodiments, a ribonucleoprotein particle (RNP) containing an RNA-guided nuclease (e.g., a Cas nuclease, such as a Cas9 nuclease) and a gRNA targeting the CD70 gene (or any other gene of interest) are delivered to T cells (e.g., primary T cells). In other embodiments, the RNA-guided nuclease and gRNA are delivered separately to T cells. A ribonucleoprotein particle (RNP) is simply an RNA-guided nuclease (e.g., Cas9) pre-complexed/complexed with (bound to) a gRNA.

In some embodiments, the gRNA targeting the CD70 gene is a synthetic modified gRNA such as but not limited to any one of the gRNAs comprising SEQ ID NO: 33-39. In some embodiments, the gRNA targeting the CD70 gene is a synthetic unmodified gRNA such as but not limited to any one of the gRNAs comprising SEQ ID NO: 23-29.

In some embodiments, gRNAs targeting the CD70 genomic region and RNA-guided nuclease create double stranded breaks in the CD70 gene. Repair of the break results in Indels in the CD70 gene wherein the CD70 gene sequence may comprises a nucleotide sequence selected from the group consisting of: SEQ ID NOs: 129-134.

Multi-Gene Editing

The engineered T cells of the present disclosure, in some embodiments, include more than one disrupted gene (e.g.: more than one gene edit), for example, in more than one gene. For example, an engineered T cell may comprise a disrupted CD70 gene, a disrupted T cell receptor alpha chain constant region (TRAC) gene, a disrupted beta-2-microglobulin (β2M) gene, a disrupted programmed cell death-1 (PD-1 or PDCD1) gene, or any combination of two or more of the foregoing disrupted genes. In some embodiments, an engineered T cell comprises a disrupted TRAC gene, a disrupted β2M gene, and a disrupted CD70 gene. In some embodiments, an engineered T cell comprises a disrupted TRAC gene, a disrupted β2M gene, and a disrupted PD-1 gene. In some embodiments, an engineered T cell comprises a disrupted TRAC gene, a disrupted β2M gene, a disrupted CD70 gene and a disrupted PD-1 gene.

TRAC Gene Edit

In some embodiments, an engineered T cell comprises a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response.

In some embodiments, a disruption in the TRAC gene expression is created by knocking a chimeric antigen receptor (CAR) into the TRAC gene (e.g., using an adeno-associated viral (AAV) vector and donor template). In some embodiments, a disruption in the TRAC gene expression is created with a nuclease and gRNAs targeting the TRAC genomic region. In some embodiments, a genomic deletion in the TRAC gene is created by HDR, wherein a chimeric antigen receptor (CAR) replaces a segment of the TRAC gene (e.g., using an adeno-associated viral (AAV) vector and donor template). In some embodiments, a disruption in the TRAC gene expression is created with a nuclease and gRNAs targeting the TRAC genomic region, and knocking a chimeric antigen receptor (CAR) into the TRAC gene.

Non-limiting examples of modified and unmodified TRAC gRNA sequences that may be used as provided herein to create a genomic in the TRAC gene are listed in Table 7 (e.g., SEQ ID NOS: 30 and 40). See also International Application No. PCT/US2018/032334, filed May 11, 2018, incorporated herein by reference. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and RNA-guided nuclease create breaks in the TRAC genomic region resulting Indels in the TRAC gene disrupting expression of the mRNA or protein.

In some embodiments, at least 50% of the engineered T cells of a population do not express a detectable level of T cell receptor (TCR) surface protein. For example, at least 55%, at least 60%, at least 70%, at least 75%, at least 80%, at least 85%, at least 90%, or at least 95% of the engineered T cells of a population may not express a detectable level of TCR surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of TCR surface protein.

In some embodiments, a ribonucleoprotein particle (RNP) containing an RNA-guided nuclease (e.g., a Cas nuclease, such as a Cas9 nuclease) and a gRNA targeting the TRAC gene (or any other gene of interest) are delivered to T cells (e.g., primary T cells). In other embodiments, the RNA-guided nuclease and gRNA are delivered separately to T cells. A ribonucleoprotein particle (RNP) is simply an RNA-guided nuclease (e.g., Cas9) pre-complexed/complexed with a gRNA.

In some embodiments, gRNAs and RNA-guided nuclease targeting the TRAC genomic region result Indels in the TRAC gene comprising a nucleotide sequence selected from the following sequences in Table 1:

TABLE 1

| Sequence | SEQ ID NO: |
|---|---|
| AAGAGCAACAAATCTGACT | 1 |
| AAGAGCAACAGTGCTGTGCCTGGAGCAACAAATCTGACTAAGAGCAACAAATCTGACT | 2 |
| AAGAGCAACAGTGCTGGAGCAACAAATCTGACTAAGAGCAACAAATCTGACT | 3 |
| AAGAGCAACAGTGCCTGGAGCAACAAATCTGACTAAGAGCAACAAATCTGACT | 4 |
| AAGAGCAACAGTGCTGACTAAGAGCAACAAATCTGACT | 5 |
| AAGAGCAACAGTGCTGTGGGCCTGGAGCAACAAATCTGACTAAGAGCAACAAATCTGACT | 6 |
| AAGAGCAACAGTGCTGGCCTGGAGCAACAAATCTGACTAAGAGCAACAAATCTGACT | 7 |
| AAGAGCAACAGTGCTGTGTGCCTGGAGCAACAAATCTGACTAAGAGCAACAAATCTGACT | 8 |

In some embodiments, an engineered T cell comprises a deletion in the TRAC gene relative to unmodified T cells. In some embodiments, an engineered T cell comprises a deletion of 15-30 base pairs in the TRAC gene relative to unmodified T cells. In some embodiments, an engineered T cell comprises a deletion of 15, 16, 17, 18, 19, 20, 21, 22, 23, 24, 25, 26, 27, 28, 29 or 30 base pairs in the TRAC gene relative to unmodified T cells. In some embodiments, an engineered T cell comprises a deletion of more than 30 base pairs in the TRAC gene relative to unmodified T cells. In some embodiments, an engineered T cell comprises a deletion of 20 base pairs in the TRAC gene relative to unmodified T cells. In some embodiments, an engineered T cell comprises a deletion of SEQ ID NO: 86 in the TRAC gene relative to unmodified T cells. In some embodiments, an engineered T cell comprises a deletion comprising SEQ ID NO: 86 in the TRAC gene relative to unmodified T cells. In some embodiments, an engineered T cell comprises a deletion of SEQ ID NO: 118 in the TRAC gene relative to unmodified T cells. In some embodiments, an engineered T cell comprises a deletion comprising SEQ ID NO: 118 in the TRAC gene relative to unmodified T cells.

β2M Gene Edit

In some embodiments, an engineered T cell comprises a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

Non-limiting examples of modified and unmodified β2M gRNA sequences that may be used as provided herein to create a genomic deletion in the β2M gene are listed in Table 7 (e.g., SEQ ID NOS: 31 and 41). See also International Application No. PCT/US2018/032334, filed May 11, 2018, incorporated herein by reference. Other gRNA sequences may be designed using the β2M gene sequence located on Chromosome 15 (GRCh38 coordinates: Chromosome 15: 44,711,477-44,718,877; Ensembl: ENSG00000166710).

In some embodiments, gRNAs targeting the β2M genomic region and RNA-guided nuclease create breaks in the β2M genomic region resulting in Indels in the β2M gene disrupting expression of the mRNA or protein.

In some embodiments, at least 50% of the engineered T cells of a population do not express a detectable level of β2M surface protein. For example, at least 55%, at least 60%, at least 70%, at least 75%, at least 80%, at least 85%, at least 90%, or at least 95% of the engineered T cells of a population may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of β2M surface protein.

In some embodiments, less than 50% of the engineered T cells of a population of cells express a detectable level of β2M surface protein. In some embodiments, less than 30% of the engineered T cells of a population of cells express a detectable level of β2M surface protein. For example, less than 50%, less than 30%, less than 25%, less than 20%, less than 15%, less than 10%, or less than 5% of the engineered T cells of a population of cells express a detectable level of β2M surface protein. In some embodiments, 40%-30%, 40%-20%, 40%-10%, 40%-5%, 30%-20%, 30%-10%, 30%-5%, 20%-10%, 20%-5%, or 10%-5% of the engineered T cells of a population of cells express a detectable level of β2M surface protein.

In some embodiments, a ribonucleoprotein particle (RNP) containing an RNA-guided nuclease (e.g., a Cas nuclease, such as a Cas9 nuclease) and a gRNA targeting the B2M gene (or any other gene of interest) are delivered to T cells (e.g., primary T cells). In other embodiments, the RNA-guided nuclease and gRNA are delivered separately to T cells. A ribonucleoprotein particle (RNP) is simply a RNA-guided nuclease (e.g., Cas9) pre-complexed/complexed with a gRNA.

In some embodiments, an edited β2M gene comprises a nucleotide sequence selected from the following sequences in Table 2.

TABLE 2

| Sequences | SEQ ID NO: |
|---|---|
| CGTGGCCTTAGCTGTGCTCGCGCTACTCTCTCTTTCTGCCTG GAGGCTATCCAGCGTGAGTCTCTCCTACCCTCCCGCT | 9 |
| CGTGGCCTTAGCTGTGCTCGCGCTACTCTCTCTTTCGCCTGG AGGCTATCCAGCGTGAGTCTCTCCTACCCTCCCGCT | 10 |
| CGTGGCCTTAGCTGTGCTCGCGCTACTCTCTCTTTCTGGAGG CTATCCAGCGTGAGTCTCTCCTACCCTCCCGCT | 11 |
| CGTGGCCTTAGCTGTGCTCGCGCTACTCTCTCTTTCTGGATA GCCTGGAGGCTATCCAGCGTGAGTCTCTCCTACCCTCCCGCT | 12 |
| CGTGGCCTTAGCTGTGCTCGCGCTATCCAGCGTGAGTCTCTC CTACCCTCCCGCT | 13 |
| CGTGGCCTTAGCTGTGCTCGCGCTACTCTCTCTTTCTGTGGC CTGGAGGCTATCCAGCGTGAGTCTCTCCTACCCTCCCGCT | 14 |

PD-1 Gene Edit

PD-1 is an immune checkpoint molecule that is upregulated in activated T cells and serves to dampen or stop T cell responses. Disrupting PD-1 by gene editing could lead to more persistent and/or potent therapeutic T cell responses and/or reduce immune suppression in a subject. In some embodiments, an engineered T cell comprises a disrupted PD-1 gene. In some embodiments, expression of the endogenous PD-1 gene is eliminated to enhance anti-tumor efficacy of the CAR T cells of the present disclosure.

Non-limiting examples of modified and unmodified PD-1 gRNA sequences that may be used as provided herein to create a genomic deletion in the PD-1 gene are listed in Table 5 (e.g., SEQ ID NOS: 32 and 42). See also International Application No. PCT/US2018/032334, filed May 11, 2018, incorporated herein by reference. Other gRNA sequences may be designed using the PD-1 gene sequence located on Chromosome 2 (GRCh38 coordinates: Chromosome 2: 241,849,881-241,858,908; Ensembl: ENSG00000188389).

In some embodiments, gRNAs targeting and RNA-guided nuclease the PD-1 genomic region create breaks in the TRAC genomic region resulting in Indels in the PD-1 gene disrupting expression of the PD-1 mRNA or protein.

In some embodiments, at least 50% of the engineered T cells of a population do not express a detectable level of PD-1 surface protein. For example, at least 55%, at least 60%, at least 70%, at least 75%, at least 80%, at least 85%, at least 90%, or at least 95% of the engineered T cells of a population may not express a detectable level of PD-1 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of PD-1 surface protein.

In some embodiments, a ribonucleoprotein particle (RNP) containing an RNA-guided nuclease (e.g., a Cas nuclease, such as a Cas9 nuclease) and a gRNA targeting the PD-1 gene (or any other gene of interest) are delivered to T cells (e.g., primary T cells). In other embodiments, the RNA-guided nuclease and gRNA are delivered separately to T cells. A ribonucleoprotein particle (RNP) is simply an RNA-guided nuclease (e.g., Cas9) pre-complexed/complexed with a gRNA.

Cellular Phenotypes

In some embodiments, one or more gene edits within a population of cells results in a phenotype associated with changes in cellular proliferative capacity, cellular exhaustion, cellular viability, cellular lysis capability (e.g., increase cytokine production and/or release), or any combination thereof.

In some embodiments, engineered T cells of a population comprise a CAR that includes an anti-CD70 scFv ectodomain. In some embodiments, engineered T cells of a population comprise a CAR that includes an anti-BCMA scFv ectodomain. In some embodiments, engineered T cells of a population comprise a CAR that includes an anti-CD19 scFv ectodomain. In some embodiments, engineered T cells of a population comprise a CAR that includes an anti-CD33 scFv ectodomain. Any of the foregoing engineered T cells may also comprise a disruption in one or more of the following genes: TRAC, β2M, PD-1, and/or CD70 (e.g., TRAC$^-$/β2M$^-$/CD70$^-$; TRAC$^-$/β2M$^-$/PD-1$^-$; or TRAC$^-$/β2M$^-$/PD-1$^-$/CD70$^-$).

In some embodiments, engineered T cells of the present disclosure exhibit increased cellular proliferative capacity relative to control cells. In some embodiments, engineered T cells of the present disclosure exhibit at least 20% greater cellular proliferative capacity, relative to control T cells. For example, engineered T cells (e.g., TRAC$^-$/β2M$^-$/CD70$^-$; TRAC$^-$/β2M$^-$/PD-1$^-$; or TRAC$^-$/β2M$^-$/PD-1$^-$/CD70$^-$; with or without a CAR) may exhibit at least 25%, at least 30%, at least 35%, at least 40%, at least 45%, at least 50%, at least 55%, at least 60%, at least 65%, at least 70%, at least 75%, at least 80%, or at least 90% greater cellular proliferative capacity, relative to control T cells. In some embodiments, engineered T cells of the present disclosure exhibit 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% greater cellular proliferative capacity, relative to control T cells. Methods of measuring cell proliferation are known to those of skill in the art and described herein.

In some embodiments, engineered T cells of the present disclosure exhibit reduced exhaustion, relative to control T cells. For example, the engineered T cells may express reduced levels of LAG3 (or other exhaustion markers), relative to control T cells. In some embodiments, the levels of LAG3 expression are reduced by at least 20%, relative to control T cells. For example, the levels of LAG3 expression may be reduced by at least 25%, at least 30%, at least 35%, at least 40%, at least 45%, at least 50%, at least 55%, at least 60%, at least 65%, at least 70%, at least 75%, at least 80%, or at least 90%, relative to control T cells. In some embodiments, the levels of LAG3 expression are reduced by 20%400%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60%, relative to control T cells. In some embodiments, reduced exhaustion is determined by measuring decreased surface expression of exhaustion markers, including TIGIT, PD-1, LAG-3 or combinations thereof. Methods for measuring surface expression are known to those of skill in the art and described herein.

In some embodiments, engineered T cells of the present disclosure exhibit increased cellular viability relative to control cells. In some embodiments, engineered T cells of the present disclosure exhibit an at least 20% increase in cellular viability, relative to control cells. For example, engineered T cells of the present disclosure may exhibit at least 25%, at least 30%, at least 35%, at least 40%, at least 45%, at least 50%, at least 55%, at least 60%, at least 65%, at least 70%, at least 75%, at least 80%, or at least 90% increase in cellular viability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular viability, relative to control cells. Methods of measuring cell viability are known to those of skill in the art and described herein.

In some embodiments, engineered T cells of the present disclosure exhibit increased cellular lysis capability relative to control cells. In some embodiments, engineered T cells of the present disclosure exhibit an at least 20% increase in cellular lysis capability (kill at least 20% more target cells), relative to control cells. For example, engineered T cells of the present disclosure may exhibit an at least at least 25%, at least 30%, at least 35%, at least 40%, at least 45%, at least 50%, at least 55%, at least 60%, at least 65%, at least 70%, at least 75%, at least 80%, or at least 90% increase in cellular lysis capability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular lysis capability, relative to control cells.

In some embodiments, engineered T cells of the present disclosure exhibit increased cytokine secretion relative to control cells. For example, in some embodiments the level of cytokines (e.g., IL-2 and/or IFN-gamma) secreted by the engineered T cells is at least 2-fold (e.g., at least 3-fold, at least 4-fold, or at least 5-fold) greater than the level of cytokines secreted by control T cells.

Control T cells, in some embodiments, are engineered T cells (e.g., gene edited T cells) that express endogenous CD70 protein (CD70 normally expressed by T cells). In some embodiments, control T cells are engineered T cells that express endogenous CD70 protein and comprise a TRAC gene disrupted by insertion of a nucleic acid encoding a CAR (e.g., an anti-CD70 CAR or anti-BCMA CAR), a disrupted β2M gene, a disrupted PD-1 gene, or any combination of the foregoing disrupted genes. In some embodiments, control T cells are unedited T cells.

Surprisingly, the multi-gene edited CAR T cells of the present disclosure (e.g., TRAC$^-$/β2M$^-$/PD-1$^-$/CD70$^-$ cells) maintain cytotoxicity (ability to kill cancer cells), following multiple challenges (also referred to as rechallenges(s)) with cancer cells. In some embodiments, the engineered T cells maintain cytotoxicity following at least 1 rechallenge with a target cell, wherein the target cell expresses an antigen recognized by the CAR T cells. In some embodiments, the engineered T cells maintain cytotoxicity following at least 2 rechallenges with a target cell, wherein the target cell expresses an antigen recognized by the CAR T cells. In some embodiments, the engineered T cells maintain cytotoxicity following at least 1 rechallenge with a cancer cell. In some embodiments, the engineered T cells maintain cytotoxicity following at least 2 rechallenges with a cancer cell. In some embodiments, the engineered T cells maintain cytotoxicity following 1, 2, 3, 4, 5, 6, 7, 8, 9, or 10 rechallenges with a target cell, wherein the target cell expresses an antigen recognized by the CAR T cells. In some embodiments, the engineered T cells maintain cytotoxicity following 2, 3, 4, 5, 6, 7, 8, 9, or 10 rechallenges with a target cell, wherein the target cell expresses an antigen recognized by the CAR T cells. In some embodiments, the engineered T cells maintain cytotoxicity following 2, 3, 4, 5, 6, 7, 8, 9, or 10 rechallenges with a cancer cell. In some embodiments, the engineered T cells maintain cytotoxicity following 10 or more rechallenges with a target cell, wherein the target cell expresses an antigen recognized by the CAR T cells. In some embodiments, the engineered T cells maintain cytotoxicity following 10 or more rechallenges with a cancer cell. In some embodiments, the engineered T cells express a CAR specific for CD70 and the target cell (e.g., cancer cell) expresses CD70. In some embodiments, the engineered T cells express a CAR specific for CD19 and the target cell (e.g., cancer cell) expresses CD19. In some embodiments, the engineered T cells express a CAR specific for CD33 and the target cell (e.g., cancer cell) expresses CD33. In some embodiments, the engineered T cells express a CAR specific for BCMA and the target cell (e.g., cancer cell) expresses BCMA.

Gene Editing Methods

Gene editing (including genomic editing) is a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When a sequence of an endogenous gene is edited, for example by deletion, insertion or substitution of nucleotide(s)/nucleic acid(s), the endogenous gene comprising the affected sequence may be knocked-out or knocked-down due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present. As used herein, a "disrupted gene" refers to a gene comprising an insertion, deletion or substitution relative to an endogenous gene such that expression of a functional protein from the endogenous gene is reduced or inhibited. As used herein, "disrupting a gene" refers to a method of inserting, deleting or substituting at least one nucleotide/nucleic acid in an endogenous gene such that expression of a functional protein from the endogenous gene is reduced or inhibited. Methods of disrupting a gene are known to those of skill in the art and described herein.

Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

Available endonucleases capable of introducing specific and targeted DSBs include, but not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination.

Other non-limiting examples of targeted nucleases include naturally-occurring and recombinant nucleases, e.g., CRISPR/Cas9, restriction endonucleases, meganucleases homing endonucleases, and the like.

CRISPR-Cas9 Gene Editing

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, single-guide RNA (sgRNA), if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

In some embodiments, the Cas9 (CRISPR associated protein 9) endonuclease is from *Streptococcus pyogenes*, although other Cas9 homologs may be used. It should be understood, that wild-type Cas9 may be used or modified versions of Cas9 may be used (e.g., evolved versions of Cas9, or Cas9 orthologues or variants), as provided herein.

In some embodiments, Cas9 may be substituted with another RNA-guided endonuclease, such as Cpf1 (of a class II CRISPR/Cas system).

In some embodiments, the CRISPR/Cas system comprise components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease is from a Type-II CRISPR/Cas system (e.g., a Cas9 protein from a CRISPR/Cas9 system). In some embodiments, the Cas nuclease is from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

In some embodiments, a Cas nuclease may comprise more than one nuclease domain. For example, a Cas9 nuclease may comprise at least one RuvC-like nuclease domain (e.g. Cpf1) and at least one HNH-like nuclease domain (e.g. Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease).

In some embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

Guide RNAs

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA comprises at least a spacer sequence that hybridizes to a target nucleic acid sequence of interest, and a CRISPR repeat sequence. In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

A single-molecule guide RNA in a Type V system comprises, in the 5' to 3' direction, a minimum CRISPR repeat sequence and a spacer sequence.

In some embodiments, the sgRNA comprises a 20 nucleotide spacer sequence at the 5' end of the sgRNA sequence. In some embodiments, the sgRNA comprises a less than 20 nucleotide spacer sequence at the 5' end of the sgRNA sequence. In some embodiments, the sgRNA comprises a more than 20 nucleotide spacer sequence at the 5' end of the sgRNA sequence. In some embodiments, the sgRNA comprises a variable length spacer sequence with 17-30 nucleotides at the 5' end of the sgRNA sequence (see Table 3).

In some embodiments, the sgRNA comprises comprise no uracil at the 3' end of the sgRNA sequence. In some embodiments, the sgRNA comprises comprise one or more uracil at the 3' end of the sgRNA sequence. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 3

| SEQ ID NO. | sgRNA sequence |
|---|---|
| 15 | nnnnnnnnnnnnnnnnnnnguuuuagagcuagaaauag caaguuaaaauaaggcuaguccguuaucaacuugaaaaa guggcaccgagucggugcuuuu |
| 16 | nnnnnnnnnnnnnnnnnnnguuuuagagcuagaaauag caaguuaaaauaaggcuaguccguuaucaacuugaaaaa guggcaccgagucggugc |
| 17 | n$_{(17-30)}$guuuuagagcuagaaauagcaaguuaaaauaag gcuaguccguuaucaacuugaaaaaguggcaccgagucg gugcu$_{(1-8)}$ |

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some embodiments, indel frequency (editing frequency) may be determined using a TIDE analysis, which can be used to identify highly efficient gRNA molecules. In some embodiments, a highly efficient gRNA yields a gene editing frequency of higher than 80%. For example, a gRNA is considered to be highly efficient if it yields a gene editing frequency of at least 80%, at least 85%, at least 90%, at least 95%, or 100%.

In some embodiments, gene disruption may occur by deletion of a genomic sequence using two guide RNAs. Methods of using CRISPR-Cas gene editing technology to create a genomic deletion in a cell (e.g., to knock out a gene in a cell) are known (Bauer D E et al. Vis. Exp. 2015; 95; e52118).

Spacer Sequence

In some embodiments, a gRNA comprises a spacer sequence. A spacer sequence is a sequence (e.g., a 20 nucleotide sequence) that defines the target sequence (e.g., a DNA target sequences, such as a genomic target sequence) of a target nucleic acid of interest. In some embodiments, the spacer sequence is 15 to 30 nucleotides. In some embodiments, the spacer sequence is 15, 16, 17, 18, 19, 29, 21, 22, 23, 24, 25, 26, 27, 28, 29, or 30 nucleotides. In some embodiments, a spacer sequence is 20 nucleotides.

The "target sequence" is adjacent to a PAM sequence and is the sequence modified by an RNA-guided nuclease (e.g., Cas9). The "target nucleic acid" is a double-stranded molecule: one strand comprises the target sequence and is referred to as the "PAM strand," and the other complementary strand is referred to as the "non-PAM strand." One of skill in the art recognizes that the gRNA spacer sequence hybridizes to the reverse complement of the target sequence, which is located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 86), then the gRNA spacer sequence is 5'-AGAGCAACAGUGCUGUGGCC-3' (SEQ ID NO: 98). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence comprises 20 nucleotides. In some embodiments, the target nucleic acid comprises less than 20 nucleotides. In some embodiments, the target nucleic acid comprises more than 20 nucleotides. In some embodiments, the target nucleic acid comprises at least: 5, 10, 15, 16, 17, 18, 19, 20, 21, 22, 23, 24, 25, 30 or more nucleotides. In some embodiments, the target nucleic acid comprises at most: 5, 10, 15, 16, 17, 18, 19, 20, 21, 22, 23, 24, 25, 30 or more nucleotides. In some embodiments, the target nucleic acid sequence comprises 20 bases immediately 5' of the first nucleotide of the PAM. For example, in a sequence comprising 5'-NNNNNNNNNNNNNNNNNNNNNRG-3', the target nucleic acid comprises the sequence that corresponds to the Ns, wherein N is any nucleotide, and the underlined NRG sequence is the S. pyogenes PAM.

Non-limiting examples of gRNAs that may be used as provided herein are provided in PCT/IB2018/001619, filed May 11, 2018, herein incorporated by this reference.

Methods of Making gRNAs

The gRNAs of the present disclosure are produced by a suitable means available in the art, including but not limited to in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in International Application PCT/US2013/30062. Accordingly, the present disclosure also includes polynucleotides, e.g., DNA, constructs and vectors are used to in vitro transcribe a gRNA described herein.

In some embodiments, non-natural modified nucleobases are introduced into polynucleotides, e.g., gRNA, during synthesis or post-synthesis. In certain embodiments, modifications are on internucleoside linkages, purine or pyrimidine bases, or sugar. In some embodiments, a modification is introduced at the terminal of a polynucleotide; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

In some embodiments, enzymatic or chemical ligation methods are used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

Certain embodiments of the invention also provide nucleic acids, e.g., vectors, encoding gRNAs described herein. In some embodiments, the nucleic acid is a DNA molecule. In other embodiments, the nucleic acid is an RNA molecule. In some embodiments, the nucleic acid comprises a nucleotide sequence encoding a crRNA. In some embodiments, the nucleotide sequence encoding the crRNA comprises a spacer flanked by all or a portion of a repeat sequence from a naturally-occurring CRISPR/Cas system. In some embodiments, the nucleic acid comprises a nucleotide sequence encoding a tracrRNA. In some embodiments, the crRNA and the tracrRNA is encoded by two separate nucleic acids. In other embodiments, the crRNA and the tracrRNA is encoded by a single nucleic acid. In some embodiments, the crRNA and the tracrRNA is encoded by opposite strands of a single nucleic acid. In other embodiments, the crRNA and the tracrRNA is encoded by the same strand of a single nucleic acid.

In some embodiments, the gRNAs provided by the disclosure are chemically synthesized by any means described in the art (see e.g., WO/2005/01248). While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together.

In some embodiments, the gRNAs provided by the disclosure are synthesized by enzymatic methods (e.g., in vitro transcription, IVT).

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In certain embodiments, more than one guide RNA can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

The guide RNA may target any sequence of interest via the targeting sequence (e.g., spacer sequence) of the crRNA. In some embodiments, the degree of complementarity between the targeting sequence of the guide RNA and the target sequence on the target nucleic acid molecule is about 60%, 65%, 70%, 75%, 80%, 85%, 90%, 95%, 97%, 98%, 99%, or 100%. In some embodiments, the targeting sequence of the guide RNA and the target sequence on the target nucleic acid molecule is 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches. In some embodiments, the targeting sequence of the guide RNA and the target sequence on the target nucleic acid molecule may contain 5 or 6 mismatches.

The length of the targeting sequence may depend on the CRISPR/Cas9 system and components used. For example, different Cas9 proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence may comprise 18-24 nucleotides in length. In some embodiments, the targeting sequence may comprise 19-21 nucleotides in length. In some embodiments, the targeting sequence may comprise 20 nucleotides in length.

In some embodiments of the present disclosure, a CRISPR/Cas nuclease system includes at least one guide RNA. In some embodiments, the guide RNA and the Cas protein may form a ribonucleoprotein (RNP), e.g., a CRISPR/Cas complex. The guide RNA may guide the Cas protein to a target sequence on a target nucleic acid molecule (e.g., a genomic DNA molecule), where the the Cas protein cleaves the target nucleic acid. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

Delivery of Guide RNA and Nuclease

In some embodiments, a gRNA and an RNA-guided nuclease are delivered to a cell separately, either simultaneously or sequentially. In some embodiments, a gRNA and an RNA-guided nuclease are delivered to a cell together. In some embodiments, a gRNA and an RNA-guided nuclease are pre-complexed together to form a ribonucleoprotein (RNP).

RNPs are useful for gene editing, at least because they minimize the risk of promiscuous interactions in a nucleic acid-rich cellular environment and protect the RNA from degradation. Methods for forming RNPs are known in the art. In some embodiments, an RNP containing an RNA-guided nuclease (e.g., a Cas nuclease, such as a Cas9 nuclease) and a gRNA targeting a gene of interest is delivered a cell (e.g.: a T cell). In some embodiments, an RNP is delivered to a T cell by electroporation.

As used herein, a "TRAC targeting RNP" refers to a gRNA that targets the TRAC gene pre-complexed with an RNA-guided nuclease. As used herein, a "β2M targeting RNP" refers to a gRNA that targets the β2M gene pre-complexed with an RNA-guided nuclease. As used herein, a "CD70 targeting RNP" refers to a gRNA that targets the CD70 gene pre-complexed with an RNA-guided nuclease. As used herein, a "PD-1 targeting RNP" refers to a gRNA that targets the PD-1 gene pre-complexed with an RNA-guided nuclease.

In some embodiments, a TRAC targeting RNP is delivered to a cell. In some embodiments, a β2M targeting RNP is delivered to a cell. In some embodiments, a CD70 targeting RNP is delivered to a cell. In some embodiments, a PD-1 targeting RNP is delivered to a cell.

In some embodiments, more than one RNP is delivered to a cell. In some embodiments, more than on RNP is delivered to a cell separately. In some embodiments, more than one RNP is delivered to a cell simultaneously. In some embodiments, at least one of the following RNPs is delivered to a cell:
  (i) a TRAC targeting RNP;
  (ii) a β2M targeting RNP;
  (iii) a CD70 targeting RNP; or
  (iv) a PD-1 targeting RNP. In some embodiments, at least two of the following RNPs are delivered to a cell:
  (i) a TRAC targeting RNP;
  (ii) a β2M targeting RNP;
  (iii) a CD70 targeting RNP; or
  (iv) a PD-1 targeting RNP.

In some embodiments, an RNA-guided nuclease is delivered to a cell in a DNA vector that expresses the RNA-guided nuclease, an RNA that encodes the RNA-guided nuclease, or a protein. In some embodiments, a gRNA targeting a gene is delivered to a cell as an RNA, or a DNA vector that expresses the gRNA.

Delivery of an RNA-guided nuclease, gRNA, and/or an RNP may be through direct injection or cell transfection using known methods, for example, electroporation or chemical transfection. Other cell transfection methods may be used.

Chimeric Antigen Receptor (CAR) T Cells

A chimeric antigen receptor refers to an artificial immune cell receptor that is engineered to recognize and bind to an antigen expressed by tumor cells. Generally, a CAR is designed for a T cell and is a chimera of a signaling domain of the T-cell receptor (TCR) complex and an antigen-recognizing domain (e.g., a single chain fragment (scFv) of an antibody or other antibody fragment) (Enblad et al., Human Gene Therapy. 2015; 26(8):498-505). A T cell that expresses a CAR is referred to as a CAR T cell. CARs have the ability to redirect T-cell specificity and reactivity toward a selected target in a non-MHC-restricted manner. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. CARs are often referenced to by the antigen they bind. For example, a "CD19 CAR", a "CD70 CAR", a "CD33 CAR" and a "BCMA CAR" are CARs comprising antigen binding domains that specifically bind to CD19, CD70, CD33 or BCMA, respectively. Accordingly, such terms are interchangeable with anti-CD19 CAR, anti-CD70 CAR, anti-CD33 CAR and anti-BCMA CAR. It will be understood by those of ordinary skill in the art that a CAR that specifically binds an antigen can be referred to with either terminology.

There are four generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TCR CD3ζ chain. Third-generation costimulatory domains may include, e.g., a combination of CD3ζ, CD27, CD28, 4-1BB, ICOS, or OX40. CARs, in some embodiments, contain an ectodomain, commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155).

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency.

In some embodiments, a chimeric antigen receptor is a first generation CAR. In other embodiments, a chimeric antigen receptor is a second generation CAR. In yet other embodiments, a chimeric antigen receptor is a third generation CAR.

A CAR, in some embodiments, comprises an extracellular (ecto) domain comprising an antigen binding domain (e.g., an antibody, such as an scFv), a transmembrane domain, and a cytoplasmic (endo) domain Ectodomain The ectodomain is the region of the CAR that is exposed to the extracellular fluid and, in some embodiments, includes an antigen binding domain, and optionally a signal peptide, a spacer domain, and/or a hinge domain. In some embodiments, the antigen binding domain is a single-chain variable fragment (scFv) that includes the VL and VH of immunoglobulins connected with a short linker peptide. The linker, in some embodiments, includes hydrophilic residues with stretches of glycine and serine for flexibility as well as stretches of glutamate and lysine for added solubility. A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. In some embodiments, the scFv of the present disclosure is humanized. In other embodiments, the scFv is fully human. In yet other embodiments, the scFv is a chimera (e.g., of mouse and human sequence).

In some embodiments, the scFv is an anti-CD70 scFv (binds specifically to CD70). Non-limiting examples of anti-CD70 scFv proteins that may be used as provided herein may include the amino acid sequence of SEQ ID NO: 48 or SEQ ID NO: 50.

In some embodiments, the scFv is an anti-BCMA scFv (binds specifically to BCMA). Non-limiting examples of anti-BCMA scFv proteins that may be used as provided herein may include the amino acid sequence of SEQ ID NO: 59.

In some embodiments, the scFv is an anti-CD19 scFv (binds specifically to CD19). Non-limiting examples of anti-CD19 scFv proteins that may be used as provided herein may include the amino acid sequence of SEQ ID NO: 151.

In some embodiments, the scFv is an anti-CD33 scFv (binds specifically to CD33). Non-limiting examples of anti-CD33 scFv proteins that may be used as provided herein may include the amino acid sequence of SEQ ID NO: 137.

Other scFv proteins may be used.

The signal peptide can enhance the antigen specificity of CAR binding. Signal peptides can be derived from antibodies, such as, but not limited to, CD8, as well as epitope tags such as, but not limited to, GST or FLAG. Examples of signal peptides include MLLLVTSLLLCELPHPAFLLIP (SEQ ID NO: 88) and MALPVTALLLPLALLLHAARP (SEQ ID NO: 89). Other signal peptides may be used.

In some embodiments, a spacer domain or hinge domain is located between an extracellular domain (comprising the antigen binding domain) and a transmembrane domain of a CAR, or between a cytoplasmic domain and a transmembrane domain of the CAR. A spacer domain is any oligopeptide or polypeptide that functions to link the transmembrane domain to the extracellular domain and/or the cytoplasmic domain in the polypeptide chain. A hinge domain is any oligopeptide or polypeptide that functions to provide flexibility to the CAR, or domains thereof, or to prevent steric hindrance of the CAR, or domains thereof. In some embodiments, a spacer domain or a hinge domain may comprise up to 300 amino acids (e.g., 10 to 100 amino acids, or 5 to 20 amino acids). In some embodiments, one or more spacer domain(s) may be included in other regions of a CAR. In some embodiments, the hinge domain is a CD8 hinge domain. Other hinge domains may be used.

Transmembrane Domain

The transmembrane domain is a hydrophobic alpha helix that spans the membrane. The transmembrane domain provides stability of the CAR. In some embodiments, the transmembrane domain of a CAR as provided herein is a CD8 transmembrane domain. In other embodiments, the transmembrane domain is a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain: FVPVFLPAKPTTTPAPRPPT-PAPTIASQPLSLRPEACRPAAGG AVHTRGLD-FACDIYIWAPLAGTCGVLLLSLVITLYCNHRNR (SEQ ID NO: 90). Other transmembrane domains may be used.

In some embodiments, the transmembrane domain is a CD8a transmembrane domain comprising the amino acid sequence: IYIWAPLAGTCGVLLLSLVITLY (SEQ ID NO: 126).

Endodomain

The endodomain is the functional end of the receptor. Following antigen recognition, receptors cluster and a signal is transmitted to the cell. The most commonly used endodomain component is CD3-zeta, which contains three (3) immunoreceptor tyrosine-based activation motif (ITAM)s. This transmits an activation signal to the T cell after the antigen is bound. In many cases, CD3-zeta may not provide a fully competent activation signal and, thus, a co-stimulatory signaling is used. For example, CD28 and/or 4-1BB may be used with CD3-zeta (CD3ζ) to transmit a proliferative/survival signal. Thus, in some embodiments, the co-stimulatory molecule of a CAR as provided herein is a CD28 co-stimulatory molecule. In other embodiments, the co-stimulatory molecule is a 4-1BB co-stimulatory molecule. In some embodiments, a CAR includes CD3 and CD28. In other embodiments, a CAR includes CD3-zeta and 4-1BB. In still other embodiments, a CAR includes CD3ζ, CD28, and 4-1BB. Table 4 provides examples of signaling domains derived from 4-1BB, CD28 and CD3-zeta that may be used herein.

TABLE 4

| Name | Sequence | SEQ ID NO: |
|---|---|---|
| 4-1BB | AAACGGGGCAGAAAGAAACTCCTGTATATATTC AAACAACCATTTATGAGACCAGTACAAACTACT CAAGAGGAAGATGGCTGTAGCTGCCGATTTCCA GAAGAAGAAGAAGGAGGATGTGAACTG | 18 |
|  | KRGRKKLLYIFKQPFMRPVQTTQEEDGCSCRFP EEEEGGCEL | 19 |
| CD28 | TCAAAGCGGAGTAGGTTGTTGCATTCCGATTAC ATGAATATGACTCCTCGCCGGCCTGGGCCGACA AGAAAACATTACCAACCCTATGCCCCCCCACGA GACTTCGCTGCGTACAGGTCC | 121 |
|  | SKRSRLLHSDYMNMTPRRPGPTRKHYQPYAPPR DFAAYRS | 20 |
| CD3-zeta | CGAGTGAAGTTTTCCCGAAGCGCAGACGCTCCG GCATATCAGCAAGGACAGAATCAGCTGTATAAC GAACTGAATTTGGGACGCCGCGAGGAGTATGAC GTGCTTGATAAACGCCGGGGAGAGACCCGGAA ATGGGGGGTAAACCCCGAAGAAAGAATCCCCAA GAAGGACTCTACAATGAACTCCAGAAGGATAAG ATGGCGGAGGCCTACTCAGAAATAGGTATGAAG GGCGAACGACGACGGGGAAAAGGTCACGATGGC CTCTACCAAGGGTTGAGTACGGCAACCAAAGAT ACGTACGATGCACTGCATATGCAGGCCCTGCCT CCCAGA | 21 |
|  | RVKFSRSADAPAYQQGQNQLYNELNLGRREEYD VLDKRRGRDPEMGGKPRRKNPQEGLYNELQKDK MAEAYSEIGMKGERRRGKGHDGLYQGLSTATKD TYDALHMQALPPR | 22 |

Cancer Antigens

CD70

In some embodiments, the T cells of the present disclosure are engineered with a chimeric antigen receptor (CAR) designed to target CD70. CD70 was initially identified as the ligand for CD27, a co-stimulatory receptor involved in T cell proliferation and survival. CD70 is only found on a small percentage of activated T cells and antigen presenting cells in draining lymph nodes during viral infection. Many human tumors also express CD70 including, but not limited to, solid cancers such as clear cell renal cancer, breast cancer, gastric cancer, ovarian cancer, glioblastoma, and hematological malignancies. Due to its restricted expression pattern on normal tissues and overexpression in numerous cancers, CD70 is an attractive therapeutic target.

Thus, in some embodiments, T cells of the present disclosure are engineered to express a CAR comprising an anti-CD70 antibody (e.g., anti-CD70 scFv). In some embodiments, the anti-CD70 antibody is an anti-CD70 scFv encoded by the sequence of SEQ ID NO: 47 or 49. In some embodiments, the anti-CD70 antibody is an anti-CD70 scFv comprising the sequence of SEQ ID NO: 48 or 50. In some embodiments, the anti-CD70 antibody is an anti-CD70 scFv comprising a VH comprising the sequence of SEQ ID NO: 51. In some embodiments, the anti-CD70 antibody is an anti-CD70 scFv comprising a VL comprising the sequence of SEQ ID NO: 52. In some embodiments, a CAR comprising an anti-CD70 antibody is encoded by the sequence of SEQ ID NO: 45. In some embodiments, a CAR comprising an anti-CD70 antibody comprises the sequence of SEQ ID NO: 46.

In some embodiments, the anti-CD70 antibody is an anti-CD70 scFv encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 47 or 49. In some embodiments, the anti-CD70 antibody is an anti-CD70 scFv comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 48 or 50. In some embodiments, the anti-CD70 antibody is an anti-CD70 scFv comprising a VH comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 51. In some embodiments, the anti-CD70 antibody is an anti-CD70 scFv comprising a VL comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 52. In some embodiments, a CAR comprising an anti-CD70 antibody is encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 45. In some embodiments, a CAR comprising an anti-CD70 antibody comprises an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 46.

BCMA

In some embodiments, the T cells of the present disclosure are engineered with a CAR designed to target BCMA. B-cell maturation antigen (BCMA, CD269) is a member of the tumor necrosis factor receptor (TNF) superfamily BCMA binds B-cell activating factor (BAFF) and a proliferation inducing ligand (APRIL). Among nonmalignant cells, BCMA is expressed primarily by plasma cells and subsets of mature B cells. BCMA is selectively expressed by B-lineage cells including multiple myeloma cells and non-Hodgkin's lymphoma, thus BCMA is also an attractive therapeutic target.

Thus, in some embodiments, T cells of the present disclosure are engineered to express a CAR comprising an anti-BCMA antibody (e.g., anti-BCMA scFv). In some embodiments, the anti-BCMA antibody is an anti-BCMA scFv encoded by the sequence of SEQ ID NO: 58. In some embodiments, the anti-BCMA antibody is an anti-BCMA scFv comprising the sequence of SEQ ID NO: 59. In some embodiments, the anti-BCMA antibody is an anti-BCMA scFv comprising a VH comprising the sequence of SEQ ID NO: 60. In some embodiments, the anti-BCMA antibody is an anti-BCMA scFv comprising a VL comprising the sequence of SEQ ID NO: 61. In some embodiments, a CAR comprising an anti-BCMA antibody is encoded by the sequence of SEQ ID NO: 56. In some embodiments, a CAR comprising an anti-BCMA antibody comprises the sequence of SEQ ID NO: 57.

In some embodiments, the anti-BCMA antibody is an anti-BCMA scFv encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 58. In some embodiments, the anti-BCMA antibody is an anti-BCMA scFv comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 59. In some embodiments, the anti-BCMA antibody is an anti-BCMA scFv comprising a VH comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 60. In some embodiments, the anti-BCMA antibody is an anti-BCMA scFv comprising a VL comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 61. In some embodiments, a CAR comprising an anti-BCMA antibody is encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 56. In some embodiments, a CAR comprising an anti-BCMA antibody comprises an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 57.

CD19

In some embodiments, the T cells of the present disclosure are engineered with a CAR designed to target CD19. Cluster of Differentiation 19 (CD19) is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM-001178098. CD19 is expressed on most B lineage cancers, including, e.g., acute lymphoblastic leukemia, chronic lymphocyte leukemia and non-Hodgkin's lymphoma. It is also an early marker of B cell progenitors. See, e.g., Nicholson et al. Mol. Immun 34 (16-17): 1157-1165 (1997).

Thus, in some embodiments, T cells of the present disclosure are engineered to express a CAR comprising an anti-CD19 antibody (e.g., anti-CD19 scFv). In some embodiments, the anti-CD19 antibody is an anti-CD19 scFv encoded by the sequence of SEQ ID NO: 150. In some embodiments, the anti-CD19 antibody is an anti-CD19 scFv comprising the sequence of SEQ ID NO: 151. In some embodiments, the anti-CD19 antibody is an anti-CD19 scFv comprising a VH comprising the sequence of SEQ ID NO: 152. In some embodiments, the anti-CD19 antibody is an anti-CD19 scFv comprising a VL comprising the sequence of SEQ ID NO: 153. In some embodiments, a CAR comprising an anti-CD19 antibody is encoded by the sequence of SEQ ID NO: 148. In some embodiments, a CAR comprising an anti-CD19 antibody comprises the sequence of SEQ ID NO: 149.

In some embodiments, the anti-CD19 antibody is an anti-CD19 scFv encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 150. In some embodiments, the anti-CD19 antibody is an anti-CD19 scFv comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 151. In some embodiments, the anti-CD19 antibody is an anti-CD19 scFv comprising a VH comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 152. In some embodiments, the anti-CD19 antibody is an anti-CD19 scFv comprising a VL comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 153. In some embodiments, a CAR comprising an anti-CD19 antibody is encoded by a nucleotide having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 148. In some embodiments, a CAR comprising an anti-CD19 antibody comprises an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 149.

CD33

In some embodiments, the T cells of the present disclosure are engineered with a CAR designed to target CD33. CD33, also known as Siglec3, is a transmembrane receptor expressed on cells of myeloid lineage that is known to bind sialic acids. As CD33 is expressed in cancer cells (e.g., acute myeloid leukemia), it is thought that CD33 represents a cell surface marker for targeting these malignancies.

Thus, in some embodiments, T cells of the present disclosure are engineered to express a CAR comprising an anti-CD33 antibody (e.g., anti-CD33 scFv). In some embodiments, the anti-CD33 antibody is an anti-CD33 scFv encoded by the sequence of SEQ ID NO: 138. In some embodiments, the anti-CD33 antibody is an anti-CD33 scFv comprising the sequence of SEQ ID NO: 137. In some embodiments, the anti-CD33 antibody is an anti-CD19 scFv comprising a VH comprising the sequence of SEQ ID NO: 140. In some embodiments, the anti-CD33 antibody is an anti-CD33 scFv comprising a VL comprising the sequence of SEQ ID NO: 141. In some embodiments, a CAR comprising an anti-CD33 antibody is encoded by the sequence of SEQ ID NO: 136. In some embodiments, a CAR comprising an anti-CD33 antibody comprises the sequence of SEQ ID NO: 139.

In some embodiments, the anti-CD33 antibody is an anti-CD33 scFv encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 138. In some embodiments, the anti-CD33 antibody is an anti-CD33 scFv comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 137. In some embodiments, the anti-CD33 antibody is an anti-CD19 scFv comprising a VH comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 140. In some embodiments, the anti-CD33 antibody is an anti-CD33 scFv comprising a VL comprising an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 141. In some embodiments, a CAR comprising an anti-CD33 antibody is encoded by a nucleotide sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 136. In some embodiments, a CAR comprising an anti-CD33 antibody comprises an amino acid sequence having at least 80%, 81%, 82%, 83%, 84%, 85%, 86%, 87%, 88%, 89%, 90%, 91%, 92%, 93%, 94%, 95%, 96%, 97% 98% or 99% identity to SEQ ID NO: 139.

Antibodies

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) monoclonal antibodies, but also antigen-binding fragments (such as Fab, Fab', F(ab')2, Fv), single chain variable fragment (scFv), mutants thereof, fusion proteins comprising an antibody portion, humanized antibodies, chimeric antibodies, diabodies, linear antibodies, single chain antibodies, single domain antibodies (e.g., camel or llama VHH antibodies), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies.

A typical antibody molecule comprises a heavy chain variable region (VH) and a light chain variable region (VL), which are usually involved in antigen binding. These regions/residues that are responsible for antigen-binding can be identified from amino acid sequences of the VH/VL sequences of a reference antibody (e.g., an anti-CD70 antibody or an anti-BCMA antibody as described herein) by methods known in the art. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. As used herein, a CDR may refer to the CDR defined by any method known in the art. Two antibodies having the same CDR means that the two antibodies have the same amino acid sequence of that CDR as determined by the same method. See, e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273: 927-948; and Almagro, J. Mol. Recognit. 17:132-143 (2004). See also hgmp.mrc.ac.uk and bioinf.org.uk/abs.

In some embodiments, an antibody is an scFv, such as an anti-CD70 scFv, an anti-BCMA scFv, an anti-CD19 scFv or an anti-CD33 scFv. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used as provided herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC).

In some embodiments, an antibody of the present disclosure is a humanized antibody. Humanized antibodies refer to forms of non-human (e g, murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody optimally also will comprise at least a portion of an immunoglobulin constant region or domain (Fc), typically that of a human immunoglobulin. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

In some embodiments, an antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, an antibody of the present disclosure specifically binds a target antigen, such as human CD70, human BCMA, human CD19 or human CD33. An antibody that "specifically binds" to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a CD70, BCMA, CD19 or CD33 epitope is an antibody that binds this CD70, BCMA, CD19 or CD33 epitope with greater affinity, avidity, more readily, and/or with greater duration than it binds to other CD70, BCMA, CD19 or CD33 epitopes or non-CD70, non-BCMA, non-CD19 or non-CD33 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, the equilibrium dissociation constant ($K_D$) between the antibody and CD70 is 100 pM to 1 μM. In some embodiments, the $K_D$ between the antibody and CD70 is 1 nM to 100 nM.

In some embodiments, the equilibrium dissociation constant ($K_D$) between the antibody and BCMA is 100 pM to 1 μM. In some embodiments, the $K_D$ between the antibody and BCMA is 1 nM to 100 nM.

In some embodiments, the equilibrium dissociation constant ($K_D$) between the antibody and CD19 is 100 pM to 1 μM. In some embodiments, the $K_D$ between the antibody and CD19 is 1 nM to 100 nM.

In some embodiments, the equilibrium dissociation constant ($K_D$) between the antibody and CD33 is 100 pM to 1 μM. In some embodiments, the $K_D$ between the antibody and CD33 is 1 nM to 100 nM.

Also within the scope of the present disclosure are functional variants of any of the exemplary antibodies as disclosed herein. A functional variant may contain one or more amino acid residue variations in the VH and/or VL, or in one or more of the VH CDRs and/or one or more of the VL CDRs as relative to a reference antibody, while retaining substantially similar binding and biological activities (e.g., substantially similar binding affinity, binding specificity, inhibitory activity, anti-tumor activity, or a combination thereof) as the reference antibody.

In some examples, an antibody disclosed herein comprises a VH CDR1, a VH CDR2, and a VH CDR3, which collectively contains no more than 10 amino acid variations (e.g., no more than 9, 8, 7, 6, 5, 4, 3, 2, or 1 amino acid variation) as compared with the VH CDR1, VH CDR2, and VH CDR3 of a reference antibody such as Antibody A (VH: SEQ ID NO: 51; VL: SEQ ID NO: 52) or Antibody B (VH: SEQ ID NO: 60; VL: SEQ ID NO: 61). "Collectively" means that the total number of amino acid variations in all of the three VH CDRs is within the defined range. Alternatively or in addition, antibody may comprise a VL CDR1, a VL CDR2, and a VL CDR3, which collectively contains no more than 10 amino acid variations (e.g., no more than 9, 8, 7, 6, 5, 4, 3, 2 or 1 amino acid variation) as compared with the VL CDR1, VL CDR2, and VL CDR3 of the reference antibody.

In some examples, an antibody disclosed herein may comprise a VH CDR1, a VH CDR2, and a VH CDR3, at least one of which contains no more than 5 amino acid variations (e.g., no more than 4, 3, 2, or 1 amino acid variation) as the counterpart VH CDR of a reference antibody such as Antibody A (VH: SEQ ID NO: 51; VL: SEQ ID NO: 52) or Antibody B (VH: SEQ ID NO: 60; VL: SEQ ID NO: 61). In specific examples, the antibody comprises a VH CDR3, which contains no more than 5 amino acid variations (e.g., no more than 4, 3, 2, or 1 amino acid variation) as the VH CDR3 of a reference antibody such as Antibody A (VH: SEQ ID NO: 51; VL: SEQ ID NO: 52) or Antibody B (VH: SEQ ID NO: 60; VL: SEQ ID NO: 61). Alternatively or in addition, an antibody may comprise a VL CDR1, a VL CDR2, and a VL CDR3, at least one of which contains no more than 5 amino acid variations (e.g., no more than 4, 3, 2, or 1 amino acid variation) as the counterpart VL CDR of the reference antibody. In specific examples, the antibody comprises a VL CDR3, which contains no more than 5 amino acid variations (e.g., no more than 4, 3, 2, or 1 amino acid variation) as the VL CDR3 of the reference antibody.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) A→G, S; (b) R→K, H; (c) N→Q, H; (d) D→E, N; (e) C→S, A; (f) Q→N; (g) E→D, Q; (h) G→A; (i) H→N, Q; (j) I→L, V; (k) L→I, V; (l) K→R, H; (m) M→L, I, Y; (n) F→Y, M, L; (o) P→A; (p) S→T; (q) T→S; (r) W→Y, F; (s) Y→W, F; and (t) V→I, L.

In some embodiments, an antibody disclosed herein may comprise VH CDRs that collectively are at least 80% (e.g., 85%, 90%, 95%, or 98%) identical to the VH CDRs of a reference antibody such as Antibody A (VH: SEQ ID NO: 51; VL: SEQ ID NO: 52) or Antibody B (VH: SEQ ID NO: 60; VL: SEQ ID NO: 61). Alternatively or in addition, the antibody may comprise VL CDRs that collectively are at least 80% (e.g., 85%, 90%, 95%, or 98%) identical to the VL CDRs of the reference antibody. In some embodiments, an antibody may comprise a VH that is at least 80% (e.g., 85%, 90%, 95%, or 98%) identical to the VH of a reference antibody such as Antibody A (VH: SEQ ID NO: 51; VL: SEQ ID NO: 52) or Antibody B (VH: SEQ ID NO: 60; VL: SEQ ID NO: 61) and/or a VL that is at least 80% (e.g., 85%, 90%, 95%, or 98%) identical to the VL of the reference antibody.

In some embodiments, an anti-CD70 antibody (e.g., anti-CD70 scFv) comprises a VH and a VL comprising the amino acid sequences set forth in SEQ ID NOs: 51 and 52, respectively. In some embodiments, an anti-CD70 antibody (e.g., anti-CD70 scFv) comprises three CDRs (CDR1, CDR2 and CDR2) of the VH set forth in SEQ ID NO: 51, and three CDRs (CDR1, CDR2 and CDR3) of the VL set forth in SEQ ID NO: 52. In some embodiments, an anti-CD70 antibody (e.g., anti-CD70 scFv) comprises three CDRs (CDR1, CDR2 and CDR2) of the VH set forth in SEQ ID NO: 51, and three CDRs (CDR1, CDR2 and CDR3) of the VL set forth in SEQ ID NO: 52, wherein the CDRs are determined according to Kabat. In some embodiments, an anti-CD70 antibody (e.g., anti-CD70 scFv) comprises three CDRs (CDR1, CDR2 and CDR2) of the VH set forth in SEQ ID NO: 51, and three CDRs (CDR1, CDR2 and CDR3) of the VL set forth in SEQ ID NO: 52, wherein the CDRs are determined according to Chothia. In some embodiments, an anti-CD70 antibody (e.g., anti-CD70 scFv) comprises three CDRs (CDR1, CDR2 and CDR2) of the VH set forth in SEQ ID NO: 51, and three CDRs (CDR1, CDR2 and CDR3) of the VL set forth in SEQ ID NO: 52, wherein the CDRs are determined according to AbM. In some embodiments, an anti-CD70 antibody (e.g., anti-CD70 scFv) comprises heavy chain CDR1, CDR2 and CDR3 sequences set forth in SEQ ID NOs: 68, 70 and 72, respectively, and light chain CDR1, CDR2 and CDR3 sequences set forth in SEQ ID NOs: 62, 64 and 66. In some embodiments, an anti-CD70 antibody (e.g., anti-CD70 scFv) comprises heavy chain CDR1, CDR2 and CDR3 sequences set forth in SEQ ID NOs: 69, 71 and 73, respectively, and light chain CDR1, CDR2 and CDR3 sequences set forth in SEQ ID NOs: 63, 65 and 67. In some embodiments, an anti-CD70 antibody is an anti-CD70 scFv comprising the amino acid sequence set forth in SEQ ID NO: 50. In some embodiments, an anti-CD70 antibody is an anti-CD70 scFv encoded by the nucleotide sequence set forth in SEQ ID NO: 49. In some embodiments, an anti-CD70 antibody is an anti-CD70 scFv comprising the amino acid sequence set forth in SEQ ID NO: 48. In some embodiments, an anti-CD70 antibody is an anti-CD70 scFv encoded by the nucleotide sequence set forth in SEQ ID NO: 47.

In some embodiments, an anti-BCMA antibody (e.g., anti-BCMA scFv) comprises a VH and a VL comprising the amino acid sequences set forth in SEQ ID NOs: 60 and 61, respectively. In some embodiments, an anti-BCMA antibody (e.g., anti-BCMA scFv) comprises three CDRs (CDR1, CDR2 and CDR2) of the VH set forth in SEQ ID NO: 60, and three CDRs (CDR1, CDR2 and CDR3) of the VL set forth in SEQ ID NO: 61. In some embodiments, an anti-BCMA antibody (e.g., anti-BCMA scFv) comprises three CDRs (CDR1, CDR2 and CDR2) of the VH set forth in SEQ ID NO: 60, and three CDRs (CDR1, CDR2 and CDR3) of the VL set forth in SEQ ID NO: 61, wherein the CDRs are determined according to Kabat. In some embodiments, an anti-BCMA antibody (e.g., anti-BCMA scFv) comprises three CDRs (CDR1, CDR2 and CDR2) of the VH set forth in SEQ ID NO: 60, and three CDRs (CDR1, CDR2 and CDR3) of the VL set forth in SEQ ID NO: 61, wherein the CDRs are determined according to Chothia. In some embodiments, an anti-BCMA antibody (e.g., anti-BCMA scFv) comprises three CDRs (CDR1, CDR2 and CDR2) of the VH set forth in SEQ ID NO: 60, and three CDRs (CDR1, CDR2 and CDR3) of the VL set forth in SEQ ID NO: 61, wherein the CDRs are determined according to AbM. In some embodiments, an anti-BCMA antibody (e.g., anti-BCMA scFv) comprises heavy chain CDR1, CDR2 and CDR3 sequences set forth in SEQ ID NOs: 80, 82 and 84, respectively, and light chain CDR1, CDR2 and CDR3 sequences set forth in SEQ ID NOs: 74, 76 and 78. In some embodiments, an anti-BCMA antibody (e.g., anti-BCMA scFv) comprises heavy chain CDR1, CDR2 and CDR3 sequences set forth in SEQ ID NOs: 81, 83 and 85, respectively, and light chain CDR1, CDR2 and CDR3 sequences set forth in SEQ ID NOs: 75, 77 and 79. In some embodiments, an anti-BCMA antibody is an anti-BCMA scFv comprising the amino acid sequence set forth in SEQ ID NO: 59 In some embodiments, an anti-BCMA antibody is an anti-BCMA scFv encoded by the nucleotide sequence set forth in SEQ ID NO: 58.

In some embodiments, an anti-CD19 antibody (e.g., anti-CD19 scFv) comprises a VH and a VL comprising the amino acid sequences set forth in SEQ ID NOs: 152 and 153, respectively. In some embodiments, an anti-CD19 antibody (e.g., anti-CD19 scFv) comprises three CDRs (CDR1, CDR2 and CDR2) of the VH set forth in SEQ ID NO: 152, and three CDRs (CDR1, CDR2 and CDR3) of the VL set forth in SEQ ID NO: 153. In some embodiments, an anti-CD19 antibody (e.g., anti-CD19 scFv) comprises three CDRs (CDR1, CDR2 and CDR2) of the VH set forth in SEQ ID NO: 152, and three CDRs (CDR1, CDR2 and CDR3) of the VL set forth in SEQ ID NO: 153, wherein the CDRs are determined according to Kabat. In some embodiments, an anti-CD19 antibody (e.g., anti-CD19 scFv) comprises three CDRs (CDR1, CDR2 and CDR2) of the VH set forth in SEQ ID NO: 152, and three CDRs (CDR1, CDR2 and CDR3) of the VL set forth in SEQ ID NO: 153, wherein the CDRs are determined according to Chothia. In some embodiments, an anti-CD19 antibody (e.g., anti-CD19 scFv) comprises three CDRs (CDR1, CDR2 and CDR2) of the VH set forth in SEQ ID NO: 152, and three CDRs (CDR1, CDR2 and CDR3) of the VL set forth in SEQ ID NO: 153, wherein the CDRs are determined according to AbM. In some embodiments, an anti-CD19 antibody (e.g., anti-CD19 scFv) comprises heavy chain CDR1, CDR2 and CDR3 sequences set forth in SEQ ID NOs: 169, 170 and 171, respectively, and light chain CDR1, CDR2 and CDR3 sequences set forth in SEQ ID NOs: 166, 167 and 168, respectively. In some embodiments, an anti-CD19 antibody (e.g., anti-CD19 scFv) comprises heavy chain CDR1, CDR2 and CDR3 sequences set forth in SEQ ID NOs: 175, 176 and 177, respectively, and light chain CDR1, CDR2 and CDR3 sequences set forth in SEQ ID NOs: 172, 173 and 174, respectively. In some embodiments, an anti-CD19 antibody is an anti-CD19 scFv comprising the amino acid sequence set forth in SEQ ID NO: 151. In some embodiments, an anti-CD19 antibody is an anti-CD19 scFv encoded by the nucleotide sequence set forth in SEQ ID NO: 150.

In some embodiments, an anti-CD33 antibody (e.g., anti-CD33 scFv) comprises a VH and a VL comprising the amino acid sequences set forth in SEQ ID NOs: 140 and 141, respectively. In some embodiments, an anti-CD33 antibody (e.g., anti-CD33 scFv) comprises three CDRs (CDR1, CDR2 and CDR2) of the VH set forth in SEQ ID NO: 140, and three CDRs (CDR1, CDR2 and CDR3) of the VL set forth in SEQ ID NO: 141. In some embodiments, an anti-CD33 antibody (e.g., anti-CD33 scFv) comprises three CDRs (CDR1, CDR2 and CDR2) of the VH set forth in SEQ ID NO: 140, and three CDRs (CDR1, CDR2 and CDR3) of the VL set forth in SEQ ID NO: 141, wherein the CDRs are determined according to Kabat. In some embodiments, an anti-CD33 antibody (e.g., anti-CD33 scFv) comprises three CDRs (CDR1, CDR2 and CDR2) of the VH set forth in SEQ ID NO: 140, and three CDRs (CDR1, CDR2 and CDR3) of the VL set forth in SEQ ID NO: 141, wherein the CDRs are determined according to Chothia. In some embodiments, an anti-CD33 antibody (e.g., anti-CD33 scFv) comprises three CDRs (CDR1, CDR2 and CDR2) of the VH set forth in SEQ ID NO: 140, and three CDRs (CDR1, CDR2 and CDR3) of the VL set forth in SEQ ID NO: 141, wherein the CDRs are determined according to AbM. In some embodiments, an anti-CD33 antibody (e.g., anti-CD33 scFv) comprises heavy chain CDR1, CDR2 and CDR3 sequences set forth in SEQ ID NOs: 142, 143 and 144, respectively, and light chain CDR1, CDR2 and CDR3 sequences set forth in SEQ ID NOs: 145, 146 and 147. In some embodiments, an anti-CD33 antibody (e.g., anti-CD33 scFv) comprises heavy chain CDR1, CDR2 and CDR3 sequences set forth in SEQ ID NOs: 178, 179 and 180, respectively, and light chain CDR1, CDR2 and CDR3 sequences set forth in SEQ ID NOs: 145, 146 and 147. In some embodiments, an anti-CD33 antibody is an anti-CD33 scFv comprising the amino acid sequence set forth in SEQ ID NO: 137. In some embodiments, an anti-CD33 antibody is an anti-CD33 scFv encoded by the nucleotide sequence set forth in SEQ ID NO: 138.

Antigen Targeting Chimeric Antigen Receptor Construct

In some embodiments, the engineered T cells described herein comprise a tumor antigen targeting CAR. In some embodiments, a tumor antigen is a "tumor associated antigen," referring an immunogenic molecule, such as a protein, that is generally expressed at a higher level in tumor cells than in non-tumor cells, in which it may not be expressed at all, or only at low levels. In some embodiments, tumor-associated structures which are recognized by the immune system of the tumor-harboring host are referred to as tumor-associated antigens. In some embodiments, a tumor-associated antigen is a universal tumor antigen if its broadly expressed by most tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells. In some embodiments, the tumor antigen is not CD70.

In some embodiments, the engineered T cells described herein comprise a non-CD70 targeting CAR (e.g., a CAR that does not bind CD70).

CD19 CAR

In some embodiments, the engineered T cells described herein comprise a CD19 targeting CAR, also referred to herein as CD19 CAR, anti-CD19 CAR or anti-CD19 CAR T cells. In some embodiments, the anti-CD19 CAR comprises (i) an ectodomain that comprises an anti-CD19 antigen-binding domain, (ii) a transmembrane domain, and (iii) an endodomain comprising at least one co-stimulatory domain.

In some embodiments, the anti-CD19 CAR comprises (i) an ectodomain that comprises an anti-CD19 antigen-binding domain, (ii) a CD8 transmembrane domain, and (iii) an endodomain that comprises a CD28 or 41BB co-stimulatory domain, and a CD3-zeta signaling domain. In some embodiments, the anti-CD19 CAR comprises (i) an ectodomain that comprises an anti-CD19 antigen-binding domain, (ii) a CD8 transmembrane domain, and (iii) an endodomain that comprises a CD28 co-stimulatory domain and a CD3-zeta signaling domain. In some embodiments, the anti-CD19 CAR comprises (i) an ectodomain that comprises an anti-CD19 antigen-binding domain, (ii) a CD8 transmembrane domain, and (iii) an endodomain that comprises a 41BB co-stimulatory domain and a CD3-zeta signaling domain.

In some embodiments, the anti-CD19 CAR comprises (i) an ectodomain that comprises an anti-CD19 antigen-binding domain, (ii) a CD8 transmembrane domain comprising the amino acid sequence set forth in SEQ ID NO: 126, and (iii) an endodomain that comprises a CD28 co-stimulatory domain comprising the amino acid sequence set forth in SEQ ID NO: 20 and a CD3-zeta signaling domain comprising the amino acid sequence set forth in SEQ ID NO: 22.

In some embodiments, the anti-CD19 CAR comprises (i) an ectodomain that comprises an anti-CD19 scFv comprising the amino acid sequence set forth in SEQ ID NO: 151, (ii) a CD8 transmembrane domain comprising the amino acid sequence set forth in SEQ ID NO: 126, and (iii) an endodomain that comprises a CD28 co-stimulatory domain comprising the amino acid sequence set forth in SEQ ID NO: 20 and a CD3-zeta signaling domain comprising the amino acid sequence set forth in SEQ ID NO: 22.

In some embodiments, the anti-CD19 CAR comprises (i) an ectodomain that comprises an anti-CD19 scFv comprising variable heavy and light chain regions comprising the amino acid sequences set forth in SEQ ID NOs: 152 and 153, respectively, (ii) a CD8 transmembrane domain comprising the amino acid sequence set forth in SEQ ID NO: 126, and (iii) an endodomain that comprises a CD28 co-stimulatory domain comprising the amino acid sequence set forth in SEQ ID NO: 20 and a CD3-zeta signaling domain comprising the amino acid sequence set forth in SEQ ID NO: 22.

In some embodiments, the anti-CD19 CAR comprises the amino acid sequence set forth in SEQ ID NO: 149. In some embodiments, the anti-CD19 CAR is encoded by the nucleotide sequence set forth in SEQ ID NO: 148. In some embodiments, the anti-CD19 CAR is encoded by a nucleotide sequence having at least 80%, 85%, 90%, 95%, 96%, 97%, 98%, 99% or 100% identity to the nucleotide sequence set forth in SEQ ID NO: 148.

CD33 CAR

In some embodiments, the engineered T cells described herein comprise a CD33 targeting CAR, also referred to herein as CD33 CAR, anti-CD33 CAR or anti-CD33 CAR T cells. In some embodiments, the anti-CD33 CAR comprises (i) an ectodomain that comprises an anti-CD33 antigen-binding domain, (ii) a transmembrane domain, and (iii) an endodomain comprising at least one co-stimulatory domain.

In some embodiments, the anti-CD33 CAR comprises (i) an ectodomain that comprises an anti-CD33 antigen-binding domain, (ii) a CD8 transmembrane domain, and (iii) an endodomain that comprises a CD28 or 41BB co-stimulatory domain, and a CD3-zeta signaling domain. In some embodiments, the anti-CD33 CAR comprises (i) an ectodomain that comprises an anti-CD33 antigen-binding domain, (ii) a CD8 transmembrane domain, and (iii) an endodomain that comprises a CD28 co-stimulatory domain and a CD3-zeta signaling domain. In some embodiments, the anti-CD33 CAR comprises (i) an ectodomain that comprises an anti-CD33 antigen-binding domain, (ii) a CD8 transmembrane domain, and (iii) an endodomain that comprises a 41BB co-stimulatory domain and a CD3-zeta signaling domain.

In some embodiments, the anti-CD33 CAR comprises (i) an ectodomain that comprises an anti-CD33 antigen-binding domain, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD33 CAR comprises (i) an ectodomain that comprises an anti-CD33 scFv comprising the amino acid sequence set forth in SEQ ID NO: 137, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD33 CAR comprises (i) an ectodomain that comprises an anti-CD33 scFv comprising variable heavy and light chain regions comprising the amino acid sequences set forth in SEQ ID NOs: 140 and 141, respectively, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD33 CAR comprises the amino acid sequence set forth in SEQ ID NO: 139. In some embodiments, the anti-CD33 CAR is encoded by the nucleotide sequence set forth in SEQ ID NO: 136. In some embodiments, the anti-CD33 CAR is encoded by a nucleotide sequence having at least 80%, 85%, 90%, 95%, 96%, 97%, 98%, 99% or 100% identity to the nucleotide sequence set forth in SEQ ID NO: 136.

BCMA CAR

In some embodiments, the engineered T cells described herein comprise a BCMA targeting CAR, also referred to herein as BCMA CAR, anti-BCMA CAR or anti-BCMA CAR T cells. In some embodiments, the anti-BCMA CAR comprises (i) an ectodomain that comprises an anti-BCMA antigen-binding domain, (ii) a transmembrane domain, and (iii) an endodomain comprising at least one co-stimulatory domain.

In some embodiments, the anti-BCMA CAR comprises (i) an ectodomain that comprises an anti-BCMA antigen-binding domain, (ii) a CD8 transmembrane domain, and (iii) an endodomain that comprises a CD28 or 41BB co-stimulatory domain, and a CD3-zeta signaling domain. In some embodiments, the anti-BCMA CAR comprises (i) an ectodomain that comprises an anti-BCMA antigen-binding domain, (ii) a CD8 transmembrane domain, and (iii) an endodomain that comprises a CD28 co-stimulatory domain and a CD3-zeta signaling domain. In some embodiments, the anti-BCMA CAR comprises (i) an ectodomain that comprises an anti-BCMA antigen-binding domain, (ii) a CD8 transmembrane domain, and (iii) an endodomain that comprises a 41BB co-stimulatory domain and a CD3-zeta signaling domain.

In some embodiments, the anti-BCMA CAR comprises (i) an ectodomain that comprises an anti-BCMA antigen-binding domain, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-BCMA CAR comprises (i) an ectodomain that comprises an anti-BCMA scFv comprising the amino acid sequence set forth in SEQ ID NO: 59, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-BCMA CAR comprises (i) an ectodomain that comprises an anti-BCMA scFv comprising variable heavy and light chain regions comprising the amino acid sequences set forth in SEQ ID NOs: 60 and 61, respectively, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-BCMA CAR comprises the amino acid sequence set forth in SEQ ID NO: 57. In some embodiments, the anti-BCMA CAR is encoded by the nucleotide sequence set forth in SEQ ID NO: 56. In some embodiments, the anti-BCMA CAR is encoded by a nucleotide sequence having at least 80%, 85%, 90%, 95%, 96%, 97%, 98%, 99% or 100% identity to the nucleotide sequence set forth in SEQ ID NO: 56.

CD70 CAR

In some embodiments, the engineered T cells described herein comprise a CD70 targeting CAR, also referred to herein as CD70 CAR, anti-CD70 CAR or anti-CD70 CAR T cells. In some embodiments, the anti-CD70 CAR comprises (i) an ectodomain that comprises an anti-CD70 antigen-binding domain, (ii) a transmembrane domain, and (iii) an endodomain comprising at least one co-stimulatory domain.

In some embodiments, the anti-CD70 CAR comprises (i) an ectodomain that comprises an anti-CD70 antigen-binding domain, (ii) a CD8 transmembrane domain, and (iii) an endodomain that comprises a CD28 or 41BB co-stimulatory domain, and a CD3-zeta signaling domain. In some embodiments, the anti-CD70 CAR comprises (i) an ectodomain that comprises an anti-CD70 antigen-binding domain, (ii) a CD8 transmembrane domain, and (iii) an endodomain that comprises a CD28 co-stimulatory domain and a CD3-zeta signaling domain. In some embodiments, the anti-CD70 CAR comprises (i) an ectodomain that comprises an anti-CD70 antigen-binding domain, (ii) a CD8 transmembrane domain, and (iii) an endodomain that comprises a 41BB co-stimulatory domain and a CD3-zeta signaling domain.

In some embodiments, the anti-CD70 CAR comprises (i) an ectodomain that comprises an anti-CD70 antigen-binding domain, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD70 CAR comprises (i) an ectodomain that comprises an anti-CD70 scFv comprising the amino acid sequence set forth in SEQ ID NO: 50, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD70 CAR comprises (i) an ectodomain that comprises an anti-CD70 scFv comprising variable heavy and light chain regions comprising the amino acid sequences set forth in SEQ ID NOs: 51 and 52, respectively, (ii) a CD8 transmembrane domain comprising the amino acid sequence set forth in SEQ ID NO: 126, and (iii) an endodomain that comprises a 41BB co-stimulatory domain comprising the amino acid sequence set forth in SEQ ID NO: 19 and a CD3-zeta signaling domain comprising the amino acid sequence set forth in SEQ ID NO: 22.

In some embodiments, the anti-CD70 CAR comprises the amino acid sequence set forth in SEQ ID NO: 46. In some embodiments, the anti-CD70 CAR is encoded by the nucleotide sequence set forth in SEQ ID NO: 45. In some embodiments, the anti-CD70 CAR is encoded by a nucleotide sequence having at least 80%, 85%, 90%, 95%, 96%, 97%, 98%, 99% or 100% identity to the nucleotide sequence set forth in SEQ ID NO: 45.

Expression of Chimeric Antigen Receptor Construct

Donor Template

The nucleic acid encoding a CAR may be delivered to a T cell that comprises what is referred to herein as a donor template (also referred to as a donor polynucleotide). A donor template can contain a non-homologous sequence, such as the nucleic acid encoding a CAR, flanked by two regions of homology to allow for efficient HDR at a genomic location of interest. Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, is inserted so that its expression is driven by the endogenous promoter at the integration site, namely the promoter that drives expression of the endogenous gene into which the donor is inserted. However, in some embodiments, the donor template comprises an exogenous promoter and/or enhancer, for example a constitutive promoter, an inducible promoter, or tissue-specific promoter. In some embodiments, the exogenous promoter is an EF1α promoter comprising a sequence of SEQ ID NO: 123. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

In some embodiments, the donor template comprises a nucleotide sequence having at least 80%, 85%, 90%, 95%, 96%, 97%, 98% or 98% identity to SEQ ID NO: 44. In some embodiments, the donor template comprises the nucleotide sequence of SEQ ID NO: 44.

In some embodiments, the donor template comprises a nucleotide sequence having at least 80%, 85%, 90%, 95%, 96%, 97%, 98% or 98% identity to SEQ ID NO: 55. In some embodiments, the donor template comprises the nucleotide sequence of SEQ ID NO: 55.

In some embodiments, the donor template comprises a nucleotide sequence having at least 80%, 85%, 90%, 95%, 96%, 97%, 98% or 98% identity to SEQ ID NO: 135. In some embodiments, the donor template comprises the nucleotide sequence of SEQ ID NO: 135.

In some embodiments, the donor template comprises a nucleotide sequence having at least 80%, 85%, 90%, 95%, 96%, 97%, 98% or 98% identity to SEQ ID NO: 156. In some embodiments, the donor template comprises the nucleotide sequence of SEQ ID NO: 156.

Other Methods

In some embodiments, a nucleic acid encoding a CAR is introduced into an engineered cell by methods known to those of skill in the art. For example, a CAR may be introduced into an engineered cell by a vector. A variety of different methods known in the art can be used to introduce any of the nucleic acids or expression vectors disclosed herein into an immune effector cell. Non-limiting examples of methods for introducing nucleic acid into a cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

Delivery Methods and Constructs

Nucleases and/or donor templates may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids. Some specific examples are provided below.

Adeno-Associated Viral Delivery

The donor nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV is AAV serotype 6 (AAV6).

Adeno-associated viruses are among the most frequently used viruses for gene therapy for several reasons. First, AAVs do not provoke an immune response upon administration to mammals, including humans Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

Homology-Directed Repair (HDR)

The donor nucleic acid encoding a CAR is inserted by homology directed repair (HDR) into the target gene locus. Both strands of the DNA at the target locus are cut by a CRISPR Cas9 enzyme. HDR then occurs to repair the double-strand break (DSB) and insert the donor DNA. For this to occur correctly, the donor sequence is designed with flanking residues which are complementary to the sequence surrounding the DSB site in the target gene (hereinafter "homology arms"). These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

The target gene can be associated with an immune response in a subject, wherein permanently deleting at least a portion of the target gene will modulate the immune response. For example, to generate a CAR T cell, the target gene can be the TCRα constant region (TRAC). Disruption of TRAC leads to loss of function of the endogenous TCR.

In some embodiments, the target gene is in a safe harbor locus.

Engineered T Cells

Engineered (gene edited) CAR T cells of the present disclosure may be autologous ("self") or non-autologous ("non-self," e.g., allogeneic, syngeneic or xenogeneic). "Autologous" refers to cells from the same subject. "Allogeneic" refers to cells of the same species as a subject, but that differ genetically to the cells in the subject. In some embodiments, the T cells are obtained from a mammal. In some embodiments, the T cells are obtained from a human.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some embodiments, an isolated population of T cells is used. In some embodiments, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, the engineered T cell populations do not express or do not substantially express one or more of the following markers: CD70, CD57, CD244, CD160, PD-1, CTLA4, HM3, and LAGS. In some embodiments, subpopulations of T cells may be isolated by positive or negative selection prior to genetic engineering and/or post genetic engineering.

In some embodiments, an isolated population of T cells expresses one or more of the markers including, but not limited to a CD3+, CD4+, CD8+, or a combination thereof. In some embodiments, the T cells are isolated from a donor, or subject, and first activated and stimulated to proliferate in vitro prior to undergoing gene editing.

To achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells.

In some embodiments, T cells are activated at the same time that genome editing compositions are introduced into the T cells. T cell populations or isolated T cells generated by any of the gene editing methods described herein are also within the scope of the present disclosure.

In some embodiments, provided herein is a population of T cells comprising genetically engineered T cells, which comprise a disrupted endogenous CD70 gene and a nucleic acid encoding a chimeric antigen receptor (CAR), e.g., those described herein. In some embodiments, the CAR binds an antigen expressed on a pathological cell. In some embodiments, the CAR binds CD70. In other embodiments, the CAR does not bind CD70. Such a T cell population may further comprise genetically engineered T cells having one or more of the following gene edits: a disrupted endogenous programmed cell death-1 (PD-1) gene, a disrupted endogenous T cell receptor alpha chain constant region (TRAC) gene, and a disrupted endogenous beta-2-microglobulin (β2M) gene. In some examples, the nucleic acid encoding the CAR may be inserted into the TRAC locus.

In some embodiments, the population of T cells disclosed herein comprises genetically engineered T cells, which comprise a disrupted CD70 gene and a nucleic acid encoding a chimeric antigen receptor (CAR) that binds an antigen expressed on a pathological cell. In some embodiments, the population of T cells disclosed herein comprises genetically engineered T cells, which comprise a disrupted CD70 gene and a nucleic acid encoding a chimeric antigen receptor (CAR), wherein the CAR binds CD70. In other embodiments, the population of T cells disclosed herein comprises genetically engineered T cells that comprise a disrupted CD70 gene and a nucleic acid encoding a CAR, wherein the CAR does not bind CD70. In some embodiments, the population of T cells disclosed herein comprises genetically engineered T cells, which comprise a disrupted CD70 gene and a nucleic acid encoding a chimeric antigen receptor (CAR) that binds an antigen expressed on a pathological cell, and further comprises a disrupted PD1 gene. In some embodiments, the CAR binds CD70. In some embodiments the CAR does not bind CD70. In some aspects, the CAR binds CD19. In some embodiments, the CAR binds CD33. In some aspects, the CAR binds BCMA. Any of the just-noted engineered T cells may further comprise a disrupted T cell receptor alpha chain constant region (TRAC) gene and/or a disrupted beta-2-microglobulin (β2M) gene.

In particular examples, provided herein is a population of T cells comprising genetically engineered T cells, which comprise a disrupted CD70 gene, a disrupted T cell receptor alpha chain constant region (TRAC) gene, a disrupted beta-2-microglobulin (β2M) gene, a nucleic acid encoding a chimeric antigen receptor (CAR), e.g., an anti-BCMA CAR, anti-CD19 CAR, anti-CD33 CAR, or anti-CD70 CAR as described herein, and optionally a disrupted programmed cell death-1 (PD-1) gene. Any of the engineered T cells disclosed herein may contain native (undisrupted) HLA genes.

In some examples, at least 50% (e.g., 60%, 70%, 80%, 90%, or 95%) of the population of T cells express the CAR as disclosed herein and do not express a detectable level of surface CD70. Such cells may further possess the features of not expressing a detectable level of surface TCR, a detectable level of surface β2M, and/or a detectable level of surface PD-1. For example, at least 50% (e.g., 60%, 70%, 80%, 90%, or 95%) of the population of T cells express the CAR as disclosed herein and do not express a detectable level of surface CD70, a detectable level of surface TCR, and a detectable level of surface β2M. In some instances, at least 50% (e.g., 60%, 70%, 80%, 90%, or 95%) of the population of T cells express the CAR as disclosed herein and do not express a detectable level of surface CD70, a detectable level of surface TCR, a detectable level of surface β2M, and a detectable level of PD-1.

An isolated cell expressing the CAR as described herein and does not express a detectable level of surface CD70 is also within the scope of the present disclosure. Such an isolated cell may not express a detectable level of surface TCR, a detectable level of surface β2M, and/or a detectable level of surface PD-1. In some examples, the isolated cell comprises a nucleic acid encoding the CAR, which is inserted into the TRAC locus.

Also provided herein are an engineered T cell population comprising engineered T cells comprising an RNA-guided nuclease, e.g., those described herein (for example, a Cas9 nuclease), and a guide RNA (gRNA) targeting a CD70 gene (e.g., those described herein). In some instances, at least 50% (e.g., 60%, 70%, 80%, 90%, or 95%) of the T cells in the T cell population comprise the RNA-guided nuclease and the gRNA targeting the CD70 gene. Such an engineered T cell population may further comprise engineered T cells comprising a gRNA targeting a PD-1 gene, a gRNA targeting a TRAC gene, a gRNA targeting a β2M gene, and/or a nucleic acid (e.g., a vector) comprising a donor template that comprises a nucleotide sequence encoding a CAR (e.g., those described herein), which optionally is flanked by left and right homology arms to the TRAC gene locus. In some examples, at least 50% (e.g., 60%, 70%, 80%, 90%, or 95%) of the T cells in the T cell population comprise the RNA-guided nuclease, the gRNA targeting the CD70 gene, and the nucleic acid coding for the CAR. When the nucleic acid coding for the CAR further comprises the left and right homology arms to the TRAC gene locus, the T cells may also comprise a gRNA targeting the TRAC gene. In addition, the T cells may further comprise a gRNA targeting a PD-1 gene, a gRNA targeting a β2M gene, or a combination thereof.

Also within the scope of the present disclosure is an isolated engineered T cell comprising the RNA-guided nuclease, the gRNA targeting the CD70 gene, and optionally one or more of a gRNA targeting a PD-1 gene, a gRNA targeting a TRAC gene, a gRNA targeting a β2M gene, and a nucleic acid (e.g., a vector) comprising a donor template that comprises a nucleotide sequence encoding a CAR (e.g., those described herein). The nucleotide sequence encoding the CAR may be flanked by left and right homology arms to the TRAC gene locus.

Generating CAR-T Cells

In some embodiments, the engineered T cells described herein are generated by modifying the genome of the cells. In some embodiments, a double stranded break (DSB) at a site in a target gene is induced. In some embodiments, the DSB is repaired using one or more endogenous DNA repair pathways. In some embodiments, a DNA repair pathway does not require a homologous sequence (e.g., the non-homologous end joining pathway or NHEJ pathway). In some embodiments, a repair pathway requires a homologous sequence (e.g., the homology-directed pathway or HDR pathway).

In some embodiments, the engineered T cells described herein are generated by inducing a DSB with CRISPR-Cas9 as an endonuclease, and one or more non-coding RNAs, and repairing the DSB using HDR and a donor polynucleotide template described herein.

In some embodiments, the engineered T cells described herein are generated using a gRNA complimentary to a sequence of a target gene that is a TRAC. In some embodiments, the engineered T cells described herein are generated using a TRAC gRNA spacer comprising the sequence set forth in SEQ ID NO: 98. In some embodiments, the engineered T cells described herein are generated using a TRAC gRNA comprising the sequence set forth in SEQ ID NO: 30. In some embodiments, the TRAC gRNA comprising the sequence set forth in SEQ ID NO: 98 targets the TRAC sequence set forth in SEQ ID NO: 118. In some embodiments, the TRAC gRNA comprising the sequence set forth in SEQ ID NO: 30 targets the TRAC sequence set forth in SEQ ID NO: 118.

In some embodiments, the engineered T cells described herein are generated using a TRAC gRNA spacer comprising the sequence set forth in SEQ ID NO: 108. In some embodiments, the engineered T cells described herein are generated using a TRAC gRNA comprising the sequence set forth in SEQ ID NO: 40. In some embodiments, the TRAC gRNA comprising the sequence set forth in SEQ ID NO: 108 targets the TRAC sequence set forth in SEQ ID NO: 118. In some embodiments, the TRAC gRNA comprising the sequence set forth in SEQ ID NO: 40 targets the TRAC sequence set forth in SEQ ID NO: 118.

In some embodiments, the engineered T cells described herein are generated using a gRNA complimentary to a sequence of a target gene that is β2M. In some embodiments, the engineered T cells described herein are generated using a β2M gRNA spacer comprising the sequence set forth in SEQ ID NO: 99. In some embodiments, the engineered T cells described herein are generated using a β2M gRNA comprising the sequence set forth in SEQ ID NO: 31. In some embodiments, the β2M gRNA comprising the sequence set forth in SEQ ID NO: 99 targets the β2M sequence set forth in SEQ ID NO: 119. In some embodiments, the β2M gRNA comprising the sequence set forth in SEQ ID NO: 31 targets the β2M sequence set forth in SEQ ID NO: 119.

In some embodiments, the engineered T cells described herein are generated using a β2M gRNA spacer comprising the sequence set forth in SEQ ID NO: 109. In some embodiments, the engineered T cells described herein are generated using a β2M gRNA comprising the sequence set forth in SEQ ID NO: 41. In some embodiments, the β2M gRNA comprising the sequence set forth in SEQ ID NO: 109 targets the β2M sequence set forth in SEQ ID NO: 119. In some embodiments, the β2M gRNA comprising the sequence set forth in SEQ ID NO: 41 targets the β2M sequence set forth in SEQ ID NO: 119.

In some embodiments, the engineered T cells described herein are generated using a gRNA complimentary to a sequence of a target gene that is a CD70. In some embodiments, the engineered T cells described herein are generated using a CD70 gRNA spacer comprising the sequence set forth in SEQ ID NO: 94. In some embodiments, the engineered T cells described herein are generated using a CD70 gRNA comprising the sequence set forth in SEQ ID NO: 26. In some embodiments, the CD70 gRNA comprising the sequence set forth in SEQ ID NO: 94 targets the CD70 sequence set forth in SEQ ID NO: 114. In some embodiments, the CD70 gRNA comprising the sequence set forth in SEQ ID NO: 26 targets the CD70 sequence set forth in SEQ ID NO: 114.

In some embodiments, the engineered T cells described herein are generated using a CD70 gRNA spacer comprising the sequence set forth in SEQ ID NO: 104. In some embodiments, the engineered T cells described herein are generated using a CD70 gRNA comprising the sequence set forth in SEQ ID NO: 36. In some embodiments, the CD70 gRNA comprising the sequence set forth in SEQ ID NO: 104 targets the CD70 sequence set forth in SEQ ID NO: 114. In some embodiments, the CD70 gRNA comprising the sequence set forth in SEQ ID NO: 36 targets the CD70 sequence set forth in SEQ ID NO: 114.

In some embodiments, the engineered T cells described herein are generated using a gRNA complimentary to a sequence of a target gene that is a CD70. In some embodiments, the engineered T cells described herein are generated using a CD70 gRNA spacer comprising the sequence set forth in SEQ ID NO: 95. In some embodiments, the engineered T cells described herein are generated using a CD70 gRNA comprising the sequence set forth in SEQ ID NO: 27. In some embodiments, the CD70 gRNA comprising the sequence set forth in SEQ ID NO: 95 targets the CD70 sequence set forth in SEQ ID NO: 115. In some embodiments, the CD70 gRNA comprising the sequence set forth in SEQ ID NO: 27 targets the CD70 sequence set forth in SEQ ID NO: 115.

In some embodiments, the engineered T cells described herein are generated using a CD70 gRNA spacer comprising the sequence set forth in SEQ ID NO: 105. In some embodiments, the engineered T cells described herein are generated using a CD70 gRNA comprising the sequence set forth in SEQ ID NO: 37. In some embodiments, the CD70 gRNA comprising the sequence set forth in SEQ ID NO: 105 targets the CD70 sequence set forth in SEQ ID NO: 115. In some embodiments, the CD70 gRNA comprising the sequence set forth in SEQ ID NO: 37 targets the CD70 sequence set forth in SEQ ID NO: 115.

In some embodiments, the engineered T cells described herein are generated using a gRNA complimentary to a sequence of a target gene that is a PD-1. In some embodiments, the engineered T cells described herein are generated using a PD-1 gRNA spacer comprising the sequence set forth in SEQ ID NO: 100. In some embodiments, the engineered T cells described herein are generated using a PD-1 gRNA comprising the sequence set forth in SEQ ID NO: 32. In some embodiments, the PD-1 gRNA comprising the sequence set forth in SEQ ID NO: 100 targets the β2M sequence set forth in SEQ ID NO: 120. In some embodiments, the PD-1 gRNA comprising the sequence set forth in SEQ ID NO: 32 targets the PD-1 sequence set forth in SEQ ID NO: 120.

In some embodiments, the engineered T cells described herein are generated using a PD-1 gRNA spacer comprising the sequence set forth in SEQ ID NO: 110. In some embodiments, the engineered T cells described herein are generated using a PD-1 gRNA comprising the sequence set forth in SEQ ID NO: 42. In some embodiments, the PD-1 gRNA comprising the sequence set forth in SEQ ID NO: 110 targets the PD-1 sequence set forth in SEQ ID NO: 120. In some embodiments, the PD-1 gRNA comprising the sequence set forth in SEQ ID NO: 42 targets the PD-1 sequence set forth in SEQ ID NO: 120.

In some embodiments, the engineered T cells described herein are generated using a TRAC gRNA comprising the sequence set forth in SEQ ID NO: 98, β2M gRNA comprising the sequence set forth in SEQ ID NO: 99, a CD70 gRNA comprising the sequence set forth in SEQ ID NO: 94 or 95, and/or a PD-1 gRNA comprising the sequence set forth in SEQ ID NO: 100. In some embodiments, the engineered T cells described herein are generated using a TRAC gRNA comprising the sequence set forth in SEQ ID NO: 108, a β2M gRNA comprising the sequence set forth in SEQ ID NO: 109, a CD70 gRNA comprising the sequence set forth in SEQ ID NO: 104 or 105, and/or a PD-1 gRNA comprising the sequence set forth in SEQ ID NO: 110.

In some embodiments, the engineered T cells described herein are generated using a TRAC gRNA comprising the sequence set forth in SEQ ID NO: 30, β2M gRNA comprising the sequence set forth in SEQ ID NO: 31, a CD70 gRNA comprising the sequence set forth in SEQ ID NO: 26 or 27, and/or a PD-1 gRNA comprising the sequence set forth in SEQ ID NO: 32. In some embodiments, the engineered T cells described herein are generated using a TRAC gRNA comprising the sequence set forth in SEQ ID NO: 40, a β2M gRNA comprising the sequence set forth in SEQ ID NO: 41, a CD70 gRNA comprising the sequence set forth in SEQ ID NO: 36 or 27, and/or a PD-1 gRNA comprising the sequence set forth in SEQ ID NO: 42.

In some embodiments, the engineered T cells are generated using a donor template comprising a non-homologous sequence that is a nucleic acid encoding a CAR. In some embodiments, a donor template is comprised of homology arms that correspond to sequences in a target gene that is a TRAC. In some embodiments, a 5' homology arm (left homology arm) of the donor template comprises the sequence set forth in SEQ ID NO: 122. In some embodiments, a 3' homology arm of the donor template comprises the sequence set forth in SEQ ID NO: 125. In some embodiments, an exogenous promoter is an EF1a promoter comprises the sequence set forth in SEQ ID NO: 123. In some embodiments, a donor template comprises the sequence set forth in SEQ ID NO: 135. In some embodiments, a donor template comprises the sequence set forth in SEQ ID NO: 156. In some embodiments, a donor template comprises the sequence set forth in SEQ ID NO: 44. In some embodiments, a donor template comprises the sequence set forth in SEQ ID NO: 55.

In some embodiments, polynucleotides encoding gRNAs, nucleases, and donor templates are introduced into cells (e.g., T cells) using conventional viral and non-viral based gene transfer methods.

In some embodiments, a polynucleotide such as a gRNA, a sgRNA, an mRNA encoding a nuclease, or a donor template are delivered to a cell using a non-viral vector delivery system. Examples of a non-viral vector delivery system include, but are not limited to, a DNA plasmid, a DNA minicircle, a naked nucleic acid, a liposome, a ribonucleoprotein particle (RNP) or a poloxamer. In some embodiments, a method of introducing polynucleotides to a cell using a non-viral vector delivery system includes electroporation, lipofection, microinjection, biolistics, or agent-enhanced uptake.

In some embodiments, a polynucleotide such as a gRNA, a sgRNA, an mRNA encoding a nuclease, or a donor template are delivered to a cell using a viral vector delivery system. Examples of a viral vector delivery system include, but are not limited to, retroviral vectors, lentiviral vectors, adenovirus vectors, poxvirus vectors, herpesvirus vectors, and adeno-associated virus (AAV) vectors.

In some embodiments, a donor template encoding a CAR construct is delivered to a cell as one or more polynucleotides. In some embodiments, a donor template encoding a CAR construct is delivered by a viral delivery vehicle. In some embodiments, a viral delivery vehicle is an adeno-associated virus (AAV) vector.

In some embodiments, an endonuclease (e.g., Cas9) is delivered to a cell as a polypeptide. In some embodiments, an endonuclease (e.g., Cas9) is delivered to a cell separately from a genome-targeting nucleic acid (e.g., a gRNA, a sgRNA). In some embodiments, an endonuclease (e.g., Cas9) is delivered to a cell as a complex with one or more genome-targeting polynucleotides (e.g., a gRNA, a sgRNA). In some embodiments, a endonuclease or a pre-complexed endonuclease is delivered by a non-viral delivery vehicle that includes, but is not limited to, a nanoparticle, a liposome, a ribonucleoprotein, a positively charged peptide, a small molecule RNA-conjugate, an aptamer-RNA chimeras, or an RNA-fusion protein complex. In some embodiments, a method of introducing an endonuclease polypeptide or a pre-complexed endonuclease polypeptide to a cell includes electroporation, lipofection, microinjection, biolistics, or agent-enhanced uptake.

In some embodiments, a Cas9 polypeptide is pre-complexed with one or more sgRNAs to form a ribonucleoprotein particle (RNP). In some embodiments, a Cas9/sgRNA RNP is formulated using a lipid nanoparticle. In some embodiments, a donor template is formulated using an AAV vector. In some embodiments, delivery to a cell of a formulated Cas9/sgRNA RNP is performed by electroporation of the cell. In some embodiments, a donor template formulated as an AAV vector is delivered prior to electroporation. In some embodiments, a donor template formulated as an AAV vector is delivered during electroporation. In some embodiments, a donor template formulated as an AAV vector is delivered following electroporation.

In some embodiments, a gene edit performed using a CRISPR/Cas9 endonuclease results in an engineered T cell with a disrupted TRAC gene. In some embodiments, a disruption of a TRAC gene results in eliminated or decreased expression of the TRAC gene. In some embodiments, a disruption of a TRAC gene disrupts or inhibits transcription and translation of an encoded gene product. In some embodiments, a disruption of a TRAC gene results in eliminated or decreased expression of a TRAC gene product. In some embodiments, eliminated or decreased expression of the TRAC gene is associated with loss of function of the TCR. In some embodiments, loss of TCR function renders an engineered T cell suitable to allogeneic transplantation (i.e., minimizing the risk of inducing GvHD). In some embodiments, a disruption of a TRAC gene is created by knocking in a CAR into the TRAC gene (e.g., using an AAV vector and a donor template). In some embodiments, a disruption in the TRAC gene expression is created by gRNAs targeting the TRAC genomic region and knocking in a CAR into the CAR gene. In some embodiments, a knock-in CAR is provided by a donor template with homology arms that correspond to sequences of the TRAC surrounding the site of a DSB.

In some embodiments, a gene edit performed using a CRISPR/Cas9 endonuclease results in an engineered T cell with a disrupted β2M gene. In some embodiments, gRNAs targeting the B2M genomic region create indels in the β2M gene that disrupt or inhibit transcription and translation of an encoded gene product. In some embodiments, a disruption of a β2M gene results in eliminated or decreased expression of the β2M polypeptide. In some embodiments, eliminated or decreased expression of the B2M polypeptide is associated with loss of function of the MHC I complex. In some embodiments, loss of MHC I function renders an engineered T cell suitable to allogeneic transplantation (i e, minimizing the risk of a host versus allogeneic T cell response). In some embodiments, loss of MHC I function results in increased persistence of an engineered T cell in an allogeneic recipient.

In some embodiments, a gene edit performed using a CRISPR/Cas9 endonuclease results in an engineered T cell with a disrupted CD70 gene. In some embodiments, gRNAs targeting the CD70 genomic region create indels in the CD70 gene that disrupt or inhibit transcription and translation of an encoded gene product. In some embodiments, a disruption of a CD70 gene results in eliminated or decreased expression of the CD70 polypeptide. In some embodiments, eliminated or decreased expression of the CD70 polypeptide is associated with enhanced cell proliferation, enhanced in vivo persistence, decreased exhaustion, and/or enhanced anti-tumor efficacy.

In some embodiments, a gene edit performed using a CRISPR/Cas9 endonuclease results in an engineered T cell with a disrupted PD-1 gene. In some embodiments, gRNAs targeting the PD-1 genomic region create indels in the PD-1 gene that disrupt or inhibit transcription and translation of an encoded gene product. In some embodiments, a disruption of a PD-1 gene results in eliminated or decreased expression of the PD-1 polypeptide.

Methods and Compositions

Provided herein, in some embodiments, are methods for treating cancer. Non-limiting examples of cancers that may be treated as provided herein include multiple myeloma, leukemia (e.g., T cell leukemia, B-cell acute lymphoblastic leukemia (B-ALL), and/or chronic lymphocytic leukemia (C-CLL)), lymphoma (e.g., B-cell non-Hodgkin's lymphoma (B-NHL), Hodgkin's lymphoma, and/or T cell lymphoma), and/or clear cell renal cell carcinoma (ccRCC). In some embodiment, the methods comprise delivering the CAR T cells (e.g., anti-BCMA, anti-CD19, anti-CD33 and/or anti-CD70 CAR T cells) of the present disclosure to a subject having multiple myeloma, leukemia, or lymphoma. Other non-limiting examples of cancers (e.g., solid tumors) that may be treated as provided herein include pancreatic cancer, gastric cancer, ovarian cancer, cervical cancer, breast cancer, renal cancer, thyroid cancer, nasopharyngeal cancer, non-small cell lung (NSCLC), glioblastoma, and/or melanoma.

CD70 has also been detected on hematological tumors and on carcinomas. The restricted expression pattern of CD70 in normal tissues and its widespread expression in various malignancies makes it an attractive target for antibody-based therapeutics. The use of CAR T cell therapy to target $CD70^+$ cancers, however, is potentially problematic because of CD70 expression in the T cells. To address this potential problem, the present disclosure also provides CAR T cells that have been engineered to disrupt endogenous CD70 expression while at the same time expressing an anti-CD70 binding moiety (e.g., an anti-CD70 scFv).

In some embodiments, the cancer is a $CD70^+$ cancer. In other embodiments, the cancer is a $BCMA^+$ cancer. In some embodiments, the cancer is a CD19+ cancer. In some embodiments, the cancer is a CD33+ cancer. It should be understood that other cancers, expressing other cancer antigens, may be treated using the engineered CD70 knockout CAR T cells of the present disclosure.

The methods, in some embodiments, comprise administering to a subject (e.g., a patient having a $CD70^+$ cancer, a $BCMA^+$ cancer, a CD19+ cancer or a CD33+ cancer) a population of CAR T cells as provided herein. In some embodiments, the methods comprise administering to a subject a population of CAR T cells comprising a CD70 gene knockout. In some embodiments, the methods comprise administering to a subject a population of CAR T cells comprising a CD70 gene knockout and a PD1 gene knockout. In some embodiments, the methods comprise implanting the cells into subject. This implanting step may be accomplished using any method of implantation known in the art. For example, the engineered cells may be injected directly in a subject's blood or otherwise administered to the subject.

As demonstrated herein, CAR T cells comprising a CD70 gene knockout exhibit extended proliferation and increased in vivo persistence. In some embodiments, CAR T cells comprising a CD70 gene knockout exhibit increased anti-tumor efficacy relative to CAR T cells expressing endogenous CD70. In some embodiments, CAR T cells comprising a CD70 gene knockout exhibit increased anti-tumor efficacy in solid tumors relative to CAR T cells expressing endogenous CD70. Without wishing to be bound by theory, the increased in vivo persistence of CAR T cells comprising a CD70 gene knockout may allow for expansion in solid tumors and therefore provide enhanced anti-tumor efficacy in such tumors relative to CAR T cells expressing endogenous CD70.

In some embodiments, the disclosure provides a method for treating a solid tumor with the CAR T cells described herein. In some embodiments, the disclosure provides a method for treating a solid tumor with the anti-CD70 CAR T cells described herein.

The step of administering may include the placement (e.g., transplantation) of cells, e.g., engineered T cells, into a subject, by a method or route that results in at least partial localization of the introduced cells at a desired site, such as tumor, such that a desired effect(s) is produced. Engineered T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of engineered T cells is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient (e.g., subject). For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various aspects described herein, an effective amount of cells (e.g., engineered T cells) comprises at least $10^2$ cells, at least $5 \times 10^2$ cells, at least $10^3$ cells, at least $5 \times 10^3$ cells, at least $10^4$ cells, at least $5 \times 10^4$ cells, at least $10^5$ cells, at least $2 \times 10^5$ cells, at least $3 \times 10^5$ cells, at least $4 \times 10^5$ cells, at least $5 \times 10^5$ cells, at least $6 \times 10^5$ cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, or multiples thereof. The cells are derived from one or more donors, or are obtained from an autologous source. In some examples described herein, the cells are expanded in culture prior to administration to a subject in need thereof.

Modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

In some embodiments, engineered T cells are administered systemically, which refers to the administration of a population of cells other than directly into a target site, tissue, or organ, such that it enters, instead, the subject's circulatory system and, thus, is subject to metabolism and other like processes.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Combination therapies are also encompassed by the present disclosure. For example, CD70 and/or CD27 antibodies can be used to bind and/or modulate the activity of CD70 and/or CD27 on CAR T cells and promote a decrease in exhaustion, enhanced CAR T cell expansion and increase efficacy of cancer cell killing. Thus, CD70 and/or CD27 antibodies can be administered with any CAR T cell known in the art to improve the CAR T cell function. For example, any of the engineered T cells provided herein may be administered in combination with anti-CD70 antibodies, anti-CD27 antibodies, or a combination of anti-CD70 antibodies and anti-CD27 antibodies. In some embodiments, $TRAC^-/\beta 2M^-$ $CAR^+$ T cells (e.g., anti-CD70 CAR or anti-BCMA CAR) are administered in combination with anti-CD70 and/or anti-CD27 antibodies. In some embodiments, $TRAC^-/\beta 2M^-/PD-1^-/CD70^-$ $CAR^+$ T cells (e.g., anti-CD70 CAR or anti-BCMA CAR) are administered in combination with anti-CD70 and/or anti-CD27 antibodies. In some embodiments, $TRAC^-/\beta 2M^-/PD-1^-$ $CAR^+$ T cells (e.g., anti-CD70 CAR or anti-BCMA CAR) are administered in combination with anti-CD70 and/or anti-CD27 antibodies. In some embodiments, $TRAC^-/\beta 2M/CD70^-$ $CAR^+$ T cells (e.g., anti-CD70 CAR or anti-BCMA CAR) are administered in combination with anti-CD70 and/or anti-CD27 antibodies. In some embodiments, the antibodies administered in combination can be Varlilumab.

In some embodiments, the disclosure provides a method of reducing exhaustion of T cells comprising disrupting the CD70 gene in the T cells. In some embodiments, the disclosure provides a method of increasing proliferation of T cells comprising disrupting the CD70 gene in the T cells. In some embodiments, the disclosure provides a method of increasing cytotoxicity of T cells comprising disrupting the CD70 gene in the T cells. In some embodiments, the disclosure provides a method of overcoming inhibitory effect of an immune checkpoint (e.g., PD-1) in T cells comprising disrupting the CD70 gene in the T cells.

OTHER EMBODIMENTS

The disclosure relates to the following embodiments. Throughout this section, the term embodiment is abbreviated as 'E' followed by an ordinal. For example, E1 is equivalent to Embodiment 1.

E1. An engineered T cell comprising a disrupted CD70 gene, a disrupted programmed cell death-1 (PD-1) gene, and a nucleic acid encoding a chimeric antigen receptor (CAR).

E2. An engineered T cell comprising a disrupted CD70 gene and a nucleic acid encoding a chimeric antigen receptor (CAR) that binds CD70.

E3. An engineered T cell comprising a disrupted CD70 gene and a nucleic acid encoding a chimeric antigen receptor (CAR) that does not bind CD70.

E4. The engineered T cell of embodiment 2 or 3, further comprising a disrupted PD-1 gene.

E5. The engineered T cell of any one of embodiments 1-4 further comprising a disrupted T cell receptor alpha chain constant region (TRAC) gene.

E6. The engineered T cell of any one of embodiments 1-5 further comprising a disrupted beta-2-microglobulin (β2M) gene.

E7. An engineered T cell, comprising a disrupted T cell receptor alpha chain constant region (TRAC) gene;
  a disrupted beta-2-microglobulin (β2M) gene;
  a disrupted CD70 gene; and
  a nucleic acid encoding a chimeric antigen receptor (CAR).

E8. The engineered T cell of embodiment 7, wherein the nucleic acid encoding the CAR is inserted into the TRAC gene.

E9. The engineered T cell of embodiment 7 or 8, further comprising a disrupted PD-1 gene.

E10. The engineered T cell of any one of embodiments 1-9, wherein the CAR comprises an ectodomain that comprises an anti-CD70 antibody, optionally wherein the anti-CD70 antibody is an anti-CD70 single-chain variable fragment (scFv).

E11. The engineered T cell of embodiment 10, wherein the anti-CD70 scFv comprises the same heavy chain variable region (VH) complementarity determining regions (CDRs) and the same light chain variable region (VL) CDRs as a reference antibody, wherein the reference antibody comprises a VH set forth as SEQ ID NO: 51 and a VL set forth as SEQ ID NO: 52.

E12. The engineered T cell of embodiment 11, wherein the anti-CD70 scFv comprises the same VH and VL chains as the reference antibody.

E13. The engineered T cell of embodiment 11, wherein the anti-CD70 scFv comprises the amino acid sequence of SEQ ID NO: 48 or 50.

E14. The engineered T cell of embodiment 11, wherein the anti-CD70 scFv comprises the amino acid sequence of SEQ ID NO: 50.

E15. The engineered T cell of any one of embodiments 1-9, wherein the CAR comprises an ectodomain that comprises an anti-BCMA antibody, optionally wherein the anti-BCMA antibody is an anti-BCMA single-chain variable fragment (scFv).

E16. The engineered T cell of embodiment 15, wherein the anti-BCMA scFv comprises the same VH complementarity determining regions (CDRs) and the same VL CDRs as a reference antibody, wherein the reference antibody comprises a VH) set forth as SEQ ID NO: 60 and a VL set forth as SEQ ID NO: 61.

E17. The engineered T cell of embodiment 16, wherein the anti-BCMA scFv comprises the same VH and VL chains as the reference antibody.

E18. The engineered T cell of embodiment 16, wherein the anti-BCMA scFv comprises the amino acid sequence of SEQ ID NO: 59.

E19. The engineered T cell of any one of embodiments 1-18, wherein the CAR comprises a CD28 or 41BB co-stimulatory domain and optionally a CD3ζ signaling domain.

E20. The engineered T cell of any one of embodiments 5-19, wherein the TRAC gene comprises the nucleotide sequence of SEQ ID NO: 44 or 55 and/or the nucleic acid encoding the CAR comprises the nucleotide sequence of SEQ ID NO: 45 or 56.

E21. The engineered T cell of any one of embodiments 6-20, wherein the disrupted β2M gene comprises gene at least one nucleotide sequence selected from any one of SEQ ID NOS: 9-14.

E22. The engineered T cell of any one of embodiments 1-21, wherein the engineered T cell maintains cytotoxicity following 5 rechallenges with a cancer cell.

E23. The engineered T cell of embodiment 22, wherein the engineered T cell maintains cytotoxicity following 10 rechallenges with a cancer cell.

E24. A population of cells comprising engineered T cells that comprise a disrupted CD70 gene, a disrupted programmed cell death-1 (PD-1) gene, and a nucleic acid encoding a chimeric antigen receptor (CAR).

E25. A population of cells comprising engineered T cells that comprise a disrupted CD70 gene, and a nucleic acid encoding a chimeric antigen receptor (CAR) that binds CD70.

E26. A population of cells comprising engineered T cells that comprise a disrupted CD70 gene and a nucleic acid encoding a chimeric antigen receptor (CAR) that does not bind CD70.

E27. The population of cells of embodiment 25 or 26 further comprising a disrupted programmed cell death-1 (PD-1) gene.

E28. The population of cells of any one of embodiments 24-27 further comprising a disrupted T cell receptor alpha chain constant region (TRAC) gene.

E29. The population of cells of any one of embodiments 24-28 further comprising a disrupted beta-2-microglobulin (β2M) gene.

E30. A population of cells comprising
  engineered T cells that comprise
  a disrupted T cell receptor alpha chain constant region (TRAC) gene;
  a disrupted beta-2-microglobulin (β2M) gene;
  a disrupted CD70 gene; and
  a nucleic acid encoding a chimeric antigen receptor (CAR).

E31. The population of cells of embodiment 30, wherein the nucleic acid encoding the CAR is inserted into the TRAC gene.

E32. The population of cells of embodiment 30 or 31, wherein the engineered T cells further comprise a disrupted programmed cell death-1 (PD-1) gene.

E33. The population of cells of any one of embodiments 24 or 27-32, wherein the CAR comprises an ectodomain that comprises an anti-CD70 antibody, optionally wherein the anti-CD70 antibody is an anti-CD70 single-chain variable fragment (scFv).

E34. The population of cells of embodiment 33, wherein the anti-CD70 scFv comprises the same VH complementarity determining regions (CDRs) and the same VL CDRs as a reference antibody, wherein the reference antibody comprises a VH set forth as SEQ ID NO: 51 and a VL set forth as SEQ ID NO: 52.

E35. The population of cells of embodiment 34, wherein the anti-CD70 scFv comprises the same VH and VL chains as the reference antibody.

E36. The population of cells of embodiment 35, wherein the anti-CD70 scFv comprises the amino acid sequence of SEQ ID NO: 48 or 50.

E37. The population of cells of embodiment 35, wherein the anti-CD70 scFv comprises the amino acid sequence of SEQ ID NO: 50.

E38. The population of cells of any one of embodiments 24-32, wherein the CAR comprises an ectodomain that comprises an anti-BCMA antibody, optionally wherein the anti-BCMA antibody is an anti-BCMA single-chain variable fragment (scFv).

E39. The population of cells of embodiment 38, wherein the anti-BCMA scFv comprises the same VH complementarity determining regions (CDRs) and the same VL CDRs as a reference antibody, wherein the reference antibody comprises a VH set forth as SEQ ID NO: 60 and a VL set forth as SEQ ID NO: 61.

E40. The population of cells of embodiment 39, wherein the anti-BCMA scFv comprises the same VH and VL chains as the reference antibody.

E41. The population of cells of embodiment 39, wherein the anti-BCMA scFv comprises the amino acid sequence of SEQ ID NO: 59.

E42. The population of cells of any one of embodiments 28-41, wherein the TRAC gene comprises the nucleotide sequence of SEQ ID NO: 44 or 55 and/or the nucleic acid encoding the CAR comprises the nucleotide sequence of SEQ ID NO: 45 or 56.

E43. The population of cells of any one of embodiments 29-42, wherein the disrupted β2M gene comprises gene at least one nucleotide sequence selected from any one of SEQ ID NOS: 9-14.

E44. The population of cells of any one of embodiments 24-43, wherein at least 50% of the engineered T cells do not express a detectable level of TCR surface protein, do not express a detectable level of β2M surface protein, do not express a detectable level of CD70 surface protein, do not express a detectable level of PD-1 surface protein, and/or express a detectable level of the CAR.

E45. The population of cells of embodiment 44, wherein 50%-70%, of the engineered T cells do not express a detectable level of TCR surface protein, do not express a detectable level of β2M surface protein, do not express a detectable level of CD70 surface protein, do not express a detectable level of PD-1 surface protein, and/or express a detectable level of the CAR.

E46. The population of cells of any one of embodiments 28-45, wherein at least 90%, optionally 90%-100%, of the engineered T cells do not express a detectable level of TCR surface protein.

E47. The population of cells of any one of embodiments 29-46, wherein at least 60%, optionally 60%-75%, of the engineered T cells do not express a detectable level of β2M surface protein.

E48. The population of cells of any one of embodiments 24-47, wherein at least 80%, optionally 80%-100%, of the engineered T cells do not express a detectable level of CD70 surface protein.

E49. The population of cells of any one of embodiments 1-48, wherein at least 80%, optionally 80%-95%, of the engineered T cells express a detectable level of the CAR.

E50. The population of cells of any one of embodiments 24-49, wherein the engineered T cells exhibit at least 20% greater cellular proliferative capacity, relative to control T cells.

E51. The population of cells of any one of embodiments 24-50, wherein the engineered T cells exhibit at least 20% greater cellular lysis capability, relative to control T cells.

E52. The population of cells of any one of embodiments 24-51, wherein the level of cytokines secreted by the engineered T cells are at least 2-fold greater than the level of cytokines secreted by control T cells.

E53. The population of any one of embodiments 24-52, wherein the engineered T cells exhibit reduced cellular exhaustion, relative to control T cells.

E54. The population of cells of embodiment 53, wherein the engineered T cells express reduced levels of LAGS, relative to control T cells.

E55. The population of cells of any one of embodiments 54, wherein the control T cells are engineered T cells that express endogenous CD70 protein.

E56. The population of cells of any one of embodiments 24-55, wherein the engineered T cells maintain cytokine-dependent proliferation.

E57. The population of cells of any one of embodiments 24-56, wherein the engineered T cells maintain cytotoxicity following 5 rechallenges with a cancer cell.

E58. The population of cells of embodiment 47, wherein the engineered T cells maintain cytotoxicity following 10 rechallenges with a cancer cell.

E59. A method comprising administering to a subject the population of cells of any one of embodiments 24-58.

E60. The method of embodiment 59, wherein the engineered T cells are engineered human T cells.

E61. The method of embodiment 59 or 60, wherein the subject has a cancer.

E62. The method of embodiment 61, wherein the cancer expresses CD70 and/or BCMA.

E63. The method of any one of embodiments 59-62, wherein the population of cells is administered to the subject in an amount effective to treat the cancer.

E64. The method of any one of embodiments 59-63, wherein the cancer is a solid tumor malignancy or a hematological malignancy.

E65. The method embodiment 64, wherein the solid tumor malignancy is selected from the group consisting of: ovarian tumor, pancreatic tumor, kidney tumor, lung tumor, and intestinal tumor.

E66. The method of embodiment 63, wherein the population of cells is administered to the subject in an amount effective to reduce the volume of a tumor in the subject.

E67. A method for producing an engineered T cell, the method comprising
  (a) delivering to a T cell
    an RNA-guided nuclease,
    a gRNA targeting a CD70 gene, and
    a vector comprising a donor template that comprises a nucleic acid encoding a CAR; and
  (b) producing an engineered T cell comprising a disrupted CD70 gene and expressing the CAR.

E68. The method of embodiment 67, further comprising in step (a) delivering to the T cell a gRNA targeting a PD-1 gene; wherein the engineered T cell of step (b) further comprises a disrupted PD-1 gene.

E69. The method of embodiment 67 or embodiment 68, further comprising in step (a) delivering to the T cell a gRNA targeting a TRAC gene; wherein the engineered T cell of step (b) further comprises a disrupted TRAC gene.

E70. The method of embodiment 69, wherein the nucleic acid encoding the CAR is flanked by left and right homology arms to the TRAC gene locus; and wherein the engineered T cell of step (b) comprises the nucleic acid encoding the CAR inserted into the TRAC gene locus.

E71. The method of any one of embodiments embodiment 67-70, further comprising in step (a) delivering to the T cell a gRNA targeting a β2M gene; wherein the engineered T cell of step (b) further comprises a disrupted β2M gene.

E72. A method for producing an engineered T cell, the method comprising
 (a) delivering to a T cell
  an RNA-guided nuclease,
  a gRNA targeting a TRAC gene,
  a gRNA targeting a β2M gene,
  a gRNA targeting a CD70 gene, and
  a vector comprising a donor template that comprises a nucleic acid encoding a CAR; and
 (b) producing an engineered T cell.

E73. The method of embodiment 72, wherein the nucleic acid encoding the CAR is flanked by left and right homology arms to the TRAC gene locus.

E74. The method of embodiment 72 or 73 further comprising delivering to the T cell a gRNA targeting a PD-1 gene.

E75. The method of any one of embodiments 67-74, wherein the RNA-guided nuclease is a Cas9 nuclease, optionally a *S. pyogenes* Cas9 nuclease.

E76. The method of any one of embodiments 69-75, wherein the gRNA targeting the TRAC gene comprises the nucleotide sequence of SEQ ID NO: 98 or targets the nucleotide sequence of SEQ ID NO: 118, and optionally wherein the gRNA targeting the TRAC gene comprises the nucleotide sequence of SEQ ID NO: 30.

E77. The method of any one of embodiments 71-76, wherein the gRNA targeting the β2M gene comprises the nucleotide sequence of SEQ ID NO: 99 or targets the nucleotide sequence of SEQ ID NO: 119, and optionally wherein the gRNA targeting the β2M gene comprises the nucleotide sequence of SEQ ID NO: 31.

E78. The method of any one of embodiments 67-77, wherein the gRNA targeting the CD70 gene comprises the nucleotide sequence of SEQ ID NOS: 94 or 95 or targets the nucleotide sequence of SEQ ID NO: 114 or 115, and optionally wherein the gRNA targeting the CD70 gene comprises the nucleotide sequence of SEQ ID NOS: 26 or 27.

E79. The method of any one of embodiments 68-71 and 74-78, wherein the gRNA targeting the PD-1 gene comprises the nucleotide sequence of SEQ ID NO: 100 or targets the nucleotide sequence of SEQ ID NO: 120, and optionally wherein the gRNA targeting the PD-1 gene comprises the nucleotide sequence of SEQ ID NO: 32.

E80. The method of any one of embodiments 67-79, wherein the CAR comprises an ectodomain that comprises an anti-CD70 antibody, optionally wherein the anti-CD70 antibody is an anti-CD70 single-chain variable fragment (scFv).

E81. The method of embodiment 80, wherein the anti-CD70 scFv comprises the same VH complementarity determining regions (CDRs) and the same VL CDRs as a reference antibody, wherein the reference antibody comprises a VH set forth as SEQ ID NO: 51 and a VL set forth as SEQ ID NO: 52.

E82. The method of embodiment 81, wherein the anti-CD70 scFv comprises the same VH and VL chains as the reference antibody.

E83. The method of embodiment 81, wherein the anti-CD70 scFv comprises the amino acid sequence of SEQ ID NO: 48 or 50.

E84. The method of embodiment 81, wherein the anti-CD70 scFv comprises the amino acid sequence of SEQ ID NO: 50.

E85. The method of any one of embodiments 67-79, wherein the CAR comprises an ectodomain that comprises an anti-BCMA antibody, optionally wherein the anti-BCMA antibody is an anti-BCMA single-chain variable fragment (scFv).

E86. The method of embodiment 85, wherein the anti-BCMA scFv comprises the same VH complementarity determining regions (CDRs) and the same VL CDRs as a reference antibody, wherein the reference antibody comprises a VH set forth as SEQ ID NO: 60 and a VL set forth as SEQ ID NO: 61.

E87. The method of embodiment 86, wherein the anti-BCMA scFv comprises the same VH and VL chains as the reference antibody.

E88. The method of embodiment 86, wherein the anti-BCMA scFv comprises the amino acid sequence of SEQ ID NO: 59.

E89. The method of any one of embodiments 67-88, wherein the CAR further comprises a CD28 or 41BB co-stimulatory domain and optionally a CD3z signaling domain.

E90. The method of embodiment 72, wherein the vector comprises a nucleic acid encoding a CAR that comprises the amino acid sequence of SEQ ID NO: 46.

E91. The method of embodiment 72, wherein the vector comprises a nucleic acid encoding a CAR that comprises the amino acid sequence of SEQ ID NO: 57.

E92. An engineered T cell comprising an RNA-guided nuclease and a gRNA targeting a CD70 gene, optionally wherein the gRNA targeting the CD70 gene comprises the nucleotide sequence of SEQ ID NOS: 94 or 95 or targets the nucleotide sequence of SEQ ID NO: 114 or 115, and optionally wherein the gRNA targeting the CD70 gene comprises the nucleotide sequence of SEQ ID NOS: 26 or 27.

E93. The engineered T cell of embodiment 92 further comprising a gRNA targeting a PD-1 gene, optionally wherein the gRNA targeting the PD-1 gene comprises the nucleotide sequence of SEQ ID NO: 100 or targets the nucleotide sequence of SEQ ID NO: 120, and optionally wherein the gRNA targeting the PD-1 gene comprises the nucleotide sequence of SEQ ID NO: 32.

E94. The engineered T cell of embodiment 92 or 93 further comprising a gRNA targeting a TRAC gene, optionally wherein the gRNA targeting the TRAC gene comprises the nucleotide sequence of SEQ ID NO: 98 or targets the nucleotide sequence of SEQ ID NO: 118, and optionally wherein the gRNA targeting the TRAC gene comprises the nucleotide sequence of SEQ ID NO: 30.

E95. The engineered T cell of any one of embodiments 92-94 further comprising a gRNA targeting a β2M gene, optionally wherein the gRNA targeting the β2M gene comprises the nucleotide sequence of SEQ ID NO: 99 or targets the nucleotide sequence of SEQ ID NO: 119, and optionally wherein the gRNA targeting the β2M gene comprises the nucleotide sequence of SEQ ID NO: 31.

E96. The engineered T cell of any one of embodiments 92-95, wherein the RNA-guided nuclease is a Cas9 nuclease, optionally a *S. pyogenes* Cas9 nuclease.

E97. The engineered T cell of any one of embodiments 92-96 further comprising a vector comprising a donor template that comprises a nucleic acid encoding a CAR, optionally wherein the nucleic acid encoding the CAR is flanked by left and right homology arms to the TRAC gene locus.

E98. The engineered T cell of embodiment 97, wherein the CAR comprises an ectodomain that comprises an anti-CD70 antibody, optionally wherein the anti-CD70 antibody is an anti-CD70 single-chain variable fragment (scFv).

E99. The engineered T cell of embodiment 98, wherein the anti-CD70 scFv comprises the same VH complementarity determining regions (CDRs) and the same VL CDRs as a reference antibody, wherein the reference antibody comprises a VH set forth as SEQ ID NO: 51 and a VL set forth as SEQ ID NO: 52.

E100. The engineered T cell of embodiment 99, wherein the anti-CD70 scFv comprises the same VH and VL chains as the reference antibody.

E101. The engineered T cell of embodiment 99, wherein the anti-CD70 scFv comprises the amino acid sequence of SEQ ID NO: 48 or 50.

E102. The engineered T cell of embodiment 99, wherein the anti-CD70 scFv comprises the amino acid sequence of SEQ ID NO: 50.

E103. The engineered T cell of embodiment 97 wherein the CAR comprises an ectodomain that comprises an anti-BCMA antibody, optionally wherein the anti-BCMA antibody is an anti-BCMA single-chain variable fragment (scFv).

E104. The engineered T cell of embodiment 103, wherein the anti-BCMA scFv comprises the same VH complementarity determining regions (CDRs) and the same VL CDRs as a reference antibody, wherein the reference antibody comprises a VH set forth as SEQ ID NO: 60 and a VL set forth as SEQ ID NO: 61.

E105. The engineered T cell of embodiment 104, wherein the anti-BCMA scFv comprises the same VH and VL chains as the reference antibody.

E106. The engineered T cell of embodiment 104, wherein the anti-BCMA scFv comprises the amino acid sequence of SEQ ID NO: 59.

E107. The engineered T cell of embodiment 97, wherein the vector comprises a nucleic acid encoding a CAR that comprises the amino acid sequence of SEQ ID NO: 46 or 57.

E108. A method of increasing proliferation or reducing exhaustion of T cells, the method comprising disrupting the CD70 gene in the T cells.

E109. The method of embodiment 108 further comprising disrupting in the T cells at least one gene selected from the group consisting of: programmed cell death-1 (PD-1) gene, T cell receptor alpha chain constant region (TRAC) gene, and beta-2-microglobulin (β2M) gene.

E110. The method of any one of embodiments 108-109 further comprising expressing in the T cells a nucleic acid encoding a chimeric antigen receptor (CAR).

E111. The method of any one of embodiments 108-110, wherein the CD70 gene is disrupted by CRISPR/Cas gene editing.

E112. The method of any one of embodiments 110-111, wherein the PD-1, TRAC, and/or β2M gene is disrupted by CRISPR/Cas gene editing.

E113. A method for treating cancer in a subject, comprising administering to the patient a population of cells comprising engineered T cells, wherein the engineered T cells comprise a disrupted CD70 gene and a nucleic acid encoding a CAR, thereby treating cancer in the subject.

E114. The method of embodiment 113, wherein the CAR binds CD70.

E115. The method of embodiment 113, wherein the CAR does not bind CD70.

E116. The method of any one of embodiments 113-115, wherein the engineered T cells further comprise a disrupted TRAC gene.

E117. The method of any one of embodiments 113-116, wherein the engineered T cells further comprise a disrupted B2M gene.

E118. The method of any one of embodiments 113-116, wherein the engineered T cells further comprise a disrupted PD-1 gene.

E119. A method for treating cancer in a subject, comprising administering to the patient a population of cells comprising engineered T cells, wherein the engineered T cells comprise:
(i) a disrupted TRAC gene;
(ii) a disrupted B2M gene;
(iii) a disrupted CD70 gene; and
(iv) a nucleic acid encoding a CAR;
thereby treating the cancer in the subject.

E120. The method of any one of embodiments 113-114 and 116-119, wherein the CAR comprises (a) an ectodomain that comprises an anti-CD70 antigen-binding fragment, (b) a CD8 transmembrane domain, and (c) an endodomain that comprises a 41BB co-stimulatory domain and a CD3z co-stimulatory domain.

E121. The method of embodiment 119 or 120, wherein the disrupted TRAC gene comprises the nucleic acid encoding the CAR.

E122. The method of any one of embodiments 120-121, wherein the anti-CD70 antibody is an anti-CD70 scFv.

E123. The method of embodiment 122, wherein the anti-CD70 scFv comprises the same heavy chain variable region (VH) complementarity determining regions (CDRs) and the same light chain variable region (VL) CDRs as a reference antibody, wherein the reference antibody comprises a VH set forth as SEQ ID NO: 51 and a VL set forth as SEQ ID NO: 52.

E124. The method of embodiment 123, wherein the anti-CD70 scFv comprises the same VH and VL chains as the reference antibody.

E125. The method of embodiment 122, wherein the anti-CD70 scFv comprises the amino acid sequence of SEQ ID NO: 48 or 50.

E126. The method of embodiment 122, wherein the anti-CD70 scFv comprises the amino acid sequence of SEQ ID NO: 50.

E127. The method of any one of embodiments 113 and 115-118, wherein the CAR comprises an ectodomain that comprises an anti-BCMA antibody, optionally wherein the anti-BCMA antibody is an anti-BCMA single-chain variable fragment (scFv).

E128. The method of embodiment 127, wherein the anti-BCMA scFv comprises the same VH complementarity determining regions (CDRs) and the same VL CDRs as a reference antibody, wherein the reference antibody comprises a VH) set forth as SEQ ID NO: 60 and a VL set forth as SEQ ID NO: 61.

E129. The method of embodiment 128, wherein the anti-BCMA scFv comprises the same VH and VL chains as the reference antibody.

E130. The method of embodiment 127, wherein the anti-BCMA scFv comprises the amino acid sequence of SEQ ID NO: 59.

E131. The method of any one of embodiments 113-130, wherein the engineered T cells are engineered human T cells.

E132. The method of any one of embodiments 113-131, wherein the cancer expresses CD70 and/or BCMA.

E133. The method of any one of embodiments 113-132, wherein the population of cells is administered to the subject in an amount effective to treat the cancer.

E134. The method of any one of embodiments 113-133, wherein the cancer is a solid tumor malignancy or a hematological malignancy.

E135. The method embodiment 134, wherein the solid tumor malignancy is selected from the group consisting of: ovarian tumor, pancreatic tumor, kidney tumor, lung tumor, and intestinal tumor.

E136. A population of cells comprising engineered T cells, wherein the engineered T cells comprise:
(i) a disrupted TRAC gene;
(ii) a disrupted beta-2-microglobulin (B2M) gene;
(iii) a disrupted CD70 gene
(iv) a nucleic acid encoding a CAR comprising (a) an ectodomain that comprises an anti-CD70 antigen-binding fragment, (b) a CD8 transmembrane domain, and (c) an endodomain that comprises a 41BB co-stimulatory domain and a CD3z co-stimulatory domain.

E137. The population of cells of embodiment 136, wherein the disrupted TRAC gene comprises the nucleic acid encoding the CAR.

E138. The population of cells of any one of embodiments 136-137, wherein the engineered T cells are human T cells.

E139. An engineered T cell comprising:
(i) a disrupted TRAC gene, wherein the disrupted TRAC gene comprises a nucleic acid encoding a CAR comprising the amino acid sequence set forth in SEQ ID NO: 46;
(ii) a disrupted B2M gene; and
(iii) a disrupted CD70 gene.

E140. The engineered T cell of embodiment 139, wherein the nucleic acid encoding the CAR comprises a sequence at least 80%, at least 90%, at least 95%, at least 96%, at least 97%, at least 98% or at least 99% identical to SEQ ID NO: 45.

E141. An engineered T cell comprising:
(i) a disrupted TRAC gene, wherein the disrupted TRAC gene comprises a nucleic acid encoding a CAR, wherein the nucleic acid sequence is at least 90% identical to SEQ ID NO: 45;
(ii) a disrupted B2M gene; and
(iii) a disrupted CD70 gene.

E142. The engineered T cell of any one of embodiments 139-141, wherein the disrupted TRAC gene comprises a donor sequence comprising the nucleotide sequence set forth in SEQ ID NO: 45 or SEQ ID NO: 44.

E143. An engineered T cell comprising:
(i) a disrupted TRAC gene comprising the nucleic acid sequence of SEQ ID NO: 44;
(ii) a disrupted B2M gene; and
(iii) a disrupted CD70 gene.

E144. The engineered T cell of any one of embodiments 139-143, wherein the T cell is a human T cell.

EXAMPLES

Example 1. Efficient Knockout of CD70 by Cas9:sgRNA RNPs in T Cells

This example describes efficient editing of the CD70 gene in primary human T cells ex vivo using CRISPR/Cas9 gene editing. Genomic segments of the CD70 gene containing the first three (3) protein coding exons were used as input in gRNA design software. The genomic segments also included flanking splice site acceptor/donor sequences. Desired gRNAs were those that would lead to insertions or deletions in the coding sequence, disrupting the amino acid sequence of CD70, leading to out of frame/loss of function allele(s) (referred to as "CD70 knockout" alleles). All seven (7) in silico-identified gRNA spacer sequences targeting the CD70 gene were synthesized, and the gRNAs were specifically modified, as indicated in Table 5. While the gRNAs in Table 5 were modified with 2'-O-methyl phosphorothioate modifications, unmodified gRNAs, or gRNAs with other modifications, may be used. See also PCT/IB2018/001619, filed May 11, 2018, herein incorporated in its entirety by this reference.

TABLE 5

| CD70 gRNA Sequences/Target Sequences |||
|---|---|---|
| gRNA Sequences |||
| Name | Unmodified Sequence | Modified Sequence |
| CD70 sgRNA (E1_T1) | UCACCAAGCCCGCGACCAAUguuuuagagc uagaaauagcaaguuaaaauaaggcuaguc cguuaucaacuugaaaaaguggcaccgagu cggugcUUUU (SEQ ID NO: 23) | U*C*A*CCAAGCCCGCGACCAAUguuuuag agcuagaaauagcaaguuaaaauaaggcua guccguuaucaacuugaaaaaguggcaccg agucggugcU*U*U*U (SEQ ID NO: 33) |
| CD70 sgRNA (E1_T1) spacer | UCACCAAGCCCGCGACCAAU (SEQ ID NO: 91) | U*C*A*CCAAGCCCGCGACCAAU (SEQ ID NO: 101) |
| CD70 sgRNA (E1_T3) | AUCACCAAGCCCGCGACCAAguuuuagagc uagaaauagcaaguuaaaauaaggcuaguc cguuaucaacuugaaaaaguggcaccgagu cggugcUUUU (SEQ ID NO: 24) | A*U*C*ACCAAGCCCGCGACCAAguuuuag agcuagaaauagcaaguuaaaauaaggcua guccguuaucaacuugaaaaaguggcaccg agucggugcU*U*U*U (SEQ ID NO: 34) |
| CD70 sgRNA (E1_T3) spacer | AUCACCAAGCCCGCGACCAA (SEQ ID NO: 92) | A*U*C*ACCAAGCCCGCGACCAA (SEQ ID NO: 102) |
| CD70 sgRNA (E1_T4) | CGGUGCGGCGCAGGCCCUAUguuuuagagc uagaaauagcaaguuaaaauaaggcuaguc cguuaucaacuugaaaaaguggcaccgagu cggugcUUUU (SEQ ID NO: 25) | C*G*G*UGCGGCGCAGGCCCUAUguuuuag agcuagaaauagcaaguuaaaauaaggcua guccguuaucaacuugaaaaaguggcaccg agucggugcU*U*U*U (SEQ ID NO: 35) |
| CD70 sgRNA (E1_T4) spacer | CGGUGCGGCGCAGGCCCUAU (SEQ ID NO: 93) | C*G*G*UGCGGCGCAGGCCCUAU (SEQ ID NO: 103) |
| CD70 sgRNA (E1_T7)); also referred to as: T7 | GCUUUGGUCCCAUUGGUCGCguuuuagagc uagaaauagcaaguuaaaauaaggcuaguc cguuaucaacuugaaaaaguggcaccgagu cggugcUUUU (SEQ ID NO: 26) | G*C*U*UUGGUCCCAUUGGUCGCguuuuag agcuagaaauagcaaguuaaaauaaggcua guccguuaucaacuugaaaaaguggcaccg agucggugcU*U*U*U (SEQ ID NO: 36) |

TABLE 5-continued

CD70 gRNA Sequences/Target Sequences

| | | |
|---|---|---|
| CD70 sgRNA (E1_T7) spacer | GCUUUGGUCCCAUUGGUCGC<br>(SEQ ID NO: 94) | G*C*U*UUGGUCCCAUUGGUCGC<br>(SEQ ID NO: 104) |
| CD70 sgRNA (E1_T8); also referred to as: T8 | GCCCGCAGGACGCACCCAUAguuuuagagc<br>uagaaauagcaaguuaaaauaaggcuaguc<br>cguuaucaacuugaaaaaguggcaccgagu<br>cggugcUUUU<br>(SEQ ID NO: 27) | G*C*C*CGCAGGACGCACCCAUAguuuuag<br>agcuagaaauagcaaguuaaaauaaggcua<br>guccguuaucaacuugaaaaaguggcaccg<br>agucggugcU*U*U*U<br>(SEQ ID NO: 37) |
| CD70 sgRNA (E1_T8) spacer | GCCCGCAGGACGCACCCAUA<br>(SEQ ID NO: 95) | G*C*C*CGCAGGACGCACCCAUA<br>(SEQ ID NO: 105) |
| CD70 sgRNA (E1_T10) | GUGCAUCCAGCGCUUCGCACguuuuagagc<br>uagaaauagcaaguuaaaauaaggcuaguc<br>cguuaucaacuugaaaaaguggcaccgagu<br>cggugcUUUU<br>(SEQ ID NO: 28) | G*U*G*CAUCCAGCGCUUCGCACguuuuag<br>agcuagaaauagcaaguuaaaauaaggcua<br>guccguuaucaacuugaaaaaguggcaccg<br>agucggugcU*U*U*U<br>(SEQ ID NO: 38) |
| CD70 sgRNA (E1_T10) spacer | GUGCAUCCAGCGCUUCGCA C<br>(SEQ ID NO: 96) | G*U*G*CAUCCAGCGCUUCGCAC<br>(SEQ ID NO: 106) |
| CD70 sgRNA (E3_T1) | CAGCUACGUAUCCAUCGUGAguuuuagagc<br>uagaaauagcaaguuaaaauaaggcuaguc<br>cguuaucaacuugaaaaaguggcaccgagu<br>cggugcUUUU<br>(SEQ ID NO: 29) | C*A*G*CUACGUAUCCAUCGUGAguuuuag<br>agcuagaaauagcaaguuaaaauaaggcua<br>guccguuaucaacuugaaaaaguggcaccg<br>agucggugcU*U*U*U<br>(SEQ ID NO: 39) |
| CD70 sgRNA (E3_T1) spacer | CAGCUACGUAUCCAUCGUGA<br>(SEQ ID NO: 97) | C*A*G*CUACGUAUCCAUCGUGA<br>(SEQ ID NO: 107) |

Target Sequences

| Name | Target Sequence (PAM) |
|---|---|
| CD70 sgRNA (E1_T1) | TCACCAAGCCCGCGACCAAT (GGG) (SEQ ID NO: 111) |
| CD70 sgRNA (E1_T3) | ATCACCAAGCCCGCGACCAA (TGG) (SEQ ID NO: 112) |
| CD70 sgRNA (E1_T4) | CGGTGCGGCGCAGGCCCTAT (GGG) (SEQ ID NO: 113) |
| CD70 sgRNA (E1_T7) | GCTTTGGTCCCATTGGTCGC (GGG) (SEQ ID NO: 114) |
| CD70 sgRNA (E1_T8) | GCCCGCAGGACGCACCCATA (GGG) (SEQ ID NO: 115) |
| CD70 sgRNA (E1_T10) | GTGCATCCAGCGCTTCGCAC (AGG) (SEQ ID NO: 116) |
| CD70 sgRNA (E3_T1) | CAGCTACGTATCCATCGTGA (TGG) (SEQ ID NO: 117) |
| TRAC sgRNA | AGAGCAACAGTGCTGTGGCC (TGG) (SEQ ID NO: 118) |
| β2M sgRNA | GCTACTCTCTCTTTCTGGCC (TGG) (SEQ ID NO: 199) |
| PD-1 sgRNA | CTGCAGCTTCTCCAACACAT (CGG) (SEQ ID NO: 120) |

*2'-O-methyl phosphorothioate residue

Primary human T cells were transfected (electroporated) with a ribonucleoprotein particle (RNP) containing Cas9 nuclease and a synthetic modified sgRNA targeting the CD70 gene (sequences in Table 5) or controls (no Cas9, no gRNA). Four to six (4-6) days post transfection, cells were (1) subjected to a TIDE analysis to assess indel frequency and (2) processed by flow cytometry (primary antibody: FITC anti-human CD70 antibody, clone 113-16, Biolegend) to assess CD70 expression levels at the cell surface.

Seven (7) gRNAs yielded measurable data by TIDE analysis, as indicated in Table 6. Four (4) gRNA sequences yielded indel percentages (editing frequencies) above 85% with protein expression knockdown above 80% (SEQ ID NOS: 23, 26, 27 and 29), indicating highly efficient gene editing. The data in Table 6 are from one (1) donor. The level of CD70 protein expression (assessed by median fluorescent intensity (MFI)) per test sample was normalized to the level of CD70 protein expression present in control cells.

TABLE 6

CD70 gRNA sequences, cutting efficiencies, and CD70 surface protein expression in gene edited T cells

| gRNA Name | gRNA Spacer Sequence | Indel % | $R^2$ | Protein expression knockdown % |
|---|---|---|---|---|
| CD70 EXON1_T1 (E1_T1) | UCACCAAGCCCGCGACCAAU<br>(SEQ ID NO: 91) | 89.3% | 0.97 | 84.8% |
| CD70 EXON1_T3 (E1_T3) | AUCACCAAGCCCGCGACCAA<br>(SEQ ID NO: 92) | 65.2% | 0.93 | 84.0% |
| CD70 EXON1_T4 (E1_T4) | CGGUGCGGCGCAGGCCCUAU<br>(SEQ ID NO: 93) | 81.6% | 0.83 | 87.5% |
| CD70 EXON1_T7 (E1_T7) | GCUUUGGUCCCAUUGGUCGC<br>(SEQ ID NO: 94) | 97.8% | 0.98 | 87.7% |
| CD70 EXON1_T8 (E1_T8) | GCCCGCAGGACGCACCCAUA<br>(SEQ ID NO: 95) | 90.1% | 0.94 | 88.1% |

TABLE 6-continued

CD70 gRNA sequences, cutting efficiencies, and CD70 surface protein expression in gene edited T cells

| gRNA Name | gRNA Spacer Sequence | Indel % | $R^2$ | Protein expression knockdown % |
|---|---|---|---|---|
| CD70_EXON1_T10 (E1_T10) | GUGCAUCCAGCGCUUCGCAC (SEQ ID NO: 96) | 28.3% | 0.30 | 83.9% |
| CD70_EXON3_T1 (E3_T1) | CAGCUACGUAUCCAUCGUGA (SEQ ID NO: 97) | 85.6% | 0.93 | 87.2% |

Analysis of On-Target Indel Profiles in T Cells

On-target amplicon analysis was conducted at the CD70 locus following gene editing using the T7 guide (SEQ ID NO: 26; SEQ ID NO: 36), targeting the CD70 gene: GCTTTGGTCCCATTGGTCGC (SEQ ID NO: 160; target sequence, with PAM SEQ ID NO: 114).

Following gene editing, on-target amplicon analysis was conducted around the CD70 locus in TRAC−/β2M−/CD70−/anti-CD70 CAR+ cells (generated as described in Example 3).

An initial PCR was performed using the KAPA HiFi PCR kit (Kapa Biosystems, Wilmington, Mass.). 100 ng of input gDNA was combined with 10 uM of each primer. The CD70_F and CD70_R primers were paired to amplify the CD70 locus (Table 7).

Analysis of the CD70 locus in a population of T cells following CRISPR/Cas9 gene editing to produce TRAC−/β2M−/anti-CD70 CAR+ T cells results in specific indel frequencies and edited gene sequences at the CD70 locus (Table 8; deletions as dashes and insertions in bold). Two cell populations of edited cells were generated from two different donor T cells (1 and 2). The populations of edited T cells from each donor were analyzed in replicate: 1A/1B and 2A/2B.

TABLE 8

| SEQ ID NO: | Gene Edited Sequence | 1A | 1B | 2A | 2B | Mean | Std. Dev. |
|---|---|---|---|---|---|---|---|
| 129 | CACACCACGAGGCAGATCACCAAGCCCGCG--CAATGGGACCAAAGCAGCCCGCAGGACG | 10.4% | 11.1% | 14.4% | 14.8% | 12.7% | 0.022 |
| 130 | CACACCACGAGGCAGATCACCAAGCCCGCGAACCAATGGGACCAAAGCAGCCCGCAGGACG | 8.7% | 10.0% | 11.3% | 11.1% | 10.3% | 0.012 |
| 131 | CACACCACGAGGCAGATC-----------ACCAATGGGACCAAAGCAGCCCGCAGGACG | 8.2% | 7.8% | 7.1% | 6.8% | 7.5% | 0.006 |
| 132 | CACACCACGAGGCAGATCACCAAGCCCGCG-CCAATGGGACCAAAGCAGCCCGCAGGACG | 3.9% | 4.5% | 4.2% | 4.3% | 4.2% | 0.002 |
| 133 | CACACCACGAGGCAGATCACCAAGCCCGC-ACCAATGGGACCAAAGCAGCCCGCAGGACG | 2.2% | 2.5% | 2.4% | 2.6% | 2.4% | 0.002 |
| 134 | CACACCACGAGGCAGATCACCA-------------------AGCCCGCAGGACG | 2.9% | 2.3% | 2.0% | 2.0% | 2.3% | 0.004 |

TABLE 7

Primers for CD70 amplicon library preparation

| CD70_F | TCGTCGGCAGCGTCAGATGTGTATAAGAGACAGcccaact taccatctcaactcaccccaagtg (SEQ ID NO: 127) |
|---|---|
| CD70_R | GTCTCGTGGGCTCGGAGATGTGTATAAGAGACAGccccctc ctgcgctagcgga (SEQ ID NO: 128) |

Example 2. Generation of T Cells with Multiple Gene Knockouts

This example describes the use of CRISPR/Cas9 gene editing technology to produce human T cells that lack expression of two, three or four genes simultaneously. Specifically, the T cell receptor (TCR) gene (gene edited in the TCR Alpha Constant (TRAC) region), the β2-microglobulin (β2M) gene, the Cluster of Differentiation 70 (CD70) gene and/or the programmed cell death 1 (PD-1 or PD1) gene were edited by CRISPR/Cas9 gene editing to produce T cells deficient in two or more of the listed genes. The following abbreviations are used in the Figures for brevity and clarity:

2×KO: TRAC−/β2M−
3×KO (PD-1): TRAC−/β2M−/PD-1−

3×KO (CD70): TRAC⁻/β2M⁻/CD70⁻
4×KO: TRAC⁻/β2M⁻/PD-1⁻/CD70⁻

Activated primary human T cells were electroporated with Cas9:gRNA RNP complexes. The nucleofection mix contained the Nucleofector™ Solution, $5\times10^6$ cells, 1 μM Cas9, and 5 μM gRNA (as described in Hendel et al., *Nat Biotechnol.* 2015; 33(9):985-989, PMID: 26121415). For the generation of double knockout T cells (2×KO), the cells were electroporated with two different RNP complexes, each containing Cas9 protein and one of the following sgRNAs: TRAC (SEQ ID NO: 40) and β2M (SEQ ID NO: 41) at the concentrations indicated above. For the generation of triple knockout T cells (3×KO), the cells were electroporated with three different RNP complexes, each RNA complex containing Cas protein and one of the following sgRNAs: (a) TRAC (SEQ ID NO: 40), β2M (SEQ ID NO: 41), and PD-1 (SEQ ID NO: 42) at the concentrations indicated above; or (b) TRAC (SEQ ID NO: 40), β2M (SEQ ID NO: 41), and CD70 (SEQ ID NO: 36 or 37) at the concentrations indicated above. For the generation of quadruple knockout T cells (4×KO), the cells were electroporated with four different RNP complexes, each RNA complex containing Cas9 protein and one the following sgRNAs: TRAC (SEQ ID NO: 40), β2M (SEQ ID NO: 41), PD-1 (SEQ ID NO: 42), and CD70 (SEQ ID NO: 36 or 37) at the concentrations indicated above. The unmodified versions (or other modified versions) of the gRNAs may also be used (e.g., SEQ ID NOS: 30, 31, 32, 26, and/or 27). Sequences in Tables 5 and 9.

Tables 11 and 12 show highly efficient multiple gene editing. For the double-knock cells (2×KO; TRAC⁻/β2M⁻), 83% of viable cells lacked expression of TCR and β2M (Table 11; 3×KO (PD1)). For the triple knockout cells, 70% of viable cells lacked expression of TCR, β2M, and PD-1 (Table 11); and 80% of viable cells lacked expression of TCR, β2M, and CD70 irrespective of the CD70 gRNA used (Table 12). For the quadruple knockout cells (4×KO), 78% of viable cells lacked expression of TCR, β2M, PD-1, and CD70 (FIG. 1).

TABLE 10

Antibodies

| Antibody | Clone | Fluor | Catalogue # | Dilution | For 1 |
|---|---|---|---|---|---|
| TCR | BW242/412 | PE | 130-091-236 (Miltenyi) | 1:100 | 1 μL |
| β2M | 2M2 | PE-Cy7 | 316318 (Biolegend) | 1:100 | 1 μL |
| PD-1 | EH12.2H7 | PE | 329906 (Biolegend) | 1:100 | 1 μL |
| CD70 | 113-16 | FITC | 355105 (Biolegend) | 1:100 | 1 μL |

TABLE 11

% of viable cells lacking expression in 2KO and 3KO (PD1) cell populations

| | TRAC KO | β2M KO | PD1 KO | 2 KO | 3 KO (PD1) |
|---|---|---|---|---|---|
| 2KO | 98% | 85% | NA | 83% | NA |
| 3 KO (PD1) | 98% | 73% | 99% | NA | 70% |

TABLE 9 gRNA Sequences/Target Sequences

| Name | Unmodified Sequence | Modified Sequence |
|---|---|---|
| TRAC sgRNA | AGAGCAACAGUGCUGUGGCCguuuuagag cuagaaauagcaaguuaaaauaaggcuag uccguuaucaacuugaaaaaguggcaccg agucggugcUUUU (SEQ ID NO: 30) | A*G*A*GCAACAGUGCUGUGGCCguuuua gagcuagaaauagcaaguuaaaauaaggc uaguccguuaucaacuugaaaaaguggca ccgagucggugcU*U*U*U (SEQ ID NO: 40) |
| TRAC sgRNA spacer | AGAGCAACAGUGCUGUGGCC (SEQ ID NO: 98) | A*G*A*GCAACAGUGCUGUGGCC (SEQ ID NO: 108) |
| β2M sgRNA | GCUACUCUCUCUUUCUGGCCguuuuagag cuagaaauagcaaguuaaaauaaggcuag uccguuaucaacuugaaaaaguggcaccg agucggugcUUUU (SEQ ID NO: 31) | G*C*U*ACUCUCUCUUUCUGGCCguuuua gagcuagaaauagcaaguuaaaauaaggc uaguccguuaucaacuugaaaaaguggca ccgagucggugcU*U*U*U (SEQ ID NO: 41) |
| β2M sgRNA spacer | GCUACUCUCUCUUUCUGGCC (SEQ ID NO: 99) | G*C*U*ACUCUCUCUUUCUGGCC (SEQ ID NO: 109) |
| PD-1 sgRNA | CUGCAGCUUCUCCAACACAUguuuuagag cuagaaauagcaaguuaaaauaaggcuag uccguuaucaacuugaaaaaguggcaccg agucggugcUUUU (SEQ IDNO: 32) | C*U*G*CAGCUUCUCCAACACAUguuuua gagcuagaaauagcaaguuaaaauaaggc uaguccguuaucaacuugaaaaaguggca ccgagucggugcU*U*U*U (SEQ ID NO: 42) |
| PD-1 sgRNA spacer | CUGCAGCUUCUCCAACACAU (SEQ ID NO: 100) | C*U*G*CAGCUUCUCCAACACAU (SEQ ID NO: 110) |

About one (1) week post electroporation, cells were either left untreated or treated with phorbol myristate acetate (PMA)/ionomycin overnight. The next day cells were processed for flow cytometry (see, e.g., Kalaitzidis D et al. *J Clin Invest* 2017; 127(4): 1405-1413) to assess TRAC, β2M, PD-1, and CD70 expression levels at the cell surface of the edited cell population. The following primary antibodies were used (Table 10):

TABLE 12

% of viable cells lacking expression in 3KO (CD70) cell populations

| | TRAC KO | β2M KO | CD70 KO | 3KO (CD70) |
|---|---|---|---|---|
| 3KO (CD70) (T7) | 99% | 79% | 99% | 80% |

TABLE 12-continued

% of viable cells lacking expression in 3KO (CD70) cell populations

|  | TRAC KO | β2M KO | CD70 KO | 3KO (CD70) |
|---|---|---|---|---|
| 3KO (CD70) (T8) | 99% | 82% | 99% | 80% |

To assess whether triple and quadruple gene editing in T cells affects cell expansion, cell numbers were enumerated among double, triple, and quadruple gene edited T cells (unedited T cells were used as a control) over a two week period of post editing. $5 \times 10^6$ cells were generated and plated for each genotype of T cells.

Figure 2:
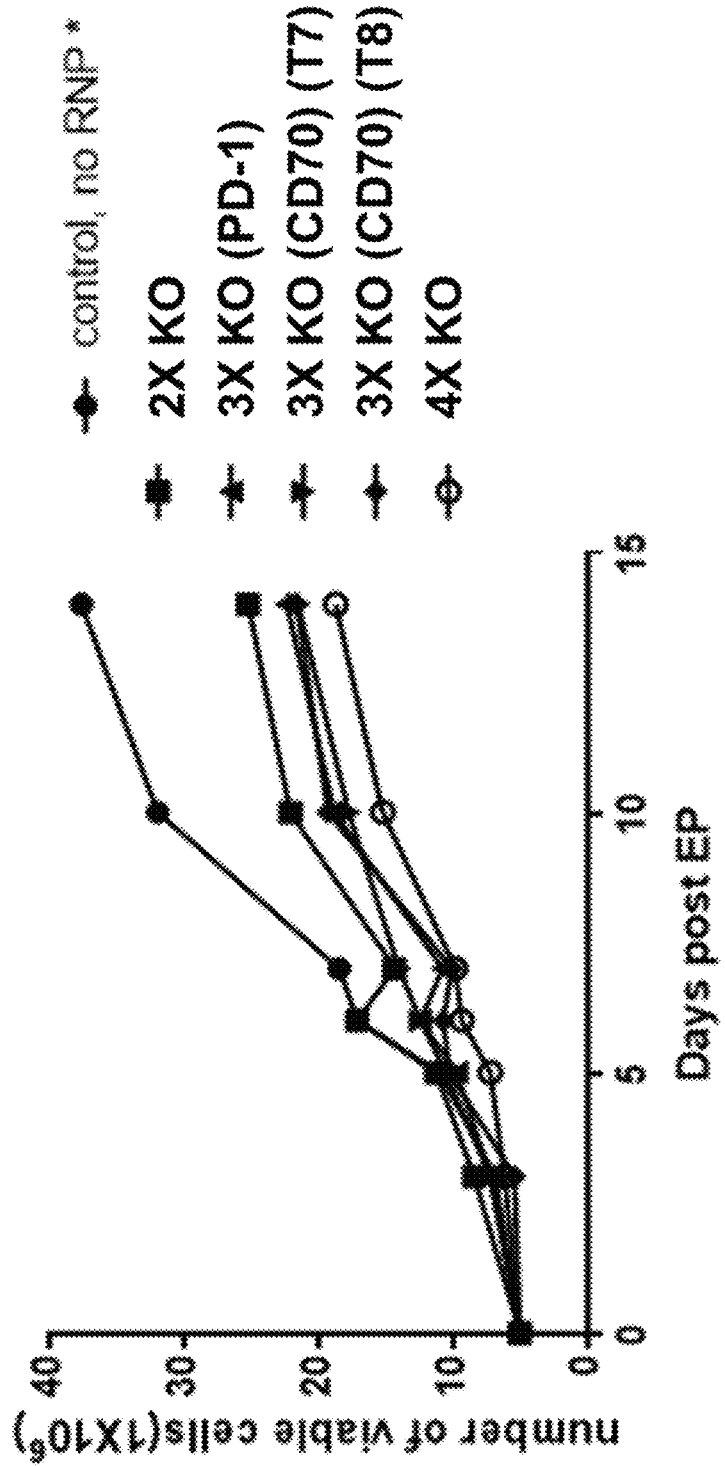
FIG. 2 includes a graph showing similar expansion among multigene-edited cells.

As shown in FIG. 2, cell proliferation (expansion) continued over the post-electroporation window test. Similar cell proliferation was observed among the double (β2M−/TRAC−), triple (β2M−/TRAC−/PD-1−, or β2M−/TRAC−/CD70−), and quadruple (β2M−/TRAC−/PD-1−/CD70) knockout T cells, as indicated by the number of viable cells. These data suggest that multiple gene editing (up to triple and quadruple, with CD70 and PD-1 genes) does not impact T cell health as measured by T cell proliferation.

Example 3. Generation of CAR T Cells Lacking CD70 and/or PD1

Generation of Anti-CD70 CAR T Cells with Multiple Knockouts

This example describes the production of allogeneic human T cells that lack expression of the TCR gene, β2M gene, CD70 gene and/or PD1 gene, and express a chimeric antigen receptor (CAR) targeting CD70. These cells are designated TCR−/β2M−/CD70−/anti-CD70 CAR+ or 3×KO (CD70) CD70 CARP; TCR−/β2M−/PD1−/anti-CD70 CAR+ or 3×KO (PD1) CD70 CAR+; TCR−/β2M−/PD1−/CD70−/anti-CD70 CAR+ or 4×KO CD70 CARP in the Figures.

A recombinant adeno-associated adenoviral vector, serotype 6 (AAV6) (MOI 50,000) comprising the nucleotide sequence of SEQ ID NO: 43 (comprising the donor template in SEQ ID NO: 44, encoding anti-CD70 CAR comprising the amino acid sequence of SEQ ID NO: 46) was delivered with Cas9:sgRNA RNPs (1 μM Cas9, 5 μM gRNA) to activated allogeneic human T cells. The following sgRNAs were used: TRAC (SEQ ID NO: 40), β2M (SEQ ID NO: 41), CD70 (SEQ ID NO: 36 or 37) and PD1 (SEQ ID NO: 42). The unmodified versions (or other modified versions) of the gRNAs may also be used (e.g., SEQ ID NOS: 30, 31, 32, 26, and/or 27). About one (1) week post electroporation, cells were processed for flow cytometry to assess TRAC, β2M, CD70, and PD1 expression levels at the cell surface of the edited cell population. The following primary antibodies were used (Table 13):

TABLE 13

| Antibodies | | | | |
|---|---|---|---|---|
| Antibody | Clone | Fluor | Catalogue # | Dilution |
| TCR | BW242/412 | PE | 130-091-236 (Miltenyi) | 1:100 |
| β2M | 2M2 | PE-Cy7 | 316318 (Biolegend) | 1:100 |
| CD70 | 113-16 | FITC | 355105 (Biolegend) | 1:100 |
| PD-1 | EH12.2H7 | PE | 329906 (Biolegend) | 1:100 |

T cell Proportion Assay. The proportions of CD4+ and CD8+ cells were then assessed in the edited T cell populations by flow cytometry using the following antibodies (Table 14):

TABLE 14

| Antibodies | | | | |
|---|---|---|---|---|
| Antibody | Clone | Fluor | Catalogue # | Dilution |
| CD4 | RPA-T4 | BV510 | 300545 (Biolegend) | 1:100 |
| CD8 | SK1 | BV605 | 344741 (Biolegend) | 1:100 |

Figure 3:
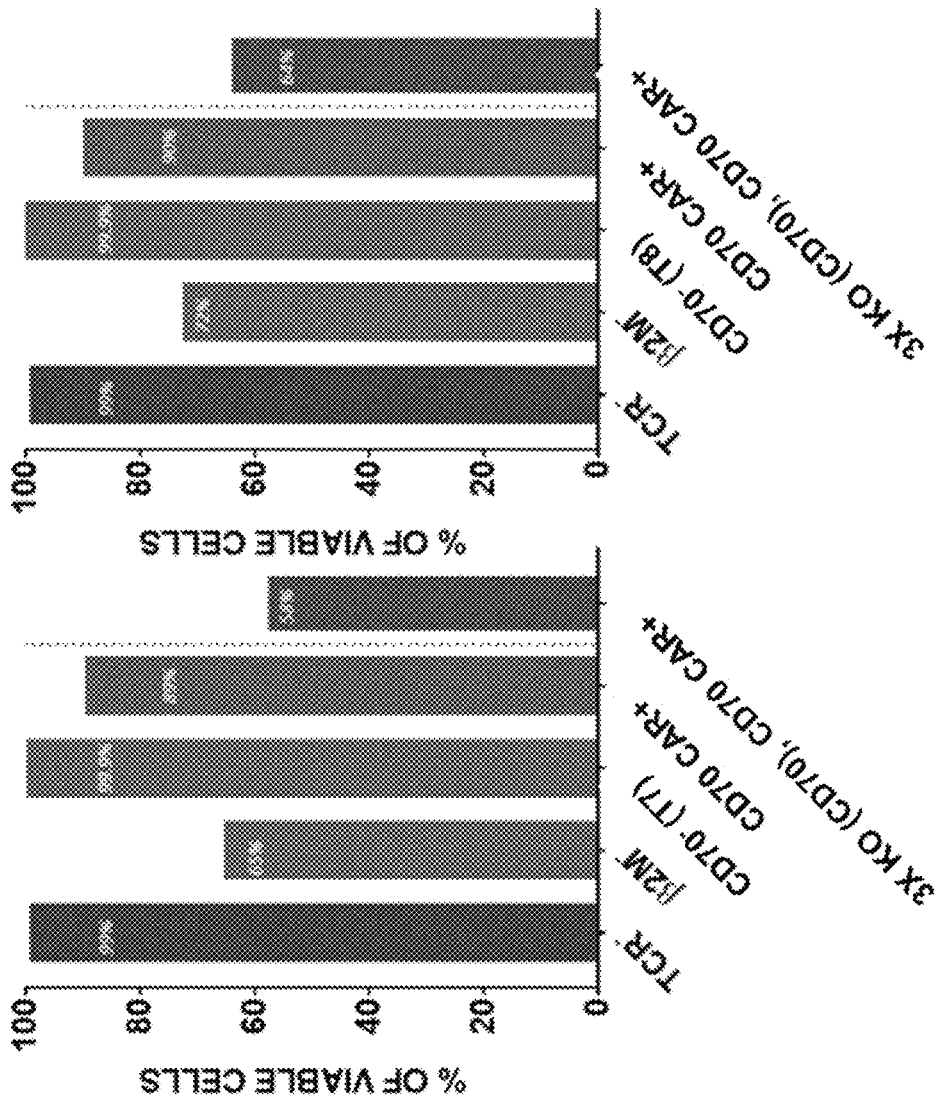
FIG. 3 includes graphs showing efficient multiple gene editing in TRAC$^-$/β2M$^-$/CD70$^-$/anti-CD70 CAR$^+$ (i.e., 3×KO (CD70), CD70 CAR$^+$) T cells.
Figure 4:
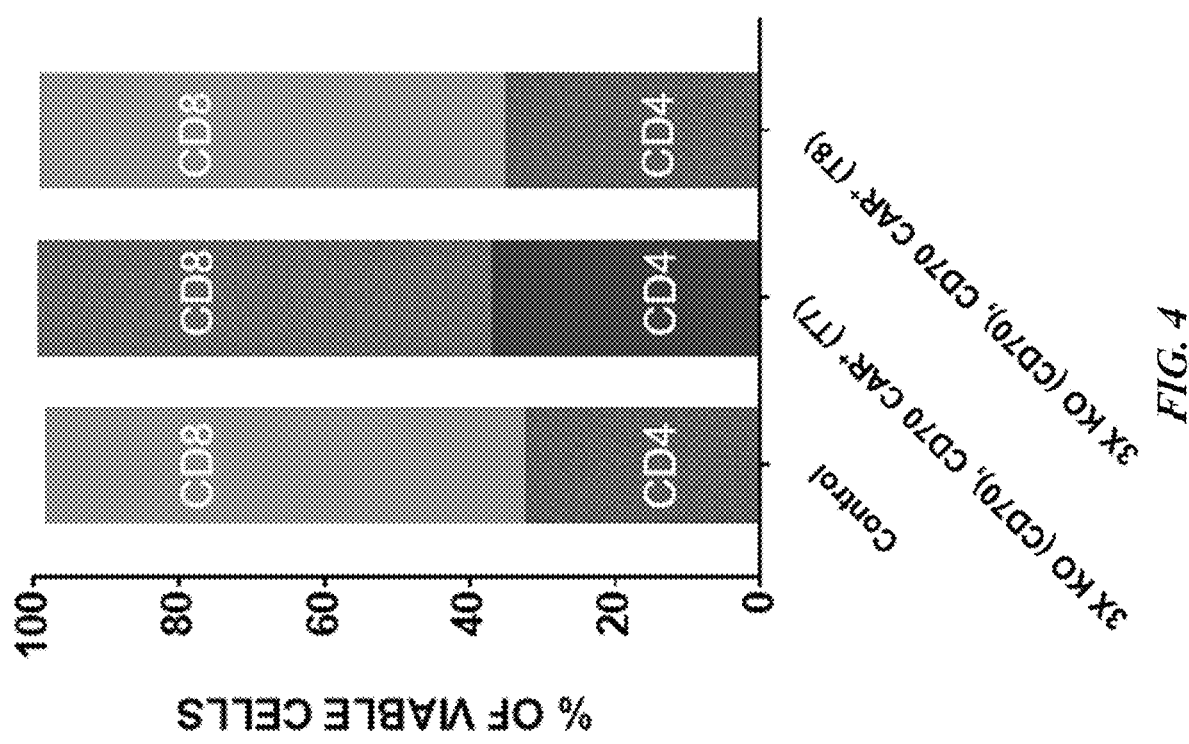
FIG. 4 includes a graph showing that normal proportions of CD4+ and CD8+ T cells are maintained among the TRAC$^-$/β2M$^-$/CD70$^-$/anti-CD70 CAR$^+$ T cell population.

High efficiency gene editing and CAR expression was achieved in the edited anti-CD70 CAR T cell populations. In addition, editing did not adversely alter CD4/CD8 T cell populations. FIG. 3 shows highly efficient gene editing and anti-CD70 CAR expression in the triple knockout CAR T cell. More than 55% of viable cells lacked expression of TCR, β2M, and CD70, and also expressed the anti-CD70 CAR. FIG. 4 shows that normal proportions of CD4/CD8 T cell subsets were maintained in the TRAC−/β2M−/CD70−/anti-CD70 CAR+ cells, suggesting that these multiple gene edits do not affect T cell biology as measured by the proportion of CD4/CD8 T cell subsets.

Figure 5:
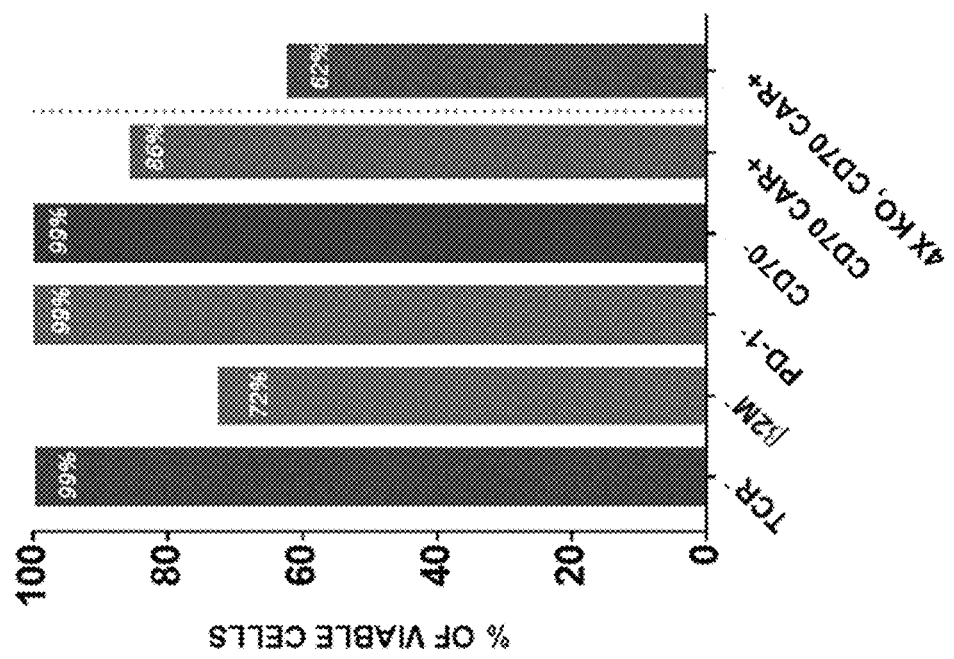
FIG. 5 includes a graph showing efficient multiple gene editing in TRAC$^-$/β2M$^-$/PD-1$^-$/CD70$^-$/anti-CD70 CAR$^+$ T cells.
Figure 6:
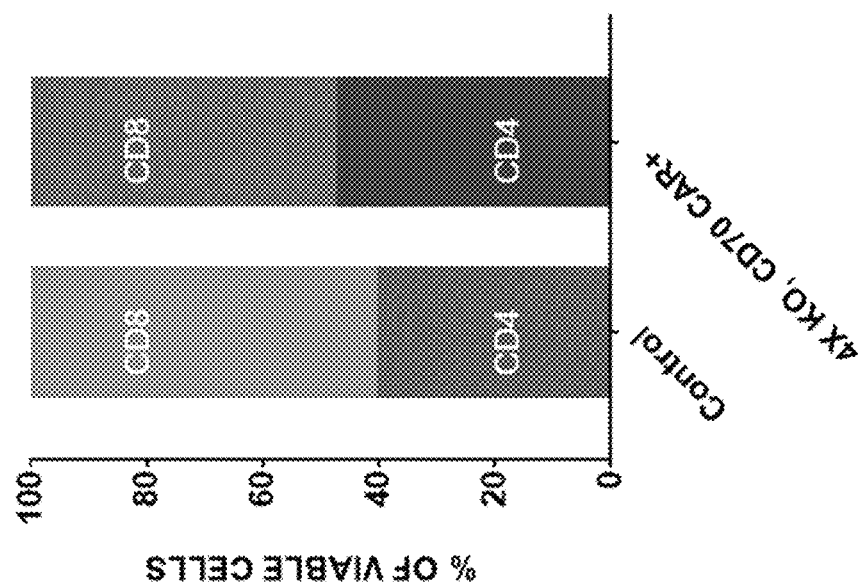
FIG. 6 includes a graph showing that normal proportions of CD4+ and CD8+ T cells are maintained among the TRAC$^-$/β2M$^-$/PD-1$^-$/CD70$^-$/anti-CD70 CAR$^+$ (i.e., 4×KO, CD70 CAR$^+$) T cell population.

FIG. 5 shows show highly efficient gene editing and anti-CD70 CAR expression in the quadruple knockout CAR T cell. Greater than 60% of viable cells lacked expression of TCR, β2M, PD-1, and CD70, and expressed the anti-CD70 CAR. FIG. 6 shows that normal proportions of CD4/CD8 T cell subsets were maintained in the TRAC−/β2M−/PD-1−/CD70−/anti-CD70 CAR+ cells, suggesting that these multiple gene editing do not affect T cell biology as measured by the proportion of CD4+/CD8+ T cell subsets.

Generation of Anti-BCMA CAR T Cells with Multiple Knockouts

This example describes the production of allogeneic human T cells that lack expression of the TCR gene, the β2M gene, the PD-1 gene, and/or the CD70 gene, and also express a chimeric antigen receptor (CAR) targeting B-cell maturation antigen (BCMA).

A recombinant adeno-associated adenoviral vector, serotype 6 (AAV6) comprising the nucleotide sequence of SEQ ID NO: 54 (comprising the donor template in SEQ ID NO: 55, encoding anti-BCMA CAR comprising the amino acid sequence of SEQ ID NO: 57) was delivered with Cas9:gRNA RNPs (1 μM Cas9, and 5 μM gRNA) to activated allogeneic human T cells. The following gRNAs were used: TRAC (SEQ ID NO: 40), β2M (SEQ ID NO: 41), PD-1 (SEQ ID NO: 42), and CD70 (SEQ ID NO: 36 or 37). The unmodified versions (or other modified versions) of the gRNAs may also be used (e.g., SEQ ID NOS: 30, 31, 32, 26 and/or 27). About one (1) week post electroporation, cells were processed for flow cytometry as described above for anti-CD70 CAR+ T cells, with the following difference. Anti-BCMA CAR expression was detected using biotinylated recombinant human BCMA (ACROS Cat #BC7-H82F0). The double and quadruple knockout anti-BCMA CAR+ cells were then characterized as described herein.

Figure 7A:
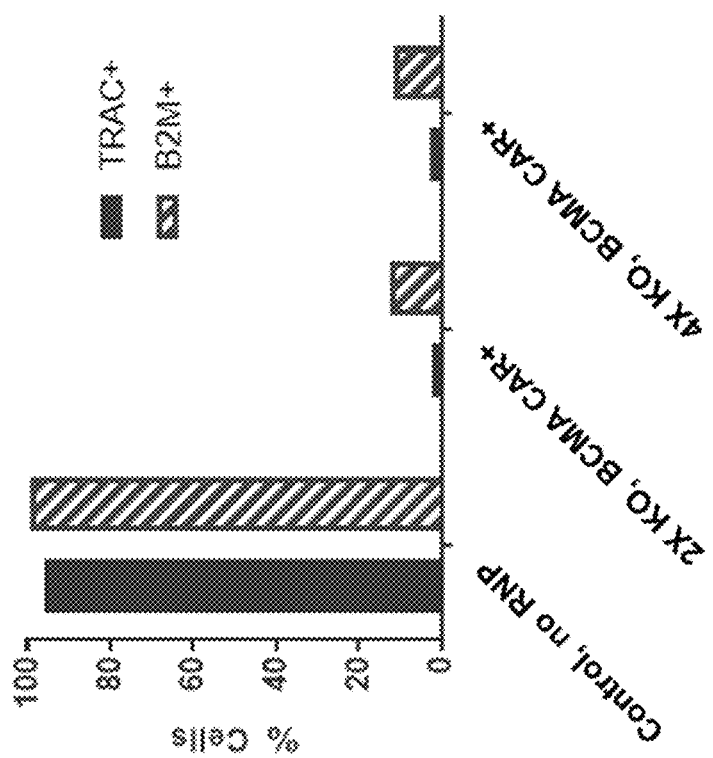
FIGS. 7A-7C include graphs showing data relating to the characterization of anti-BCMA CAR+ T cells with multi-gene edits. Double knockout TRAC$^-$/β2M$^-$/anti-BCMA CAR+ T cells and quadruple knockout TRAC$^-$/β2M$^-$/PD-1$^-$/CD70$^-$/anti-BCMA CAR+ T cells were stained for TRAC and β2M (FIG. 7A), PD-1 and CD70 (FIG. 7B), and BCMA CAR (FIG. 7C) expression. The anti-BCMA CAR was expressed at approximately 80% in both the double and quadruple knockout CAR T cells.
Figure 7B:
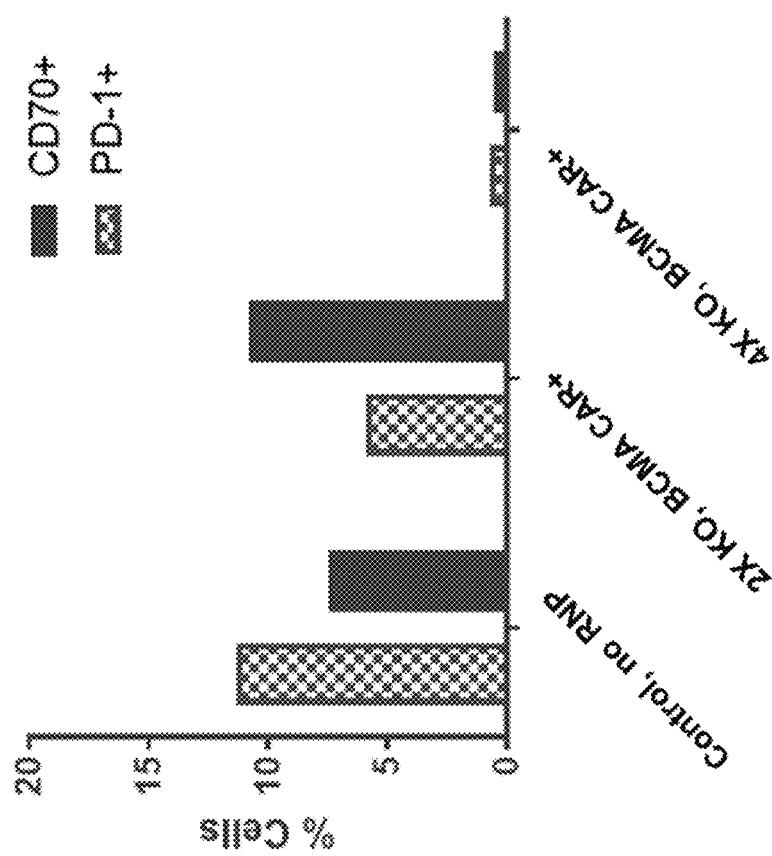
Figure 7C:
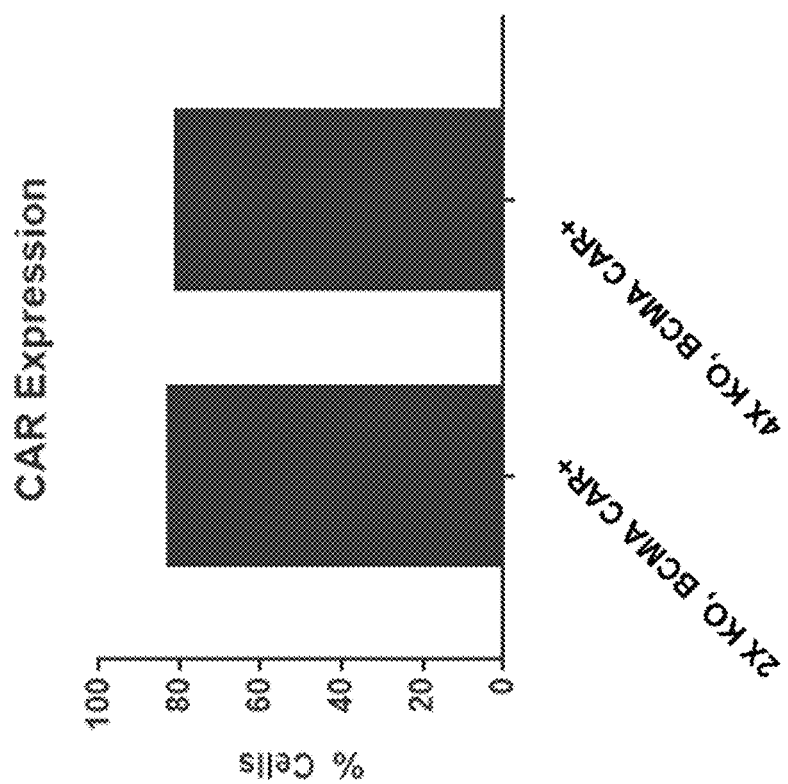

FIGS. 7A-7B shows highly efficient gene editing of the TRAC gene, β2M gene, the CD70 gene and the PD-1 gene. FIG. 7C shows high expression of the anti-BCMA CAR+ cells in double knockout and quadruple knockout cells.

Generation of Anti-CD19 CAR T Cells with Multiple Knockouts

Allogeneic human T cells were generated that express a chimeric antigen receptor (CAR) targeting CD19 and lack the expression of the TCR gene, the β2M gene, and optionally the CD70 gene.

To generate the allogeneic T cells, activated primary human T cells were electroporated with Cas9:gRNA RNP complexes and infected with adeno-associated adenoviral vectors (AAVs) containing anti-CD19 CAR donor template with homology to the TRAC locus. Recombinant AAV serotype 6 (AAV6) comprising the nucleotide sequence of SEQ ID NO: 155 (comprising the donor template in SEQ ID NO: 156, encoding anti-CD19 CAR comprising the amino acid sequence of SEQ ID NO: 149) was delivered with Cas9:sgRNA RNPs (1 µM Cas9, 5 µM gRNA) to activated human T cells. The following sgRNAs were used to knockout the respective genes: TRAC (SEQ ID NO: 40), β2M (SEQ ID NO: 41), CD70 (SEQ ID NO: 36). The unmodified versions (or other modified versions) of the gRNAs may also be used (e.g., SEQ ID NOs: 30, 21 or 27). About one (1) week post electroporation, cells were processed for flow cytometry as described above for anti-CD70 CAR+ T cells, with the following difference. Anti-CD19 CAR expression was detected using biotinylated recombinant human CD19 (ACROBIOSYSTEMS INC; CD9-H825). The CD70 deficient anti-CD19 CAR+ T cells were then characterized as described herein.

Generation of Anti-CD33 CAR T Cells with Multiple Knockouts

Allogeneic human T cells were generated that express a chimeric antigen receptor (CAR) targeting CD33 and lack the expression of the T cell receptor (TCR) gene (gene edited in the TCR Alpha Constant (TRAC) region), the β2-microglobulin (β2M) gene, and optionally the CD70 gene.

To generate the allogeneic T cells, activated primary human T cells were electroporated with Cas9:gRNA RNP complexes and infected with adeno-associated adenoviral vectors (AAVs) containing anti-CD33 CAR donor template with homology to the TRAC locus. Recombinant AAV serotype 6 (AAV6) comprising the nucleotide sequence of SEQ ID NO: 87 (comprising the donor template in SEQ ID NO: 135, encoding anti-CD33 CAR comprising the amino acid sequence of SEQ ID NO: 139 was delivered with Cas9:sgRNA RNPs (1 µM Cas9, 5 µM gRNA) to activated human T cells. The following sgRNAs were used to knockout the respective genes: TRAC (SEQ ID NO: 40), β2M (SEQ ID NO: 41), CD70 (SEQ ID NO: 36). The unmodified versions (or other modified versions) of the gRNAs may also be used (e.g., SEQ ID NOs: 30, 21 or 27).

Populations of TCR+ T cells (no RNP) and TRAC−/β2M− T cells (TCR and β2M deficient cells without a CAR) were similarly generated for use as controls. About one (1) week post electroporation, cells were processed for flow cytometry as described above for anti-CD70 CAR+ T cells, with the following difference. Anti-CD33 CAR expression was detected using biotinylated recombinant human CD33 (data not shown). The CD70 knockout anti-CD33 CAR+ T cells were then characterized as described herein.

Figure 8:
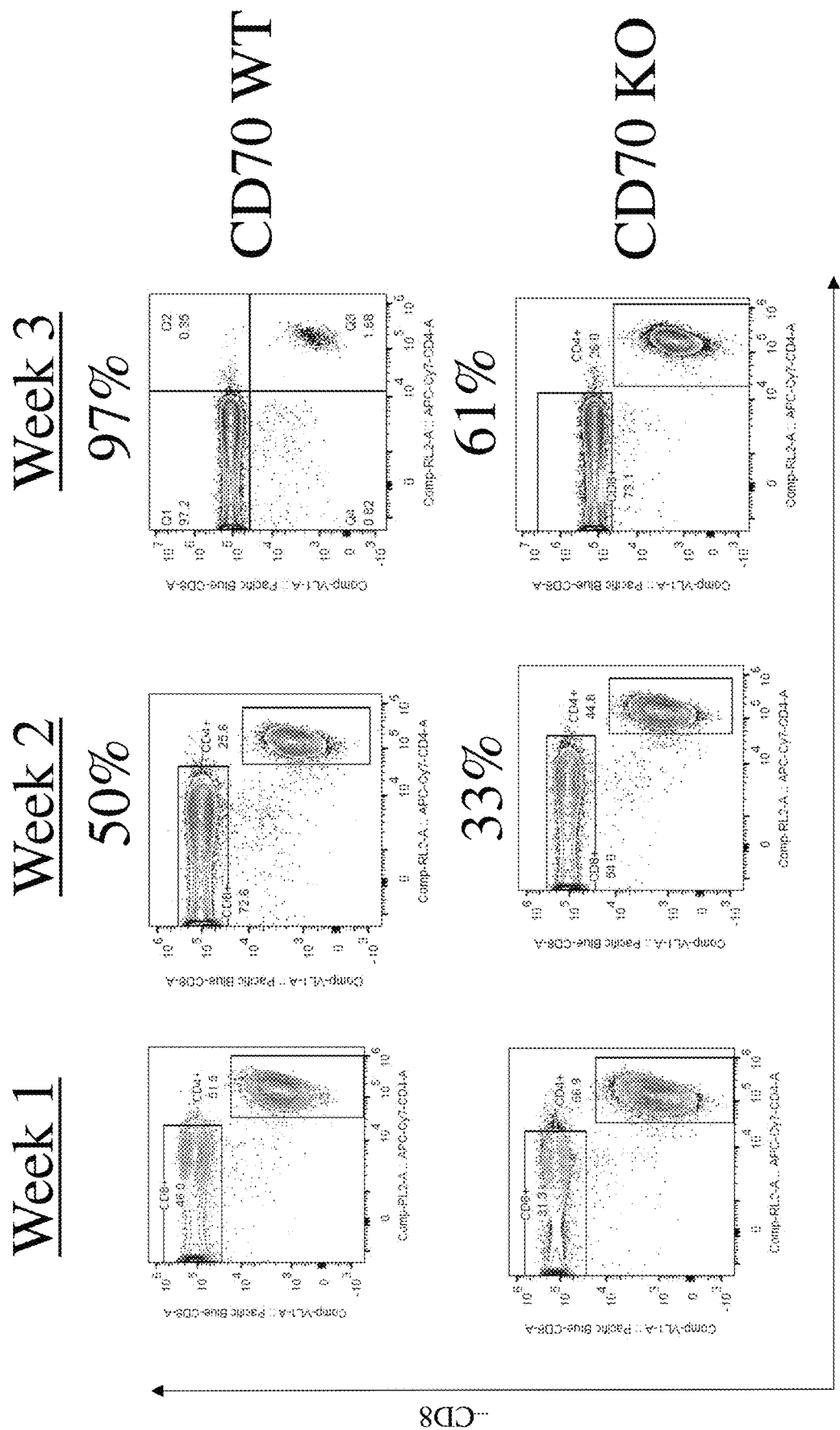
FIG. 8 includes flow cytometry plots showing prevention of loss of CD4+ cells in 3×KO (TRAC-/β2M-/CD70-) anti-CD33 CAR T cells compared 2×KO (TRAC-/β2M-) anti-CD33 CAR T cells over three weeks.

Characterization of CD4/CD8 Cell Populations in Anti-CD33 CAR T Cells with CD70 Knock-Out CD33 can be expressed on T cells with higher levels observed on cultured CD4 cells than CD8 cells. During the course of producing anti-CD33 CAR-T cells CD4 cells become substantially reduced due to fratricide. As shown in FIG. 8, anti-CD33 CAR-T cell cultures with intact CD70 displayed a 97% reduction in CD4+ cells over a 3 week culture period, while cultures of cells with disrupted CD70 showed only a 61% reduction over this time course. Thus disrupting the CD70 gene appears to reduce the fratricide observed in the anti-CD33 CAR-T cell cultures. Without wishing to be bound by theory, this effect may occur through an immune stimulatory function which could be potentiated by CD70/CD27 interactions, and genetic disruption of CD70 results in more balanced CD4/CD8 ratios that may be more optimal for therapeutic benefit in malignancy.

Example 4. CD70 KO Improves Cell Proliferation

Effect of CD70 KO on Cell Proliferation of Anti-CD33 CAR T Cells In Vitro

Figure 9:
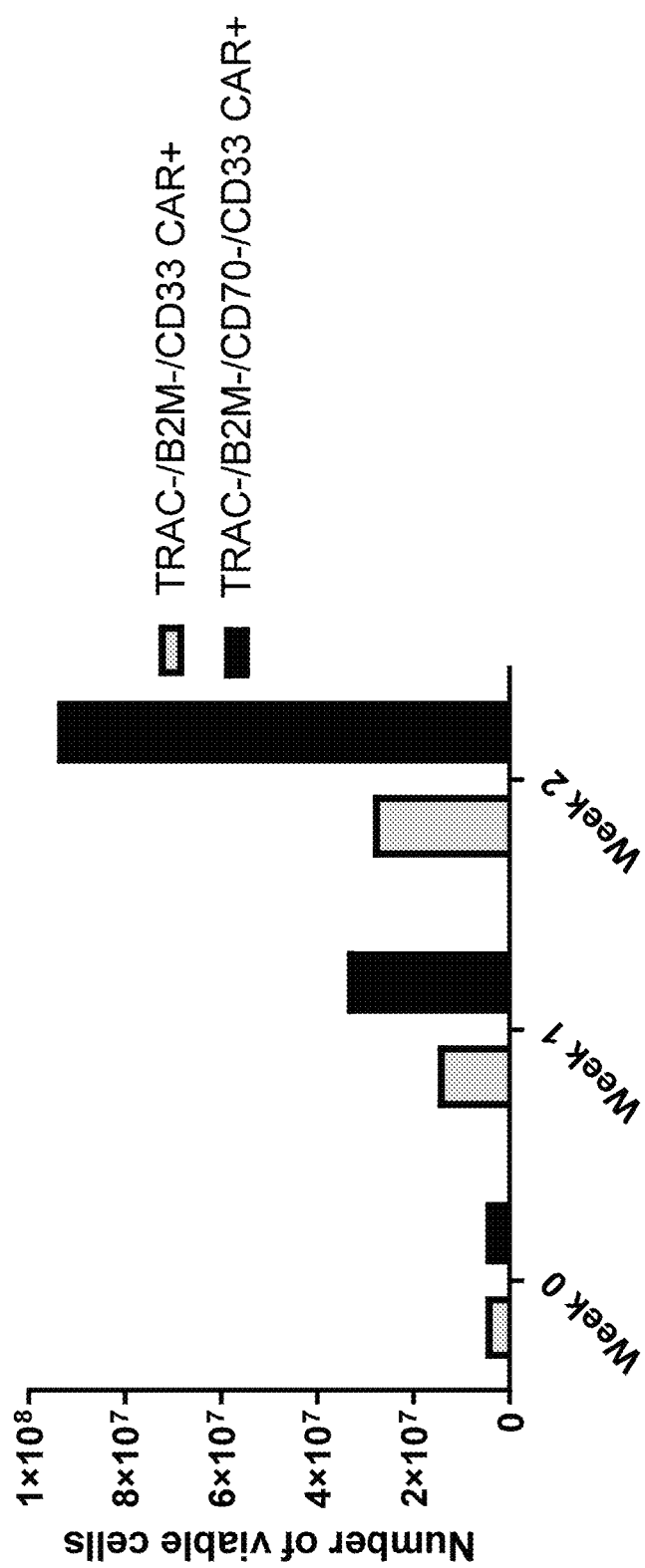
FIG. 9 includes a graph showing CD70 KO enhanced cell proliferation in anti-CD33 CAR T cells over two weeks. The total number of viable cells was quantified in 3×KO (TRAC-/β2M-/CD70-) and 2×KO (TRAC-/β2M-) anti-CD33 CAR T cells.

To assess the ability of cells to expand in cytokine containing media (IL-2+IL-7), anti-CD33 CAR T cells were utilized. Specifically, $5 \times 10^6$ total anti-CD33 CAR T cells comprising a double knockout (TRAC−/B2M−) or triple knockout (TRAC−/B2M−/CD70−) were generated as described in Example 3, plated and allowed to grow in a 10 mL volume of cytokine containing media. After 1 week cells were counted. $5 \times 10^6$ cells from the previous culture were then replated in 10 mL volume (fresh cytokine containing media) and 1 week later the total number of cells were enumerated. Allogeneic anti-CD33 CAR-T cells containing a disruption in the CD70 gene expanded to greater levels on the first and second week of replating (FIG. 9). These data show that CD70 knockout can result in greater cell yields in culture.

Effect of CD70 KO on Cell Proliferation of Anti-CD19 CAR T Cells In Vitro

Figure 10:
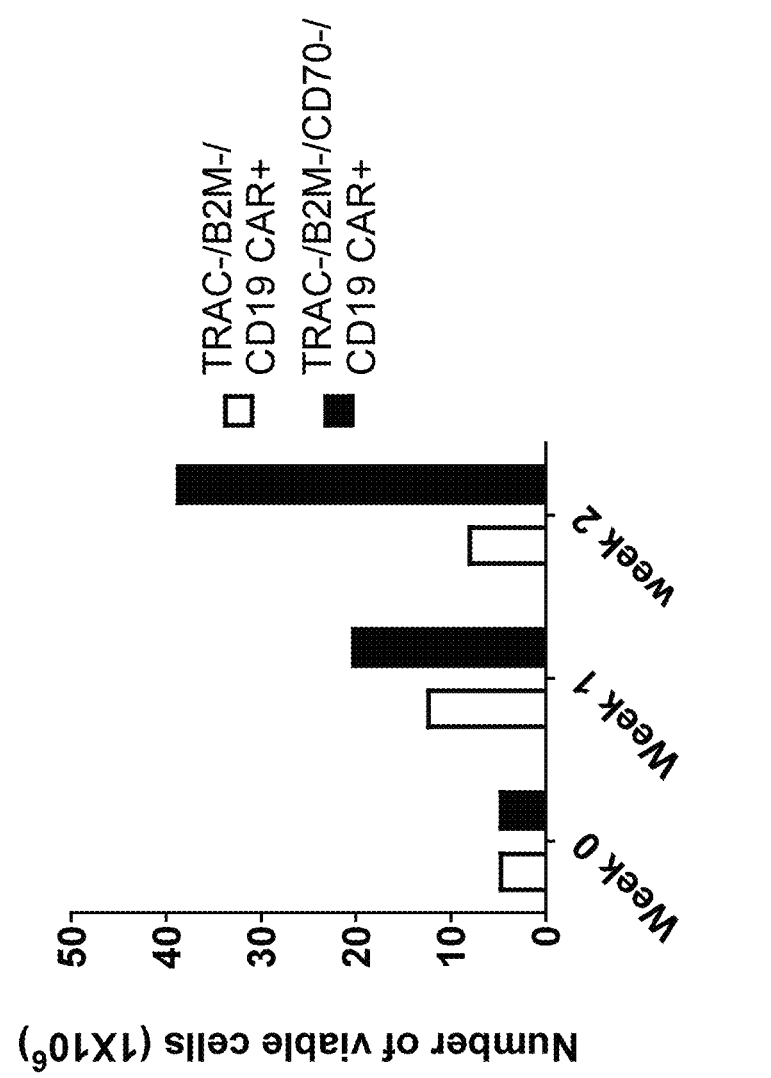
FIG. 10 includes a graph showing CD70 KO enhanced cell proliferation in anti-CD19 CAR T cells over two weeks. The total number of viable cells was quantified in 3×KO (TRAC-/β2M-/CD70-) and 2×KO (TRAC-/β2M-) anti-CD33 CAR T cells.

To further assess the ability of cells to expand in cytokine containing media (IL-2+IL-7), anti-CD19 CAR T cells were utilized. Specifically, $5 \times 10^6$ total anti-CD19 CAR T cells comprising a double knockout (TRAC−/B2M−) or triple knockout (TRAC−/B2M−/CD70−) were generated as described in Example 3, plated and allowed to grow in a 10 mL volume of cytokine containing media. After 1 week cells were counted. $5 \times 10^6$ cells from the previous culture were then replated in 10 mL volume (fresh cytokine containing media) and 1 week later the total number of cells were enumerated. Allogeneic anti-CD19 CAR-T cells containing a disruption in the CD70 gene expanded to greater levels on the first and second week of replating as compared to control cells without a CD70 gene disruption (FIG. 10). These data show that CD70 knockout can result in greater cell yields in culture.

Effect of CD70 KO on Cytokine Driven Proliferation and Apoptosis of Anti-BCMA CAR T Cells In Vitro Cytokine driven proliferation. To evaluate the effect of CD70 and/or PD1 knockout on cell proliferation, anti-BCMA CAR T cells were utilized. Anti-BCMA CAR T cells were generated as described in Example 3. The following groups of edited T cells were generated:

TRAC−/B2M−/anti-BCMA CAR+ (Control; 2KO, BCMA CAR+)

TRAC−/B2M−/CD70−/anti-BCMA CAR+ (3KO (CD70), BCMA CAR+)

TRAC−/B2M−/PD1−/anti-BCMA CAR+ (3KO (PD1), BCMA CAR+)

TRAC−/B2M−/CD70−/PD1−/anti-BCMA CAR+ (4KO, BCMA CAR+)

Edited cells were enriched for TRAC−/B2M− cells by magnetic depletion of CD3+B2M+ cells. Briefly, cells were labelled with anti-CD3 Biotin (Biolegend Cat #300404) anti-02M Biotin (Biolegend Cat #316308) antibodies, each at 0.5 µg per $1 \times 10^6$ cells in 100 µl volume at 4° C. for 15 min, washed and incubated with Streptavidin labelled magnetic microbeads (Miltenyi Biotech, 130-048-101) for 15 min at 4° C. Cells were resuspended in buffer and passed through LS columns (Miltenyi Biotech, 130-042-401) according to the manufacturer's protocol. To determine the effect of CD70 or PD1 on IL-2/IL-7 driven T cell proliferation, the edited T cells (1E6 cells/ml) were cultured in growth medium (X-vivo medium (04-744, Lonza), supplemented with 5% human AB serum (HP1022, Valley Biomedical)), 50 ng/ml IL-2 (rhIL-2; 130-097-745, Miltenyi Biotech) and 10 ng/ml IL-7 (rhIL-7; Cellgenix 001410-050) for up to four weeks. At indicated days, the cells were counted and re-seeded in fresh medium at 1.5E6 cells/ml in appropriate culture dishes.

Figure 11:
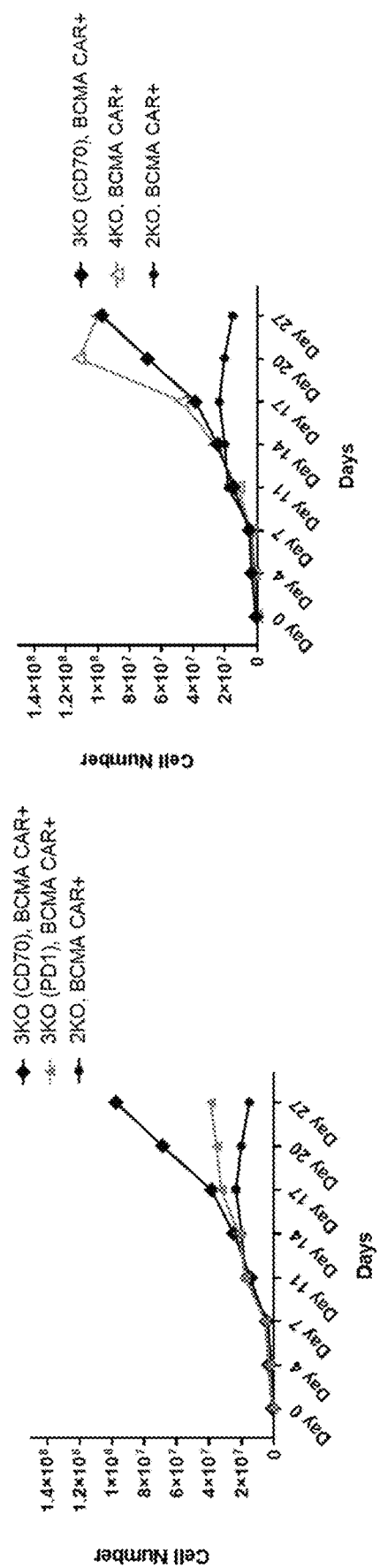
FIG. 11 includes graphs showing CD70 KO enhanced cell proliferation in anti-BCMA CAR T cells and rescued the detrimental effect of PD1 KO on BCMA CAR cell proliferation. The total number of viable cells was quantified in 4×KO (TRAC-/β2M-/CD70-/PD1-), 3×KO (CD70) (TRAC-/β2M-/CD70-), 3×KO (PD1) (TRAC-/β2M-/PD1-) and 2×KO (TRAC-/β2M-) anti-CD33 CAR T cells.
Figure 12:
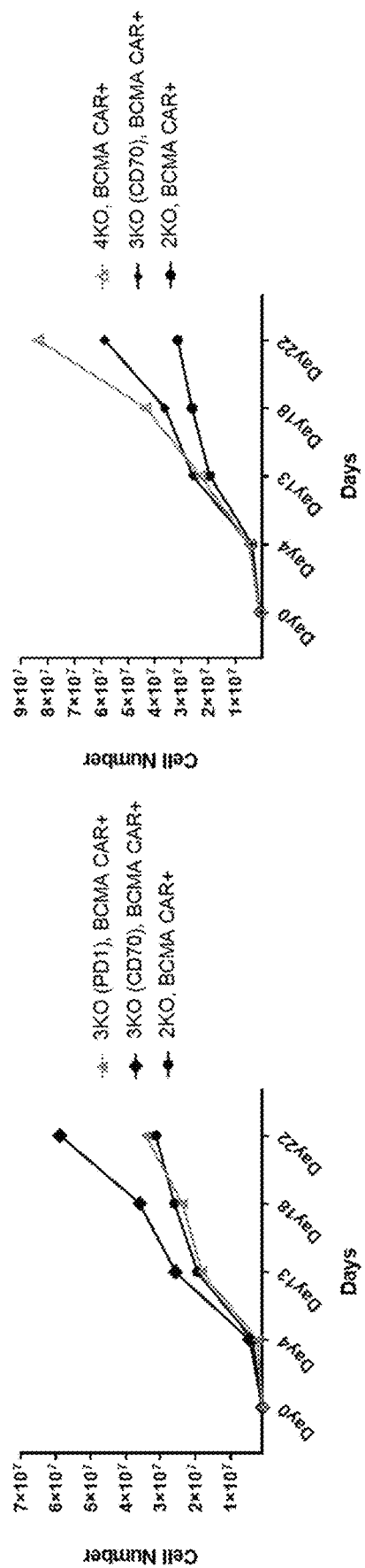
FIG. 12 includes graphs showing CD70 KO enhanced cell proliferation in anti-BCMA CAR T cells and rescued the detrimental effect of PD1 KO on BCMA CAR cell proliferation. The total number of viable cells was quantified in 4×KO (TRAC-/β2M-/CD70-/PD1-), 3×KO (CD70) (TRAC-/β2M-/CD70-), 3×KO (PD1) (TRAC-/β2M-/PD1-) and 2×KO (TRAC-/β2M-) anti-CD33 CAR T cells. The anti-BCMA CAR T cells were derived from a different donor T cells as the CAR T cells shown in FIG. 11.

FIGS. 11 and 12 show that knockout of CD70 improved IL-2/IL-7 driven proliferation of anti-BCMA CAR T cells in vitro, as compared to CD70 sufficient controls (i.e. anti-BCMA CAR T cells comprising endogenous CD70). FIG. 11 also shows the CD70 KO can improve health and proliferation competence of anti-BCMA CAR T cells even when the T cells from this donor appear to be in significant decline after 17 days when the CD70 gene is intact (as shown by the reduced cell numbers of donor 1 (FIG. 11) compared to donor 2 (FIG. 12)). This property of maintaining T cell health (enabled by KO of the CD70 gene) is broadly applicable to many aspects of CAR T development including: extended expansion during manufacturing increasing yield and consistency, rescue of exhausted/unhealthy T cells enabling potentially lower doses in patients and more robust responses, combination with other KOs that may be more detrimental to T cell health but have other advantages such as overcoming suppression of T cell activity (e.g. PD1 KO). As shown in FIGS. 11 and 12, deleting the PD1 gene by itself shows no benefit to CAR T cell expansion but when combined with a CD70 KO shows synergistic effects.

Apoptosis. The effect of CD70 KO on apoptotic cell death of anti-BCMA CAR+ T cells following exposure to antigen was evaluated in an antigen rechallenge assay. Briefly, to achieve antigen exposure, anti-BCMA CAR+ T cells were exposed to plate-adhered recombinant BCMA protein. Plates with adhered antigen were prepared by coating 24 well plates with recombinant BCMA protein in 1×PBS (1 µg/ml; biotinylated Human BCMA Protein, ACRO Biosystems) overnight at 4° C. and then washing away unbound antigen. Following the wash, antigen-bound plates were then used to challenge anti-BCMA CAR+ T cells either with or without a CD70 knockout. The 2×KO (TRAC−/B2M−) anti-BCMA CAR+ T cells and 3×KO (TRAC−/B2M−/CD70−) anti-BCMA CAR+ T cells (1×10$^6$ cells/ml) were exposed to plate-bound recombinant BCMA protein (1 µg/ml) for 24 hours in growth medium (X-vivo medium (04-744, Lonza), 5% human AB serum (HP1022, Valley Biomedical)) supplemented with IL-2 (rhIL-2; 130-097-745, Miltenyi Biotech). Cells were then washed, counted and re-challenged (1×10$^6$ cells/ml) with fresh plate-bound antigen every 24 hours for a total of three consecutive re-challenges (24 hr, 48 hr, and 72 hr). At the end of each re-challenge, an aliquot of cells was washed and stained with fluorochrome-conjugated annexin V along with propidium iodide in annexin V binding buffer (BioLegend) for 15 minutes at room temperature. Cells were then washed and resuspend in annexin V binding buffer for analysis by flow cytometry. The cells were counted at each time point and the cell count per ml was derived. For the calculation of fold-expansion at each time point, the initial fold-expansion at time 0 was set at 1. Fold-expansion for all other time points were calculated by multiplying the cell count per ml at each time point by the fold-expansion per ml for the prior time point. For example, the fold expansion at 72 hr was calculated by multiplying the cell count per ml at 72 hr by the fold expansion per ml at 48 hr.

Figure 13:
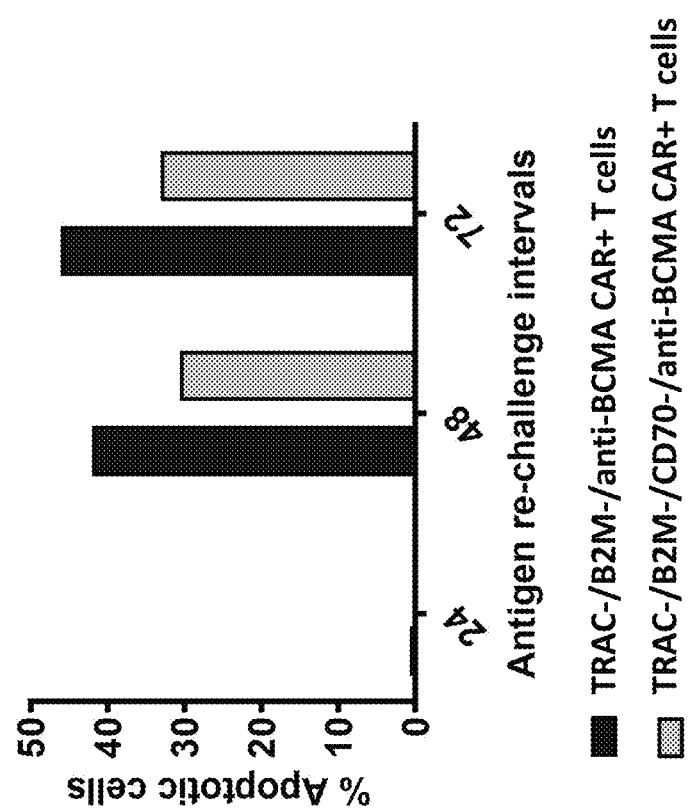
FIG. 13 includes a graph showing a comparison of apoptotic cell death due to antigen exposure in 2×KO (TRAC-/B2M-) anti-BCMA CAR+ T cells and 3×KO (TRAC-/B2M-/CD70-) anti-BCMA CAR+ T cells. CAR+ T cells were exposed to plate-bound BCMA antigen for 24 hours with a re-challenge every 24 hours and apoptosis was assessed following each antigen challenge by flow cytometry. Induction of apoptosis due to antigen challenge was lower in anti-BCMA CAR+ T cells with a CD70 KO compared to those without.
Figure 14:
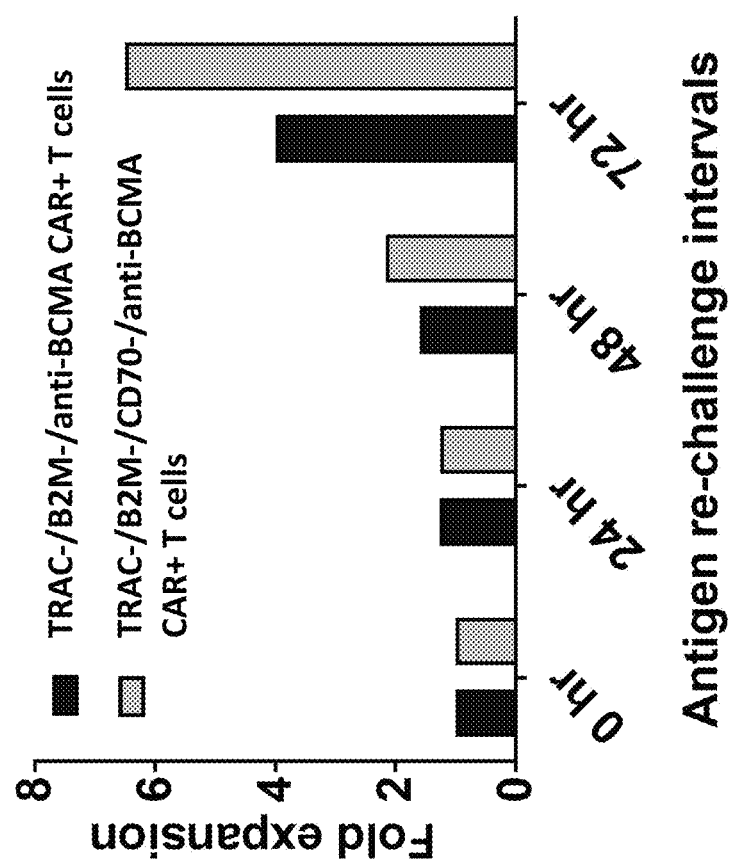
FIG. 14 includes a graph showing a comparison of CAR T cell expansion following antigen exposure in 2×KO (TRAC-/B2M-) anti-BCMA CAR+ T cells and 3×KO (TRAC-/B2M-/CD70-) anti-BCMA CAR+ T cells. CAR+ T cells were exposed to plate-bound BCMA antigen for 24 hours with a re-challenge every 24 hours and cell expansion was assessed following each antigen challenge and normalized to the population at time 0 h. Population expansion following antigen challenge was higher in anti-BCMA CAR+ T cells with a CD70 KO compared to those without.

FIG. 13 demonstrates that the deletion of CD70 (CD70 KO) rescues anti-BCMA CAR+ T cells from apoptosis, as shown by the decrease in the percentage of apoptotic cells following the second (48 hr) and third (72 hr) rechallenge. Furthermore, the absence of CD70 expression in anti-BCMA CAR+ T cells surprisingly enhances the expansion of the anti-BCMA CAR+ T cells in response to antigen exposure (FIG. 14).

Effect of CD70 KO on Cell Proliferation of Anti-CD70 CAR T Cells In Vitro

Figure 15:
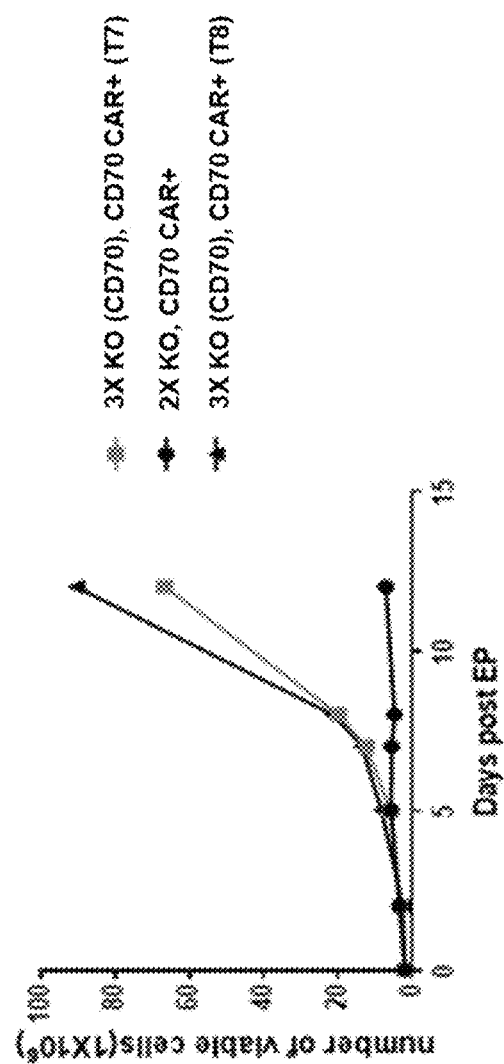
FIG. 15 includes a graph showing robust cell expansion in TRAC$^-$/β2M$^-$/CD70$^-$/anti-CD70 CAR$^+$ T cells. The total number of viable cells was quantified in 3×KO (TRAC-/β2M-/CD70-) and 2×KO (TRAC-/β2M-) anti-CD70 CAR T cells. 3×KO cells were generated with either CD70 sgRNA T7 or T8.

To further assess the impact of disrupting the CD70 gene in CAR T cells, anti-CD70 CAR T cells were generated as described in Example 3. Specifically, 3×KO (TRAC−/β2M−/CD70−) anti-CD70 CAR T cells were generated using two different gRNAs (T7 (SEQ ID NO: 36 and T8 (SEQ ID NO: 37)). After electroporation, cell expansion was assessed as described in Example 2 by counting viable cells. FIG. 15 shows that triple knockout TRAC−/β2M−/CD70−/anti-CD70 CAR$^+$ T cells generated with either T7 or T8 gRNAs exhibited greater cell expansion relative to double knockout TRAC−/β2M−/anti-CD70 CAR$^+$ T cells. These data suggest that knocking-out the CD70 gene gives a cell proliferation advantage to anti-CD70 CAR+ T cells.

Figure 16:
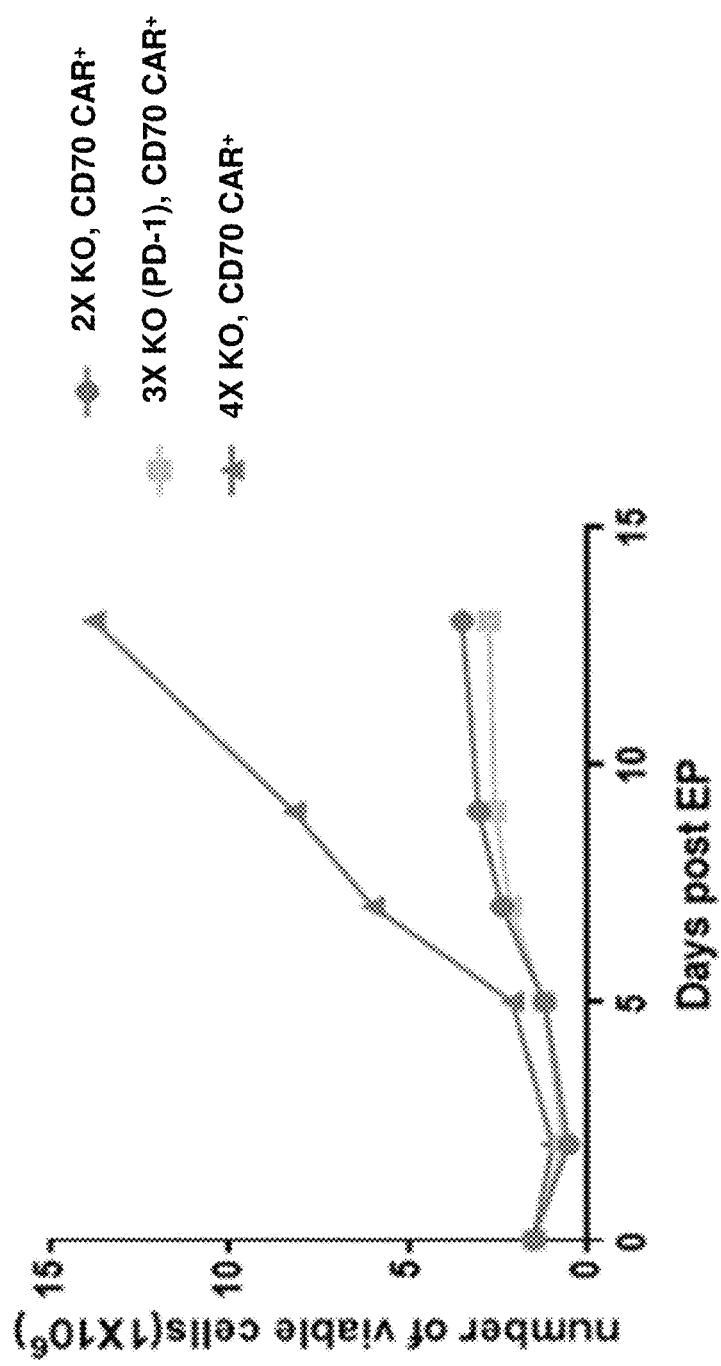
FIG. 16 includes a graph showing robust cell expansion of TRAC$^-$/β2M$^-$/PD-1$^-$/CD70$^-$/anti-CD70 CAR+ T cells. The total number of viable cells was quantified in 4×KO (TRAC-/β2M-/PD1-/CD70-), 3×KO (TRAC-/β2M-/PD1-) and 2×KO (TRAC-/β2M-) anti-CD70 CAR T cells.

Cell expansion was also assessed in the quadruple knockout, TRAC−/β2M−/PD-1−/CD70−/anti-CD70 CAR+ T cells. These cells exhibited greater expansion relative to triple knockout TRAC−/β2M−/PD-1−/anti-CD70 CAR+ T cells and to double knockout TRAC−/β2M−/anti-CD70 CAR+ T cells (FIG. 16).

Example 5. CD70 KO Increases Durability and Potency of CAR T Cells In Vitro

Cell Killing Function of Anti-CD19 CAR T Cells with CD70 Knock-Out

Following preparation of edited anti-CD19 CAR T cells as described in Example 3, the functional activity of the CAR T cells was verified using a flow cytometry-based cytotoxicity assay. The anti-CD19 CAR T cells (TRAC−/β2M−/CD19 CAR+ and TRAC−/β2M−/CD70−/CD19 CAR+) were co-cultured with one of two CD19-expressing cancer cell lines (target cells): Nalm6 (ATCC cr13273) or Raji (ATCC ccl-86). The target cells were labeled with 5 µM efluor670 (eBiosciences), washed and incubated in co-cultures with the TRAC−/β2M−/anti-CD19 CAR+, or TRAC−/β2M−/CD70−/anti-CD19 CAR+ at varying ratios (0.01, 0.05, 0.1, 0.5, 1:1 T cells:target cells). The target cells were seeded at 50,000 cells per well in a 96-well, U-bottom plate. The co-culture was incubated overnight. After incubation, wells were washed and media was replaced with 200 µL of media containing a 1:500 dilution of 5 mg/mL DAPI (Molecular Probes). 25 µL of CountBright beads (Life Technologies) were then added to each well and the cell cultures were analyzed for cell viability by flow cytometry (i.e., viable cells being negative for DAPI staining)

Percent cell lysis of the target cells (e.g.: Nalm6 or Raji cells) was then determined using the following formula:

Percent cell lysis=(1−((total number of target cells in a test sample)÷(total number of target cells in a control sample))×100;

wherein a test sample was target cells (e.g.: Nalm6 or Raji cells) co-cultured with 1) TRAC−/β2M−/CD19 CAR+ T cells or 2) TRAC−/β2M−/CD70−/CD19 CAR+ T cells; and a control sample was target cells alone that had not been co-cultured.

Figure 17:
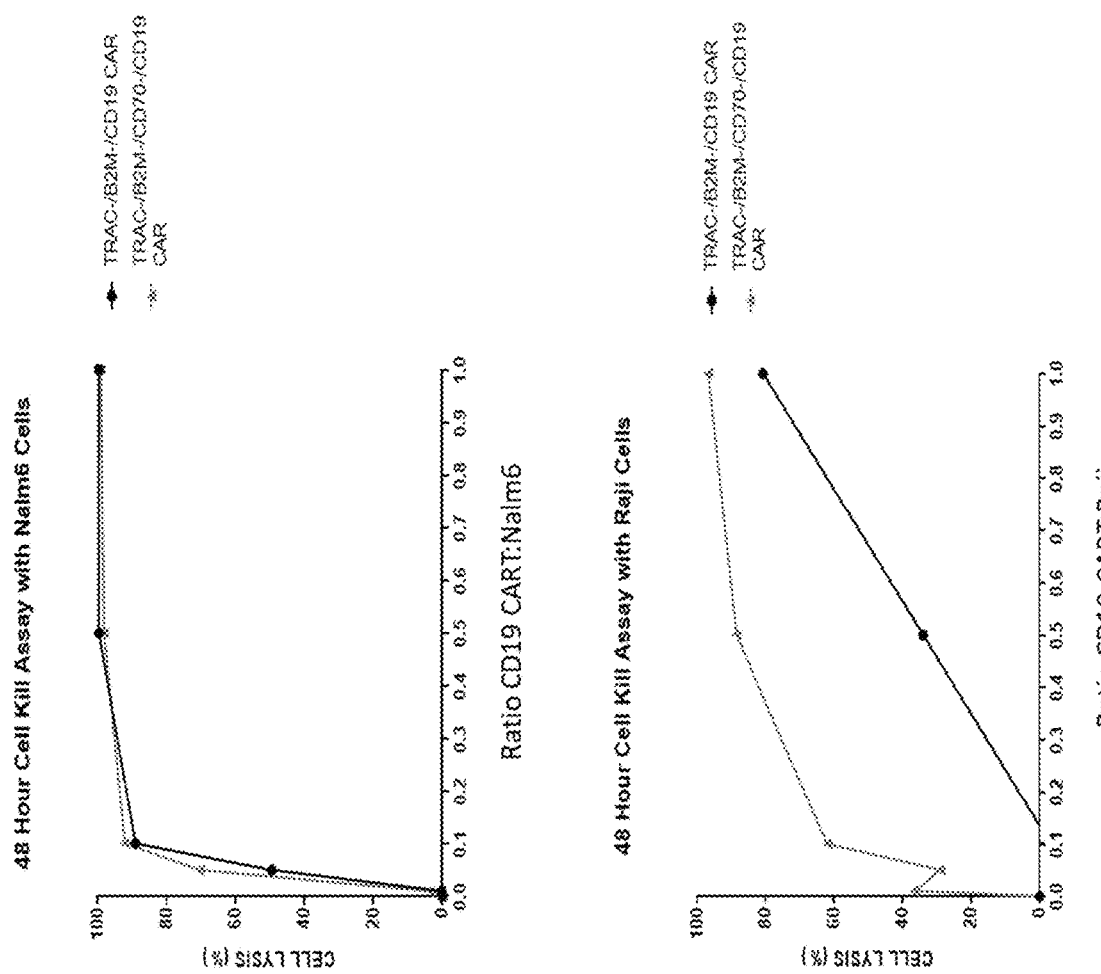
FIG. 17 includes graphs showing robust cell killing of both Nalm6 (top panel) cells and Raji (bottom panel) cells by anti-CD19 CAR T cells (TRAC$^-$/β2M$^-$/CD70$^-$/anti-CD19 CARP or TRAC$^-$/β2M$^-$/anti-CD19 CAR$^+$ T cells).

Disruption of the CD70 gene led to enhanced cytolytic activity of the anti-CD19 CAR-T cells against the Raji cell line at low CAR-T to target ratios (FIG. 17, bottom panel).

Disruption of CD70 did not enhance anti-CD19 CAR-T activity against the Nalm6 cell line (FIG. 17, top panel). Of note, the Nalm6 cell line is relatively easier to lyse by these CAR-T cells (>80% lyses at 0.1:1 CAR-T cell to target ratio for Nalm6 vs 0% for Raji at this ratio for the wild-type cells) likely explaining the lack of resulting increased efficacy due to CD70 disruption in this assay against Nalm6 cells. The increased activity conferred by CD70 loss against the Raji cell line indicates that in challenging tumor environments, particularly when CAR-T to tumor ratios are low, CD70 loss may have substantial benefit to the CAR-T cells in eradicating tumor cells.

Cell Killing Function of Anti-CD33 CAR T Cells with CD70 Knock-Out

Following preparation of the edited anti-CD33 CAR+ T cells as described in Example 3, the functional activity of the CAR T cells was verified using a flow cytometry-based cytotoxicity assay. The anti-CD33 CAR T cells (TRAC−/β2M−/CD33 CAR+ and TRAC−/β2M−/CD70−/CD33 CAR+) or control T cells (no RNP) were co-cultured with the CD33-expressing cancer cell line MV4-11 (ATCC CRL-9591). The target cells were labeled with 5 µM efluor670 (eBiosciences), washed and incubated in co-cultures with the TRAC−/B2M−/anti-CD33 CAR+, TRAC−/β2M−/CD70−/anti-CD33 CAR+, or controls at varying ratios (0.01:1, 0.03:1, 0.06:1, 0.125:1, 0.25:1, 0.5:1, or 1:1 T cells:target cells). The target cells were seeded at 50,000 cells per well in a 96-well, U-bottom plate. The co-culture was incubated overnight. After 48 hrs, wells were washed and media was replaced with 200 µL of media containing a 1:500 dilution of 5 mg/mL DAPI (Molecular Probes). 25 µL of CountBright beads (Life Technologies) were then added to each well and the cell cultures were analyzed for cell viability by flow cytometry (i.e., viable cells being negative for DAPI staining).

Percent cell lysis of the target cells (e.g.: MV4-11) was then determined using the following formula:

$$\text{Percent cell lysis} = (1 - ((\text{total number of target cells in a test sample}) \div (\text{total number of target cells in a control sample}))) \times 100;$$

wherein a test sample was target cells (e.g.: MV4-11 cells) co-cultured with 1) TRAC−/B2M−/CD33 CAR+ T cells; or 2) TRAC−/B2M−/CD70−/CD33 CAR+ T cells, and a control sample was target cells alone that had not been co-cultured.

Figure 18:
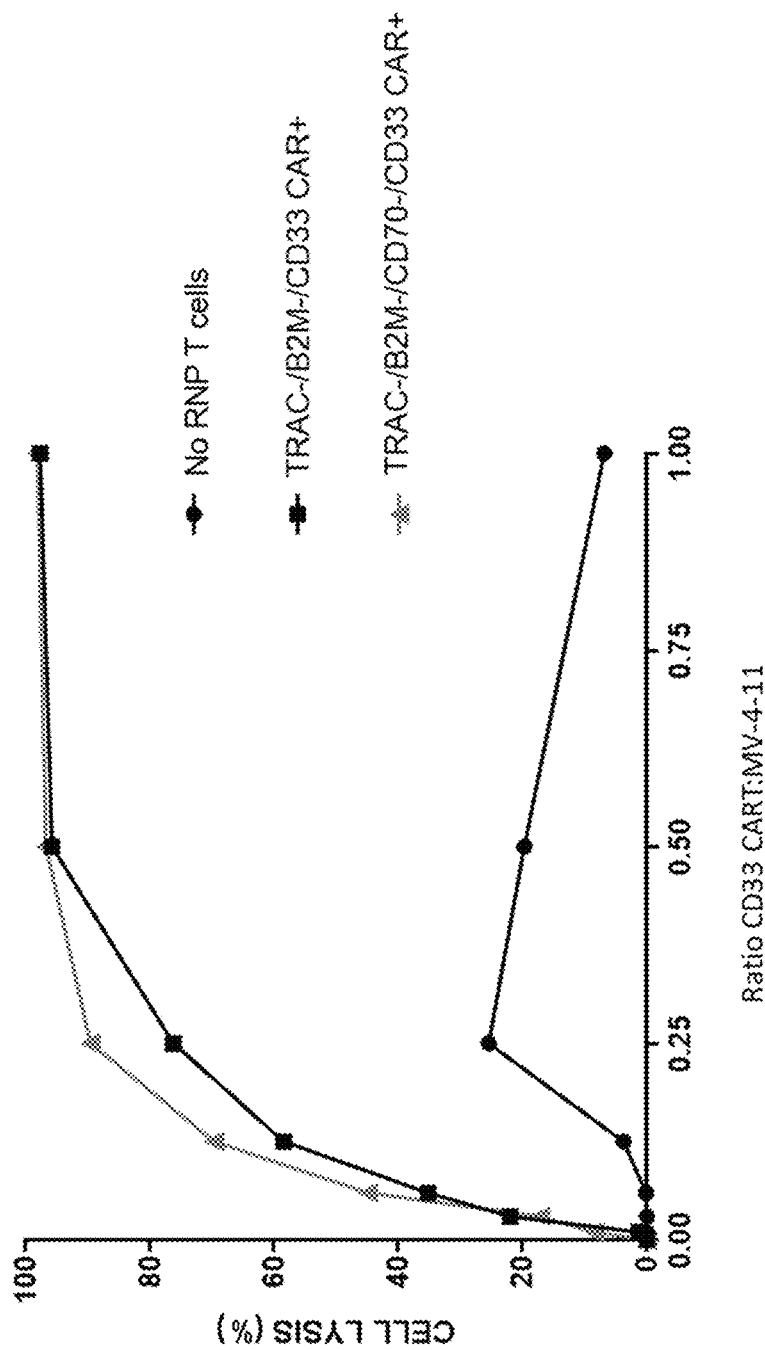
FIG. 18 includes a graph showing robust cell killing of MV411 cells by anti-CD33 CAR T cells (TRAC$^-$/β2M$^-$/CD70$^-$/anti-CD33 CARP or TRAC$^-$/β2M$^-$/anti-CD33 CAR$^+$ T cells).

Although both populations of anti-CD33 CAR T cells effectively killed MV4-11 cells, reaching nearly 100% cells kill at ratios of 0.5 CAR T cell: MV4-11 cell, the TRAC−/B2M−/CD70−/CD33 CAR+ T cells demonstrated higher cell killing at lower CAR T to cancer cell rations (FIG. 18). These data demonstrate that allogeneic anti-CD33 CAR T cells with the additional CD70 knock-out are more efficacious at lower CAR T cell to target cell ratios.

Cell Killing Function of Anti-CD70 CAR T Cells with CD70 Knock-Out

Figure 19:
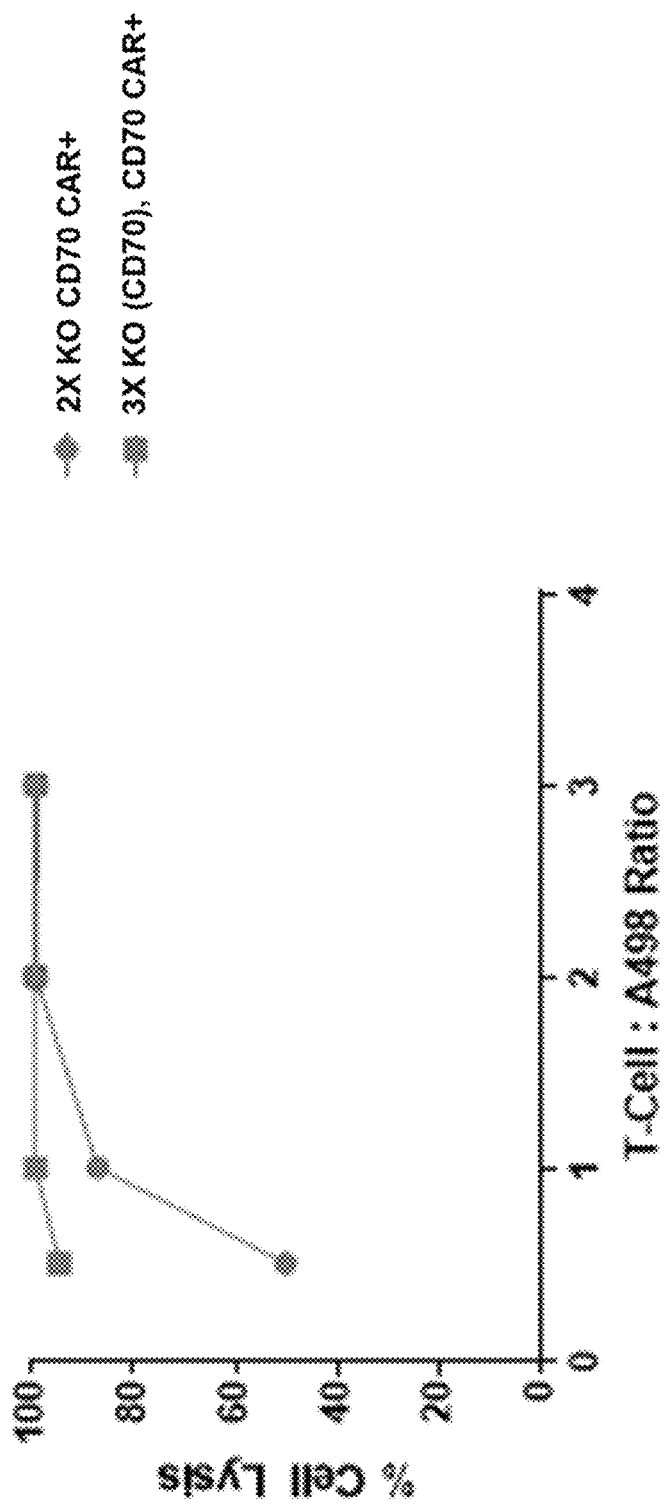
FIG. 19 includes a graph showing robust cell killing of A498 cells by 3×KO (TRAC$^-$/β2M$^-$/CD70$^-$) anti-CD70 CAR$^+$ T cells compared to 2×KO (TRAC$^-$/β2M$^-$) anti-CD70 CAR$^+$ T cells.

A cell killing assay was used to assess the ability of the TRAC−/β2M−/CD70−/anti-CD70 CAR+ cells and TRAC−/β2M−/PD-1−/CD70−/anti-CD70 CAR+ cells to kill a CD70+ adherent renal cell carcinoma (RCC)-derived cell line (A498 cells). Adherent cells were seeded in 96-well plates at 50,000 cells per well and left overnight at 37° C. The next day edited anti-CD70 CAR T cells were added to the wells containing target cells at the indicated ratios. After the indicated incubation period, CAR T cells were removed from the culture by aspiration and 100 µL Cell titer-Glo (Promega) was added to each well of the plate to assess the number of remaining viable cells. The amount of light emitted per well was then quantified using a plate reader. The cells exhibited potent cell killing of RCC-derived cells following 24-hour co-incubation (FIG. 19). The anti-CD70 CAR T cells demonstrated higher potency when CD70 was knocked out, which is clearly visible at low T cell: A498 ratios (1:1 and 0.5:1) where cell lysis remains above 90% for TRAC−/β2M−/CD70−/anti-CD70 CAR+, while cells lysis drops below 90% for the TRAC−/β2M−/anti-CD70 CAR+. This suggests that knocking-out the CD70 gene gives a higher cell kill potency to anti-CD70 CAR+ T cells.

Example 6. Rechallenge of CD70 Deficient CAR T Cells In Vitro

CD70 Knockout Improves Anti-CD33 CAR+ T Cell Killing Upon Serial Rechallenge

Figure 20:
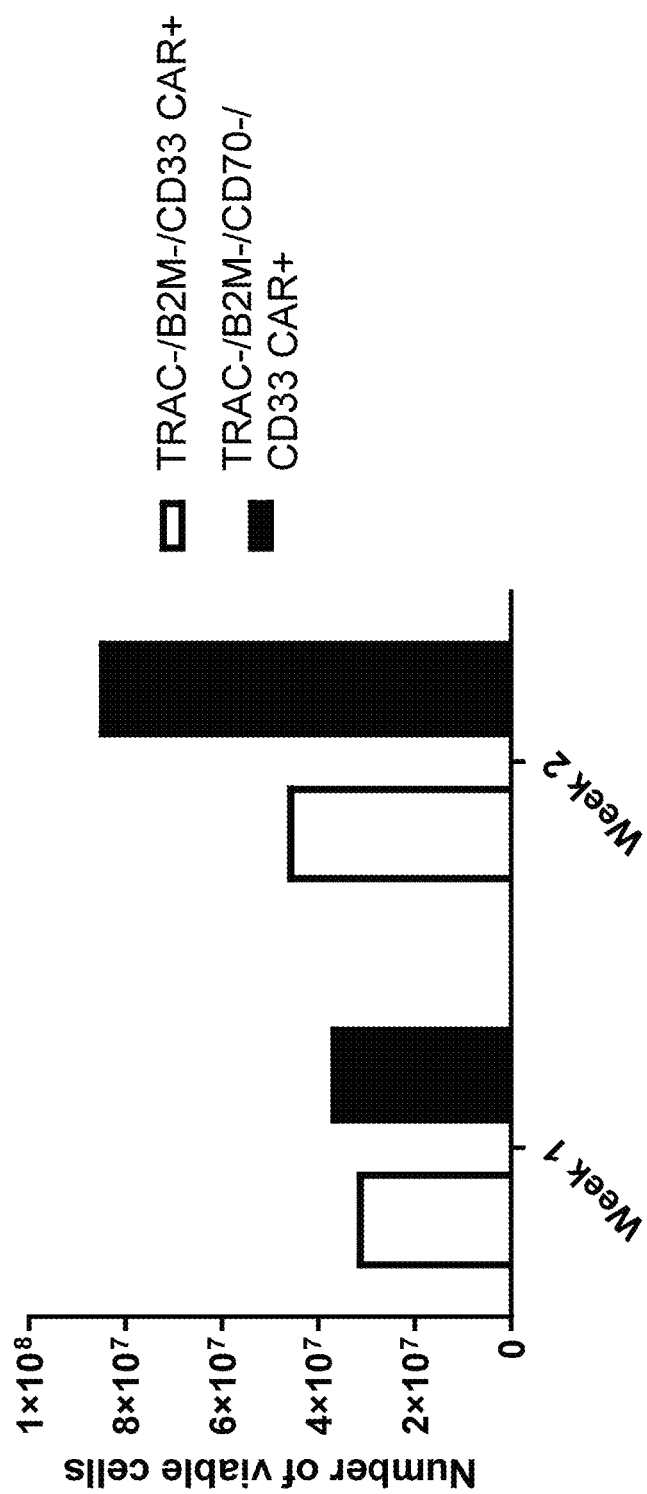
FIG. 20 includes a graph showing cell expansion of 3×KO (TRAC-/β2M-/CD70-) or 2×KO (TRAC-/β2M-) anti-CD33 CAR T cells after challenge with MV411 target cells.

To assess the ability of cells to expand after challenge and rechallenge with antigen-expressing cells (e.g.: target cells) anti-CD33 CAR T cells were generated as described in Example 3 and utilized. Specifically, $5 \times 10^6$ total T cells were plated in the presence of $5 \times 10^6$ irradiated target cells (MV-4-11) and allowed to grow in a 10 mL volume. After 1 week, cells were counted, $5 \times 10^6$ cells from the previous culture were then replated in 10 mL volume along with a fresh aliquot of $5 \times 10^6$ irradiated target cells and 1 week later the total number of cells were enumerated. The process was repeated as indicated, each rechallenge started with $5 \times 10^6$ cells. The number of viable cells were counted as described in Example 2. Allogeneic anti-CD33 CAR-T cells containing a disruption in the CD70 gene expanded to greater levels on the second week of after 2 challenges with MV-4-11 cells (FIG. 20). These data show that CD70 can limit T-cell expansion in the presence of antigen expressing cells and its loss can result in greater cell expansion after antigen stimulation.

CD70 Knockout Improves Anti-CD19 CAR+ T Cell Killing Upon Serial Rechallenge

Figure 21:
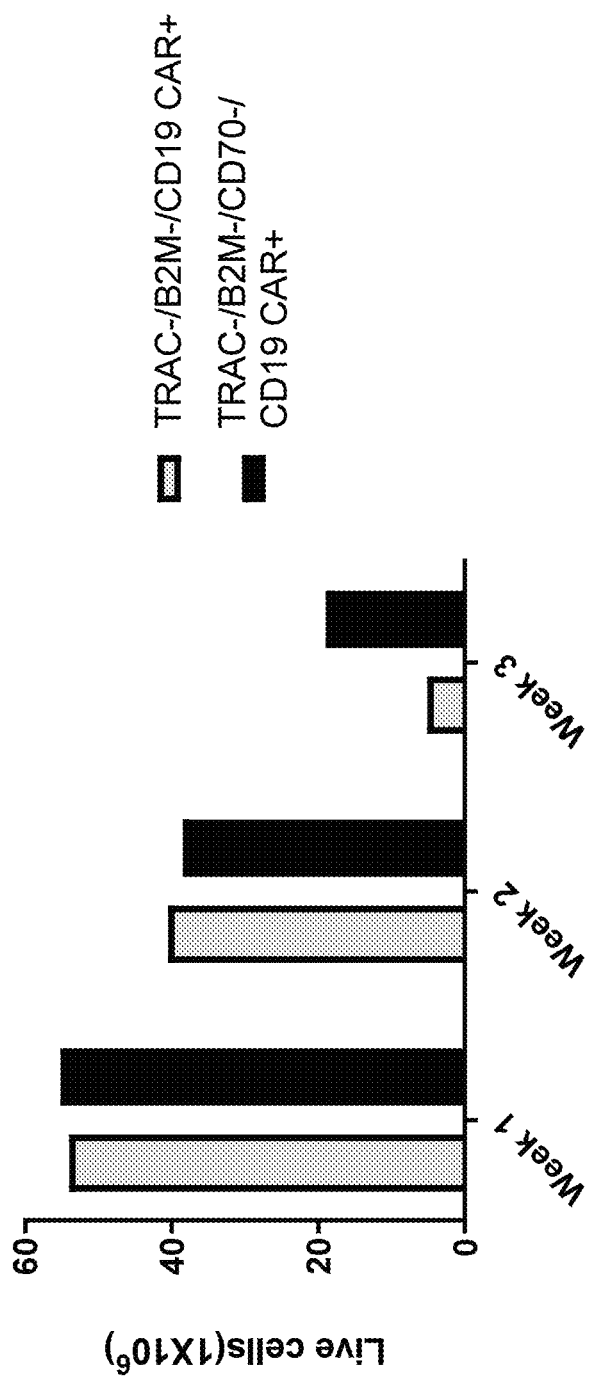
FIG. 21 includes a graph showing cell expansion of 3×KO (TRAC-/β2M-/CD70-) or 2×KO (TRAC-/β2M-) anti-CD70 CAR T cells after challenge with Nalm6 target cells.

To further assess the ability of cells to expand after challenge and rechallenge with antigen-expressing cells (e.g.: target cells) anti-CD19 CAR T cells were generated as described in Example 3 and utilized. Specifically, $5 \times 10^6$ total T cells were plated in the presence of $5 \times 10^6$ irradiated target cells (Nalm6) and allowed to grow in a 10 mL volume. After 1 week, cells were counted, $5 \times 10^6$ cells from the previous culture were then replated in 10 mL volume along with a fresh aliquot of $5 \times 10^6$ irradiated target cells and 1 week later the total number of cells were enumerated. The process was repeated as indicated, each rechallenge started with $5 \times 10^6$ cells. The number of viable cells were counted as described in Example 2. Allogeneic anti-CD19 CAR-T cells containing a disruption in the CD70 gene expanded to similar amounts during the first 2 challenges. However, at three challenges allogeneic anti-CD19 CAR-T cells containing a disruption in the CD70 gene expanded to greater level on the third challenge with Nalm6 cells (FIG. 21). These data show that the presence of CD70 can limit T-cell expansion in the presence of antigen expressing cells and its loss can result in greater cell expansion after repeated antigen stimulation.

Knockout of CD70, or PD-1 Plus CD70, Maintain Anti-CD70 CAR+ T Cell Killing Upon Serial Rechallenge The anti-CD70 CAR+ T cells generated above were serially rechallenged with CD70+ kidney cancer cell line, A498, and evaluated for their ability to kill the CD70+ kidney cancer cell lines A498 or ACHN.

A498 cells were plated in a T25 flask and mixed at a ratio of 2:1 (T-cell to A498) with 10×10$^6$ anti-CD70 CAR+ T cells containing either two (TRAC$^-$/β2M$^-$), three (TRAC$^-$/(32M$^-$/PD-1$^-$) or (TRAC$^-$/β2M$^-$/CD70$^-$)), or four (TRAC$^-$/β2M$^-$/PD-1$^-$/CD70$^-$) gRNA edits.

Figure 22A:
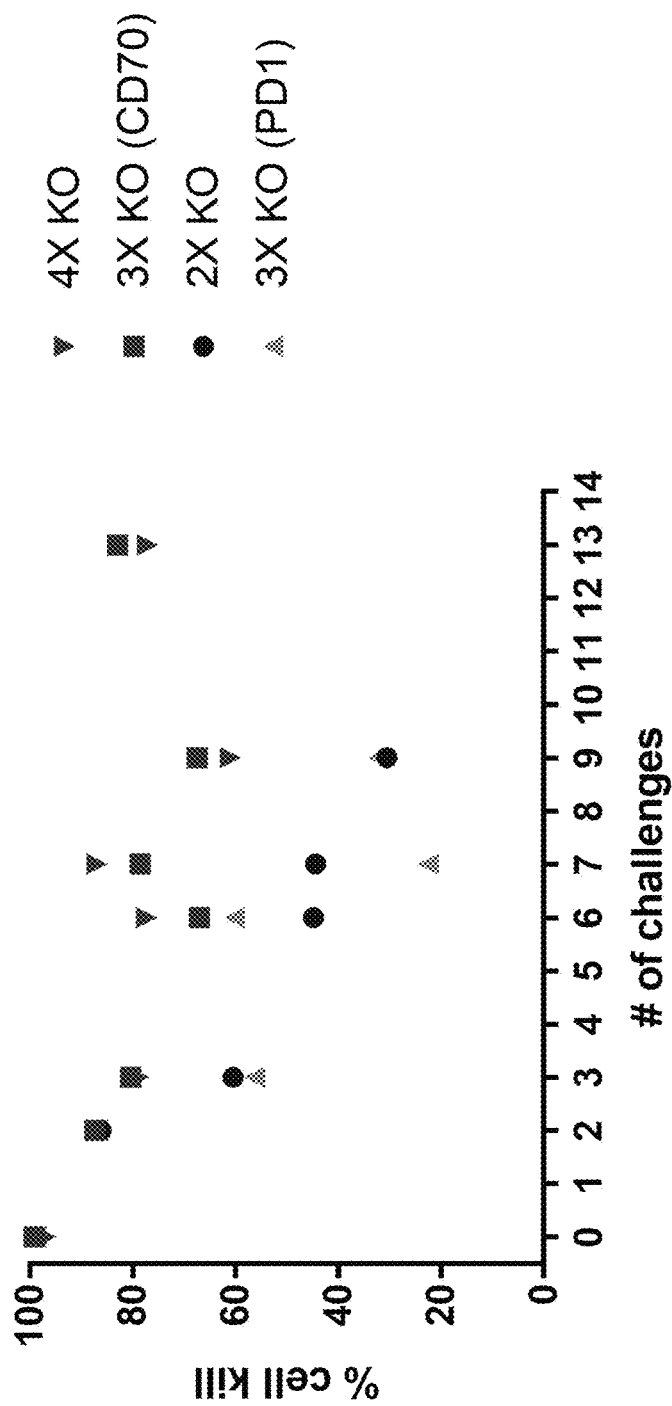
FIG. 22A includes a graph showing A498 cell killing by anti-CD70 CAR T cells after serial rechallenge. 4×KO (TRAC$^-$/β2M$^-$/CD70$^-$/PD1$^-$), 3×KO (CD70) (TRAC$^-$/β2M$^-$/CD70$^-$), 3×KO (PD1) (TRAC$^-$/β2M$^-$/PD1$^-$) and 2×KO (TRAC$^-$/β2M$^-$) anti-CD70 CAR+ T cells were utilized. 3×KO (CD70), CD70 CAR$^+$ T cells, and 4×KO, CD70 CAR+ T cells were the most effective.

Two or three days after each challenge, cells were counted, washed, resuspended in fresh T cell media, and re-challenged the next day with the same ratio of two anti-CD70 CAR$^+$ T cell per one A498 cell (2:1, CAR$^+$ T:target). Challenging of anti-CD70 CAR$^+$ T cells with CD70+ A498 cells was repeated 13 times. Three to four days following each exposure to A498 cells (and prior to the next rechallenge), aliquots of the culture were taken and analyzed for the ability of the CAR T Cells to kill A498 or ACHN target cells at a ratio of 2:1 (CAR T cell: Target cell). Cell kill was measured using Cell titer-glo (Promega). Prior to the first challenge with A498, anti-CD70 CAR+ T cells with 2×KO (TRAC$^-$/β2M$^-$), 3×KO (TRAC$^-$/β2M/CD70), 3×KO (TRAC$^-$/β2M$^-$/PD-1$^-$), and 4×KO (TRAC$^-$/β2M$^-$/PD-1$^-$/CD70$^-$) each exhibited a target cell killing of A498 cells approaching 100%. By challenge nine however, the 2×KO (TRAC$^-$/β2M$^-$) and 3×KO (TRAC$^-$/β2M$^-$/PD-1$^-$) anti-CD70 CAR+ T cells induced target cell killing of A498 cells below 40%, while 3×KO (TRAC$^-$/β2M$^-$/CD70) and 4×KO (TRAC$^-$/β2M$^-$/PD-1$^-$/CD70$^-$) anti-CD70 CAR$^+$ T cells exhibited target cell killing above 60% (FIG. 22A). The target cell killing for 3×KO (TRAC$^-$/β2M$^-$/CD70) and 4×KO (TRAC$^-$/β2M$^-$/PD-1$^-$/CD70$^-$) anti-CD70 CAR$^+$ T cells remained above 60% even following 13 re-challenges with A498 cells, demonstrating that these CAR+ T cells were resistant to exhaustion.

Figure 22B:
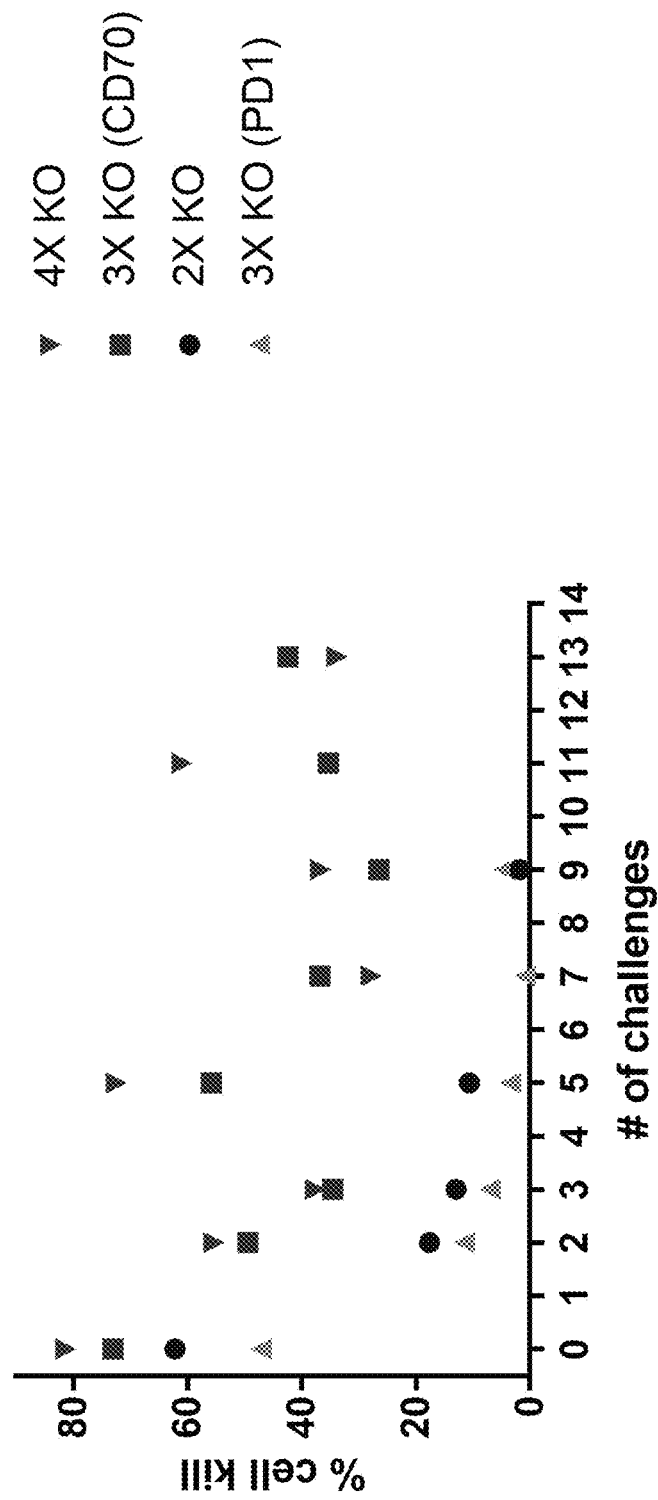
FIG. 22B includes a graph showing ACHN cell killing by anti-CD70 CAR T cells after serial rechallenge. The same cells as FIG. 22A were utilized. 3×KO (CD70), CD70 CAR$^+$ T cells and 4×KO, CD70 CAR$^+$ T cells were the most effective.

Anti-CD70 CAR T cells were also evaluated for their ability to kill ACHN cells at a ratio of 2:1 (T-cell to ACHN) following serial rechallenge with A498 renal carcinoma cells (FIG. 22B). Prior to the first challenge with A498, the double knockout TRAC$^-$/β2M$^-$/anti-CD70 CAR$^+$ T cells, the triple knockout TRAC$^-$/β2M$^-$/PD-1$^-$/anti-CD70 CAR$^+$ T, the triple knockout TRAC$^-$/β2M$^-$/CD70$^-$/anti-CD70 CAR$^+$ T cells and the quadruple knockout TRAC$^-$/β2M$^-$/PD-1$^-$/CD70$^-$/anti-CD70 CAR$^+$ T exhibited a cell kill efficiency above 62%, 47%, 73% and 81%, respectively.

After challenge five, the triple knockout TRAC$^-$/β2M$^-$/CD70$^-$/anti-CD70 CAR$^+$ T cells and the quadruple knockout TRAC$^-$/β2M$^-$/PD-1$^-$/CD70$^-$/anti-CD70 CAR$^+$ T cells still efficiently killed above 55% of ACHN cells at a ratio of 2:1 (T-cell to ACHN), while the double knockout TRAC$^-$/β2M$^-$/anti-CD70 CAR$^+$ T cells and the triple knockout TRAC$^-$/β2M$^-$/PD-1$^-$/anti-CD70 CAR$^+$ T cell kill dropped below 11% of ACHN cells. This trend continued, wherein the double knockout TRAC$^-$/β2M$^-$/anti-CD70 CAR$^+$ T cells and the triple knockout TRAC$^-$/β2M$^-$/PD-1$^-$/anti-CD70 CAR$^+$ T cells failed to survive beyond 10 rechallenges. In contrast, the triple knockout TRAC$^-$/β2M$^-$/CD70$^-$/anti-CD70 CAR$^+$ T cells and the quadruple knockout TRAC$^-$/β2M$^-$/PD-1$^-$/CD70$^-$/anti-CD70 CAR$^+$ T cells continued to expand in culture and to kill greater than 30% of ACHN cells at a ratio of 2:1 (T-cell to ACHN) following two rechallenges.

The data demonstrate that the 4×KO, CD70 CAR$^+$ T cells and the 3×KO (CD70), CD70 CAR$^+$ cells are more potent than the 2×KO, CD70 CAR$^+$ T or 3×KO (PD1), CD70 CAR+ T cells. In addition, the 3× (CD70) KO and 4×KO prevents T cell exhaustion.

Figure 23A:
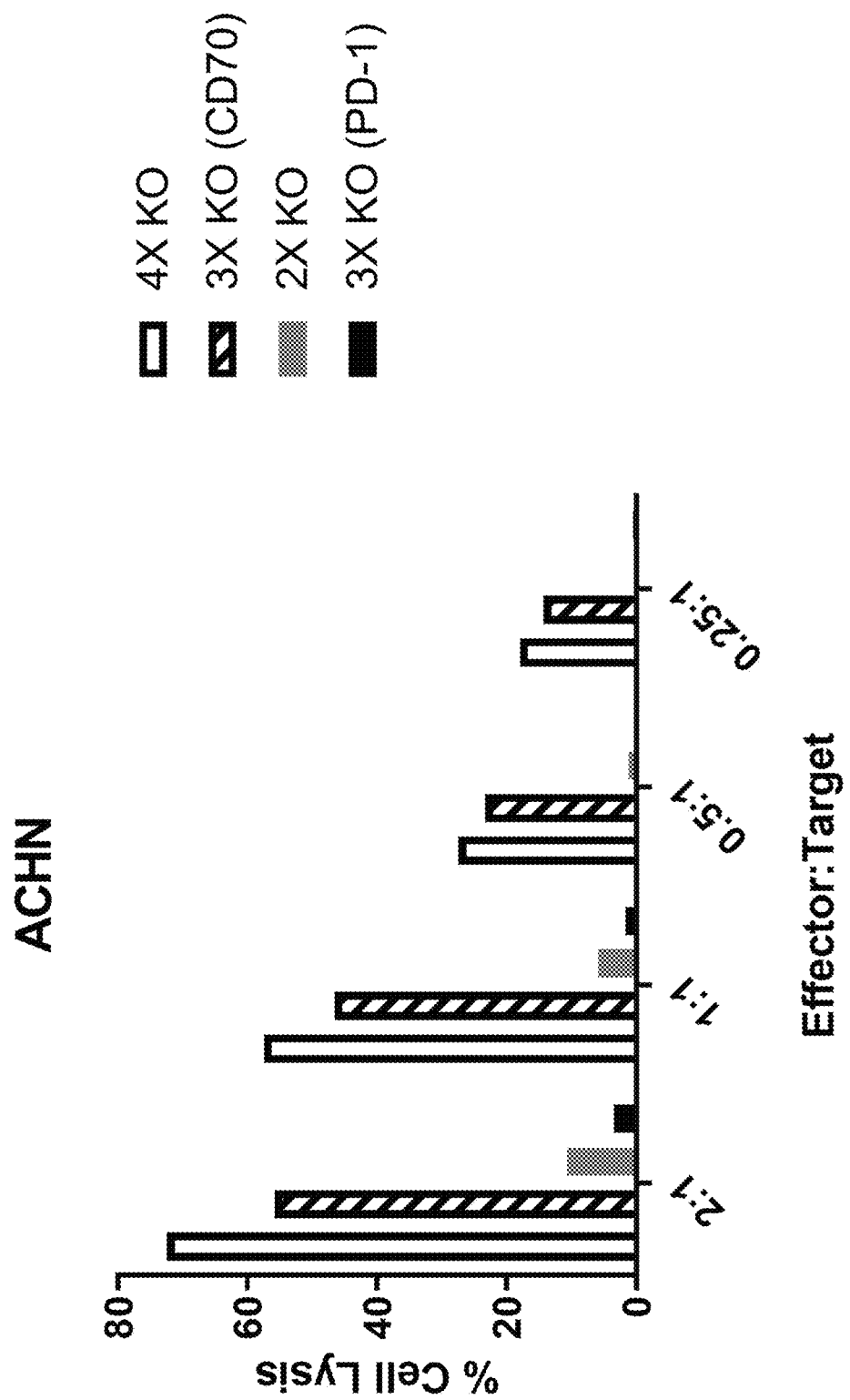
FIG. 23A includes a graph showing ACHN cell killing by anti-CD70 CAR T cells at various effector:target ratios. 4×KO (TRAC$^-$/β2M$^-$/CD70$^-$/PD1$^-$), 3×KO (CD70) (TRAC$^-$/β2M$^-$/CD70$^-$), 3×KO (PD1) (TRAC$^-$/β2M$^-$/PD1$^-$) and 2×KO (TRAC$^-$/β2M$^-$) anti-CD70 CAR+ T cells were utilized. 3×KO (CD70), CD70 CAR+ T cells and 4×KO, CD70 CAR+ T cells were superior killers following multiple serial rechallenges.

After 5 rechallenges the cells were evaluated for their ability to kill cancer cells. Surprisingly, the 3KO and 4KO anti-CD70 CAR+ T cells remained highly effective at killing cancer cells (FIG. 23A) even after multiple cancer cell challenges. The cell killing effect of the anti-CD70 CAR+ T cells on ACHN cells is reproducible at even at reduced effector to target cell ratios of 1:1, 0.5:1, and 0.25:1. (FIG. 23A).

To ensure long-term benefit upon CAR T treatment, CAR T cells should be able to identify and eradicate their target cells over a long period of time, to rule out the possibility of cancer cell escape from CAR-T mediated cell kill. The in vitro re-challenge assay mimics a recurrent encounter of CAR-T cells with target cells over several cycles of CAR-T cell activation. These data demonstrate the superiority of the triple knockout TRAC$^-$/β2M$^-$/CD70$^-$/anti-CD70 CAR$^+$ T cells and of the quadruple knockout TRAC$^-$/β2M$^-$/PD-1$^-$/CD70$^-$/anti-CD70 CAR$^+$ T cells, in sustaining multiple challenges with kidney cancer cells, without showing reduction of their target cell killing ability, as compared to the double knockout TRAC$^-$/β2M$^-$/anti-CD70 CAR$^+$ T cells and the triple knockout TRAC$^-$/β2M$^-$/PD-1$^-$/anti-CD70 CAR$^+$ T cells.

Figure 23B:
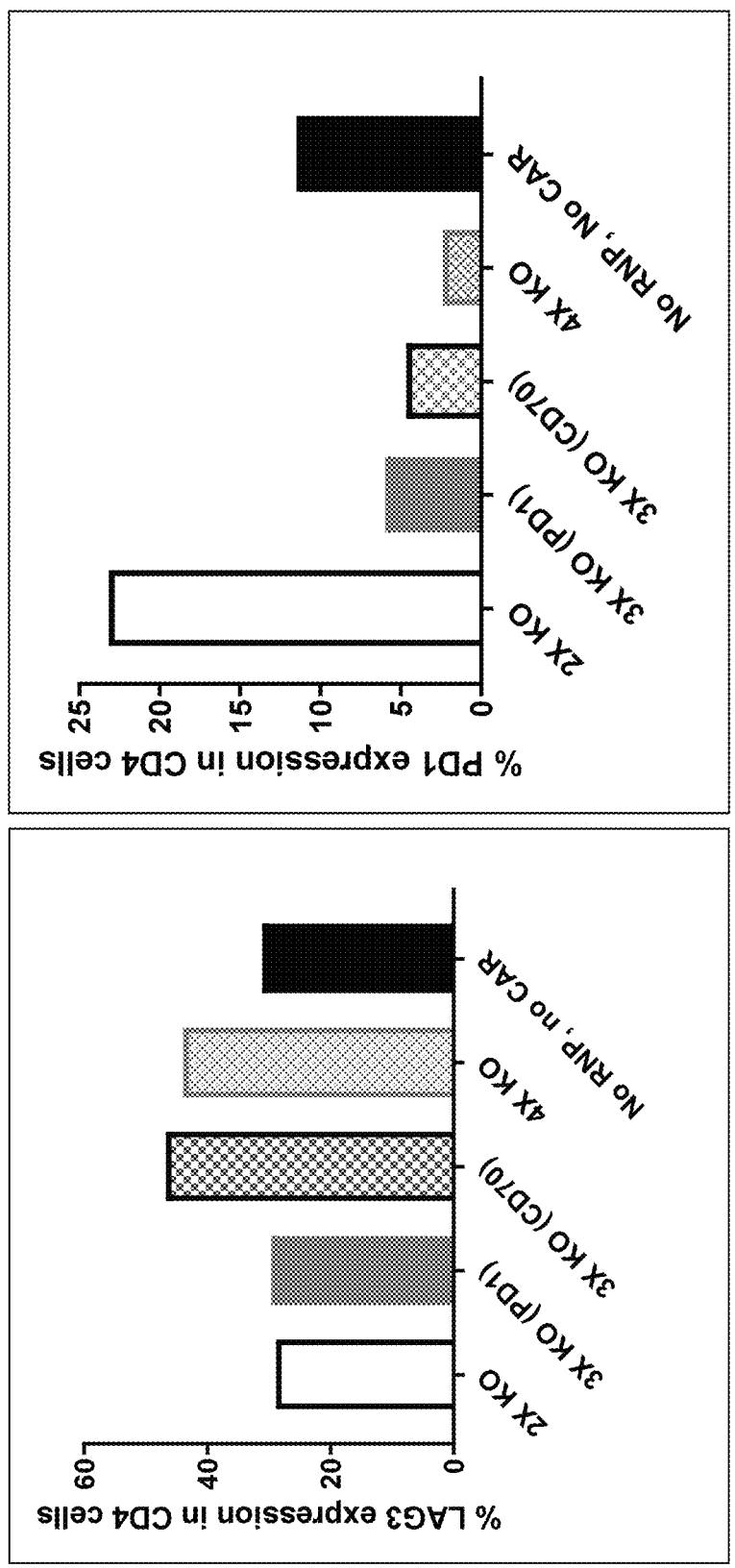
FIG. 23B includes a graph showing LAG5 (left) and PD1 (right) expression in the cells from FIG. 23A following eight rechallenges.

Exhaustion and activation markers were also measured by flow cytometry in the anti-CD70 CAR$^+$ T cells following rechallenge. After 8 challenges, the Triple (TRAC–/β2M–/CD70–) and Quadruple (TRAC–/β2M–/PD1–/CD70–) KO anti-CD70 CAR+ T cells exhibited higher activation marker LAGS expression than the Double (TRAC–/β2M–) and Quadruple (TRAC–/β2M–/PD1–/CD70–) KO anti-CD70 CAR+ T cells, consistent with their level of high cell kill activity. It was observed that PD1 expression was lower in the Triple (TRAC–/β2M–/CD70–) anti-CD70 CAR+T cells (similar to Triple (TRAC–/β2M–/PD1–) and Quadruple (TRAC–/β2M–/PD1–/CD70–) KO anti-CD70 CAR+ T cells) compared to the Double (TRAC–/β2M–) anti-CD70 CAR+ T cells, suggesting that knocking-out CD70 has an effect on the downregulation of the exhaustion marker PD1 expression in the Anti-CD70 CAR+T cells. (FIG. 23B).

Knockout of PD-1 and CD70 Maintains Anti-BCMA CAR+ T Cell Killing Upon Serial Rechallenge The anti-BCMA CAR$^+$ T cells generated as described in Example 3 were serially rechallenged with and evaluated for their ability to kill the BCMA+ multiple myeloma cell line MM.1S (ATCC CRL-2974). The ability to secrete cytokines upon serial T cell activation through CAR engagement was also measured after each rechallenge. MM.1S cells were labeled with 5 μM eFlour670 and mixed at a ratio of 2:1 (MM.1S to T-cell) in a 6 well tissue culture dish with 1×10$^6$ anti-BCMA CAR+ T cells containing either two (TRAC$^-$/β2M$^-$) or four ((TRAC$^-$/β2M$^-$/PD-1$^-$/CD70$^-$) gRNA edits. One day following exposure to MM.1S cells, an aliquot of the culture was taken and analyzed for both target cell kill & IFN-g secretion by CAR-T cells. To measure cytokine release, T cells and target cells were co-incubated for 24 hours at the ratios indicated. Supernatant media was collected for use in IL-2 or IFNγ ELISAs (RD Systems) on a new plate following the manufacturer's instructions (RD Systems). To quantify cell killing, cells were washed, media was replaced with 200 mL of media containing a 1:500 dilution of 5 mg/mL DAPI (Molecular Probes) (to enumerate dead/dying cells). Finally, 25 mL of CountBright beads (Life Technologies) was added to each well. Cells were then processed by flow cytometry.

$$\text{Cells/mL} = ((\text{number of live target cell events})/(\text{number of bead events})) \times ((\text{Assigned bead count of lot(beads}/50 \text{ μL}))/(\text{volume of sample})) \quad 1)$$

Total target cells were calculated by multiplying cells/mL×the total volume of cells.  2)

The percent cell lysis was then calculated with the following equation: % Cell lysis=(1−((Total Number of Target Cells in Test Sample)/(Total Number of Target Cells in Control Sample))× 100     3)

Figure 24B:
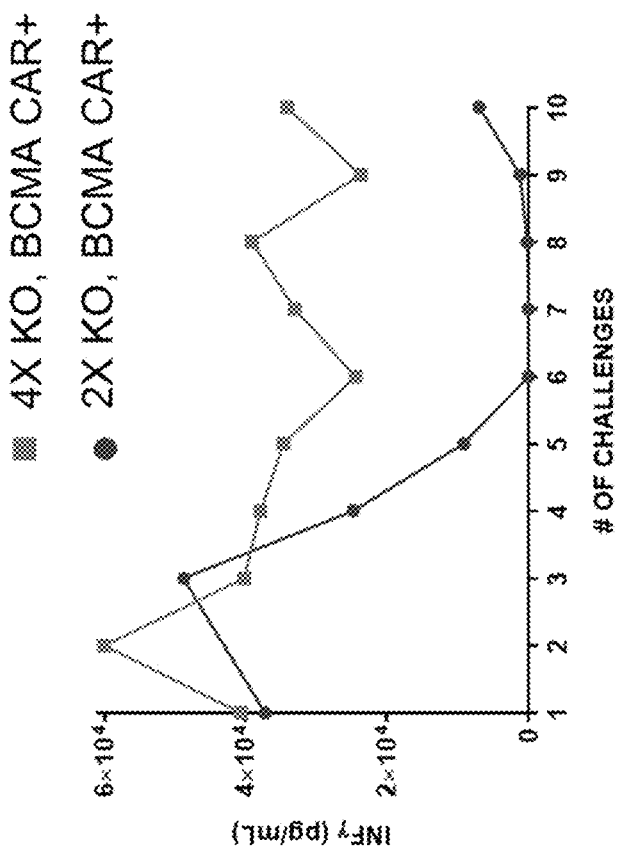
FIGS. 24A-24C include graphs showing that knockout of PD-1 and CD70 enhances cell killing activity of anti-BCMA CAR+ T cells as measured through serial rechallenges with a multiple myeloma cell line (MM.1S). Double knockout (2×KO (TRAC$^-$/β2M$^-$) anti-BCMA CAR+ T cells (circles) began to lose their potency towards MM.1S cells after approximately 4 rechallenges, while quadruple knockout (4×KO (TRAC$^-$/β2M$^-$/CD70$^-$/PD1$^-$) anti-BCMA CAR$^+$ T cells (squares) were capable of killing 100% of the MM.1S cells after 10 rechallenges (FIG. 24A). Consistent with this, the quadruple knockout anti-BCMA CAR$^+$ T cells continued to secrete IFN-g in response to target cells after 10 rechallenges, while the double knockout anti-BCMA CAR$^+$ T cells showed reduced IFN-g secretion after the third rechallenge (FIG. 24B). The quadruple knockout anti-BCMA CAR$^+$ T cells also showed higher proliferation in response to exposure to target cells than the double knockout anti-BCMA CAR$^+$ T cells (FIG. 24C).
Figure 24A:
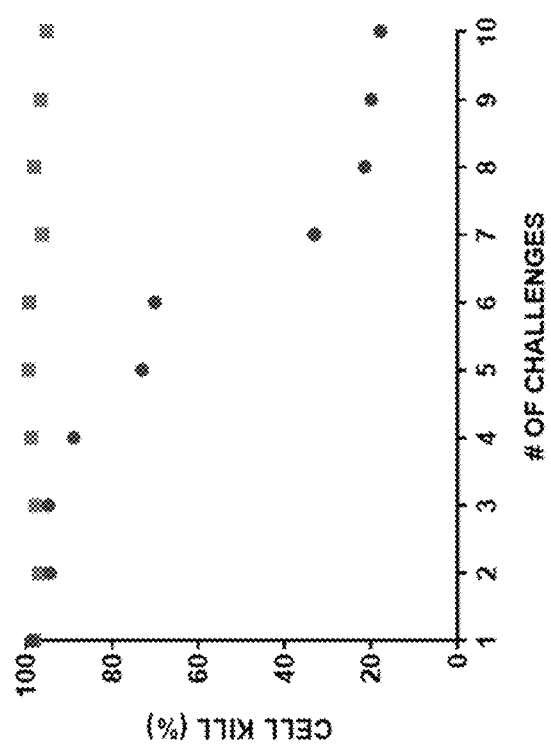
Figure 24C:
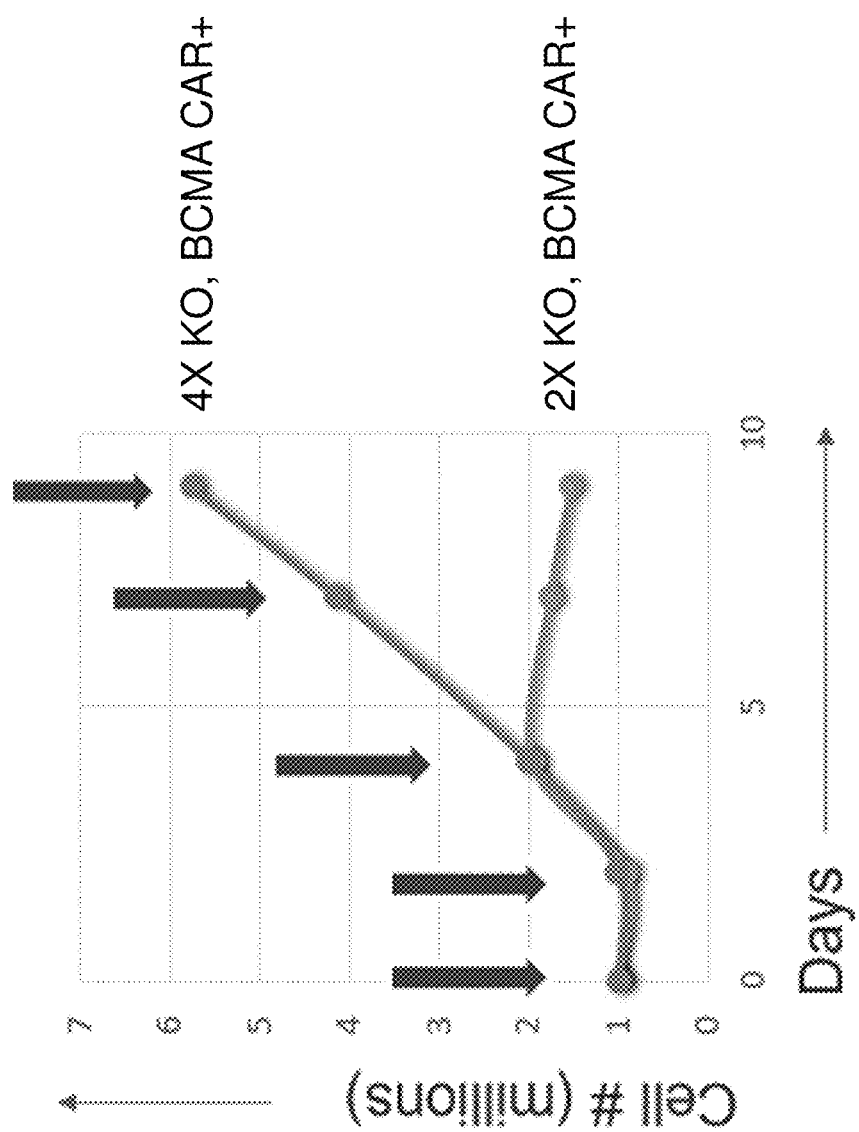

Two or three days after each challenge, cells were counted, washed, resuspended in fresh T cell media, and rechallenged with the same ratio of one anti-BCMA CAR$^+$ T cell per two eFlour670 labeled MM.1S cells. Challenging of anti-BCMA CAR$^+$ T cells with BCMA+ MM.1S cells was repeated 10 sequential times. Prior to any challenge with MM.1S cells, co-incubation of either 2×KO (TRAC−/B2M−) or 4×KO (TRAC−/B2M−/CD70−/PD-1−) anti-BCMA CAR+ T cells with MM.1S cells resulted in complete killing of target cells. Additionally, IFNγ production by both 2×KO and 4×KO anti-BCMA CAR+ T cells was similar. Following a 4th rechallenge with MM.1S cells however, target cell killing and IFNγ production by 2×KO anti-BCMA CAR+ T cells decreased relative to that induced by 4×KO anti-BCMA CAR+ T cells. By the 8th rechallenge, target cell killing was only approximately 20% for 2×KO anti-BCMA CAR+ T cells, while both IFNg and target cell killing by 4×KO anti-BCMA CAR+ T cells remained comparable to that seen prior to any challenge with MM.1S cells (FIGS. 24A-24B). In addition, the quadruple knockout anti-BCMA CAR T cells showed higher proliferation in response to exposure to target cells (FIG. 24C).

To ensure long-term benefit upon CAR T treatment, CAR T cells should be able to identify and eradicate their target cells over long period of time, to rule out the possibility of cancer cell escape from CAR-T mediated cell killing. The in vitro rechallenge assay mimics a recurrent encounter of CAR-T cells with target cells over several cycles of CAR-T cell activation, therefore demonstrating the superiority of the 4× knockout TRAC$^-$/β2M$^-$/PD-1$^-$/CD70$^-$/anti-BCMA CAR$^+$ T cells, in sustaining multiple challenges with target cells, without showing reduction of cell killing ability, as compared to the double knockout TRAC$^-$/β2M$^-$/anti-BCMA CAR$^+$ T cells (FIGS. 24A-24C).

Example 7. CD70 KO Overcomes Challenge of Excess Inhibitory Molecules

Comparison of the Effects of Multi-Knockout Anti-CD70 CAR+ T Cells on A498-PD-L1 Renal Carcinoma Cells Cell Kill Assay. The ability of multi-gene edited anti-CD70 CAR$^+$ cells to kill A498 renal carcinoma cells overexpressing PD-L1 was determined using the cell kill assay described herein. To create cells overexpressing PD-L1 (CD274), A498 cells were infected with lentivirus encoding a PD-L1 cDNA and a puromycin resistance gene (Genecopoeia). After selection with puromycin, cells were stained with an anti-PD-L1 antibody to assess expression of PD-L1. The A498 cells expressing PD-L1 are referred to as A498-PD-L1 and were used in the functional assays described.

Figure 25A:
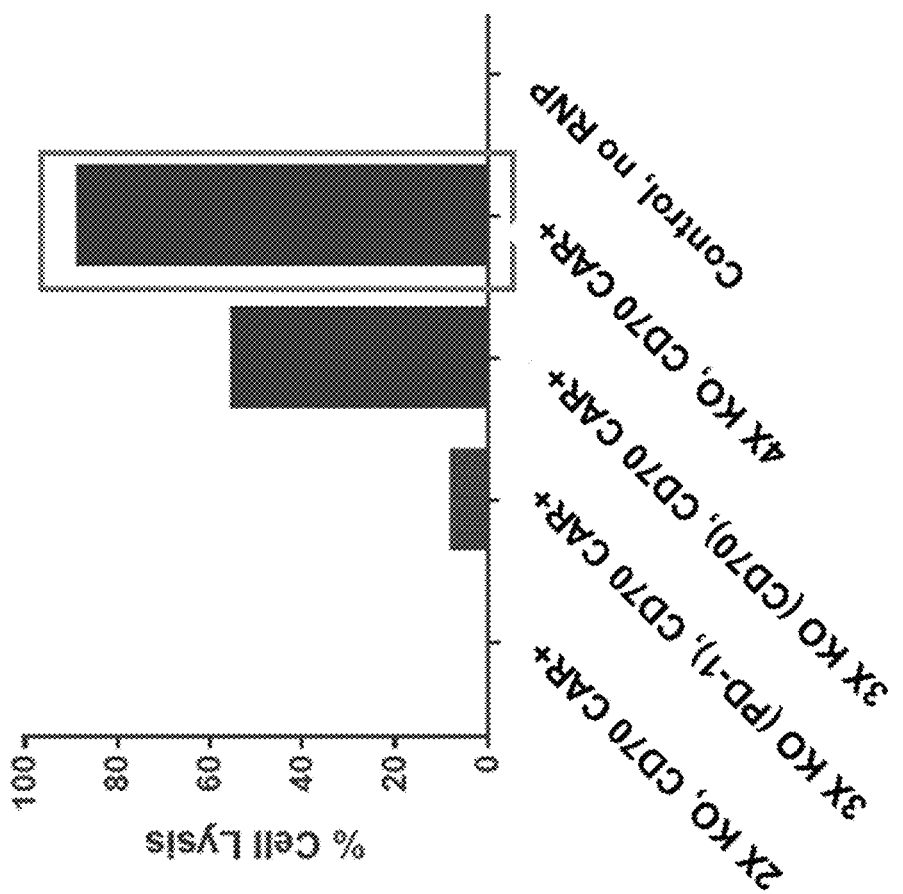
FIGS. 25A-25C include graphs showing highest cell kill activity in A498 PD-L1 kidney cancer cells (which overexpress PD-L1) using quadruple knockout (4×KO) TRAC$^-$/β2M$^-$/PD-1$^-$/CD70$^-$/anti-CD70 CAR$^+$ T cells and triple knockout (3×KO (CD70)) TRAC$^-$/β2M$^-$/CD70$^-$/anti-CD70 CAR$^+$ T cells, relative to double knockout (2×KO) TRAC$^-$/β2M$^-$/anti-CD70 CAR$^+$ T cells and triple knockout (3×KO (PD1) TRAC/β2M$^-$/PD-1$^-$/anti-CD70 CAR$^+$ T cells. A CAR T cell:A498-PD-L1 cell ratio of 2:1 was used in FIG. 25A, a CAR T cell:A498-PD-L1 cell ratio of 1:1 was used in FIG. 25B, and a CART cell:A498-PD-L1 cell ratio of 0.5:1 was used in FIG. 25C.
Figure 25B:
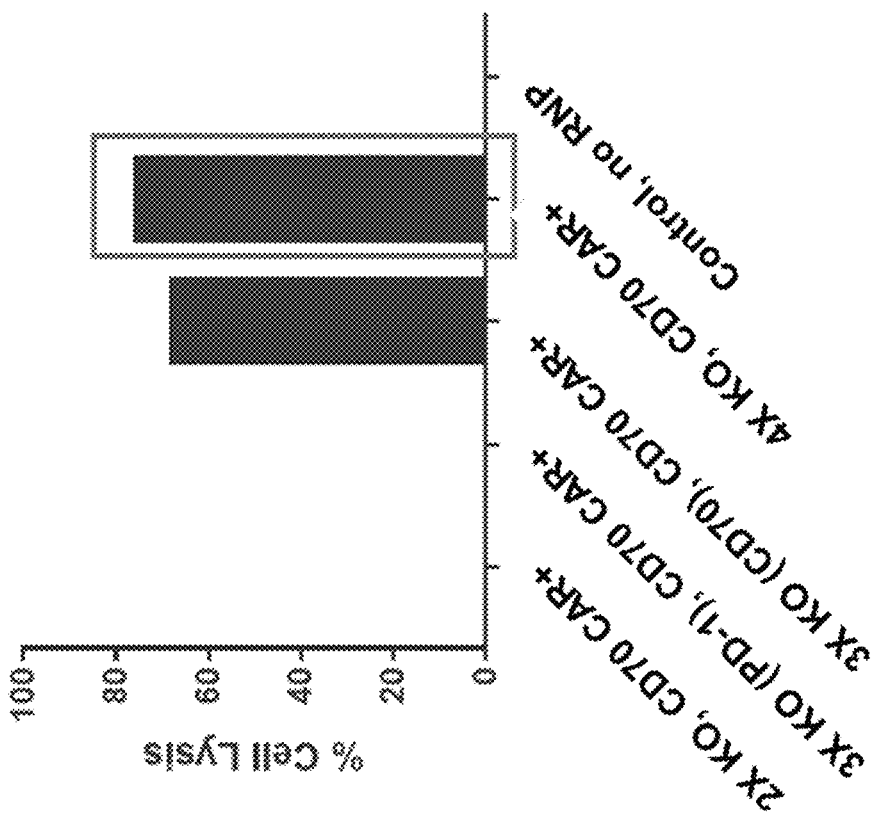
Figure 25C:
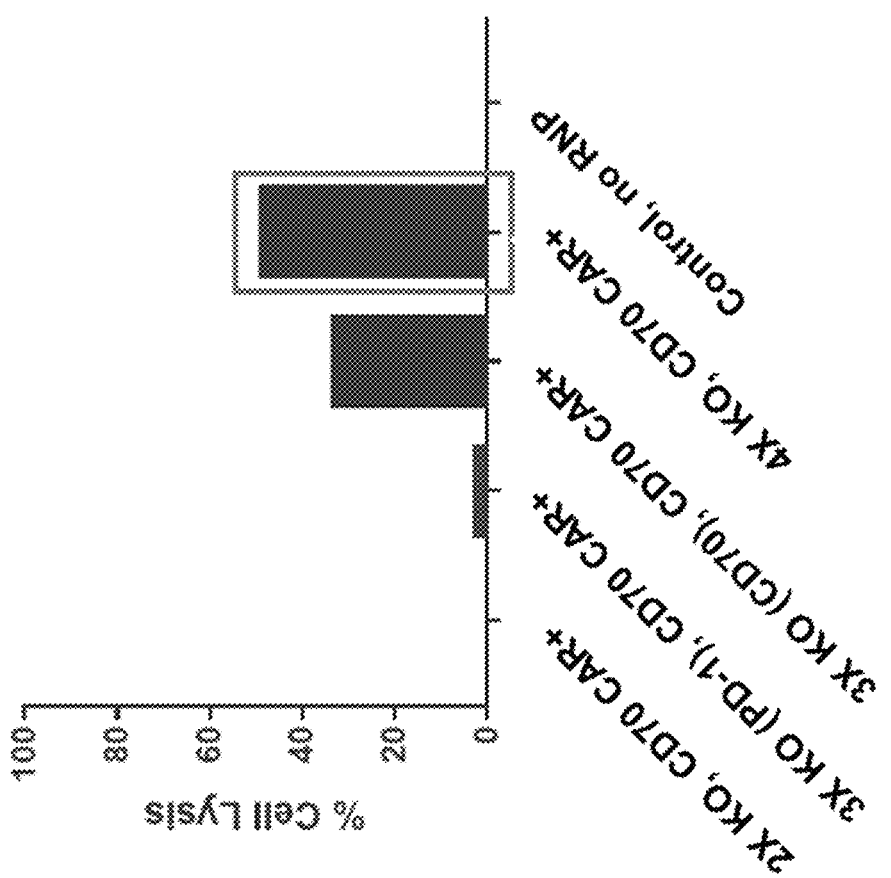

The TRAC$^-$/β2M$^-$/anti-CD70 CAR$^+$ (2×KO, CD70 CAR$^+$), TRAC$^-$/β2M$^-$/PD-1$^-$/anti-CD70 CAR$^+$ (3×KO (PD-1), CD70 CAR$^+$), TRAC$^-$/β2M$^-$/CD70$^-$/anti-CD70 CAR$^+$ (3×KO (CD70), CD70 CAR$^+$) and TRAC$^-$/β2M$^-$/PD-1$^-$/CD70$^-$/anti-CD70 CAR$^+$ (4×KO, CD70 CAR$^+$) T cells were incubated with the A498-PD-L1 cells at a CAR T cell:A498-PD-L1 target cells ratio of 2:1 (FIG. 25A), 1:1 (FIG. 25B), or 0.5:1 (FIG. 25C). The CD70 knockout cells exhibited potent cell killing of RCC-derived cells following 24-hour co-incubation (FIGS. 25A-25C). The cells with PD1 knockout alone did not effectively lyse cells in the presence of PD-L1 overexpression. However, the CD70 knockout was able to rescue the PD1 knockout and enhanced cell lysis was observed in the CART cells with CD70 KO and PD1 KO. These data demonstrate that the loss of CD70 on the surface of these CAR-T cells enhances their function even in the presence of highly immune suppressive molecules expressed by tumor cells such as PD-L1.

Figure 26A:
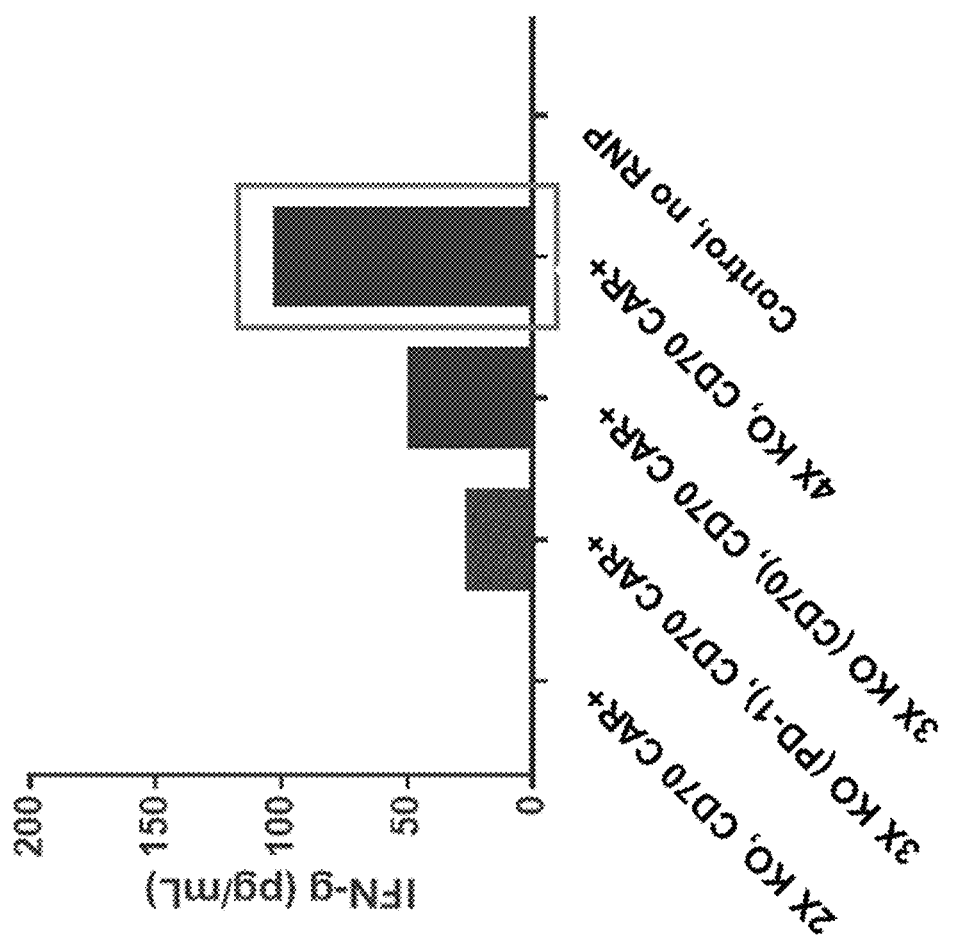
FIG. 26A and FIG. 26B include graphs showing that quadruple knockout (4×KO) TRAC$^-$/β2M$^-$/PD-1$^-$/CD70$^-$/anti-CD70 CAR+ T cells secrete the highest levels of cytokines IFN-gamma (FIG. 26A) and IL-2 (FIG. 26B), relative to triple knockout (3×KO (CD70) TRAC$^-$/β2M$^-$/CD70$^-$/anti-CD70 CAR$^+$ T cells, double knockout (2×KO) TRAC$^-$/β2M$^-$/anti-CD70 CAR$^+$ T cells and triple knockout (3×KO (PD1) TRAC$^-$/β2M$^-$/PD-1$^-$/anti-CD70 CAR$^+$ T cells. A CART cell:A498-PD-L1 cell ratio of 1:1 was used.
Figure 26B:
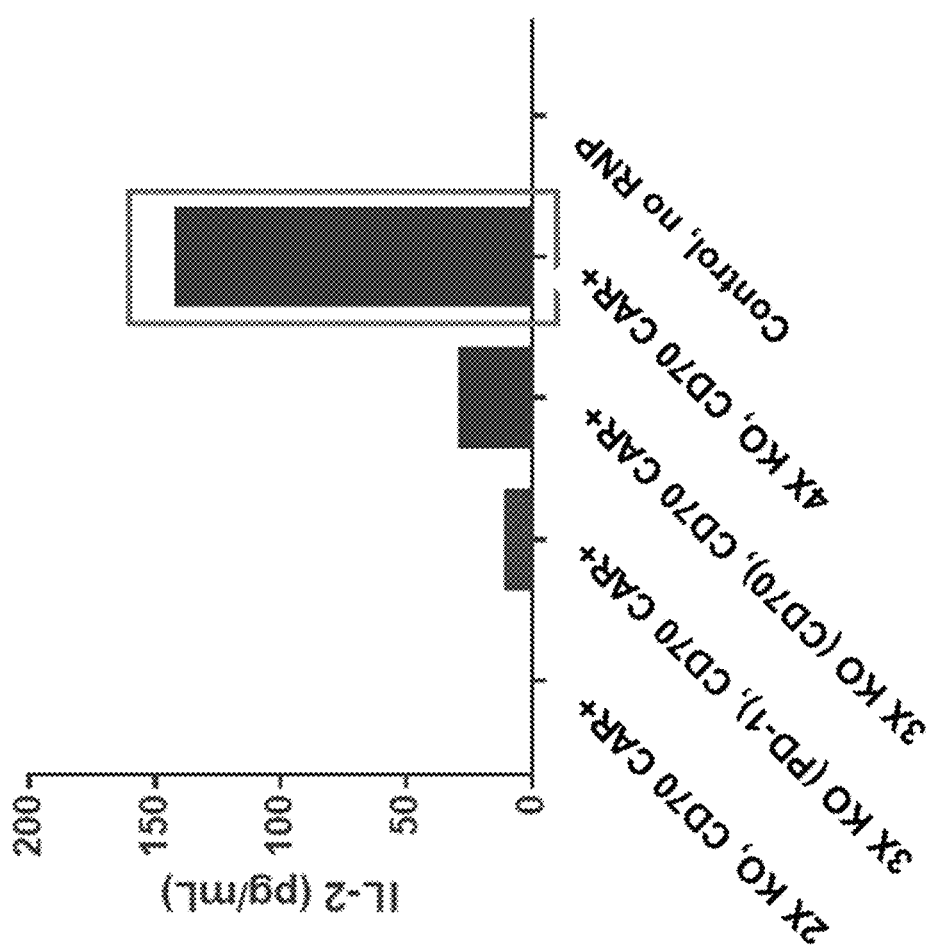

Cytokine Release Assay. A cytokine release assay was performed as described herein. The ability of the double knockout, triple knockout, and quadruple knockout anti-CD70 CAR$^+$ T cells to produce IL-2 and IFN-g when co-cultured in the presence of A948-PD-L1 cells following 24-hour co-incubation at a ratio (CAR T cell:A948-PD-L1 target cell) of 1:1 was assessed using an ELISA assay. IL-2 and IFN-g from supernatants of cell co-cultures were measured. The quadruple knockout TRAC$^-$/β2M$^-$/PD-1$^-$/CD70$^-$/anti-CD70 CAR$^+$ T cells secreted the highest levels of IFN-g (FIG. 26A) and IL-2 (FIG. 26B) when cultured with A948-PD-L1 cells. These data demonstrate the knockout of CD70 enhances CAR-T cells secretion of cytokines even in the presence of highly immune suppressive molecules expressed by tumor cells such as PD-L1. The knockout of CD70 together with a knockout of PD-1 in CAR-T cells further enhances the effect. Without wishing to be bound by theory, it is believed knocking-out CD70 in anti-CD70 CAR+ T cells can rescue the detrimental phenotypes of other cell knockouts (e.g.: PD1). These data demonstrate that knocking-out CD70 in CAR T cells enhances target cell killing and CAR T cell function in a highly immune suppressive context.

Example 8. CD70 Knockout Improves In Vivo Efficacy

Efficacy of CD70 and PD1 Knockout in Anti-CD70 CART Cells: The Subcutaneous Renal Cell Carcinoma Tumor Xenograft Model in NOG Mice Treatment in Small Tumor Model The ability of T cells expressing a CD70 CAR to eliminate kidney carcinoma cells that express high levels of CD70 was evaluated in in vivo using a subcutaneous renal cell carcinoma (A498) tumor xenograft model in mice.

CRISPR/Cas9 and AAV6 were used as above (see for example, Example 3) to create human T cells that lack expression of the TCR, β2M, CD70 and/or PD1 with concomitant expression from the TRAC locus using a CAR construct targeting CD70 (SEQ ID NO: 45; SEQ ID NO: 46). In this example activated T cells were first electroporated with 2, 3 or 4 distinct Cas9:sgRNA RNP complexes containing sgRNAs targeting TRAC (SEQ ID NO: 40), β2M (SEQ ID NO: 41), PD1 (SEQ ID NO: 42), and CD70 (SEQ ID NO: 36 or 37). The DNA double stranded break at the TRAC locus was repaired by homology directed repair with an AAV6-delivered DNA template comprising a donor template (SEQ ID NO: 44; SEQ ID NO: 45) (encoding anti-CD70 CAR comprising the amino acid sequence of SEQ ID NO: 45) containing right and left homology arms to the TRAC locus flanking a chimeric antigen receptor cassette (−/+ regulatory elements for gene expression).

The resulting modified T cells are 2×KO (TRAC−/β2M−), 3×KO (TRAC−/β2M−/PD1− or TRAC−/β2M−/CD70−) and 4×KO (TRAC−/β2M−/PD1−/CD70−) anti-CD70 CAR+(with 41BB costimulatory domain) T cells. The ability of these anti-CD70 CAR+ T cells to ameliorate disease caused by a CD70+ renal carcinoma cell line was evaluated in NOG mice using methods employed by Translational Drug Development, LLC (Scottsdale, Ariz.). In brief, 12, 5-8 week old female, CIEA NOG (NOD.Cg- Prkdc$^{scid}$Il2rg$^{tm1Sug}$/JicTac) mice were individually housed in ventilated microisolator cages, maintained under pathogen-free conditions, 5-7 days prior to the start of the study. Mice received a subcutaneous inoculation of 5×10$^6$ A498 renal carcinoma cells/mouse in the right hind flank. When mean tumor size reached 25-75 mm$^3$ (target of ≈50 mm$^3$), the mice were further divided into 5 treatment groups as shown in Table 15. On Day 1, treatment group 2 to 5 received a single 200 µl intravenous dose of anti-CD70 CAR+ T cells according to Table 15.

TABLE 15

Treatment groups

| Group | CAR-T | A498 cells | T cell treatment (i.v.) | N |
|---|---|---|---|---|
| 1 | None | 5 × 10$^6$ cells/mouse | None | 5 |
| 2 | 2X KO, anti-CD70 CAR+ T cells | 5 × 10$^6$ cells/mouse | 1 × 10$^7$ cells/mouse | 5 |
| 3 | 3X KO (PD1), anti-CD70 CAR+ T cells | 5 × 10$^6$ cells/mouse | 1 × 10$^7$ cells/mouse | 5 |
| 4 | 3X KO (CD70,) anti-CD70 CAR+ T cells | 5 × 10$^6$ cells/mouse | 1 × 10$^7$ cells/mouse | 5 |
| 5 | 4X KO (CD70, PD1), anti-CD70 CAR+ T cells | 5 × 10$^6$ cells/mouse | 1 × 10$^7$ cells/mouse | 5 |

Figure 27A:
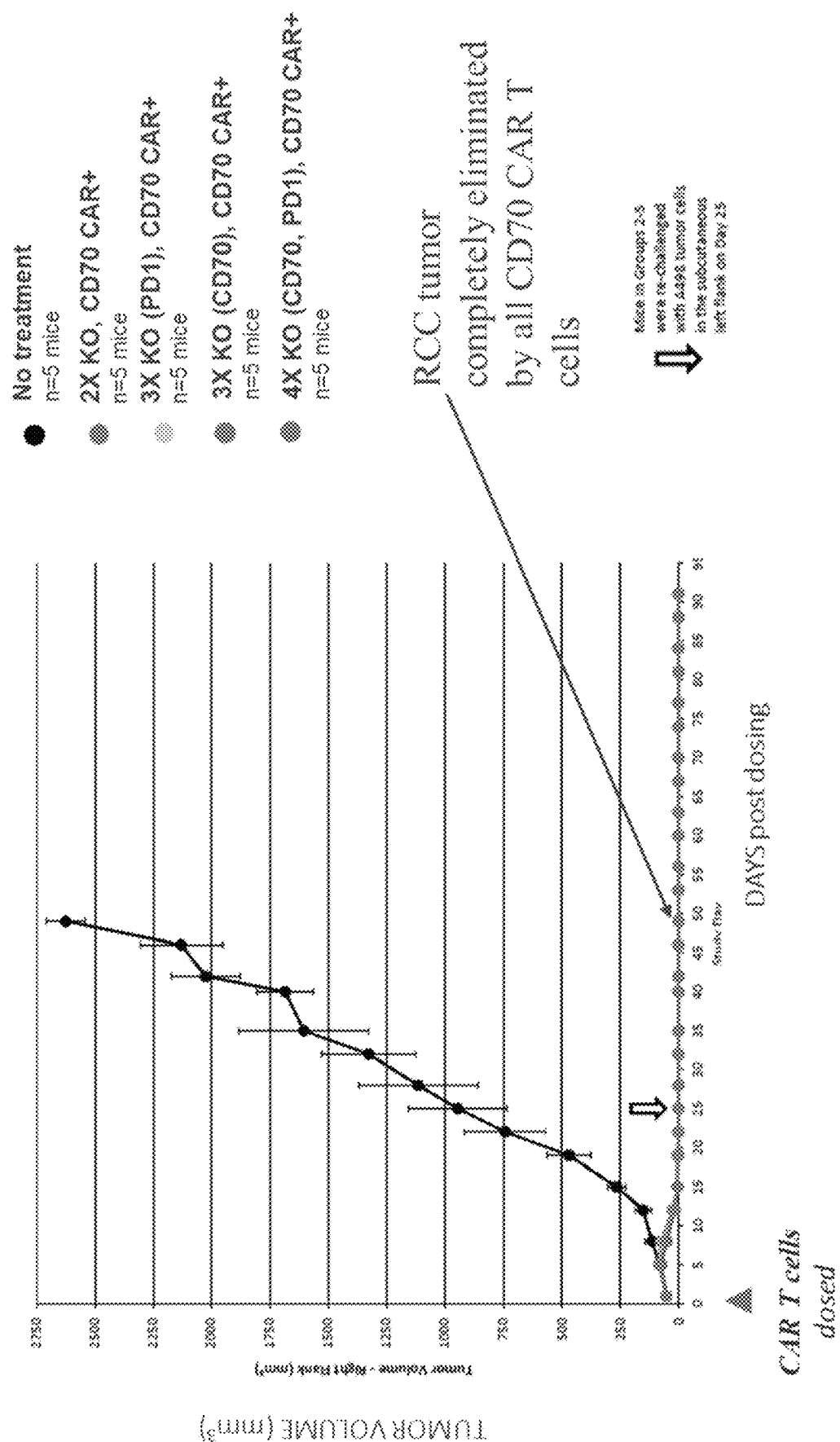
FIG. 27A includes a graph showing results from an experiment designed to assess tumor volume reduction in a subcutaneous A498 renal cell carcinoma model exposed to: 2×KO (TRAC$^-$/β2M), CD70 CAR$^+$ T cells; 3×KO (PD-1) (TRAC$^-$/β2M$^-$/PD1), CD70 CAR$^+$ T cells; 3×KO (CD70) (TRAC$^-$/β2M$^-$/CD70), CD70 CAR$^+$ T cells; or 4×KO (PD-1, CD70) (TRAC$^-$/β2M$^-$/PD1$^-$/CD70$^-$), CD70 CAR+ T cells.

Tumor volume was measured 2 times weekly from day of treatment initiation. By day 5 treatment with all four types of anti-CD70 CAR T cells began to show a decrease in tumor volume and by day 22, all four types of anti-CD70 CAR T cells completely eliminated CD70+ kidney cancer tumors during the duration of the study until day 91 (FIG. 27A). These data demonstrate that all four anti-CD70 CAR T cells can regress CD70+ kidney cancer tumors in vivo.

Figure 27B:
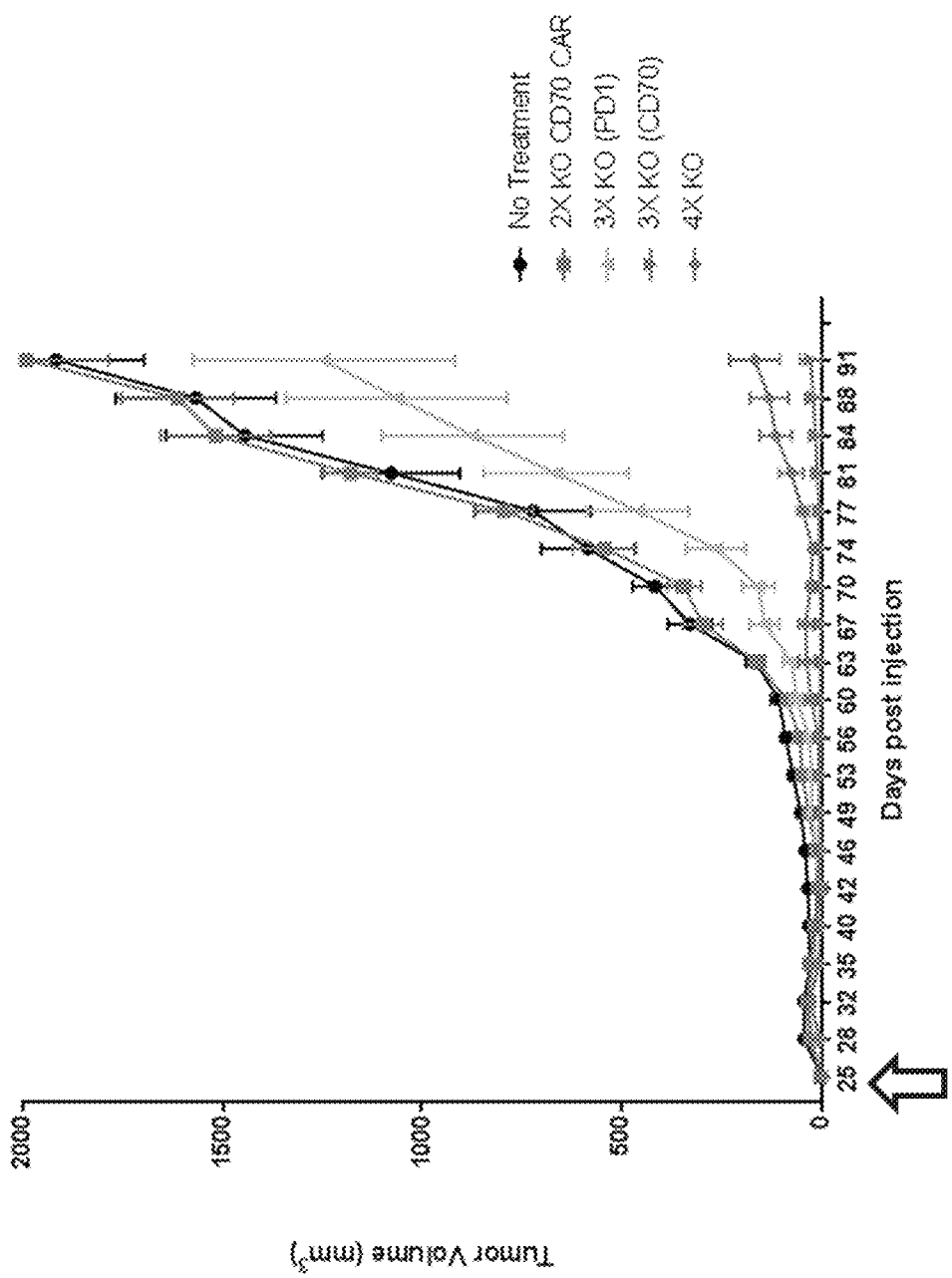
FIG. 27B includes a graph showing results from an experiment designed to assess prevention of tumor growth in a subcutaneous A498 renal cell carcinoma rechallenge model. Mice from FIG. 27A were rechallenged with A498 tumor cells on day 25 and tumor volume was assessed over time.

To test the activity of the anti-CD70 CAR T cells after rechallenge, surviving mice were inoculated in the subcutaneous left hind flank with 5×10$^6$ A498 renal carcinoma cells/mouse on day 25. (Table 16). Sustained efficacy was evaluated from day 46 onward. Results are shown in FIG. 27B. At day 56, 5 out of 5 mice treated with 2×, CD70 CAR+ T cells exhibited tumors regrowth post rechallenge, 4 out of 5 mice treated with 3× (PD1), CD70 CAR+ T cells exhibited tumors regrowth post rechallenge, 2 out of 5 mice treated with 4× (CD70,PD1), CD70 CAR+ T cells exhibited tumors regrowth post rechallenge, while none of the mice treated with 3× (CD70), CD70 CAR+ T cells exhibited tumors regrowth post rechallenge. This trend continued, at day 70, 4 out of 5 mice treated with 3× (PD1), CD70 CAR$^+$ T cells exhibited tumors regrowth post rechallenge, 4 out of 5 mice treated with 4× (CD70, PD1), CD70 CAR$^+$ T cells exhibited tumors regrowth post rechallenge, while only one of the mice treated with 3× (CD70), CD70 CAR$^+$ T cells exhibited a small tumor regrowth that began to appear at 34 days post rechallenge. Even out to day 91, only 1 of 5 mice treated with 3× (CD70), CD70 CAR$^+$ T cells was starting to exhibit tumor regrowth, indicating that TRAC$^-$/β2M$^-$/CD70$^-$/anti-CD70 CAR$^+$ T cells retain a higher in vivo efficacy after re-exposure to tumor cells.

TABLE 16

Size of rechallenge tumors in untreated mice or mice treated with CD70 CAR T cells

| CAR T treatment | Subject | Tumor volume (mm$^3$) at day post CAR T cell dosing | | | | |
|---|---|---|---|---|---|---|
| | | Day 77 | Day 81 | Day 84 | Day 88 | Day 91 |
| 2KO, CD70 CAR T | 1 | 1044 | 1265 | 1853 | 1927 | 2150 |
| | 2 | 653 | 927 | 1040 | 1123 | 1256 |
| | 3 | 899 | 1267 | 1603 | 1678 | 2167 |
| | 4 | 701 | 1287 | 1672 | 1817 | 2490 |
| | 5 | 689 | 1146 | 1423 | 1525 | 1901 |
| 3KO (PD1), CD70 CAR T | 1 | 385 | 692 | 983 | 1172 | 1369 |
| | 2 | 0 | 0 | 0 | 0 | 0 |
| | 3 | 566 | 738 | 1030 | 1537 | 1740 |
| | 4 | 712 | 1111 | 1337 | 1482 | 1832 |
| | 5 | 632 | 778 | 1017 | 1129 | 1289 |
| 3KO (CD70), CD70 CAR T | 1 | 0 | 0 | 0 | 0 | 0 |
| | 2 | 34 | 56 | 75 | 104 | 135 |
| | 3 | 0 | 0 | 0 | 0 | 0 |
| | 4 | 0 | 0 | 0 | 0 | 0 |
| | 5 | 0 | 0 | 0 | 0 | 0 |
| 4KO, CD70 CAR T | 1 | 66 | 91 | 182 | 215 | 304 |
| | 2 | 56 | 85 | 119 | 126 | 155 |
| | 3 | 0 | 0 | 0 | 0 | 0 |
| | 4 | 76 | 175 | 218 | 256 | 316 |
| | 5 | 35 | 30 | 51 | 58 | 63 |
| No treatment | 1 | 567 | 1263 | 1673 | 1751 | 2020 |
| | 2 | 882 | 1214 | 1535 | 1609 | 2047 |
| | 3 | 1158 | 1304 | 1676 | 1924 | 2389 |
| | 4 | 295 | 391 | 667 | 789 | 1078 |
| | 5 | 707 | 1213 | 1676 | 1766 | 2056 |

Treatment in Large Tumor Model

The in vivo efficacy of anti-CD70 CAR T cells against larger renal cell carcinoma tumors was investigated. As above, CRISPR/Cas9 and AAV6 were used to create human T cells that lack expression of the TCR, β2M, CD70 and/or PD1 with concomitant expression from the TRAC locus using a CAR construct targeting CD70 (SEQ ID NO: 45). In this example activated T cells were first electroporated with 2, 3 or 4 distinct Cas9:sgRNA RNP complexes containing sgRNAs targeting TRAC (SEQ ID NO: 40), β2M (SEQ ID NO: 41), PD1 (SEQ ID NO: 42), and CD70 (SEQ ID NO: 36 or 37). The DNA double stranded break at the TRAC locus was repaired by homology directed repair with an AAV6-delivered DNA template (SEQ ID NO: 43) (encoding anti-CD70 CAR comprising the amino acid sequence of SEQ ID NO: 5) containing right and left homology arms to the TRAC locus flanking a chimeric antigen receptor cassette (−/+ regulatory elements for gene expression).

The resulting modified T cells are 2×KO (TRAC−/β2M−), 3×KO (TRAC−/β2M−/PD1− or TRAC−/β2M−/CD70−) and 4×KO (TRAC−/β2M−/PD1−/CD70−) anti-CD70 CAR+ (with 41BB costimulatory domain) T cells. The ability of these anti-CD70 CAR+ T cells to ameliorate disease caused by a CD70+ renal carcinoma cell line was evaluated in NOG mice using methods employed by Translational Drug Development, LLC (Scottsdale, Ariz.). In brief, 12, 5-8 week old female mice, CIEA NOG (NOD.Cg-Prkdc$^{scid}$Il2rg$^{tm1Sug}$/JicTac) were individually housed in ventilated microisolator cages, maintained under pathogen-free conditions, 5-7 days prior to the start of the study. Mice received a subcutaneous inoculation of 5×10$^6$ A498 renal carcinoma cells/mouse. When mean tumor size reached 125-175 mm$^3$ (target of ~150 mm$^3$), the mice were further divided into 5 treatment groups as shown in Table 17. On day 1, treatment group 2 to 5 received a single 200 µl intravenous dose of anti-CD70 CAR+ T cells according to Table 17.

TABLE 17

Treatment groups

| Group | CAR-T | A498 cells | T cell treatment (i.v.) | N |
|---|---|---|---|---|
| 1 | None | 5 × 10⁶ cells/mouse | None | 5 |
| 2 | 2X KO, CD70 CAR+ T cells | 5 × 10⁶ cells/mouse | 1 × 10⁷ cells/mouse | 5 |
| 3 | 3X KO (PD1), CD70 CAR+ T cells | 5 × 10⁶ cells/mouse | 1 × 10⁷ cells/mouse | 4 |
| 4 | 3X KO (CD70,) CD70 CAR+ T cells | 5 × 10⁶ cells/mouse | 1 × 10⁷ cells/mouse | 5 |
| 5 | 4X KO (CD70, PD1), CD70 CAR+ T cells | 5 × 10⁶ cells/mouse | 1 × 10⁷ cells/mouse | 5 |

Figure 27C:
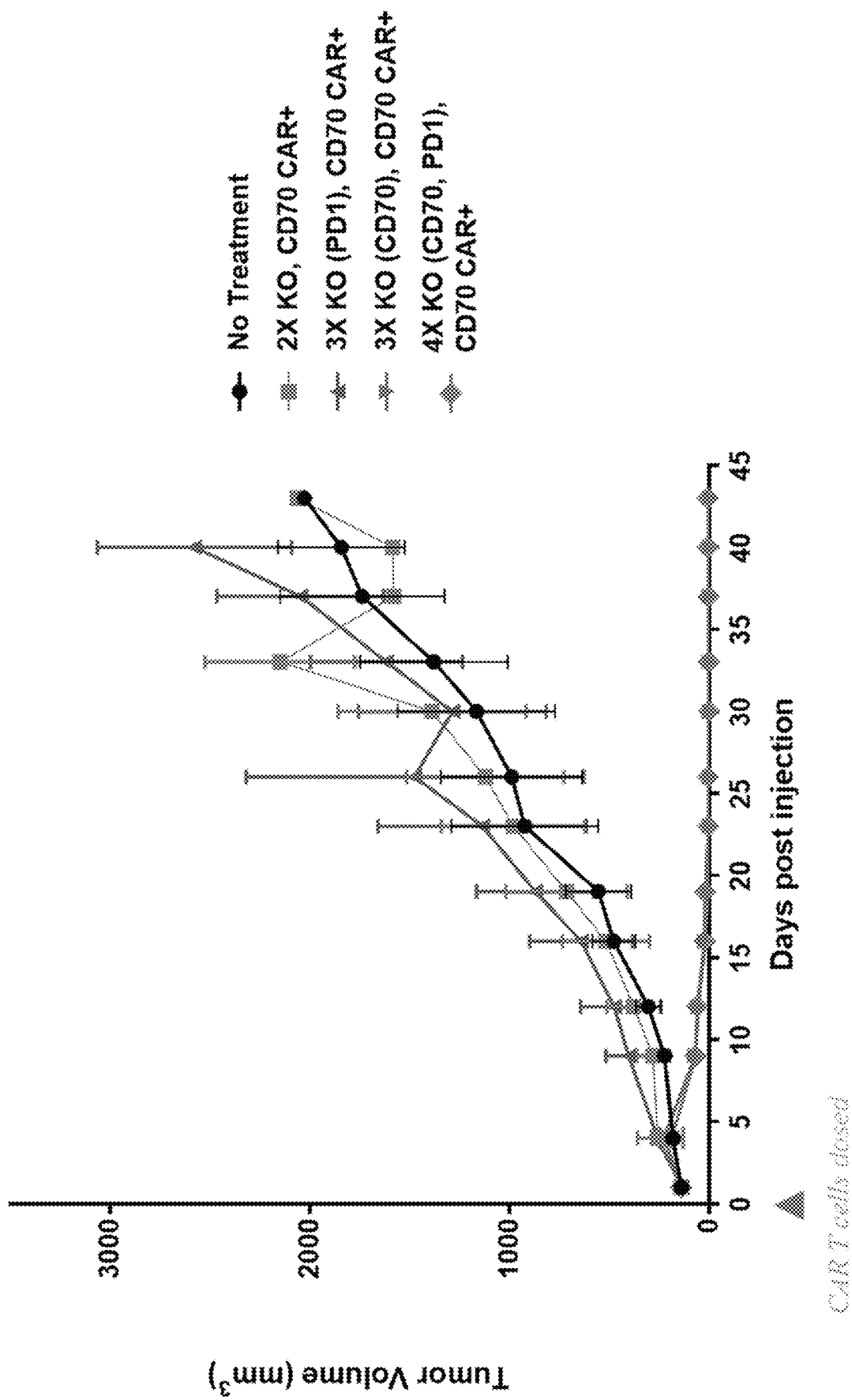
FIG. 27C includes a graph showing results from an experiment designed to assess tumor volume reduction in a subcutaneous A498 renal cell carcinoma model (large tumor of ~150 mm3 at time of CAR-T injection) exposed to: 3×KO (CD70) (TRAC$^-$/β2M$^-$/CD70$^-$), CD70 CAR$^+$ T cells; 4×KO (PD-1, CD70) (TRAC$^-$/β2M$^-$/PD1$^-$/CD70$^-$), CD70 CAR$^+$ T cells; 2×KO (TRAC$^-$/β2M$^-$), CD70 CAR$^+$ T cells; or 3×KO (PD-1) (TRAC$^-$/β2M$^-$/PD1), CD70 CAR$^+$ T cells.

Tumor volume was measured 2 times weekly from day of treatment initiation. By day 4 treatment only the 3×KO (TRAC−/β2M−/CD70−) anti-CD70 CAR+ T cells and 4×KO (TRAC−/β2M−/PD1−/CD70−) anti-CD70 CAR+ T cells began to show a decrease in tumor volume (FIG. 27C). In contrast, the tumor growth for animals treated with 2×KO (TRAC−/β2M−) anti-CD70 CAR+ T cells or 3×KO (TRAC−/β2M−/PD1−) anti-CD70 CAR+ T cells was similar to the no treatment group. By day 23 treatment, the 3×KO (TRAC−/β2M−/CD70−) anti-CD70 CAR+ T cells completely eliminated CD70+ kidney cancer tumors in vivo. By day 23 treatment, elimination of the tumors in response to the 4×KO (TRAC−/β2M−/PD1−/CD70−) anti-CD70 CAR+ T cells was almost complete, with 4 of 5 mice exhibiting no detectable kidney cancer tumors in vivo.

These data show that 3×KO (TRAC−/β2M−/CD70−) anti-CD70 CAR+ T cells and 4×KO (TRAC−/β2M−/PD1−/CD70−) anti-CD70 CAR+ T cells can significantly regress large CD70+ kidney cancer tumors in vivo.

In Vivo Tumor Model for Anti-BCMA CAR in Context of PD1, CD70, and PD1 with CD70 Knock Outs.

The efficacy of TRAC−/β2M−/anti-BCMA (4-1BB co-stim) CAR+ T cells, TRAC−/β2M−/PD-1−/anti-BCMA (4-1BB co-stim), TRAC−/β2M−/CD70−/anti-BCMA (4-1BB co-stim), and TRAC−/β2M−/PD-1−/CD70−/anti-BCMA (4-1BB co-stim) CAR+ T cells against the subcutaneous MM.1S tumor xenograft model in NOG mice was evaluated. In brief, 25, 5-8 week old female, CIEA NOG (NOD.Cg-Prkdc$^{scid}$I12rg$^{tm1Sug}$/JicTac) mice were individually housed in ventilated microisolator cages, maintained under pathogen-free conditions, 5-7 days prior to the start of the study. On day 1, 25 mice received a subcutaneous inoculation in the right flank of 5×10⁶ MM.1S cells in 50% Matrigel/mouse. When the mean tumor volume reached between 75 and 125 mm³, the mice were divided into 5 treatment groups (N=5) and dosed with T cell populations comprising ~50% anti-BCMA CAR+ T cells, as indicated in Table 18.

TABLE 18

Dosing

| Group | CAR T Cell | # of T Cells injected | Anti-BCMA CAR+ T cells | N |
|---|---|---|---|---|
| 1 | N/A | N/A | N/A | 5 |
| 2 | TRAC−/β2M−/anti-BCMA | 1 × 10⁷ cells/mouse | 5 × 10⁶ (5 million) | 5 |
| 3 | TRAC−/β2M−/PD-1−/anti-BCMA | 1 × 10⁷ cells/mouse | 5 × 10⁶ (5 million) | 5 |
| 4 | TRAC−/β2M−/CD70−/anti-BCMA | 1 × 10⁷ cells/mouse | 5 × 10⁶ (5 million) | 5 |
| 5 | TRAC−/β2M−/PD-1−/CD70−/anti-BCMA | 1 × 10⁷ cells/mouse | 5 × 10⁶ (5 million) | 5 |

Tumor volume and body weights were measured twice weekly and individual mice were euthanized when their tumor volume reached ≥2000 mm³.

Figure 28A:
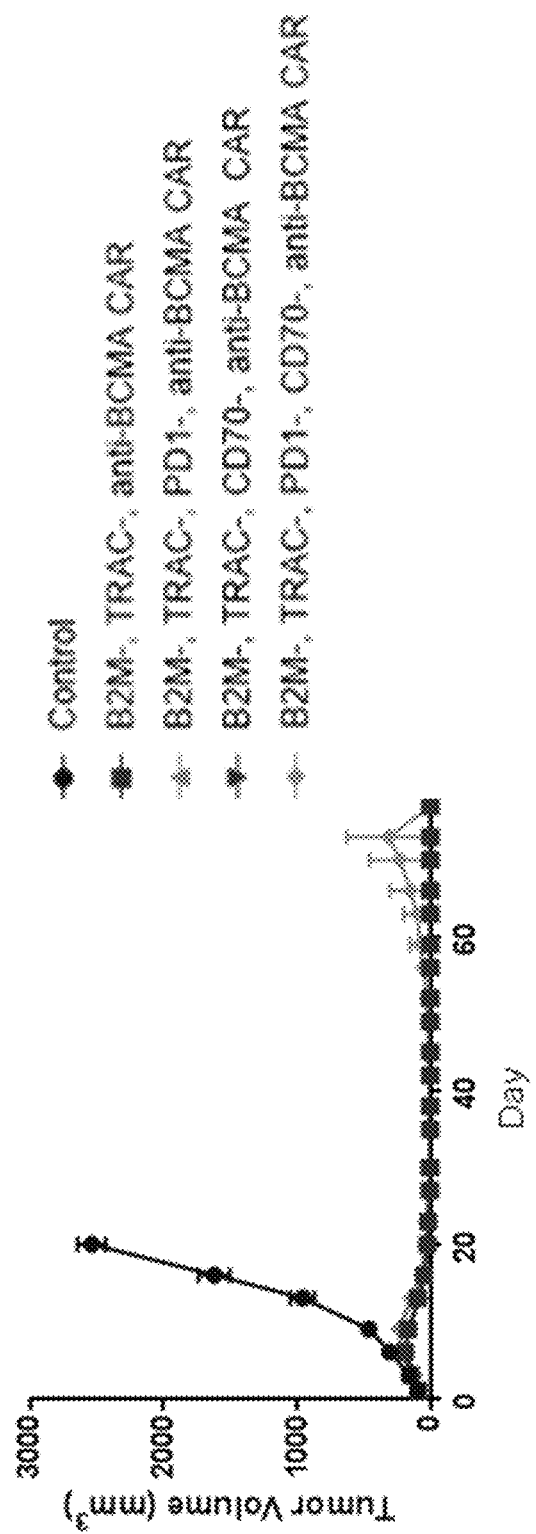
FIG. 28A includes a graph showing tumor volume reduction in a subcutaneous MM.18 model exposed to: 2×KO (TRAC$^-$/β2M), BCMA CAR$^+$ T cells; 3×KO (PD-1) (TRAC$^-$/β2M$^-$/PD1$^-$), BCMA CAR$^+$ T cells; 3×KO (CD70) (TRAC$^-$/β2M$^-$/CD70$^-$), BCMA CAR$^+$ T cells; or 4×KO (PD-1, CD70) (TRAC$^-$/β2M$^-$/PD1$^-$/CD70$^-$), BCMA CAR+ T cells.

By day 16, all treatment groups showed tumor regression from the starting volumes while animals in the control group had tumors averaging greater than 1500 mm³. By day 27, all animals in the control group had reached the tumor volume endpoint of ≥2000 mm³ while all treatment groups had an average tumor volume less than 20 mm³ (FIG. 28A). On day 45, all mice from each treatment group (Groups 2-5) were further subjected to a secondary tumor challenge (re-challenge). The mice received a second subcutaneous inoculation in the left flank of 5×10⁶ MM.1S cells in 50% Matrigel/mouse. A new group of control mice were entered (N=5) and also received an inoculation of 5×10⁶ MM.1S cells in 50% Matrigel/mouse in the left flank.

All mice were monitored for tumor growth in both the initial right flank tumor and the rechallenge tumor in the left flank. All treatment groups successfully inhibited tumor growth in the initial right flank tumor in most subjects (FIG. 28A; Table 19). Tumor growth was inhibited by all treatments both before and after tumor re-challenge for the duration of the experiment to day 77. Only one subject treated with TRAC−/β2M−/CD70−/PD1−/anti-BCMA CAR⁺ T cells exhibited tumor growth from the initial cancer cell challenge (Table 19).

Figure 28B:
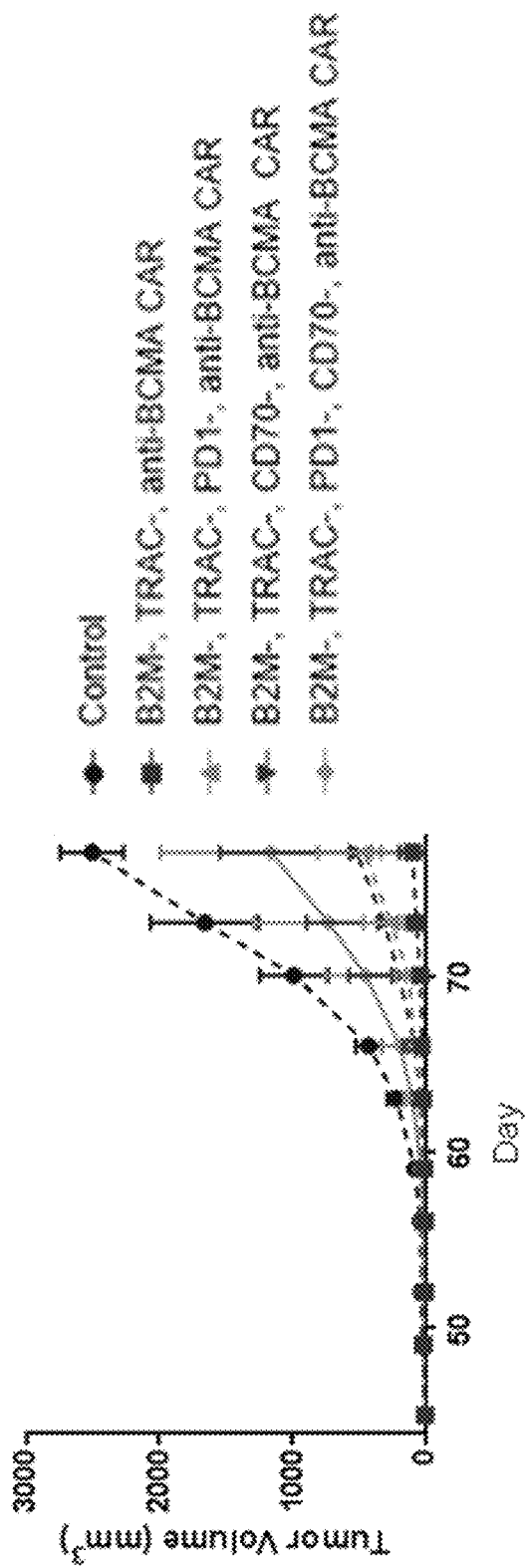
FIG. 28B includes a graph showing tumor volume reduction in a subcutaneous MM.18 model following a tumor cell re-challenge. Mice from FIG. 28A were re-challenged with a second inoculation of MM.18 cells on day 45 and tumor volume was assessed over time.

Surprisingly, tumor growth after re-challenge in the left flank was also significantly inhibited by all treatment groups from the date of re-challenge (day 45) to day 77 (FIG. 28B; Table 19). These data demonstrate that the CAR+ T cells persist in vivo to inhibit initial tumor growth, as well as inhibiting growth of new tumors following a re-challenge with additional cancer cells even though no further CAR-T cells were delivered to these mice. For example, three of the four mice initially treated with populations of TRAC−/β2M−/anti-BCMA CAR⁺ T cells, three of the five mice initially treated with TRAC−/β2M−/CD70−/anti-BCMA CAR⁺ T cells, and three of the five mice initially treated with TRAC−/β2M−/PD1−/anti-BCMA CAR⁺ T cells, exhibited no new tumor growth despite a second challenge (re-challenge) to new cancer cells. These data demonstrate that, unexpectedly, anti-BCMA CAR⁺ T cells are capable of persisting for long periods of time in vivo, e.g., up to at least 77 days following injection, and retain their ability to inhibit tumor cell growth and reduce tumor volumes for long periods in vivo. These surprising results indicate that use of such TRAC−/β2M−/anti-BCMA CAR⁺ T cells would achieve superior long-term anti-cancer effect in vivo.

Figure 29:
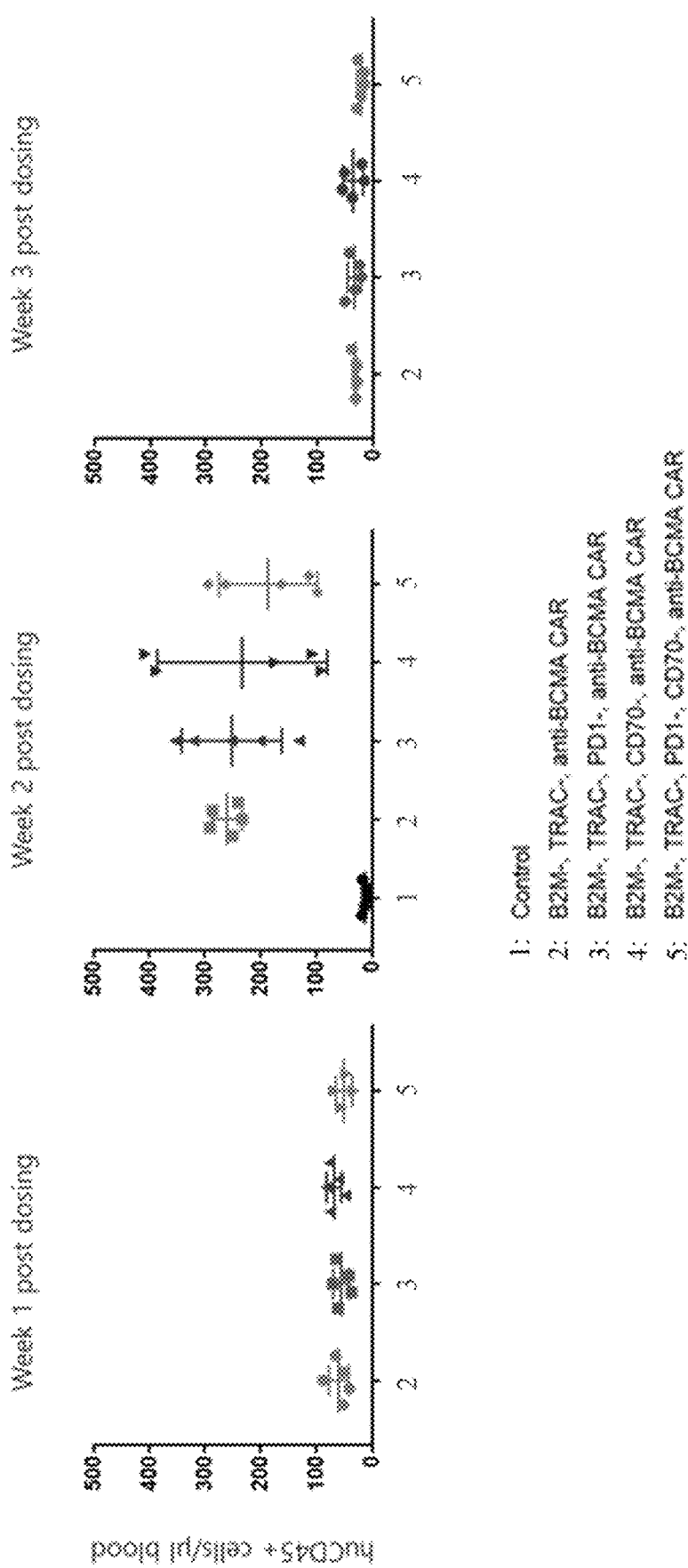
FIG. 29 includes graphs showing the number of human CD45+ 2×KO (TRAC$^-$/β2M$^-$), BCMA CAR+ T cells; human CD45$^+$ 3×KO (PD-1) (TRAC$^-$/β2M$^-$/PD1$^-$), BCMA CAR$^+$ T cells; human CD45$^+$ 3×KO (CD70) (TRAC$^-$/β2M$^-$/CD70$^-$), BCMA CAR$^+$ T cells; and human CD45$^+$ 4×KO (PD-1, CD70) (TRAC$^-$/β2M$^-$/PD1$^-$/CD70$^-$), BCMA CAR$^+$ T cells 1 week (right graph), 2 weeks (middle graph), and 3 weeks (left graph) post dosing.

Human CD45+ cells were quantified from mouse blood using BD Trucount tubes following the manufacturers protocol and detected using Brilliant Violet 786 conjugated anti-human CD45 (Biolegend Cat #368528). All groups showed values of less than 100 huCD45+ cells/μl at 1 week. Two weeks post dosing, the number of circulating CD45+ in all groups peaked before falling to pre-week 1 values by week 3 (FIG. 29). Upon re-challenge at Day 45, the anti-BCMA CAR+ T cell treated subjects were able to eliminate or inhibit tumor growth without subsequent expansion of circulating CAR T cells following cancer rechallenge. These data further demonstrate that, unexpectedly, anti-BCMA CAR+ T cells are capable of persisting for long periods of time in vivo, e.g., up to at least 77 days following injection, and retain their ability to inhibit tumor cell growth and reduce tumor volumes for long periods in vivo. These surprising results indicate that use of TRAC−/β2M−/anti-BCMA CAR+ T cells, TRAC−/β2M−/CD70−/anti-BCMA CAR+ T cells and TRAC−/β2M−/PD1−/anti-BCMA CAR+ T cells would achieve superior long-term anti-cancer effect in vivo.

TABLE 19

Size of tumors in untreated mice or mice treated with anti-BCMA CAR T cells

| Treatment | Mouse | Tumor volume at Day 45 (mm³) Right Flank | Tumor volume at Day 77 (mm³) | |
|---|---|---|---|---|
| | | | Right Flank | Left Flank |
| No Treatment | 1 | TS | TS | TS |
| | 2 | TS | TS | TS |
| | 3 | TS | TS | TS |
| | 4 | TS | TS | TS |
| | 5 | TS | TS | TS |
| TRAC−/β2M−/anti-BCMA | 1 | 0 | 0 (MS at Day 59) | 0 (MS at Day 59:) |
| | 2 | 0 | 0 | 0 |
| | 3 | 0 | 0 | 0 |
| | 4 | 0 | 0 | 297 |
| | 5 | FD-T at day 16 | FD-T at day 16 | 14D-T at day 16 |
| TRAC−/β2M−/PD1−/anti-BCMA | 1 | 0 | 0 | 1820 |
| | 2 | 0 | 0 | 0 |
| | 3 | 0 | 0 | 487 |
| | 4 | 0 | 0 | 0 |
| | 5 | 0 | 0 | 0 |
| TRAC−/β2M−/CD70−/anti-BCMA | 1 | 10 | 0 | 0 |
| | 2 | 0 | 0 | 0 |
| | 3 | 0 | 0 | 2349 (TS at day 77) (TS at day 77) |
| | 4 | 0 | 0 | 0 |
| | 5 | 0 | 0 | 258 |
| TRAC−/β2M−/PD1−/CD70−/anti-BCMA | 1 | 0 | 0 | 1157 |
| | 2 | 0 | 0 | 1842 |
| | 3 | 0 | 0 | 1664 |
| | 4 | 0 | 0 | 0 |
| | 5 | 89 | 1583 (TS at day 73) | 1560 (TS at day 73) |

TS = sacrificed because of tumor volume;
MS = Moribund sacrifice;
FD-T = animal found dead.

In Vivo Tumor Model for Anti-BCMA CAR in Context of CD70 Knockout: Effect of CD70 KO on Moderate CAR T Dosing The efficacy of several anti-BCMA CAR⁺ T cell genotypes, both with and without CD70 knockouts, was evaluated against the subcutaneous RPMI-8226 tumor xenograft model in NOG mice. In brief, eighty five (85), 5-8 week old female, CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. On day 1 mice received a subcutaneous inoculation of $10 \times 10^6$ RPMI-8226 cells/mouse. Ten (10) days post inoculation with RPMI-8226 cells, the mice were divided into 17 treatment groups (N=5) and dosed with T cell populations comprising ~80% anti-BCMA CAR⁺ T cells, as indicated in Table 20.

TABLE 20

| Group | Anti-BCMA CAR T Cell | # of T Cells injected | Anti-BCMA CAR+ T cells | N |
|---|---|---|---|---|
| 1 | N/A | N/A | N/A | 5 |
| 2 | TRAC−/β2M−/anti-BCMA | $3 \times 10^6$ cells/mouse | $2.4 \times 10^6$ (2.4 million) | 5 |
| 3 | TRAC−/β2M−/anti-BCMA | $1 \times 10^6$ cells/mouse | $8 \times 10^5$ (0.8 million) | 5 |
| 4 | TRAC−/β2M−/anti-BCMA | $3 \times 10^5$ cells/mouse | $2.4 \times 10^5$ (0.24 million) | 5 |
| 5 | TRAC−/β2M−/anti-BCMA | $1 \times 10^5$ cells/mouse | $8 \times 10^4$ (0.08 million) | 5 |
| 6 | TRAC−/β2M−/PD1−/anti-BCMA | $3 \times 10^6$ cells/mouse | $2.4 \times 10^6$ (2.4 million) | 5 |
| 7 | TRAC−/β2M−/PD1−/anti-BCMA | $1 \times 10^6$ cells/mouse | $8 \times 10^5$ (0.8 million) | 5 |
| 8 | TRAC−/β2M−/PD1−/anti-BCMA | $3 \times 10^5$ cells/mouse | $2.4 \times 10^5$ (0.24 million) | 5 |
| 9 | TRAC−/β2M−/PD1−/anti-BCMA | $1 \times 10^5$ cells/mouse | $8 \times 10^4$ (0.08 million) | 5 |
| 10 | TRAC−/β2M−/CD70−/anti-BCMA | $3 \times 10^6$ cells/mouse | $2.4 \times 10^6$ (2.4 million) | 5 |
| 11 | TRAC−/β2M−/CD70−/anti-BCMA | $1 \times 10^6$ cells/mouse | $8 \times 10^5$ (0.8 million) | 5 |
| 12 | TRAC−/β2M−/CD70−/anti-BCMA | $3 \times 10^5$ cells/mouse | $2.4 \times 10^5$ (0.24 million) | 5 |
| 13 | TRAC−/β2M−/CD70−/anti-BCMA | $1 \times 10^5$ cells/mouse | $8 \times 10^4$ (0.08 million) | 5 |
| 14 | TRAC−/β2M−/PD1−/CD70−/anti-BCMA | $3 \times 10^6$ cells/mouse | $2.4 \times 10^6$ (2.4 million) | 5 |
| 15 | TRAC−/β2M−/PD1−/CD70−/anti-BCMA | $1 \times 10^6$ cells/mouse | $8 \times 10^5$ (0.8 million) | 5 |
| 16 | TRAC−/β2M−/PD1−/CD70−/anti-BCMA | $3 \times 10^5$ cells/mouse | $2.4 \times 10^5$ (0.24 million) | 5 |
| 17 | TRAC−/β2M−/PD1−/CD70−/anti-BCMA | $1 \times 10^5$ cells/mouse | $8 \times 10^4$ (0.08 million) | 5 |

Tumor volume and body weight was measured twice weekly, and individual mice were euthanized when tumor volume was ≥2000 mm³. By day 22, the data show a statistically significant decrease in the tumor volume in response to higher doses of anti-BCMA CAR T cells ($1 \times 10^5$-$3 \times 10^6$ cell doses) compared to any anti-BCMA CAR T cell genotype dosed at 100,000 cells (groups 5, 9, 13 and 17) (FIG. 30; Table 21).

Figure 30:
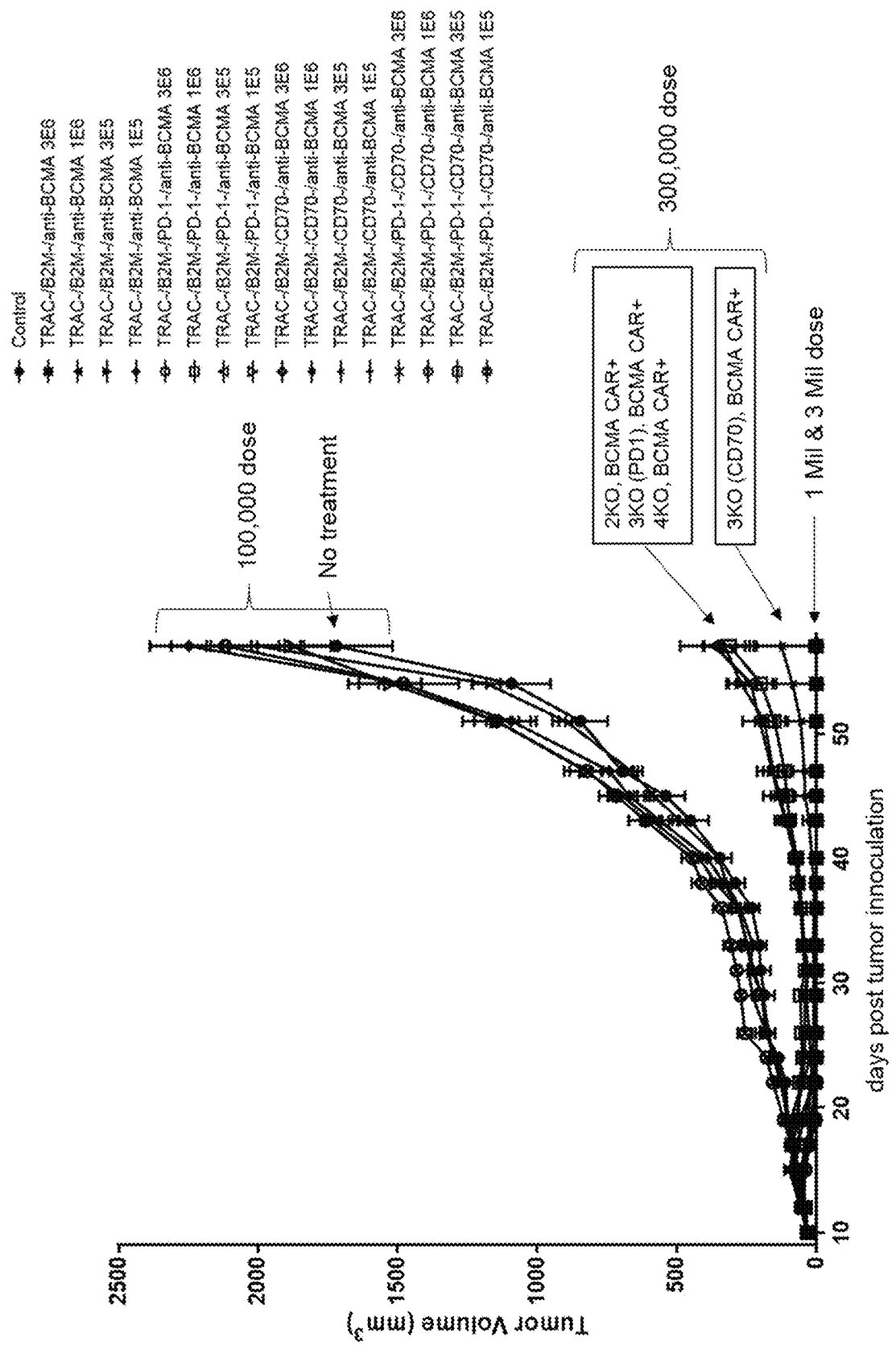
FIG. 30 includes graphs showing the results from an experiment designed to assess tumor volume reduction in a subcutaneous RPMI-8226 tumor xenograft model exposed to: TRAC$^-$/β2M/-anti-BCMA CAR$^+$ T cells (2×KO, BCMA CAR$^+$ T cells); TRAC$^-$/β2M$^-$/PD1$^-$/anti-BCMA CAR$^+$ T cells (3×KO (PD-1), BCMA CAR$^+$ T cells); TRAC$^-$/β2M$^-$/CD70$^-$/anti-BCMA CAR$^+$ T cells (3×KO (CD70), BCMA CAR$^+$ T cells); or TRAC$^-$/β2M$^-$/PD1$^-$/CD70$^-$/anti-BCMA CAR$^+$ T cells (4×KO (PD-1, CD70), BCMA CAR$^+$ T cells), at doses of 1×10$^5$, 3×10$^5$, 1×10$^6$, or 3×10$^6$ cells/mouse.

At day 36, the TRAC−/β2M−/CD70−/anti-BCMA CAR+ T cells dosed at a moderate dose of $3 \times 10^5$ cells exhibited a greater effect on decreasing tumor volume than the anti-BCMA CAR+ T cells without a CD70 KO (e.g., TRAC−/β2M−/anti-BCMA CAR+ T cells, TRAC−/β2M−/PD1−/anti-BCMA CAR+ T cells, or TRAC−/β2M−/PD1−/CD70−/anti-BCMA CAR+ T cells) (FIG. 30). All of the higher doses of $1 \times 10^6$ or greater all anti-BCMA CAR+ T cells (FIG. 30; 1 Mil, 3 Mil), showed complete regression in tumor volume. This trend continued out to Day 57 of the study.

These results demonstrate that inhibiting the activity of CD70 (e.g., by knocking out CD70) increases the efficacy and potency of CAR⁺ T cells in vivo. This effect is independent of the presence of an anti-CD70 CAR.

TABLE 21

| Group | Treatment | Anti-BCMA CAR+ T cells/dose | Tumor Volume (mm³) at Day 36 | | | | | Tumor Volume (mm³) at Day 57 | | | | |
|---|---|---|---|---|---|---|---|---|---|---|---|---|
| 1 | No Treatment | N/A | 220 | 220 | 186 | 173 | 278 | 1790 | 1794 | 938 | 2055 | 2029 |
| 2 | TRAC-/β2M-/anti-BCMA | 2.4 × 10⁶ (2.4 million) | 0 | 0 | 0 | 0 | 0 | 0 | 0 | 0 | 0 | 0 |
| 3 | | 8 × 10⁵ (0.8 million) | 0 | 0 | 0 | 0 | 0 | 0 | 0 | 0 | 0 | 0 |
| 4 | | 2.4 × 10⁵ (0.24 million) | 65 | 65 | 77 | 56 | 0 | 516 | 441 | 257 | 97 | 337 |
| 5 | | 8 × 10⁴ (0.08 million) | 264 | 264 | 386 | 276 | 185 | 2391 | 2283 | 2058 | 2147 | 2359 |
| 6 | TRAC-/β2M-/PD1-/anti-BCMA | 2.4 × 10⁶ (2.4 million) | 0 | 0 | 0 | 0 | 0 | 0 | 0 | 0 | 0 | 0 |
| 7 | | 8 × 10⁵ (0.8 million) | 0 | 0 | 0 | 0 | 0 | 0 | 0 | 0 | 0 | 0 |
| 8 | | 2.4 × 10⁵ (0.24 million) | 135 | 135 | 59 | 57 | 28 | 764 | 518 | 280 | 181 | 79 |
| 9 | | 8 × 10⁴ (0.08 million) | 261 | 261 | 265 | 287 | 312 | 1532 | 1557 | 2218 | 2010 | 2098 |
| 10 | TRAC-/β2M-/CD70-/anti-BCMA | 2.4 × 10⁶ (2.4 million) | 0 | 0 | 0 | 0 | 0 | 0 | 0 | 0 | 0 | 0 |
| 11 | | 8 × 10⁵ (0.8 million) | 0 | 0 | 0 | 0 | 0 | 0 | 0 | 0 | 0 | 0 |
| 12 | | 2.4 × 10⁵ (0.24 million) | 47 | 47 | 0 | 0 | 0 | 526 | 58 | 47 | 0 | 0 |
| 13 | | 8 × 10⁴ (0.08 million) | 292 | 292 | 267 | 313 | 235 | 2075 | 2127 | 2096 | 1365 | 2354 |
| 14 | TRAC-/β2M-/PD1-/CD70-/anti-BCMA | 2.4 × 10⁶ (2.4 million) | 0 | 0 | 0 | 0 | 0 | 0 | 0 | 0 | 0 | 0 |
| 15 | | 8 × 10⁵ (0.8 million) | 0 | 0 | 0 | 0 | 0 | 0 | 0 | 0 | 0 | 0 |
| 16 | | 2.4 × 10⁵ (0.24 million) | 100 | 100 | 91 | 19 | 20 | 478 | 576 | 82 | 131 | 289 |
| 17 | | 8 × 10⁴ (0.08 million) | 310 | 310 | 319 | 345 | 451 | 1528 | 2160 | 2843 | 2557 | 1499 |

Example 9. Multi Knockout CAR T Cells Retain Cytokine Dependency

Cytokine Dependency. To determine whether gene editing resulted in unwanted off-target editing that could generate cells with adverse properties, such as uncontrolled cell growth, the ability gene edited CAR T cells to grow in the absence of cytokines and/or serum was assessed.

Figure 31:
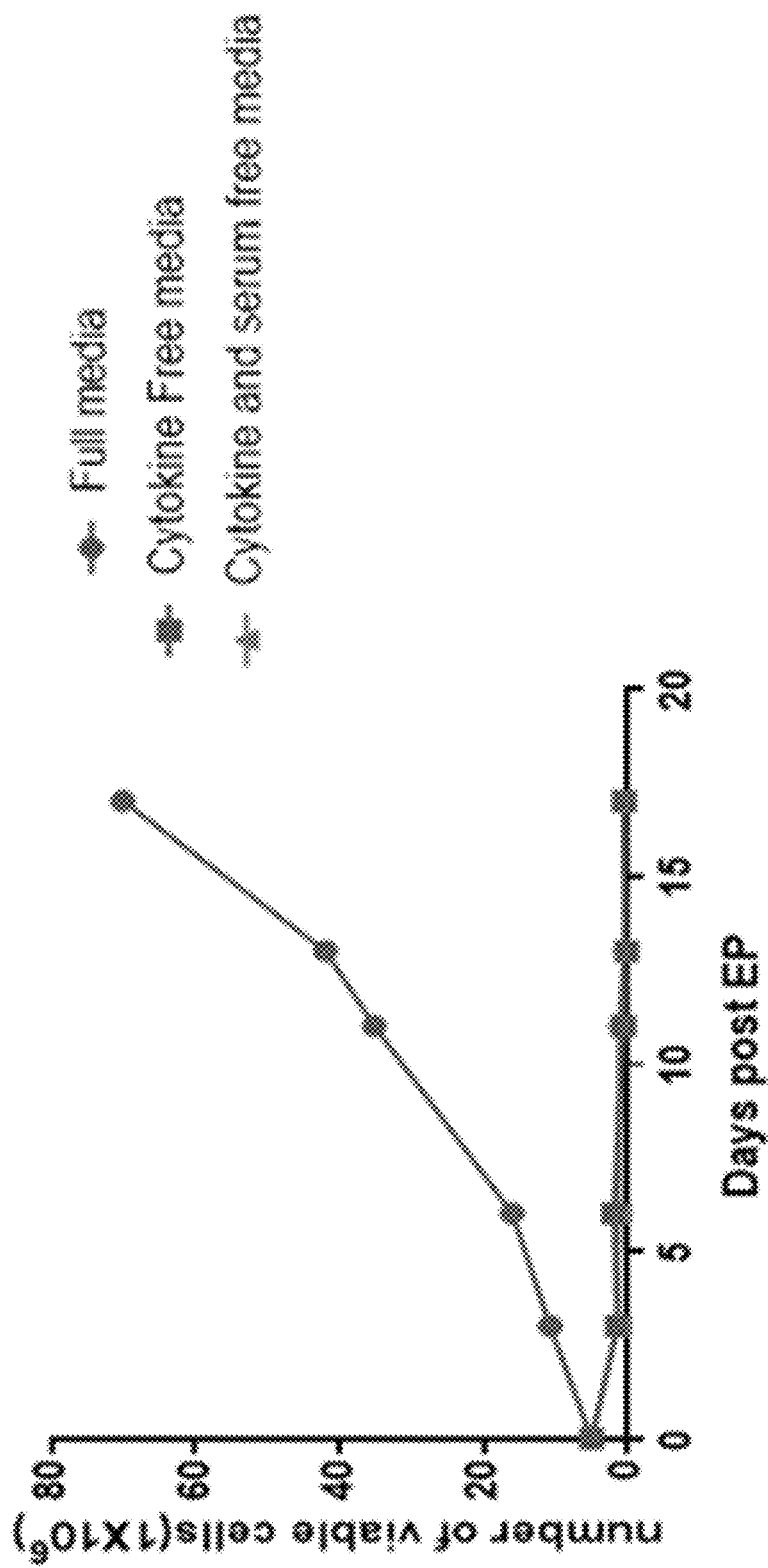
FIG. 31 includes a graph showing that TRAC$^-$/β2M$^-$/CD70$^-$/anti-CD70 CAR$^+$ T cell maintain cytokine-dependent proliferation.

Anti-CD70 CAR T cells: The ability of TRAC⁻/β2M⁻/CD70⁻/anti-CD70 CAR⁺ cells to grow in the absence of cytokines and/or serum was assessed. 5×10⁶ TRAC⁻/β2M⁻/CD70⁻/anti-CD70 CAR⁺ cells were plated ~2 weeks post cell production (Day 0). The number of viable cells were enumerated 7 and 14 days post plating in either full media, 5% human serum without cytokines (IL-2 and IL-7), or base media lacking serum and cytokines. No cells were detected at 14 days plated in the cultures that lacked cytokines, suggesting that any potential off-target effects due to genome editing did not induce growth factor independent growth/proliferation to the cells (FIG. 31). The cells only proliferated in the presence of cytokines (full media that contains cytokines) and did not proliferate in the presence of serum alone. Thus, in vivo, the cells would likely not grow in the absence of cytokine, growth factor or antigen stimulation due to any off-target genome editing.

Figure 32:
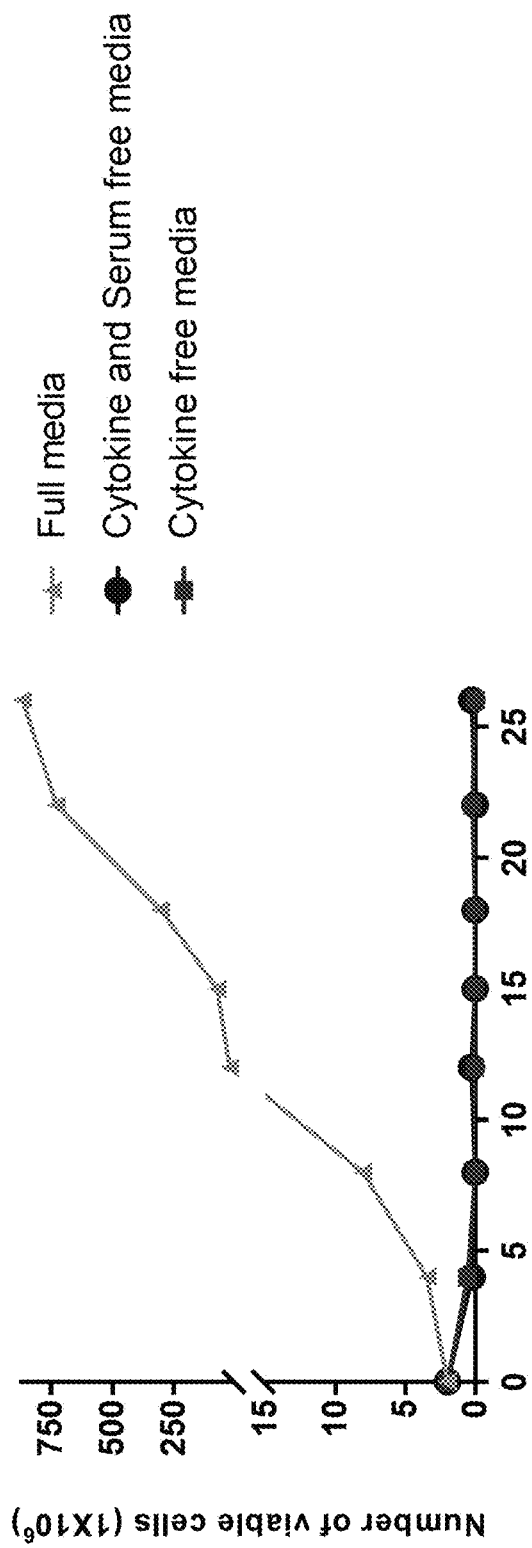
FIG. 32 shows cytokine-dependent growth of the TRAC$^-$/β2M$^-$/PD-1$^-$/CD70$^-$/anti-CD70 CAR$^+$ T cells.

The ability of TRAC$^-$/β2M$^-$/CD70$^-$/PD1$^-$ anti-CD70 CAR$^+$ cells to grow in the absence of cytokines and/or serum was also assessed. 2×10$^6$ cells were plated ~2 weeks post cell production (Day 0). The number of viable cells were enumerated until 26 days post plating in either full media, 5% human serum without cytokines (IL-2 and IL-7), or base media lacking serum and cytokines. No cells were detected at 26 days plated in the cultures that lacked cytokines, suggesting that any potential off-target effects due to genome editing did not induce growth factor independent growth/proliferation to the cells (FIG. 32). The cells only proliferated in the presence of cytokines (full media that contains cytokines) and did not proliferate in the presence of serum alone. Thus, genome editing did not induce any adverse events that allow the cells to grow in the absence of cytokine, growth factor or antigen stimulation.

Figure 33:
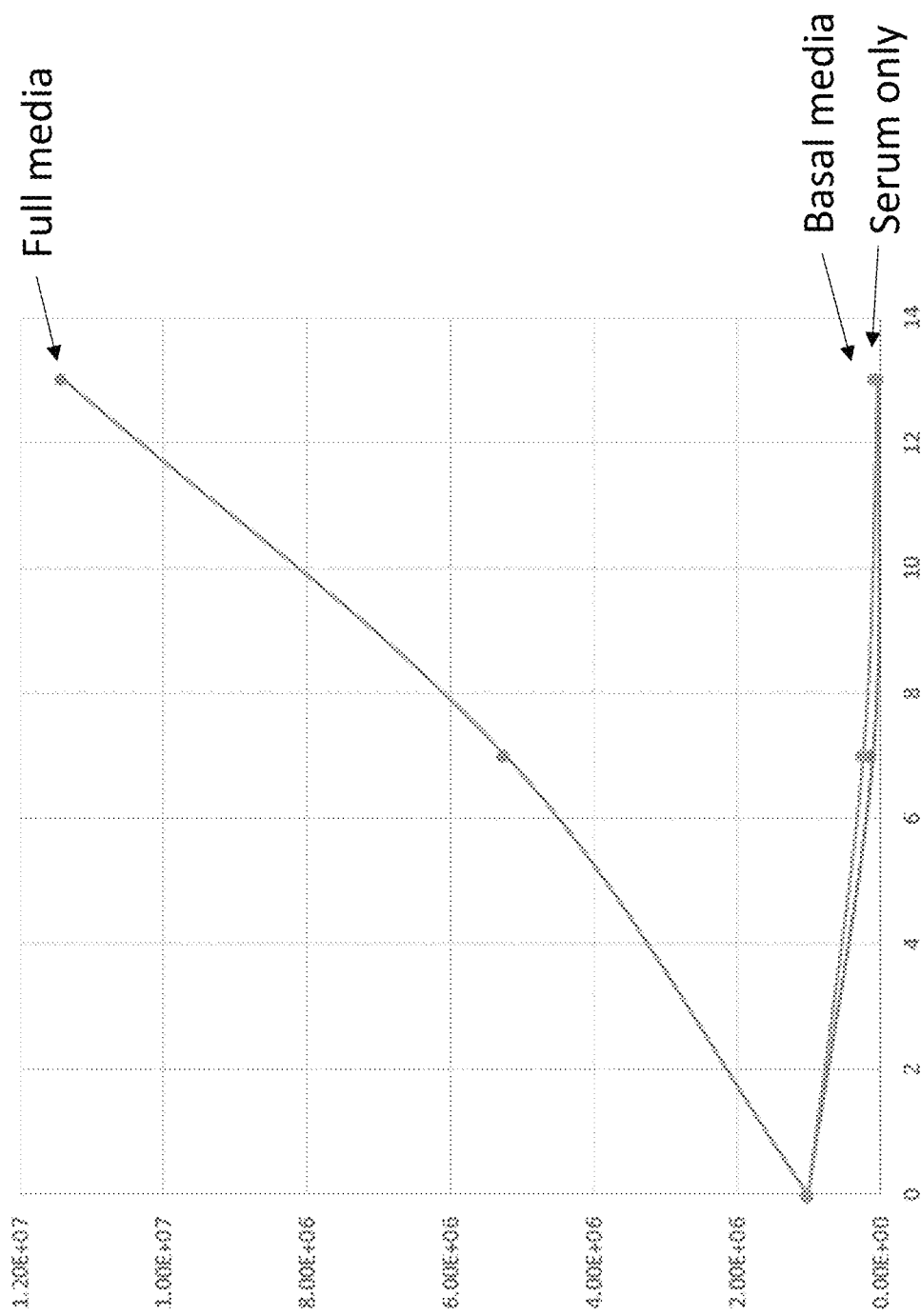
FIG. 33 includes a graph showing 4×KO (TRAC$^-$/β2M$^-$/PD-1$^-$/CD70$^-$), BCMA CAR$^+$ T cells maintain cytokine dependency.

Anti-BCMA CAR+ T cells: The ability of TRAC$^-$/β2M$^-$/CD70$^-$/PD-1$^-$/anti-BCMA CARP cells to grow in the absence of cytokines and/or serum was assessed. TRAC$^-$/β2M$^-$/CD70$^-$/PD-1$^-$/anti-BCMA CAR$^+$ cells are also referred to as 4×KO, BCMA CARP cells. 1×10$^6$ 4×KO, BCMA CAR+ cells were plated following the 10 rechallenges described in Example 6. The number of viable cells were enumerated 7 and 14 days post plating in either full media, 5% human serum without cytokines (IL-2 and IL-7), or base media lacking serum and cytokines. No cells were detected at 13 days plated in the cultures that lacked cytokines, suggesting that any potential off-target effects due to genome editing did not induce growth factor independent growth/proliferation to the cells (FIG. 33). The cells only proliferated in the presence of cytokines (full media that contains cytokines) and did not proliferate in the presence of serum alone. Thus, in vivo, the cells would likely not grow in an uncontrolled way.

Other CAR T cells: It has previously been shown that the anti-CD33 CAR+ T cells and anti-CD19 CAR+ T cells exemplified herein only proliferated in the presence of cytokines and do not proliferate in the presence of serum alone. Thus, in vivo, these cells would likely not grow in an uncontrolled way.

Cytokine Release Assay. To measure cytokine release, T cells and target cells were co-incubated for 24 hours at the ratios indicated. Supernatant media was collected for use in IL-2 or IFNγ ELISAs (RD Systems) on a new plate following the manufacturer's instructions (RD Systems).

Figure 34:
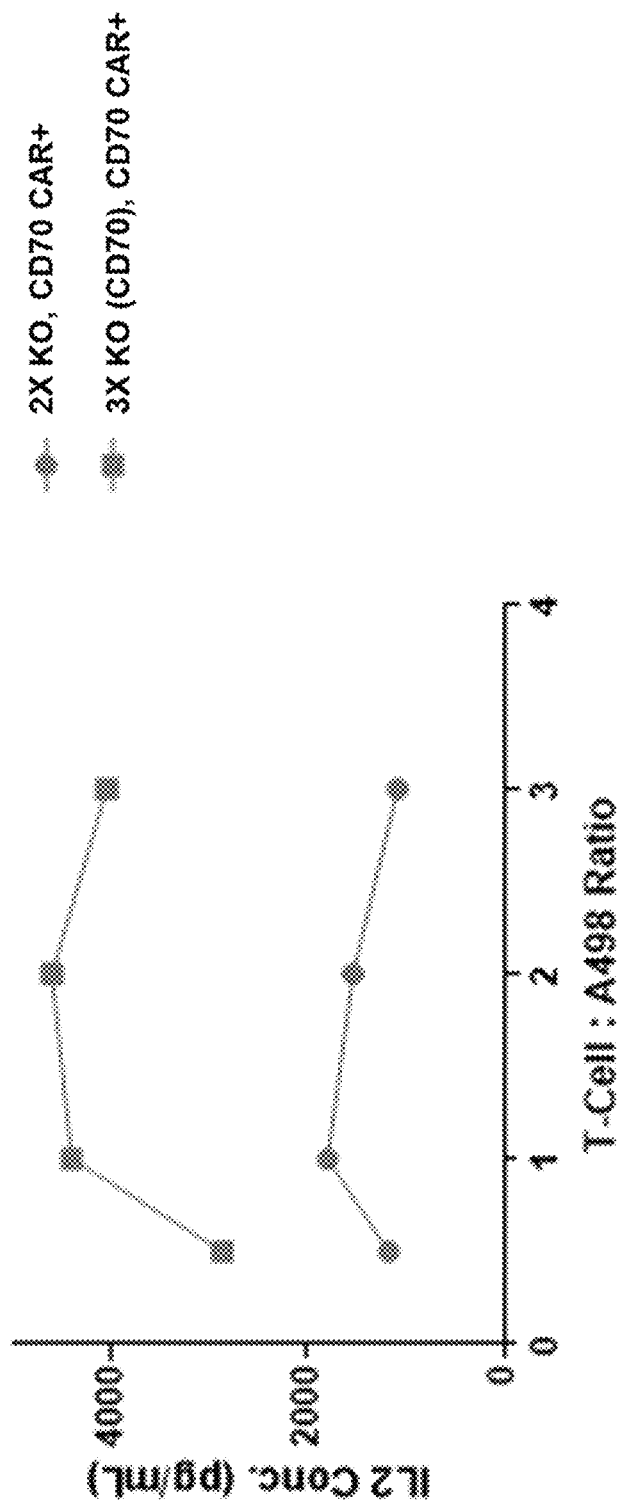
FIG. 34 includes a graph showing enhanced cytokine (IL-2) release by 3×KO (TRAC–/β2M–/CD70–) anti-CD70 CAR+ T cells compared to 2×KO (TRAC–/β2M–) anti-CD70 CAR+ T cells when co-cultured with A498 kidney cancer cells at various ratios for 24 hours.

The ability of the TRAC$^-$/β2M$^-$/CD70$^-$/anti-CD70 CARP cells to produce interleukin-2 (IL-2) when co-cultured in the presence of A498 cells was analyzed using the ELISA assay. Both the triple knockout TRAC$^-$/β2M$^-$/CD70$^-$/anti-CD70 CAR+ T cells and double knockout TRAC$^-$/β2M$^-$/anti-CD70 CAR+ T cells secreted high levels of IL-2. Strikingly, the TRAC$^-$/β2M$^-$/CD70$^-$/anti-CD70 CAR$^+$ cells secreted higher levels of IL-2 than the TRAC$^-$/β2M$^-$/anti-CD70 CAR$^+$ cells when cultured with A498 cells (FIG. 34). These results suggest that knocking-out the CD70 gene gives an advantage to anti-CD70 CAR+ T cells to secrete more IL-2.

Example 10. Effect of Multiple Knockout on Anti-CD70 CAR+ T Cells on A498 Renal Carcinoma Cells Effect of Multi Knock-Out on the Function of Anti-CD70 CAR+ T Cells.

Cell Killing Assay. The ability of multi-gene editing to kill A498 renal carcinoma cells was determined using the cell kill assay described above. In brief, the TRAC$^-$/β2M$^-$/anti-CD70 CAR$^+$ (2×KO, CD70 CAR$^+$), TRAC$^-$/β2M$^-$/PD-1$^-$/anti-CD70 CAR$^+$ (3×KO (PD-1), CD70 CAR$^+$), TRAC$^-$/β2M$^-$/CD70$^-$/anti-CD70 CAR$^+$ (3×KO (CD70), CD70 CAR$^+$) and TRAC$^-$/β2M$^-$/PD-1$^-$/CD70$^-$/anti-CD70 CAR$^+$ (4×KO, CD70 CAR$^+$) cells were incubated with a CD70$^+$ adherent RCC-derived cell line (A498 cells) at various CAR T cell:A498 target cells ratios.

Figure 35:
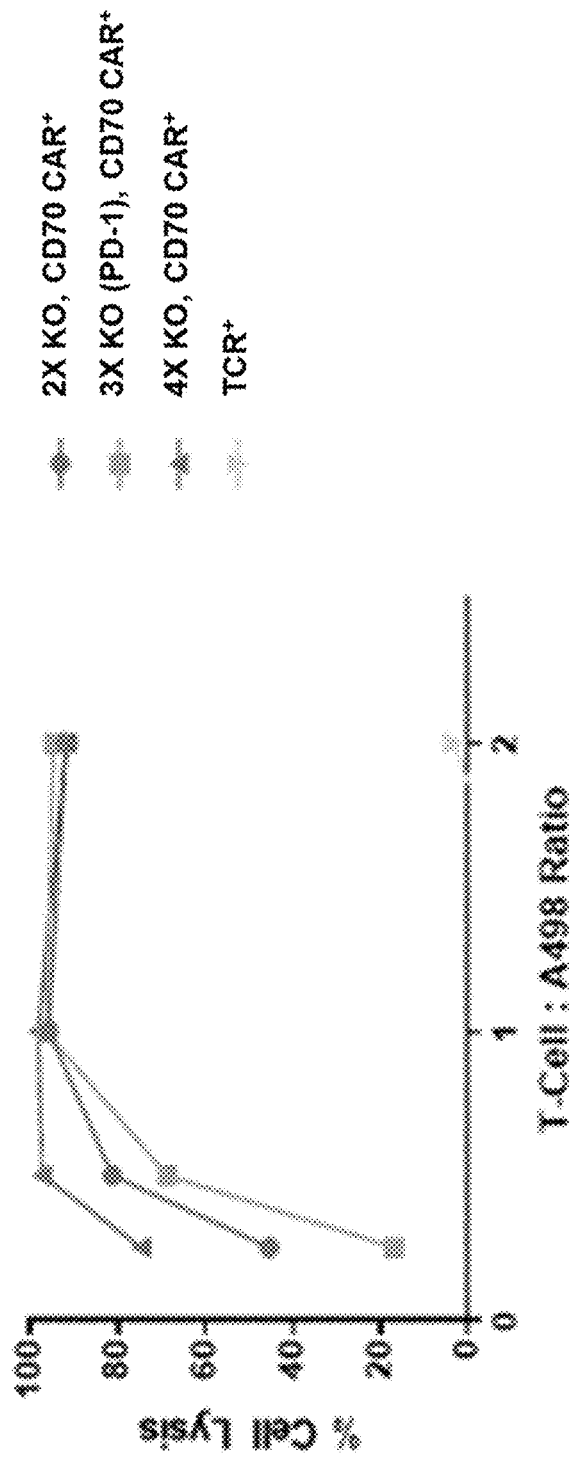
FIG. 35 includes a graph showing robust cell killing of A498 cells by anti-CD70 CAR T cells (2×KO (TRAC$^-$/β2M$^-$), CD70 CAR+; 3×KO (PD-1) (TRAC$^-$/β2M$^-$/PD-1$^-$), CD70 CAR+; and 4×KO (TRAC$^-$/β2M$^-$/PD-1$^-$/CD70$^-$) CD70 CAR$^+$) relative to TCR+ T cells. T cells were co-cultured with A498 cells at various ratios for 24 hours and percentage of cell lysis was measured.

The TRAC$^-$/β2M$^-$/PD-1$^-$/CD70$^-$/anti-CD70 CAR$^+$ cells exhibited potent cell killing of RCC-derived cells following 24-hour co-incubation (FIG. 35). The quadruple TRAC$^-$/β2M$^-$/PD-1$^-$/CD70$^-$/anti-CD70 CAR$^+$ T demonstrated higher cell kill potency than triple knockout TRAC$^-$/β2M$^-$/PD-1$^-$/anti-CD70 CAR$^+$ T cells that demonstrated higher potency than double knockout TRAC$^-$/β2M$^-$/anti-CD70 CAR$^+$ T cells (visible at low T-cell: A498 Ratio of 0.5:1 and 0.25:1). The results demonstrate knocking out both the CD70 and PD-1 genes gave the anti-CD70 CAR+ cells higher cell kill potency.

Figure 36:
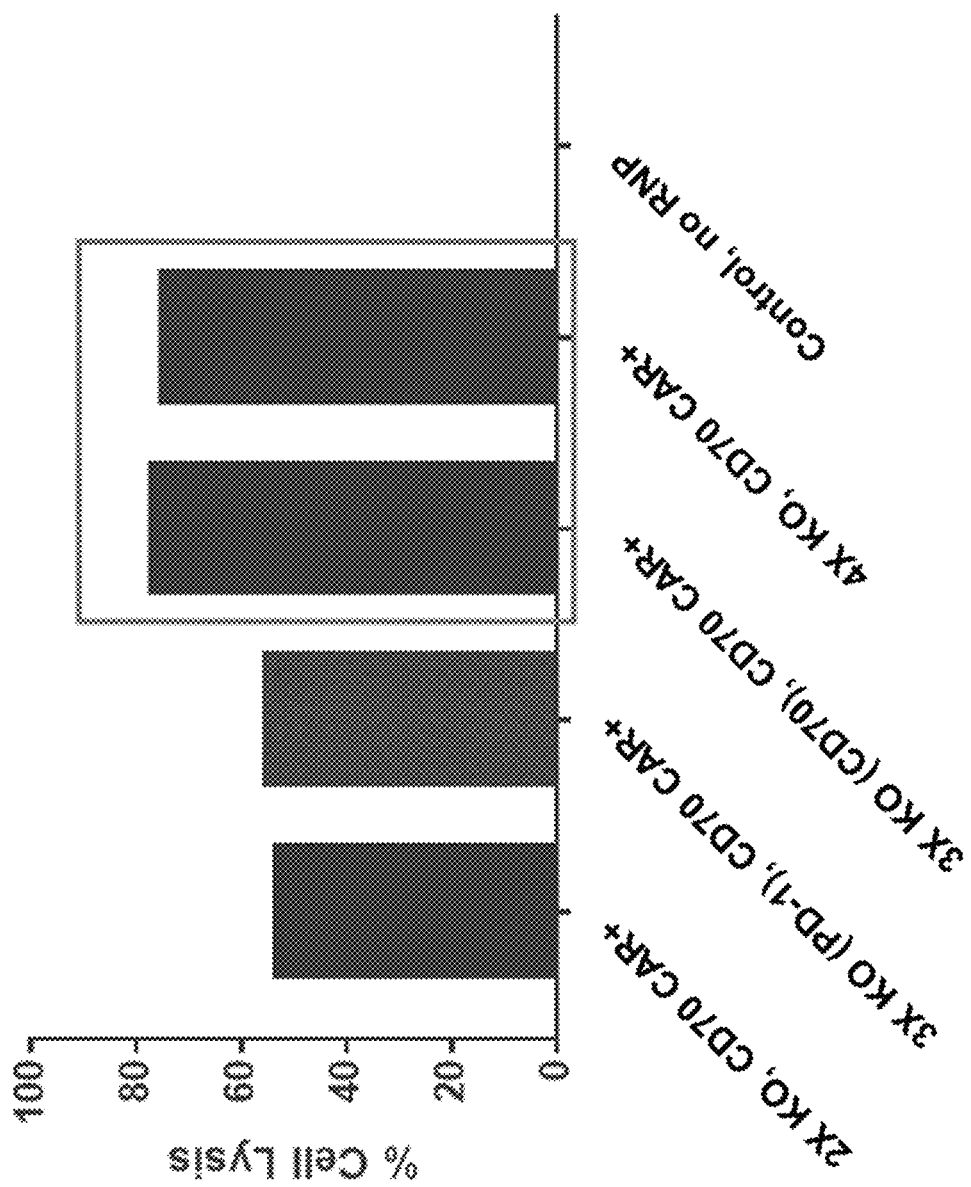
FIG. 36 includes a graph showing highest cell kill activity in A498 kidney cancer cells using quadruple knockout TRAC$^-$/β2M$^-$/PD-1$^-$/CD70$^-$/anti-CD70 CAR$^+$ T cells (4×KO, CD70 CAR+) and triple knockout TRAC$^-$/β2M$^-$/CD70$^-$/anti-CD70 CAR$^+$ T cells (3×KO (CD70), CD70 CAR+), relative to double knockout TRAC$^-$/β2M$^-$/anti-CD70 CAR$^+$ (i.e., 2×KO, CD70 CAR$^+$) T cells and triple knockout TRAC$^-$/β2M$^-$/PD-1$^-$/anti-CD70 CAR$^+$ (i.e., 3×KO (PD-1), CD70 CAR$^+$) T cells. A CAR T cell:A498 cell ratio of 0.25:1 was used. Percentage of cell lysis of A498 cells was measured 24 hours after co-culture.

The gene edited cells also exhibited potent cell killing of RCC-derived cells following 24-hour co-incubation at a CART cell:A948 target cell ratio of 0.24:1. (FIG. 36). Specifically, the triple knockout TRAC$^-$/β2M$^-$/CD70$^-$/anti-CD70 CAR$^+$ T cells and the quadruple knockout TRAC$^-$/β2M$^-$/PD-1$^-$/CD70$^-$/anti-CD70 CAR$^+$ T cells demonstrated higher potency than the double knockout TRAC$^-$/β2M$^-$/anti-CD70 CAR$^+$ T cells or the triple knockout TRAC$^-$/β2M$^-$/PD-1$^-$/anti-CD70 CAR$^+$ T cells. These data indicate that knockout of CD70 in the context of an anti-CD70 CAR improved the cell killing ability of the anti-CD70 CAR$^+$ T cells.

Figure 37A:
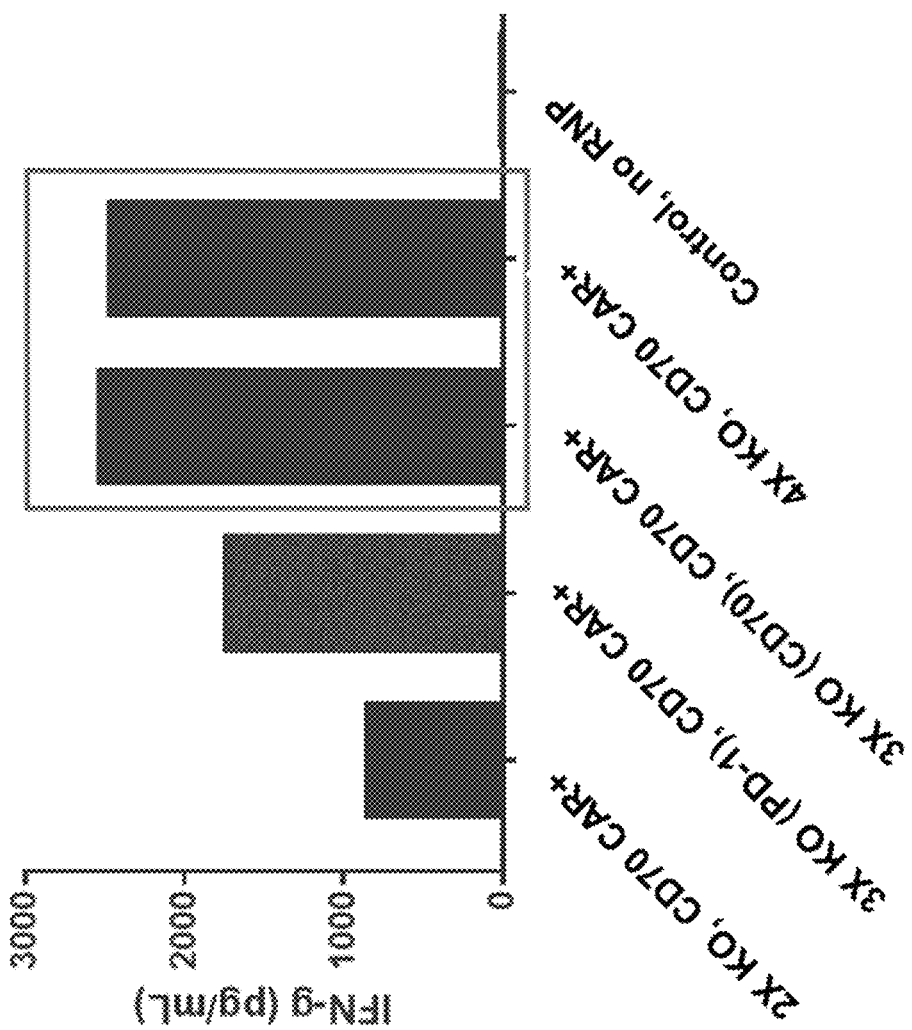
FIGS. 37A and 37B include graphs showing that quadruple knockout TRAC$^-$/β2M$^-$/PD-1$^-$/CD70$^-$/anti-CD70 CAR+ T cells (4×KO, CD70 CAR+) and triple knockout TRAC$^-$/β2M$^-$/CD70$^-$/anti-CD70 CAR$^+$ T cells (3×KO (CD70), CD70 CAR+) secrete the highest levels of cytokines IFN-gamma (FIG. 37A) and IL-2 (FIG. 37B), relative to double knockout TRAC$^-$/β2M$^-$/anti-CD70 CAR$^+$ T cells (2×KO, CD70 CAR+) and triple knockout TRAC$^-$/β2M$^-$/PD-1$^-$/anti-CD70 CAR$^+$ T cells (3×KO (PD-1), CD70 CAR+). A CART cell:A498 cell ratio of 0.25:1 was used. IFN-gamma and IL-2 secretion was measured 24 hours are co-culture.
Figure 37B:
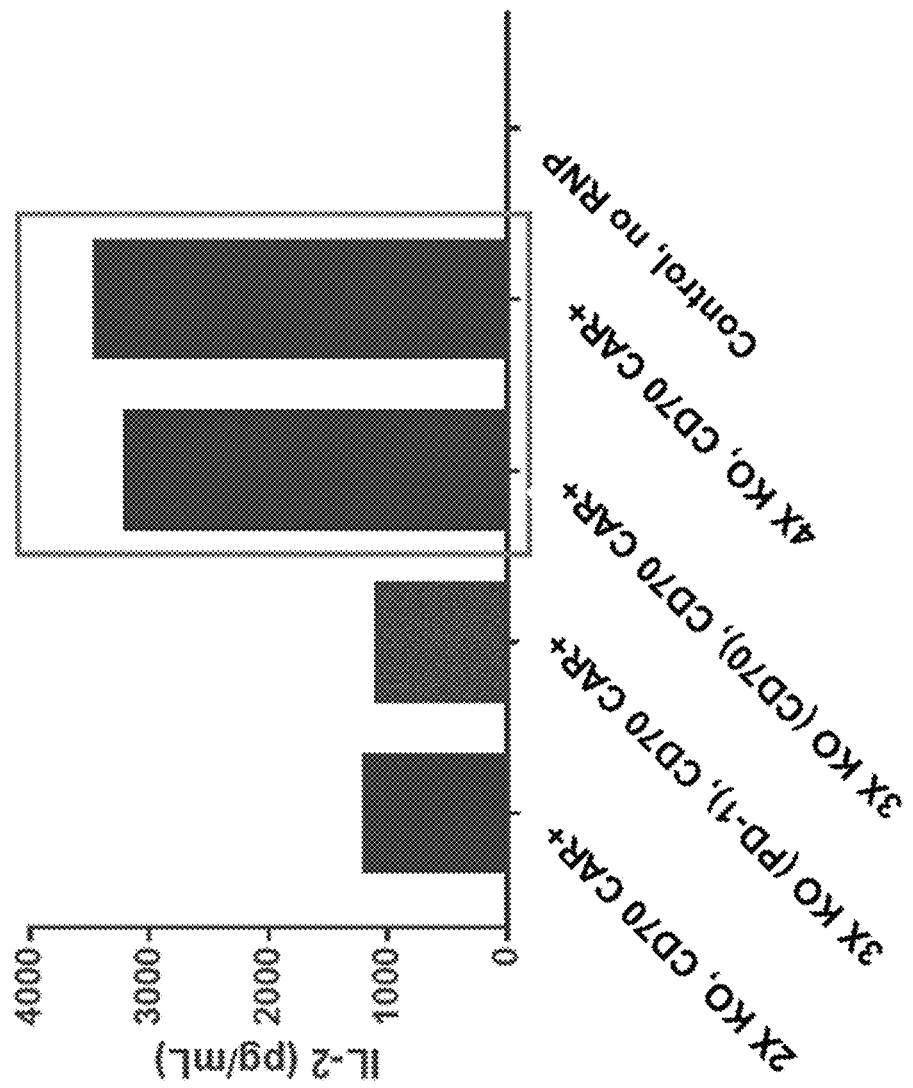

Cytokine Release Assay. A cytokine release assay was performed as described above. The ability of the double knockout, triple knockout, and quadruple knockout anti-CD70 CAR$^+$ T cells to produce IL-2 and interferon gamma (IFN-gamma (IFN-g)) when co-cultured in the presence of A498 cells following 24-hour co-incubation at a ratio (CAR T cell:A498 target cell) of 0.25:1 was assessed using an ELISA assay. IL-2 and IFN-g from supernatants of cell co-cultures were measured. The triple knockout TRAC$^-$/β2M$^-$/CD70$^-$/anti-CD70 CAR$^+$ T cells and quadruple knockout TRAC$^-$/β2M$^-$/PD-1$^-$/CD70$^-$/anti-CD70 CAR$^+$ T cells secreted the highest levels of IFN-g (FIG. 37A) and IL-2 (FIG. 37B) when cultured with A498 cells.

Effect of CD70 Knockout on Exhaustion Marker Expression

The levels of the exhaustion markers PD-1 and LAG3 were assessed on the TRAC$^-$/β2M$^-$/anti-CD70 CAR$^+$ (2×KO, CD70 CAR$^+$), TRAC$^-$/β2M$^-$/PD-1$^-$/anti-CD70 CAR$^+$ (3×KO (PD-1), CD70 CAR$^+$), TRAC$^-$/β2M$^-$/CD70$^-$/anti-CD70 CAR$^+$ (3×KO (CD70), CD70 CAR$^+$) and TRAC$^-$/β2M$^-$/PD-1$^-$/CD70$^-$/anti-CD70 CAR$^+$ (4×KO, CD70 CAR$^+$) T cells used in the Examples above. CD4$^+$ T cells were assessed for PD-1 expression (FIG. 38) and both CD8+ T cells and CD4+ T cells were assessed for LAG3 expression (FIG. 39A and FIG. 39B, respectively) by flow cytometry.

Figure 38:
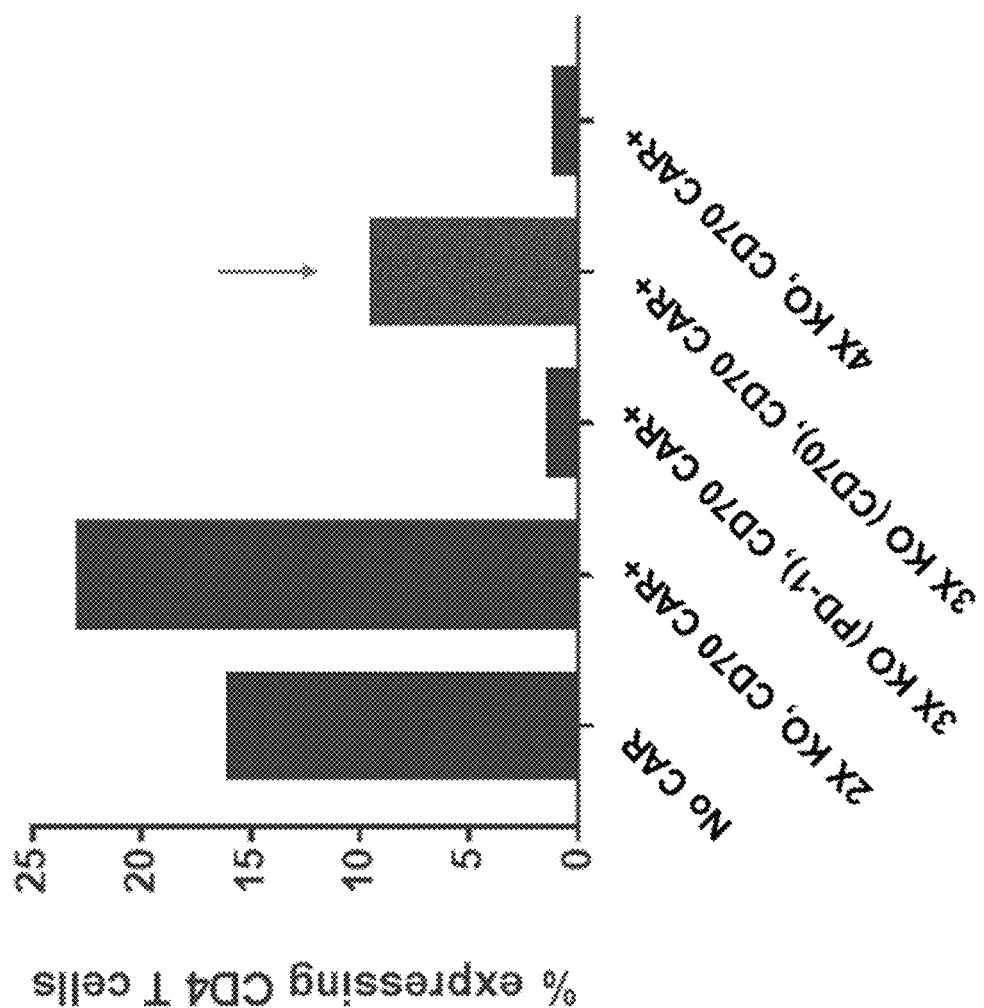
FIG. 38 includes a graph showing that knocking out CD70 in anti-CD70 CAR T cells (3×KO (CD70) (TRAC$^-$/β2M$^-$/CD70$^-$), CD70 CAR+; 3×KO (PD-1) (TRAC$^-$/β2M$^-$/PD1$^-$), CD70 CAR+; and 4×KO (TRAC$^-$/β2M$^-$/CD70$^-$/PD-1$^-$), CD70 CAR+) decreased levels of PD-1 expression in CD4+ T cells relative to anti-CD70 CAR T cells expressing endogenous CD70 (2×KO (TRAC$^-$/β2M$^-$) CD70 CAR+).

The data demonstrate that CD70 KO reduces exhaustion marker expression in CAR T cells. The data in FIG. 38 shows that PD-1 expression is decreased, as expected, when PD-1 is knocked out, and it is also decreased when CD70 is knocked out.

Figure 39A:
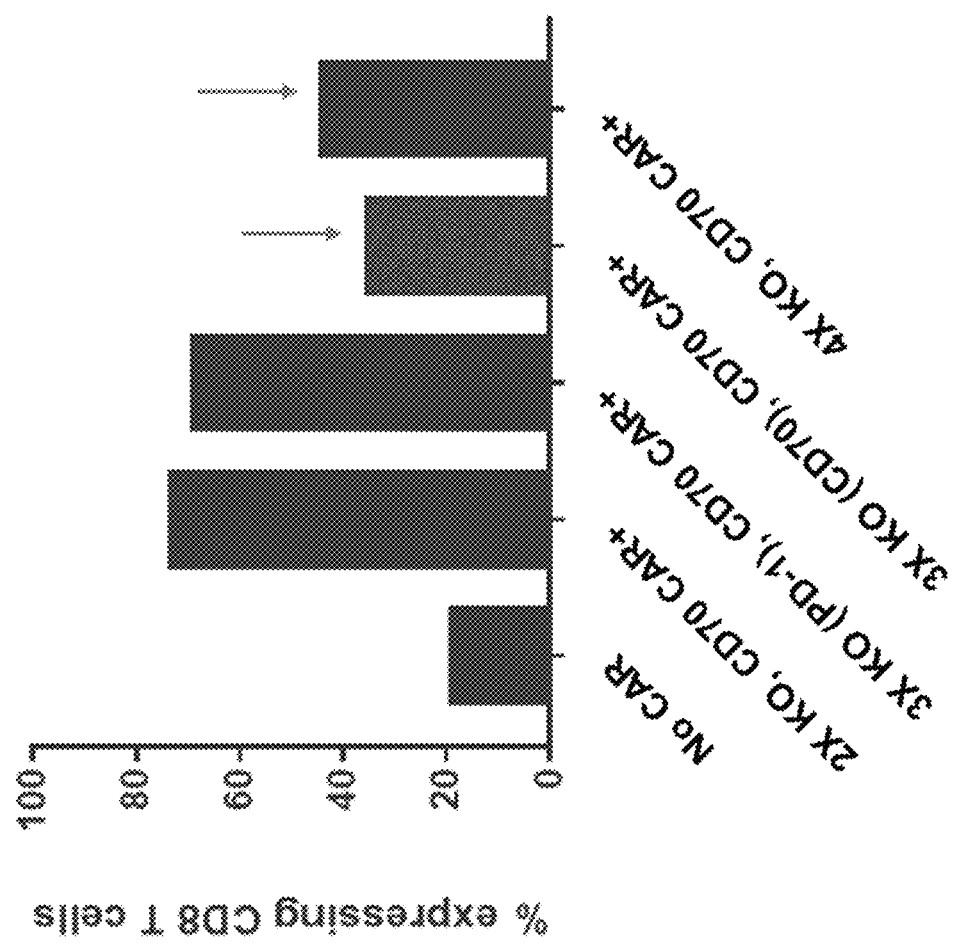
FIG. 39A and FIG. 39B include graphs showing that knocking out CD70 in anti-CD70 CAR T cells (3×KO (CD70) (TRAC$^-$/β2M$^-$/CD70$^-$), CD70 CAR+; 3×KO (PD-1) (TRAC$^-$/β2M$^-$/PD1$^-$), CD70 CAR+; and 4×KO (TRAC$^-$/β2M$^-$/CD70$^-$/PD-1$^-$), CD70 CAR+) decreased levels of exhaustion marker LAGS in CD8+ T cells (FIG. 39A) and CD4+ T cells (FIG. 39B) relative to anti-CD70 CAR T cells expressing endogenous CD70 (2×KO (TRAC$^-$/β2M$^-$) CD70 CAR+).
Figure 39B:
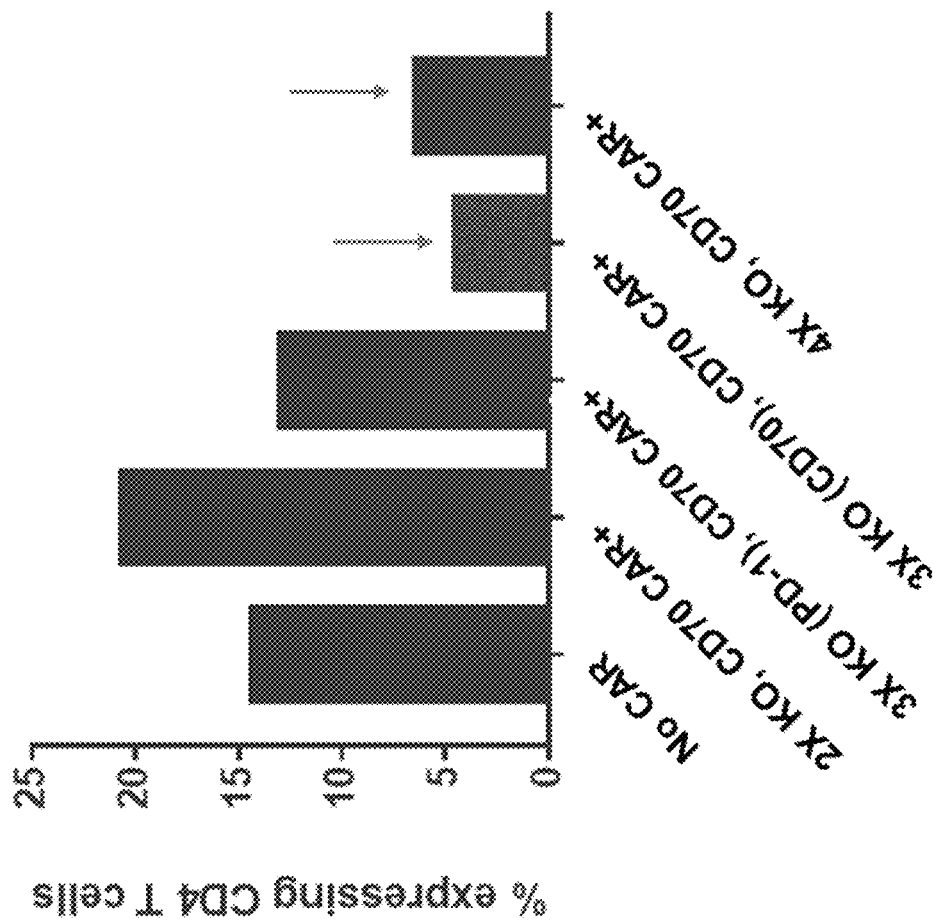

The data in FIGS. 39A and 39B show that knocking out CD70, reduces the LAG3 expression marker in CD4 and CD8 cells.

The data demonstrate that knocking out CD70, specifically, could reduce the potential exhaustion of the CD8+ and CD4+ gene edited populations of CAR+ T cells leading to better therapeutics.

Example 11. CD70 KO Improves Cell Kill in Multiple Cell Types

Figure 40A:
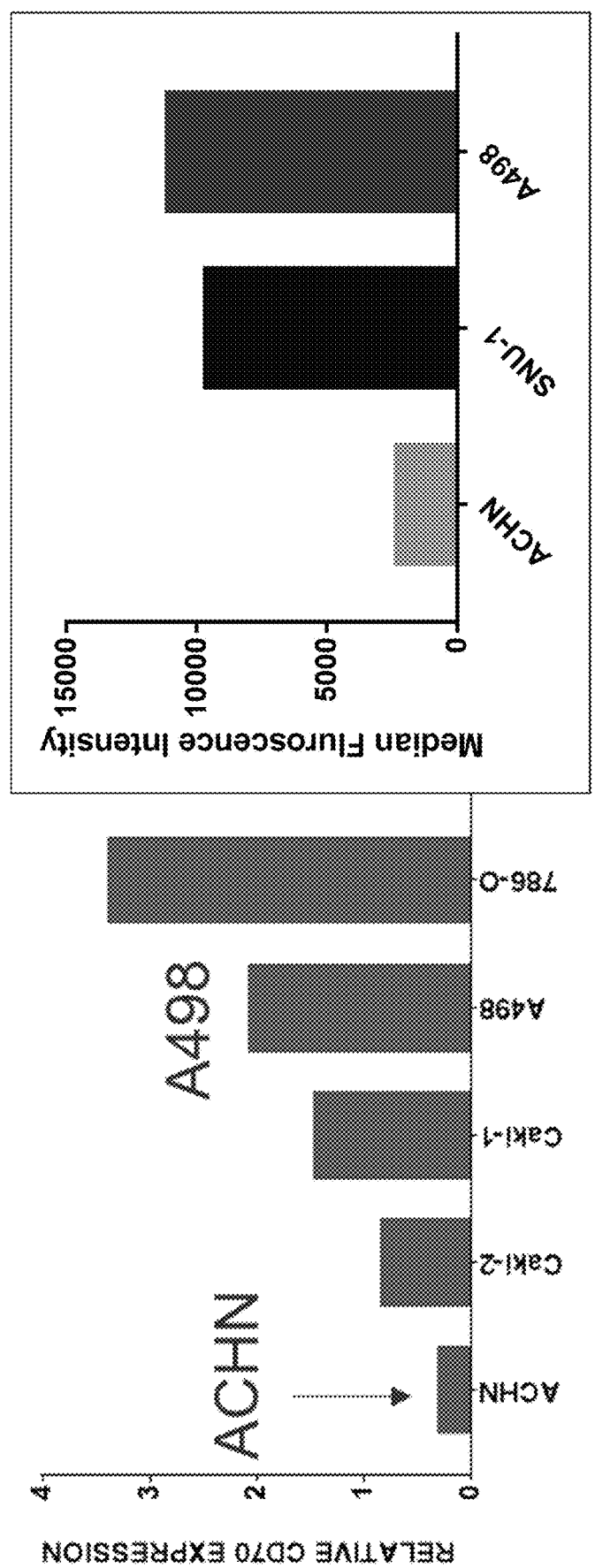
FIG. 40A includes graphs showing relative CD70 expression in five different cancer cell lines (left panel) and relative CD70 expression in three different cancel cell lines (right panel).
Figure 40B:
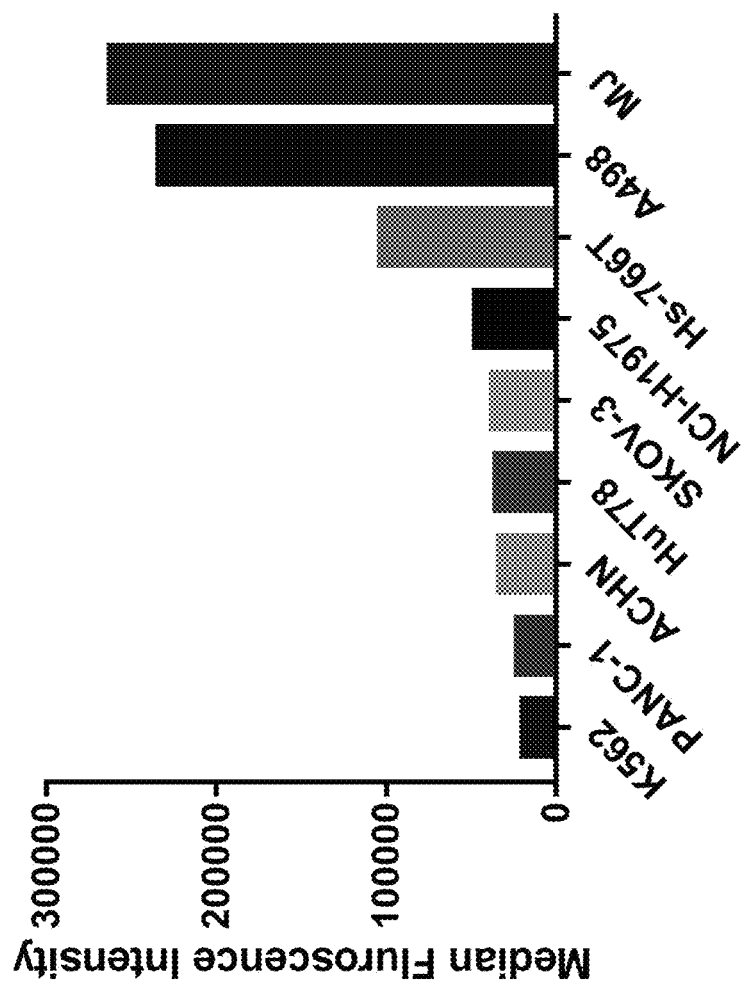
FIG. 40B includes graphs showing relative CD70 expression in nine different cancer cell lines.

CD70 Expression in Various Cancer Cell Lines. Relative CD70 expression was measured in various cancer cell lines to further evaluate the ability of anti-CD70 CAR+ T cells to kill various cancer types. CD70 expression was measured by FACS analysis using Alexa Fluor 647 anti-human CD70 antibody (BioLegend Cat. No. 355115). FIG. 40A (left graph) shows the relative expression of CD70 in ACHN cells, as measured by FACS, compared to other kidney cancer cell lines A498, 786-O, cacki-1 and Caki-2. Additionally, non-kidney cancer cell lines were evaluated for CD70 expression by FACS analysis (Table 22, FIG. 40A and FIG. 40B) using either an Alexa Fluor 647 anti-human CD70 antibody (BioLegend Cat. No. 355115; FIG. 40A, right panel) or a FITC anti-human CD70 antibody (BioLegend Cat. No. 355105) in FIG. 40B. SNU-1 (intestinal cancer cells) exhibited high levels of CD70 expression that were similar to A498 (FIG. 40A, right panel). SKOV-3 (ovarian), HuT78 (lymphoma), NCI-H1975 (lung) and Hs-766T (pancreatic) cell lines exhibited levels of CD70 expression that were similar or higher than ACHN but lower than A498 (Table 22, FIG. 40B).

TABLE 22

| Cell Line | Cancer type | Relative CD70 expression |
| --- | --- | --- |
| A498 | Kidney Carcinoma | High |
| ACHN | Kidney (derived from metastasis) | Medium-Low |
| SK-OV-3 | Ovarian Adenocarcinoma | Medium |
| NCI-H1975 | Lung Adenocarcinoma (NSCLC) | Medium |
| Calu-1 | Lung Carcinoma | Low |
| DU 145 | Prostate Carcinoma | Low |
| SNU-1 | Gastric Carcinoma | High |
| Hs 766T | Pancreatic Carcinoma | Medium |
| MJ | T cell Lymphoma | High |
| HuT78 | T cell Lymphoma | Medium |
| HuT102 | T cell Lymphoma | Medium |
| PANC-1 | Pancreatic Carcinoma | Low |
| U937 | AML | No expression |
| K562 | chronic myelogenous leukemia | No expression (Negative Control) |

Figure 40C:
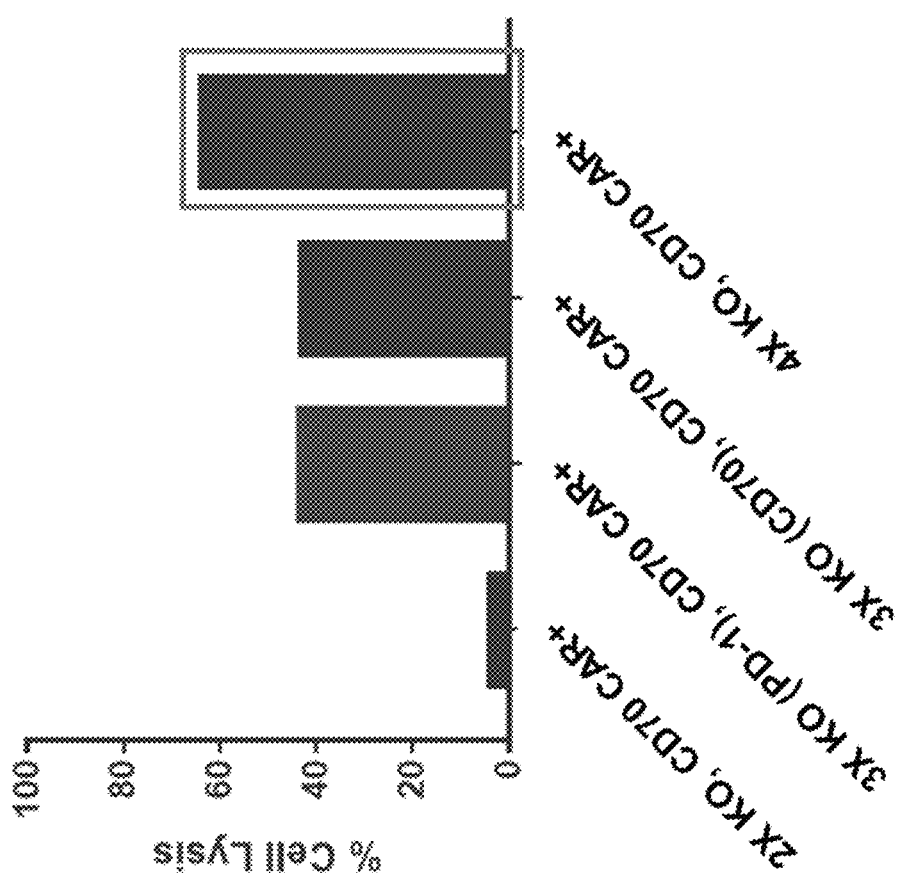
FIGS. 40C-40D include graphs showing highest cell kill activity in ACHN (ATCC® CRL-1611™) kidney cancer cells (which express low levels of CD70) using quadruple knockout TRAC$^-$/β2M$^-$/PD-1$^-$/CD70$^-$/anti-CD70 CAR+ T cells (4×KO, CD70 CAR+) and triple knockout TRAC$^-$/β2M$^-$/CD70$^-$/anti-CD70 CAR$^+$ T cells (3×KO (CD70), CD70 CAR+), relative to double knockout TRAC$^-$/β2M$^-$/anti-CD70 CAR$^+$ T cells (2×KO, CD70 CAR+) and triple knockout TRAC$^-$/β2M$^-$/PD-1$^-$/anti-CD70 CAR$^+$ T cells (3×KO (PD-1), CD70 CAR+). A CAR T cell:ACHN cell ratio of 0.5:1 was used in FIG. 40C and a CART cell:ACHN cell ratio of 0.25:1 was used in FIG. 40D.
Figure 40D:
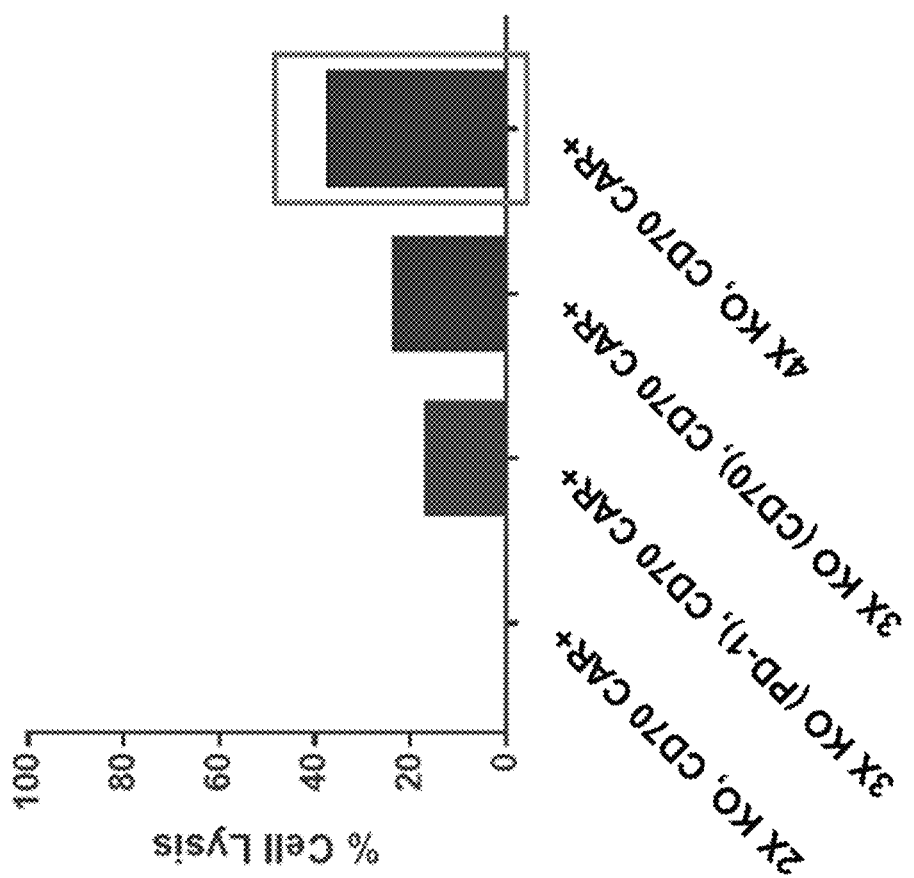

Cell Kill Assay. The ability of multi-gene edited anti-CD70 CAR+ cells to kill ACHN renal carcinoma cells was determined using the cell kill assay described above. The TRAC−/β2M−/anti-CD70 CAR+ (2×KO, CD70 CAR+), TRAC−/β2M−/PD-1−/anti-CD70 CAR+ (3×KO (PD-1), CD70 CAR+), TRAC−/β2M−/CD70−/anti-CD70 CAR+ (3×KO (CD70), CD70 CAR+) and TRAC−/β2M−/PD-1−/CD70−/anti-CD70 CAR+ (4×KO, CD70 CAR+) cells were incubated with an adherent RCC-derived cell line expressing low levels of CD70 antigen (ACHN cells) (FIG. 40A shows the relative expression of CD70 in ACHN cells, as measured by FACS, compared to other kidney cancer cell lines A498, 786-0, cacki-1 and Caki-2) at a CAR T cell:ACHN target cells ratio of 0.5:1 (FIG. 40C) and 0.25:1 (FIG. 40D). The gene edited cells exhibited potent cell killing of RCC-derived cells following 24-hour co-incubation (FIGS. 40C and 40D). The cells demonstrated higher potency when PD-1 was knocked out, when CD70 was knocked out, and even slightly higher potency when both PD-1 and CD70 were knocked out. In conclusion, knockout of PD-1 or CD70 or of both PD-1 and CD70 together improves the cell killing ability of the anti-CD70 CAR+ cells in ACHN cells.

Figure 40E:
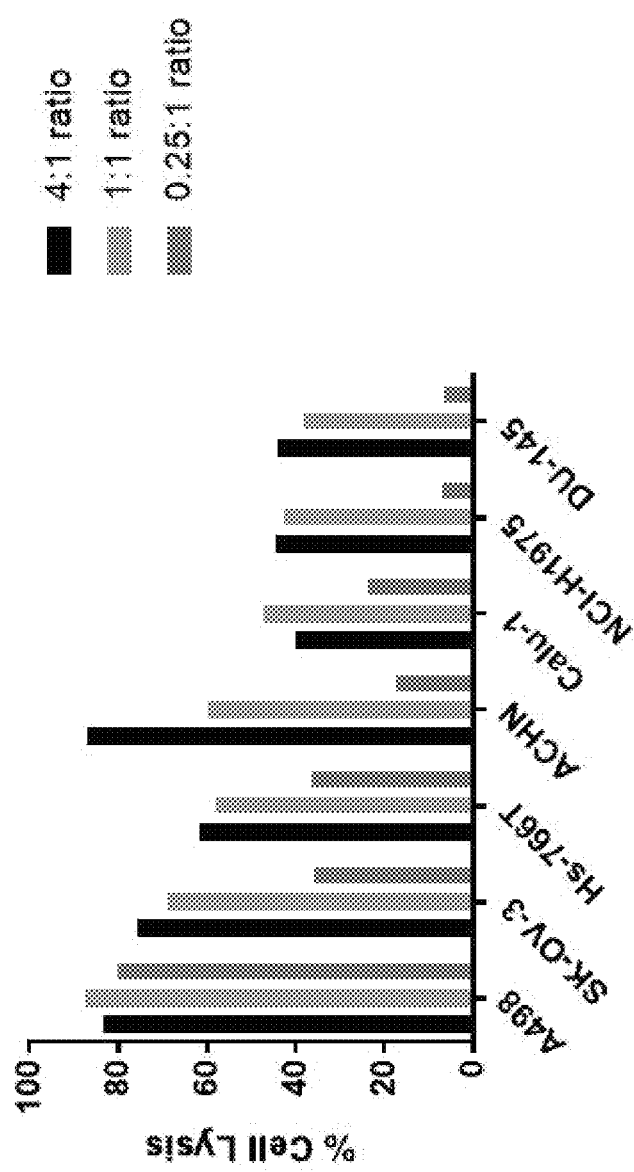
FIG. 40E and FIG. 40F include graphs showing cell kill activity using quadruple knockout TRAC$^-$/β2M$^-$/PD-1$^-$/CD70$^-$/anti-CD70 CAR$^+$ T cells (FIG. 40E) and triple knockout TRAC$^-$/β2M$^-$/CD70$^-$/anti-CD70 CAR$^+$ T cells (FIG. 40F) against additional solid tumor cell lines with varying levels of CD70 expression (4:1, 1:1, or 0.25:1 effector:target cell ratio).
Figure 40F:
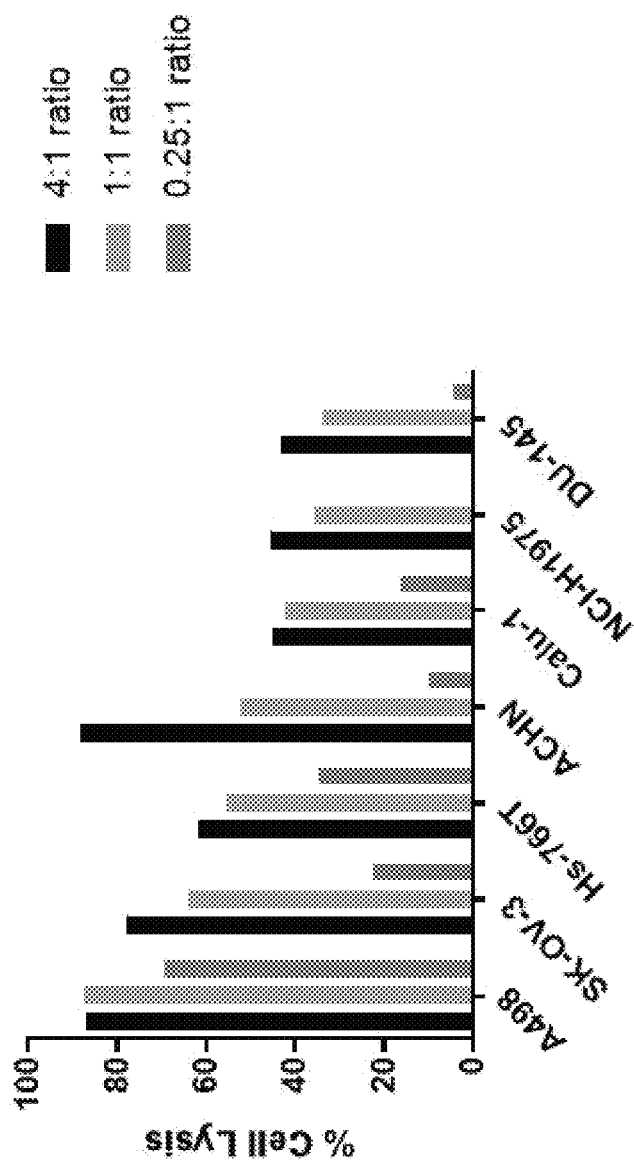
Figure 40G:
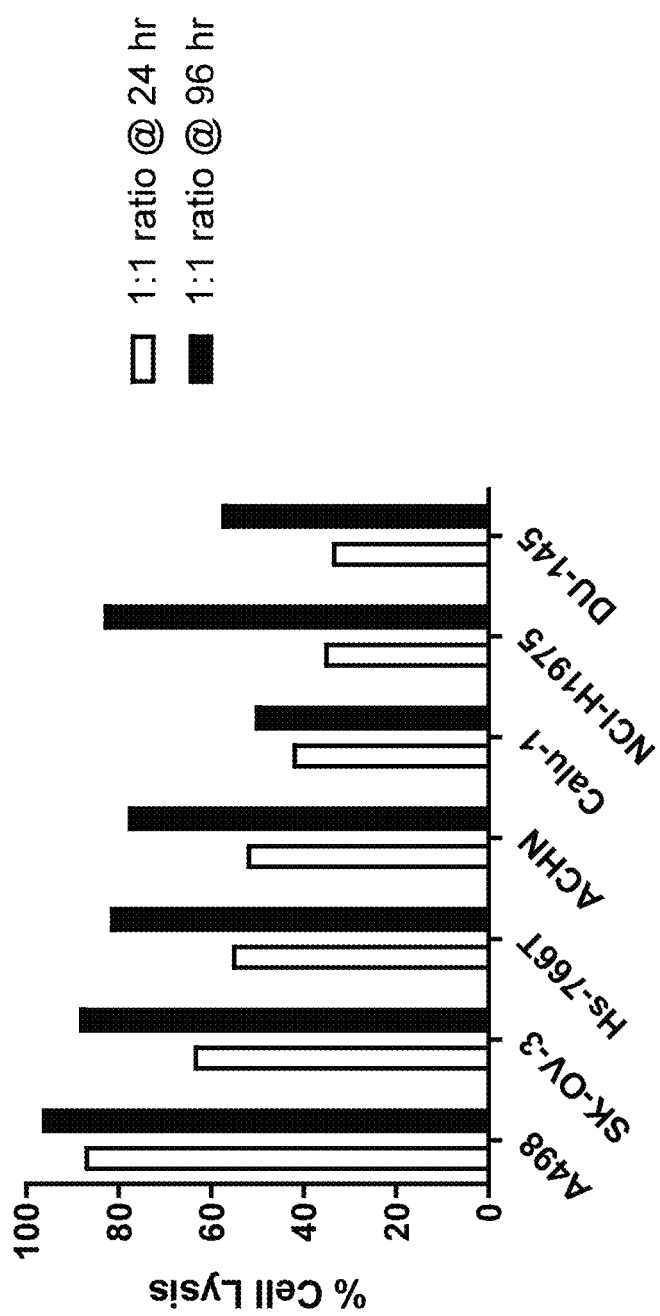
FIG. 40G includes a graph showing cell kill activity using the triple knockout TRAC$^-$/β2M$^-$/CD70$^-$/anti-CD70 CAR$^+$ T cells against solid tumor cell lines after a co-culture period of 24 hours or 96 hours.

Although ACHN cells were found to express moderate to low levels of CD70, they were surprisingly susceptible to killing by 3×KO (PD-1), CD70 CAR+ T cells, 3×KO (CD70), CD70 CAR+ T cells, and 4×KO CD70 CAR+ T cells (FIGS. 40C and 40D). This indicates that high CD70 expression is not a requirement for effective killing of a target cell by gene-edited T cells that express an anti-CD70 CAR. Additionally, given that the levels of CD70 expression on SNU-1, SK-OV-3, NCI-H1975 and HS-766T cell lines were found to be similar or higher than ACHN, it was expected that anti-CD70 CAR+ T cells would be especially efficient at killing these cancer cell types as well. Indeed, it was found that TRAC−/β2M−/PD-1−/CD70−/anti-CD70 CAR+ (4×KO, CD70 CAR+) and TRAC−/β2M−/CD70−/anti-CD70 CAR+ (3×KO (CD70), CD70 CAR+) exhibited surprisingly potent cell killing of numerous solid tumor cell lines after only 24 hours of co-culture (FIG. 40E shows killing by 4×KO CAR+ T cells and FIG. 40F shows killing by 3×KO CAR+ T cells). Both 3×KO, CD70 CAR+ and 4×KO, CD70 CAR+ T cells killed >60% of kidney, pancreatic, and ovarian tumor cells (A498, ACHN, SK-OV-3, and Hs-766T) at a 4:1 effector:target cell ratio and >50% at a 1:1 effector:target cell ratio. Cell killing of cancer cell lines that had medium to low CD70 expression (NCI-H1975, Calu-1 and DU 145) was still effective with >30% killing at an effector:target cell ratio of 4:1 within 24 hours of co-culture (FIGS. 40E and 40F). Longer exposure (i.e., 96 hours) to either 3×KO or 4×KO, CD70 CAR+ T cells resulted in an increase in cancer cell killing across all cell types, particularly for SKOV-3, Hs-766T, and NIC-H1975 cells wherein killing was >80% at an effector:target cell ratio of 1:1 (FIG. 40G).

SNU-1 Cell Kill by was Assessed by Visual Assessment.

Target cell killing following long exposure to CAR+ T cells was also assessed by microscopy for SNU-1 cancer cells. SNU-1 cells were plated at a density of 1 million cells per well in a 6 well plate and mixed at an effector:target ratio of 4:1 with 3×KO (CD70), anti-CD70 CAR+ T cells. The co-culture was incubated for six (6) days and the presence of viable cancer cells was assessed by microscope. All gastric carcinoma target cells (SNU-1) were eliminated in wells containing TRAC−/β2M−/CD70−/anti-CD70 CAR+ T cells, as compared to control wells, indicating cancer cells were completely eliminated by anti-CD70 CAR+ T cells with an extended co-culture.

The ability of anti-CD70 CAR+ T cells to selectively kill CD70-expressing cells was determined. A flow cytometry assay was designed to test killing of cancer cell suspension lines (e.g., K562, MM.1S and HuT78 cancer cells that are referred to as "target cells") by 3×KO (CD70) (TRAC−/B2M−/CD70−) anti-CD70 CAR+ T cells. Two of the target cell lines that were used were CD70-expressing cancer cells (e.g., MM.1S and HuT78), while a third that was used as negative control cancer cells lack CD70 expression (e.g., K562). The TRAC−/B2M−/CD70−/anti-CD70 CAR+ T cells were co-cultured with either the CD70-expressing MM.1S or HuT78 cell lines or the CD70-negative K562 cell line. The target cells were labeled with 5 μM efluor670 (eBiosciences), washed and seeded at a density of 50,000 target cells per well in a 96-well U-bottom plate. The target cells were co-cultured with TRAC−/B2M−/CD70− anti-CD70 CAR+ T cells at varying ratios (0.5:1, 1:1, 2:1 and 4:1 CAR+ T cells to target cells) and incubated overnight. Target cell killing was determined following a 24 hour co-culture. The cells were washed and 200 μL of media containing a 1:500 dilution of 5 mg/mL DAPI (Molecular Probes) (to enumerate dead/dying cells) was added to each well. Cells were then analyzed by flow cytometry and the amount of remaining live target cells was quantified.

Figure 40H:
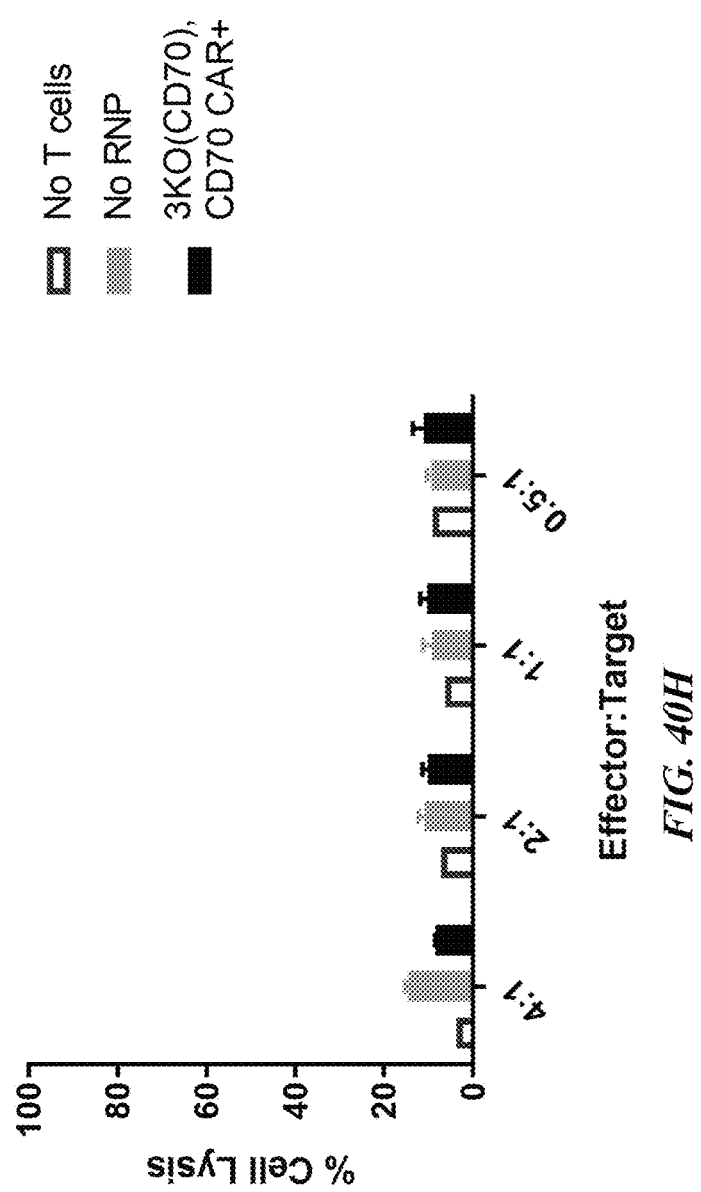
FIGS. 40H-40J include graphs showing cell kill activity using the triple knockout TRAC$^-$/β2M$^-$/CD70$^-$/anti-CD70 CAR$^+$ T cells (3KO (CD70), CD70 CAR+) against CD70-deficient chronic myelogenous leukemia (K562) cells (FIG. 40H), CD70-expressing multiple myeloma (MM.1S) cells (FIG. 40I), and CD70-expressing T cell lymphoma (HuT78) cells (FIG. 40J) at various effector:target ratios.
Figure 40I:
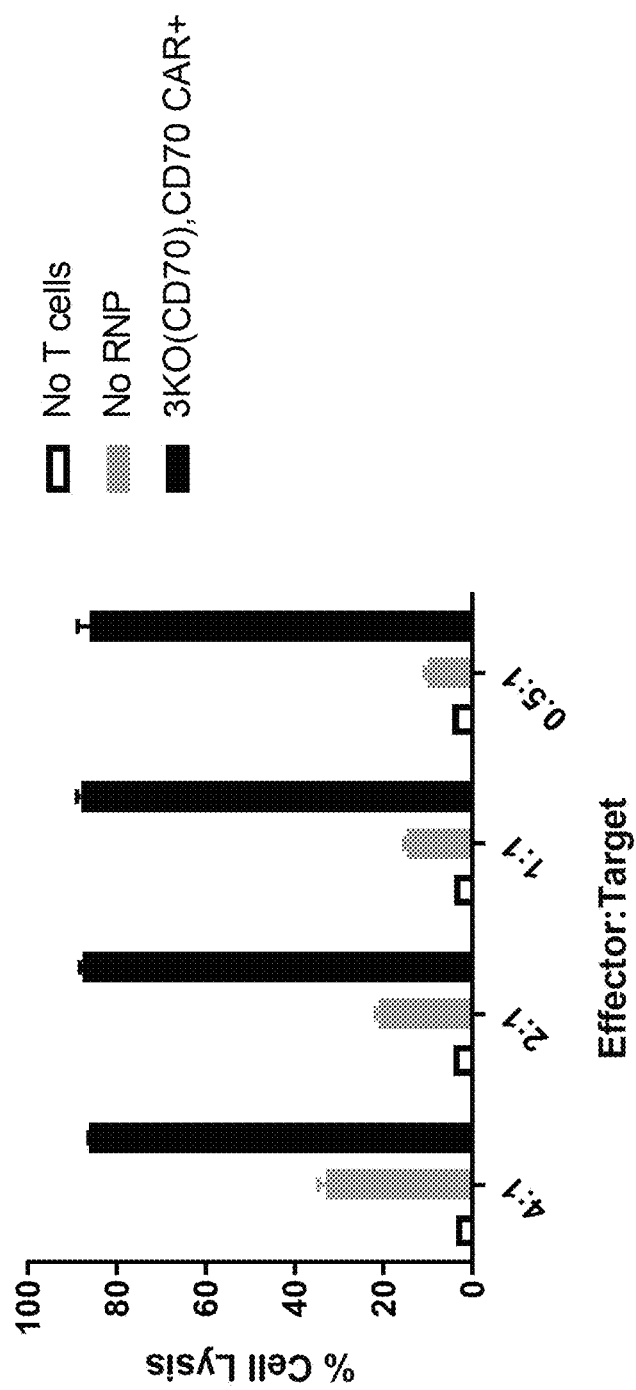
Figure 40J:
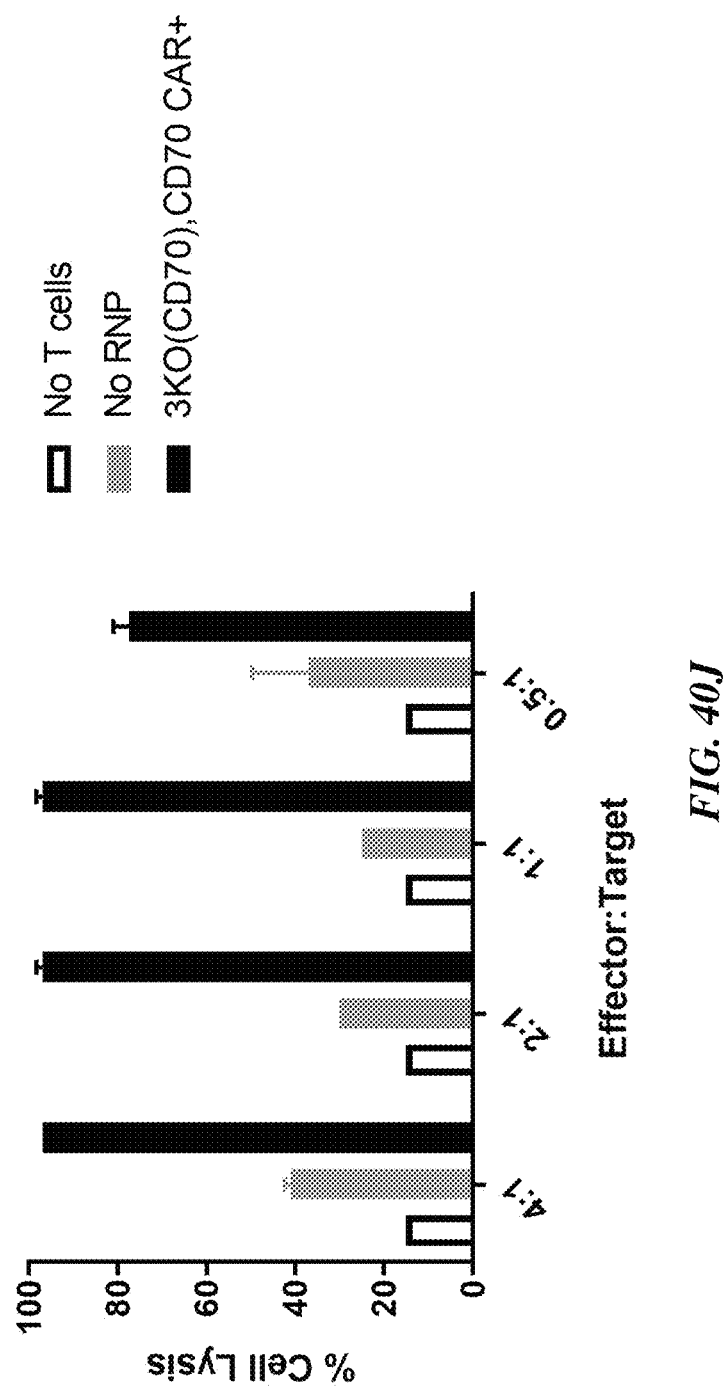

FIG. 40H, FIG. 40I, and FIG. 40J demonstrate selective target cell killing by TRAC−/B2M−/CD70− anti-CD70 CAR+ T cells. A 24 hour co-culture with 3×KO (CD70) CAR+ T cells resulted in nearly complete killing of T cell lymphoma cells (HuT78), even at a low CAR+ T cell to CD70-expressing target cell ratio of 0.5:1 (FIG. 40J). Likewise, a 24 hour co-culture resulted in nearly complete killing of multiple myeloma cells (MM.1S) at all CAR+ T cell to target cell ratios tested (FIG. 40I) Killing of target cells was found to be selective in that TRAC−/B2M−/anti-CD70 CAR+ T cells induced no killing of CD70-deficient K562 cells that was above the level of control samples (e.g., either cancer cells alone or co-culture with no RNP T cells), at any effector:target cell ratio tested (FIG. 40H).

Figure 41A:
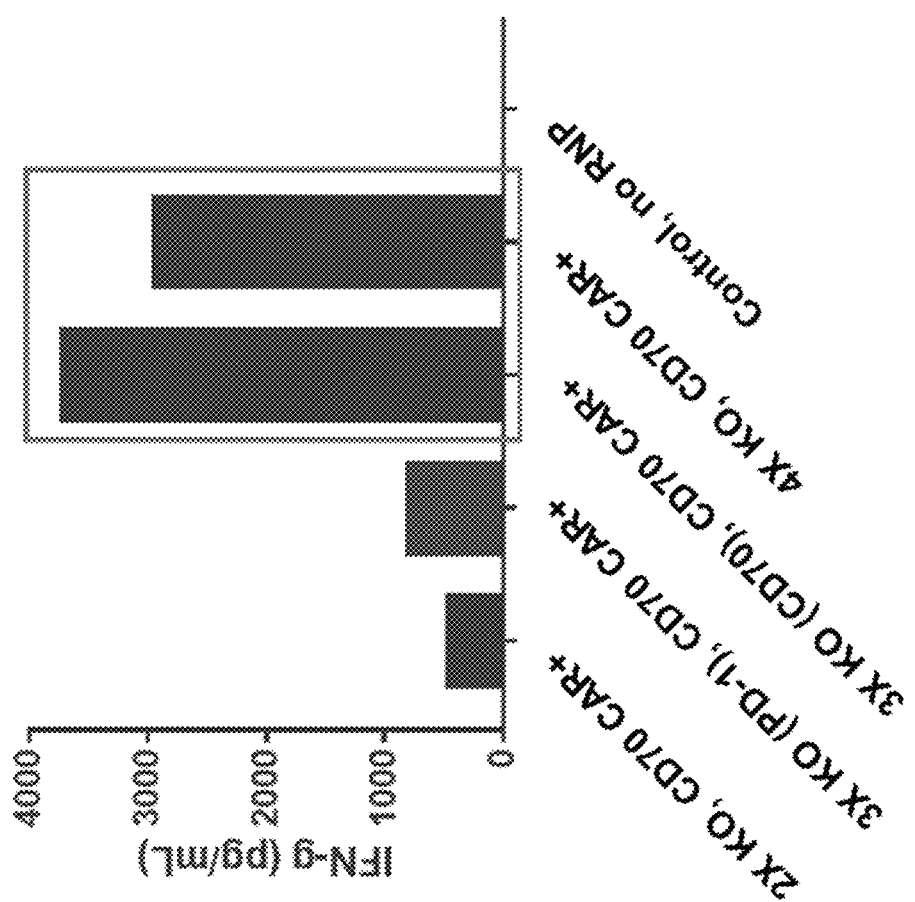
FIG. 41A and FIG. 41B include graphs showing that quadruple knockout TRAC$^-$/β2M$^-$/PD-1$^-$/CD70$^-$/anti- CD70 CAR+ T cells (4×KO, CD70 CAR+) and triple knockout TRAC$^-$/β2M$^-$/CD70$^-$/anti-CD70 CAR$^+$ T cells (3×KO (CD70), CD70 CAR+) secrete the highest levels of cytokines IFN-gamma (FIG. 41A) and IL-2 (FIG. 41B), relative to double knockout TRAC$^-$/β2M$^-$/anti-CD70 CAR$^+$ T cells (2×KO, CD70 CAR+) and triple knockout TRAC$^-$/β2M$^-$/PD-1$^-$/anti-CD70 CAR$^+$ T cells (3×KO (PD-1), CD70 CAR+). A CAR T cell:ACHN cell ratio of 0.25:1 was used.
Figure 41B:
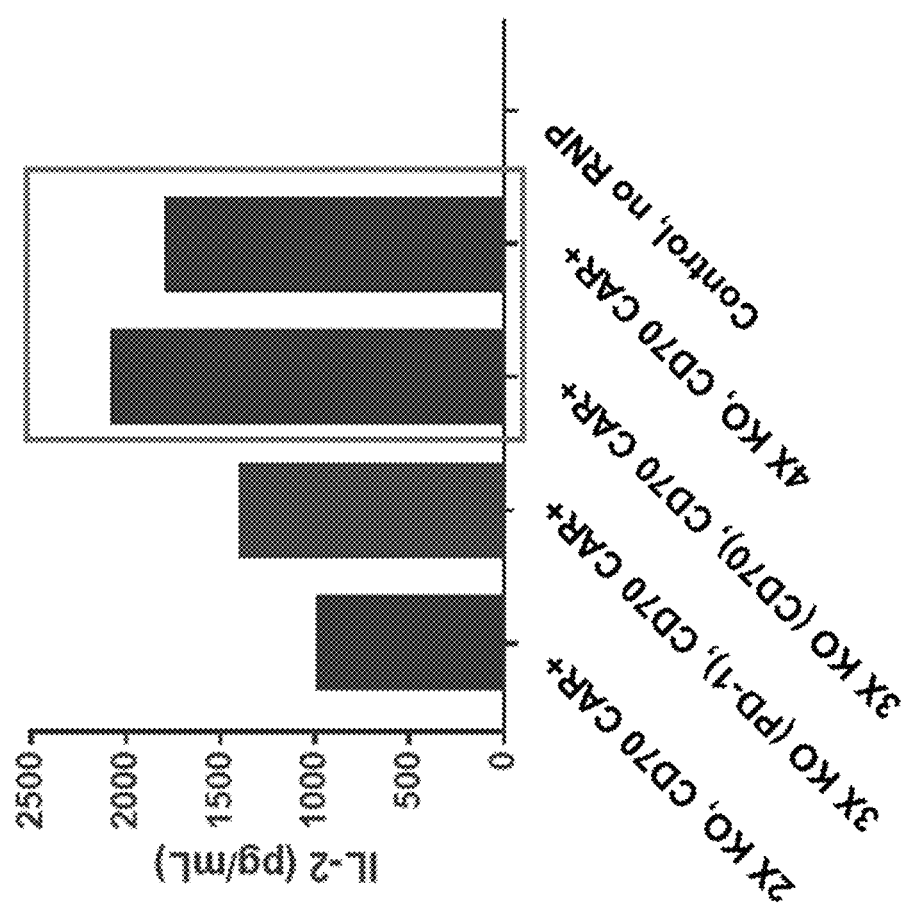

Cytokine Release Assay. A cytokine release assay was performed as described above. The ability of the double knockout, triple knockout, and quadruple knockout anti-CD70 CAR+ T cells to produce IL-2 and IFN-g when co-cultured in the presence of ACHN cells following 24-hour co-incubation at a ratio (CAR T cell:ACHN target cell) of 0.25:1 was assessed using an ELISA assay. IL-2 and IFN-g from supernatants of cell co-cultures were measured. The triple knockout TRAC−/β2M−/CD70−/anti-CD70 CAR+ T cells and quadruple knockout TRAC−/β2M−/PD-1−/CD70−/anti-CD70 CAR+ T cells secreted the highest levels of IFN-g (FIG. 41) and IL-2 (FIG. 41B) when cultured with ACHN cells. In conclusion, knockout of CD70 or of both PD-1 and CD70 together improves the cell killing ability of the anti-CD70 CAR+ cells in ACHN cells.

Example 12. Efficacy of CD70 KO in Anti-CD70 CAR+ T Cells: The Tumor Xenograft Model in NOG Mice Treatment in the Ovarian Tumor Model The ability of T cells expressing an anti-CD70 CAR to eliminate ovarian adenocarcinoma cells that express moderate levels of CD70 was evaluated in vivo using a subcutaneous ovarian carcinoma (SKOV-3) tumor xenograft model in mice.

CRISPR/Cas9 and AAV6 were used as above (see for example, Example 3) to generate human T cells that lack expression of the TCR, β2M, CD70 with concomitant expression from the TRAC locus using a CAR construct targeting CD70 (SEQ ID NO: 45; SEQ ID NO: 46. In this example activated T cells were first electroporated with 3 distinct Cas9:sgRNA RNP complexes containing sgRNAs targeting TRAC (SEQ ID NO: 40), β2M (SEQ ID NO: 41), and CD70 (SEQ ID NO: 36 or 37). The DNA double stranded break at the TRAC locus was repaired by homology directed repair with an AAV6-delivered DNA template comprising a donor template (SEQ ID NO: 44; SEQ ID NO: 45) (encoding anti-CD70 CAR comprising the amino acid sequence of SEQ ID NO: 45) containing right and left homology arms to the TRAC locus flanking a chimeric antigen receptor cassette (−/+ regulatory elements for gene expression).

The resulting modified T cells are 3×KO (TRAC−/β2M−/CD70−) anti-CD70 CAR+ T cells. The ability of these anti-CD70 CAR+ T cells to ameliorate disease caused by a CD70+ ovarian carcinoma cell line was evaluated in NOG mice using methods employed by Translational Drug Development, LLC (Scottsdale, Ariz.). In brief, 12 5-8 week old female, CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. Mice received a subcutaneous inoculation of 5×10$^6$ SKOV-3 ovarian carcinoma cells/mouse in the right hind flank. When mean tumor size reached 25-75 mm$^3$ (target of ~50 mm$^3$), the mice were further divided into two treatment groups as shown in Table 23. On Day 1, treatment group 2 received a single 200 μl intravenous dose of anti-CD70CAR+ T cells according to Table 23.

TABLE 23

Treatment groups

| Group | CAR-T | SKOV-3 cells | T cell treatment (i.v.) | N |
|---|---|---|---|---|
| 1 | None | 5 × 10$^6$ cells/mouse | None | 5 |
| 2 | 3X KO (CD70,) anti-CD70 CAR+ T cells | 5 × 10$^6$ cells/mouse | 1 × 10$^7$ cells/mouse | 5 |

Figure 42A:
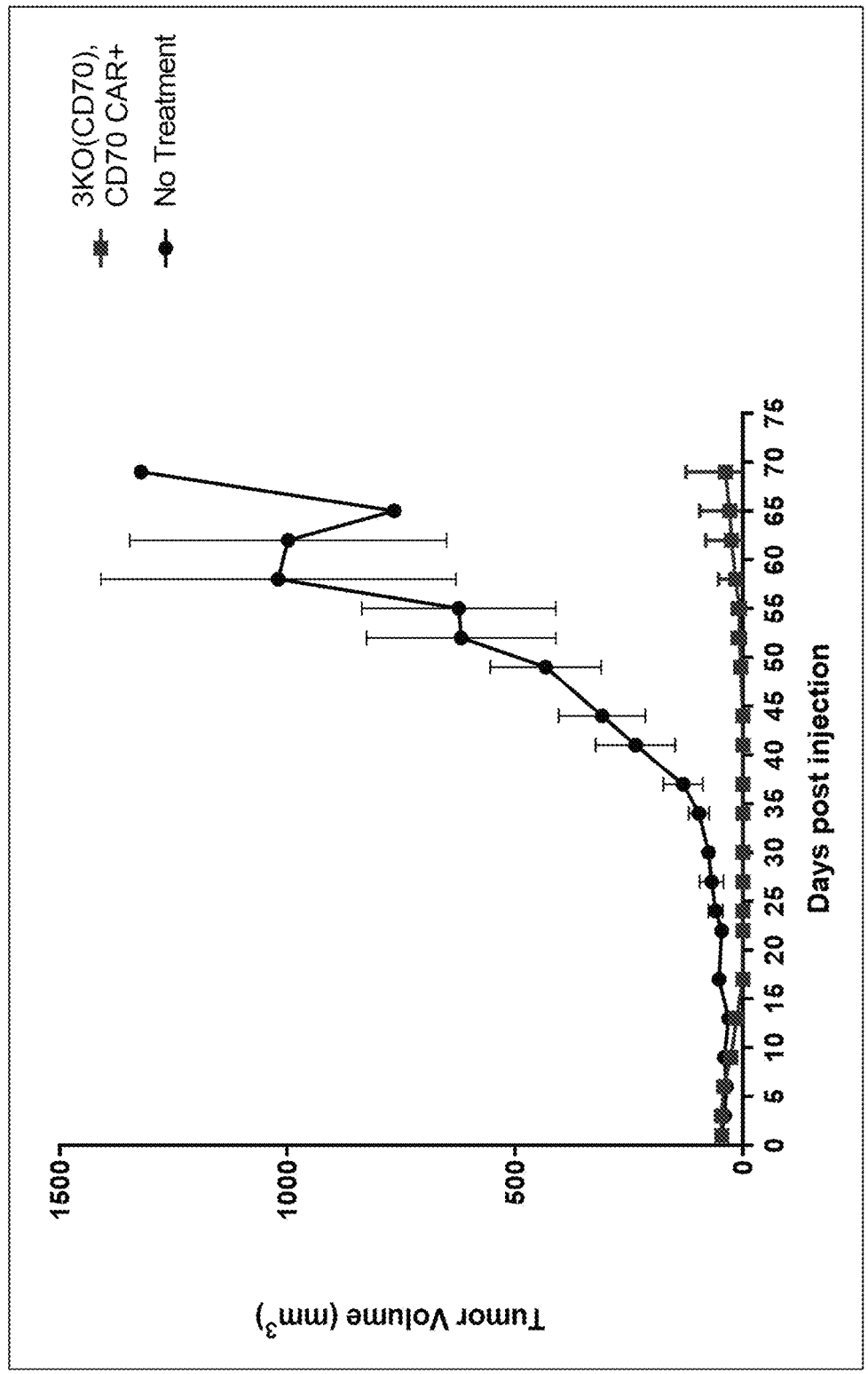
FIG. 42A includes a graph showing results from an experiment designed to assess tumor volume reduction in a human ovarian tumor xenograft model (e.g., SKOV-3 tumor cells) exposed to 3×KO (TRAC−/B2M−/CD70−) anti-CD70 CAR T cells.

Tumor volume was measured 2 times weekly from day of treatment initiation. By day 9 post-injection, tumors treated with anti-CD70 CART cells began to show a decrease in tumor volume relative to tumors in untreated animals. By day 17 post-injection, CD70+ ovarian cancer tumors in mice treated with anti-CD70 CAR T cells were completely eliminated. This complete regression of tumor growth was sustained in treated animals through day 44 post-injection, whereupon 4 out of 5 mice treated with anti-CD70 CART cells remained tumor-free until the end-of-observation (day 69) (FIG. 42A). These data demonstrate that 3×KO (TRAC−/β2M−/CD70−) anti-CD70 CAR+ cells are highly potent in vivo for treating human ovarian tumors.

Treatment in the Non-Small Cell Lung Carcinoma (NSCLC) Tumor Model

The ability of T cells expressing a CD70 CAR to eliminate lung adenocarcinma cells that express moderate levels of CD70 was evaluated in in vivo using a subcutaneous lung carcinoma (NCI-H1975) tumor xenograft model in mice.

CRISPR/Cas9 and AAV6 were used as above (see for example, Example 3) to create human T cells that lack expression of the TCR, β2M, CD70 with concomitant expression from the TRAC locus using a CAR construct targeting CD70 (SEQ ID NO: 43; SEQ ID NO: 44). In this example activated T cells were first electroporated with 3 distinct Cas9:sgRNA RNP complexes containing sgRNAs targeting TRAC (SEQ ID NO: 40), β2M (SEQ ID NO: 41), and CD70 (SEQ ID NO: 36 or 37). The DNA double stranded break at the TRAC locus was repaired by homology directed repair with an AAV6-delivered DNA template (SEQ ID NO: 43; SEQ ID NO: 44) (encoding anti-CD70 CAR comprising the amino acid sequence of SEQ ID NO: 45) containing right and left homology arms to the TRAC locus flanking a chimeric antigen receptor cassette (−/+ regulatory elements for gene expression).

The resulting modified T cells are 3×KO (TRAC−/β2M−/CD70−) anti-CD70 CAR+ (with 41BB costimulatory domain) T cells. The ability of these anti-CD70 CAR+ T cells to ameliorate disease caused by a CD70+ lung carcinoma cell line was evaluated in NOG mice using methods employed by Translational Drug Development, LLC (Scottsdale, Ariz.). In brief, 12, 5-8 week old female, CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. Mice received a subcutaneous inoculation of 5×10$^6$ NCI-H1975 lung carcinoma cells/mouse in the right hind flank. When mean tumor size reached 25-75 mm$^3$ (target of ~50 mm$^3$), the mice were further divided into 2 treatment groups as shown in Table 24. On Day 1, treatment group 2 received a single 200 µl intravenous dose of anti-CD70CAR+ T cells according to Table 24.

TABLE 24

Treatment groups

| Group | CAR-T | NCI-H1975 cells | T cell treatment (i.v.) | N |
|---|---|---|---|---|
| 1 | None | 5 × 10$^6$ cells/mouse | None | 5 |
| 2 | 3X KO (CD70,) anti-CD70 CAR+ T cells | 5 × 10$^6$ cells/mouse | 1 × 10$^7$ cells/mouse | 5 |

Figure 42B:
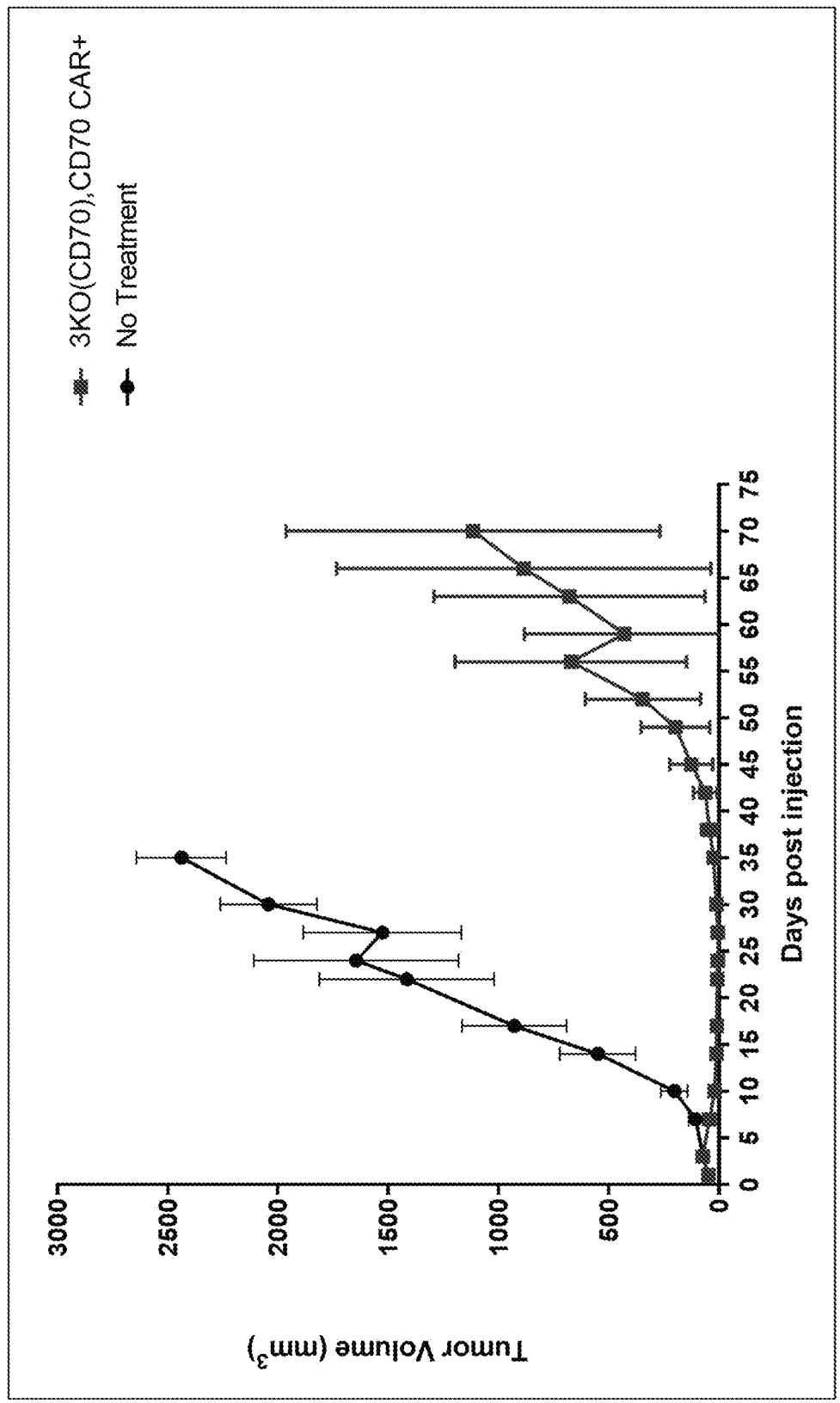
FIG. 42B includes a graph showing results from an experiment designed to assess tumor volume reduction in a human non-small cell lung tumor xenograft model (e.g., NCI-H1975 tumor cells) exposed to 3×KO (TRAC−/B2M−/CD70−) anti-CD70 CAR T cells.

Tumor volume was measured 2 times weekly from day of treatment initiation. By day 12 post-injection, tumors treated with anti-CD70 CAR T cells began to show a decrease in tumor volume relative to tumors in untreated animals. This complete regression of tumors in treated animals continue through day 33 post injection. Treatment with anti-CD70 CAR T cells resulted in potent activity against established H1975 lung cancer xenografts through 40 days post injection (tumor regrowth was suppressed in all mice up to day 40 with tumor size<100 mm$^3$), whereupon tumors began to grow. (FIG. 42B). These data demonstrate that 3×KO (TRAC−/β2M−/CD70−) anti-CD70 CAR+ cells have potent activity against human CD70+ lung cancer tumors in vivo.

Treatment in the Pancreatic Tumor Model

The ability of T cells expressing a CD70 CAR to eliminate pancreatic carcinoma cells that express moderate levels of CD70 was evaluated in in vivo using a subcutaneous pancreatic (Hs 766T) tumor xenograft model in mice.

CRISPR/Cas9 and AAV6 were used as above (see for example, Example 3) to create human T cells that lack expression of the TCR, β2M, CD70 with concomitant expression from the TRAC locus using a CAR construct targeting CD70 (SEQ ID NO: 43; SEQ ID NO: 44). In this example activated T cells were first electroporated with 3 distinct Cas9:sgRNA RNP complexes containing sgRNAs targeting TRAC (SEQ ID NO: 40), β2M (SEQ ID NO: 41), and CD70 (SEQ ID NO: 36 or 37). The DNA double stranded break at the TRAC locus was repaired by homology directed repair with an AAV6-delivered DNA template (SEQ ID NO: 43; SEQ ID NO: 44) (encoding anti-CD70 CAR comprising the amino acid sequence of SEQ ID NO: 45) containing right and left homology arms to the TRAC locus flanking a chimeric antigen receptor cassette (−/+ regulatory elements for gene expression).

The resulting modified T cells are 3×KO (TRAC−/β2M−/CD70−) anti-CD70 CAR+ T cells. The ability of these anti-CD70 CAR+ T cells to ameliorate disease caused by a CD70+ pancreatic carcinoma cell line was evaluated in NOG mice using methods employed by Translational Drug Development, LLC (Scottsdale, Ariz.). In brief, 12, 5-8 week old female, CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. Mice received a subcutaneous inoculation of 5×10$^6$ Hs766T pancreatic carcinoma cells in the right hind flank. When mean tumor size reached 25-75 mm$^3$ (target of ~50 mm$^3$), the mice were further divided into 2 treatment groups as shown in Table 25. On Day 1, treatment group 2 received a single 200 µl intravenous dose of anti-CD70 CAR+ T cells according to Table 25.

TABLE 25

Treatment groups

| Group | CAR-T | Hs766T cells | T cell treatment (i.v.) | N |
|---|---|---|---|---|
| 1 | None | 5 × 10$^6$ cells/mouse | None | 5 |
| 2 | 3X KO (CD70,) anti-CD70 CAR+ T cells | 5 × 10$^6$ cells/mouse | 1 × 10$^7$ cells/mouse | 5 |

Figure 42C:
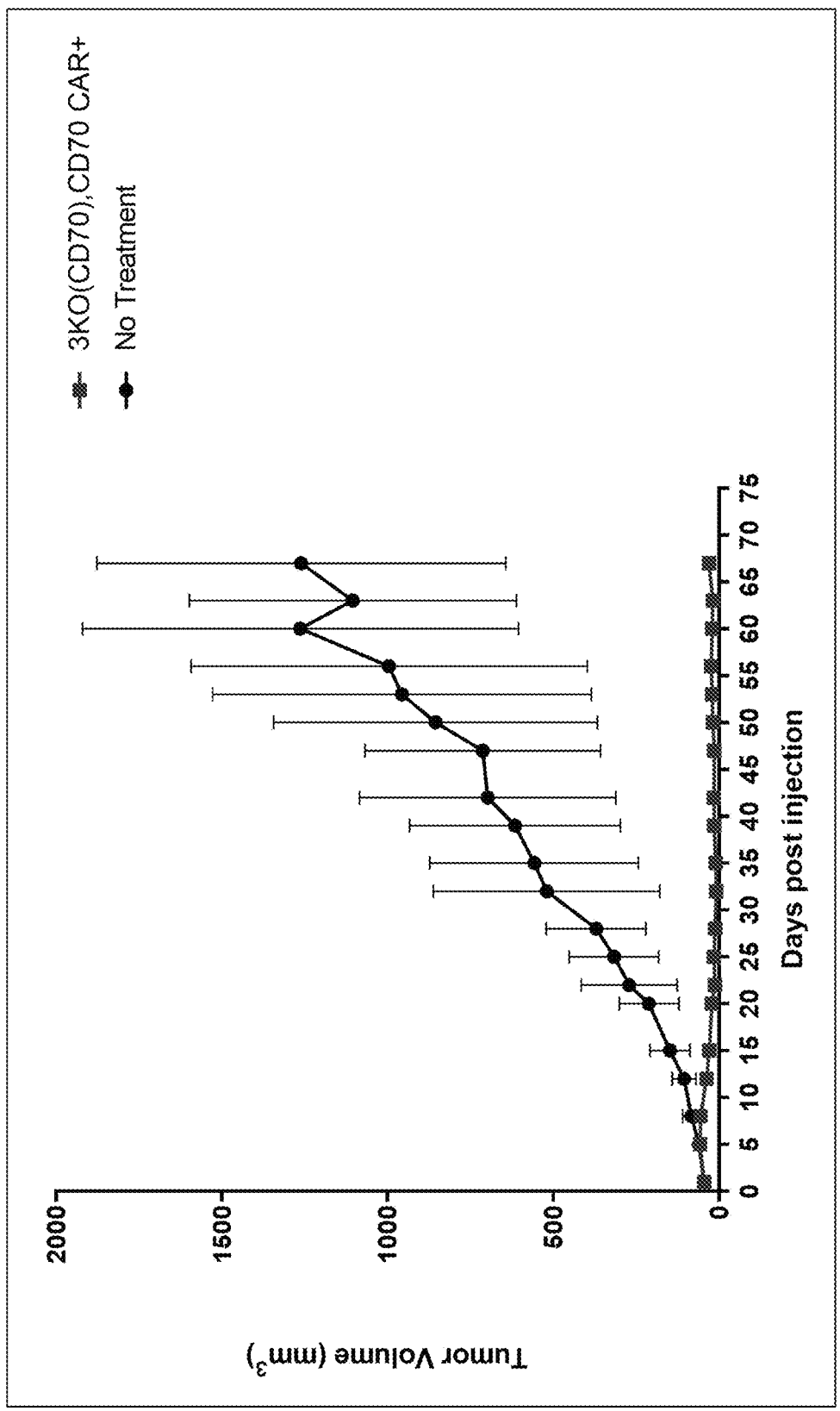
FIG. 42C includes a graph showing results from an experiment designed to assess tumor volume reduction in a human pancreatic tumor xenograft model (e.g., Hs766T tumor cells) exposed to 3×KO (TRAC−/B2M−/CD70−) anti-CD70 CAR T cells.
Figure 42D:
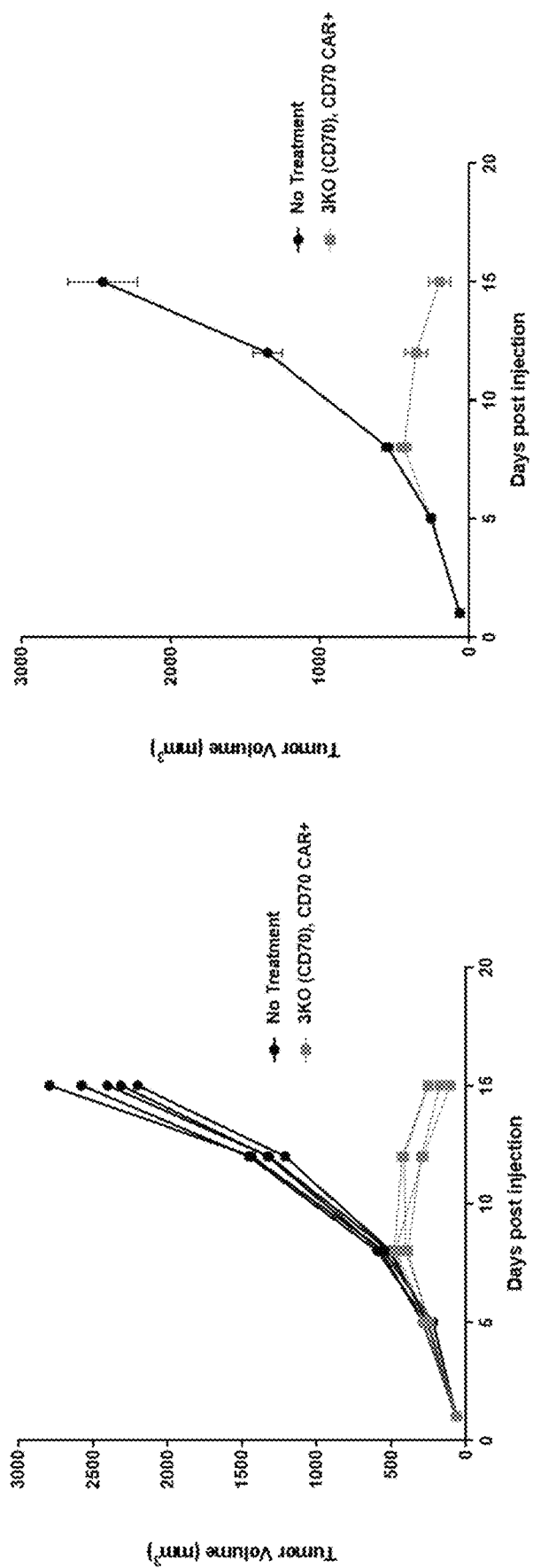
FIG. 42D includes graphs showing results from an experiment designed to assess tumor volume reduction in a human T-cell lymphoma xenograft model (e.g., HuT78 tumor cells) exposed to 3×KO (TRAC−/B2M−/CD70−) anti-CD70 CAR T cells. Tumor volumes of individual mice (left) and mean tumor volumes (right) are shown.

Tumor volume was measured 2 times weekly from day of treatment initiation. By Day 15 post-injection, tumors treated with anti-CD70 CAR T cells began to show a decrease in tumor volume in all treated mice. Treatment with anti-CD70 CAR+ T cells effectively reduced the size of the CD70+ pancreatic cancer tumors, in all mice tested (<37 mm$^3$) with no evidence of further growth for the duration of the study (through Day 67) (FIG. 42C). These data demonstrate that 3×KO (TRAC−/β2M−/CD70−) anti-CD70 CAR+ cells induce regression of human CD70+ pancreatic cancer tumors in vivo, with potent activity against established Hs766T pancreatic cancer xenografts and durable responses beyond 60 days following treatment initiation.

Treatment in the Cutaneous T-Cell Lymphoma Tumor Xenograft Model

The ability of T cells expressing an anti-CD70 CAR to eliminate T cell lymphoma was evaluated in in vivo using a subcutaneous T-cell lymphoma (Hu T78) tumor xenograft model in mice.

CRISPR/Cas9 and AAV6 were used as above (see for example, Example 3) to create human T cells that lack expression of the TCR, β2M, CD70 with concomitant expression from the TRAC locus using a CAR construct targeting CD70 (SEQ ID NO: 43; SEQ ID NO: 44). In this example activated T cells were first electroporated with 3 distinct Cas9:sgRNA RNP complexes containing sgRNAs targeting TRAC (SEQ ID NO: 40), β2M (SEQ ID NO: 41), and CD70 (SEQ ID NO: 36 or 37). The DNA double stranded break at the TRAC locus was repaired by homology directed repair with an AAV6-delivered DNA template (SEQ ID NO: 43; SEQ ID NO: 44) (encoding anti-CD70 CAR comprising the amino acid sequence of SEQ ID NO: 45) containing right and left homology arms to the TRAC locus flanking a chimeric antigen receptor cassette (−/+ regulatory elements for gene expression).

The resulting modified T cells are 3×KO (TRAC−/β2M−/CD70−) anti-CD70 CAR+ T cells. The ability of these anti-CD70 CAR+ T cells to ameliorate disease caused by a CD70+ T-cell lymphoma cell line was evaluated in NOG mice using methods employed by Translational Drug Development, LLC (Scottsdale, Ariz.). In brief, 12, 5-8 week old female, CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. Mice received a subcutaneous inoculation of 3×10$^6$ HuT78 T-cell lymphoma cells in the right hind flank. When mean tumor size reached 25-75 mm$^3$ (target of ~50 mm$^3$), the mice were further divided into 2 treatment groups as shown in Table 26. On Day 1, treatment group 2 received a single 200 µl intravenous dose of anti-CD70 CAR+ T cells according to Table 26.

TABLE 26.

| | Treatment groups | | | |
|---|---|---|---|---|
| Group | CAR-T | HuT78 cells | T cell treatment (i.v.) | N |
| 1 | None | 5 × 10$^6$ cells/mouse | None | 5 |
| 2 | 3X KO (CD70,) anti-CD70 CAR+ Tcells | 5 × 10$^6$ cells/mouse | 1 × 10$^7$ cells/mouse | 4 |

Tumor volume was measured 2 times weekly from day of treatment initiation. By Day 12 post-injection, tumors treated with anti-CD70 CAR T cells began to show a decrease in tumor volume in all treated mice. Treatment with anti-CD70 CAR+ T cells effectively reduced the size of the CD70+ T-cell lymphoma tumors, in all mice tested at Day 15 (FIG. 42C). These data demonstrate that 3×KO (TRAC−/β2M−/CD70−) anti-CD70 CAR+ cells induce regression of human CD70+ T-cell lymphoma tumors in vivo, with potent activity against established HuT78 T-cell lymphoma xenografts.

Summary of Sequences

| SEQ ID NO | Description | Sequence |
|---|---|---|
| 1 | TRAC Indel | AAGAGCAACAAATCTGACT |
| 2 | TRAC Indel | AAGAGCAACAGTGCTGTGCCTGGAGCAACAAATCTGACTAAGAGCAACAAATCTGACT |
| 3 | TRAC Indel | AAGAGCAACAGTGCTGGAGCAACAAATCTGACTAAGAGCAACAAATCTGACT |
| 4 | TRAC Indel | AAGAGCAACAGTGCCTGGAGCAACAAATCTGACTAAGAGCAACAAATCTGACT |
| 5 | TRAC Indel | AAGAGCAACAGTGCTGACTAAGAGCAACAAATCTGACT |
| 6 | TRAC Indel | AAGAGCAACAGTGCTGTGGGCCTGGAGCAACAAATCTGACTAAGAGCAACAAATCTGACT |
| 7 | TRAC Indel | AAGAGCAACAGTGCTGGCCTGGAGCAACAAATCTGACTAAGAGCAACAAATCTGACT |
| 8 | TRAC Indel | AAGAGCAACAGTGCTGTGTGCCTGGAGCAACAAATCTGACTAAGAGCAACAAATCTGACT |
| 9 | B2M Indel | CGTGGCCTTAGCTGTGCTCGCGCTACTCTCTCTTTCTGCCTGGAGGCTATCCAGCGTGAGTCTCTCCTACCCTCCCGCT |
| 10 | B2M Indel | CGTGGCCTTAGCTGTGCTCGCGCTACTCTCTCTTTCGCCTGGAGGCTATCCAGCGTGAGTCTCTCCTACCCTCCCGCT |
| 11 | B2M Indel | CGTGGCCTTAGCTGTGCTCGCGCTACTCTCTCTTTCTGGAGGCTATCCAGCGTGAGTCTCTCCTACCCTCCCGCT |
| 12 | B2M Indel | CGTGGCCTTAGCTGTGCTCGCGCTACTCTCTCTTTCTGGATAGCCTGGAGGCTATCCAGCGTGAGTCTCTCCTACCCTCCCGCT |
| 13 | B2M Indel | CGTGGCCTTAGCTGTGCTCGCGCTATCCAGCGTGAGTCTCTCCTACCCTCCCGCT |
| 14 | B2M Indel | CGTGGCCTTAGCTGTGCTCGCGCTACTCTCTCTTTCTGTGGCCTGGAGGCTATCCAGCGTGAGTCTCTCCTACCCTCCCGCT |
| 15 | sgRNA | nnnnnnnnnnnnnnnnnnnnguuuuagagcuagaaauagcaaguuaaaauaaggcuaguccguuaucaacuugaaaaaguggcaccgagucggugcuuuu |
| 16 | sgRNA | nnnnnnnnnnnnnnnnnnnnguuuuagagcuagaaauagcaaguuaaaauaaggcuaguccguuaucaacuugaaaaaguggcaccgagucggugc |
| 17 | sgRNA | n$_{(17-30)}$guuuuagagcuagaaauagcaaguuaaaauaaggcuagucguuaucaacuugaaaaaguggcaccgagucggugcu$_{(1-8)}$ |

Summary of Sequences

| SEQ ID NO | Description | Sequence |
|---|---|---|
| 18 | 4-1BB nucleotide sequence | AAACGGGGCAGAAAGAAACTCCTGTATATATTCAAACAACCATTTA TGAGACCAGTACAAACTACTCAAGAGGAAGATGGCTGTAGCTGCCG ATTTCCAGAAGAAGAAGAAGGAGGATGTGAACTG |
| 19 | 4-1BB amino acid sequence | KRGRKKLLYIFKQPFMRPVQTTQEEDGCSCRFPEEEEGGCEL |
| 20 | CD28 amino acid sequence | SKRSRLLHSDYMNMTPRRPGPTRKHYQPYAPPRDFAAYRS |
| 21 | CD3-z nucleotide sequence | CGAGTGAAGTTTTCCCGAAGCGCAGACGCTCCGGCATATCAGCAAG GACAGAATCAGCTGTATAACGAACTGAATTTGGGACGCCGCGAGGA GTATGACGTGCTTGATAAACGCCGGGGGAGAGACCCGGAAATGGGG GGTAAACCCCGAAGAAAGAATCCCCAAGAAGGACTCTACAATGAAC TCCAGAAGGATAAGATGGCGGAGGCCTACTCAGAAATAGGTATGAA GGGCGAACGACGACGGGGAAAAGGTCACGATGGCCTCTACCAAGGG TTGAGTACGGCAACCAAAGATACGTACGATGCACTGCATATGCAGG CCCTGCCTCCCAGA |
| 22 | CD3-z amino acid sequence | RVKFSRSADAPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR |
| 23 | CD70 sgRNA (E1_T1) | UCACCAAGCCCGCGACCAAUguuuuagagcuagaaauagcaaguua aaauaaggcuaguccguuaucaacuugaaaaaguggcaccgagucg gugcUUUU |
| 24 | CD70 sgRNA (E1_T3) | AUCACCAAGCCCGCGACCAAguuuuagagcuagaaauagcaaguua aaauaaggcuaguccguuaucaacuugaaaaaguggcaccgagucg gugcUUUU |
| 25 | CD70 sgRNA (E1_T4) | CGGUGCGGCGCAGGCCCUAUguuuuagagcuagaaauagcaaguua aaauaaggcuaguccguuaucaacuugaaaaaguggcaccgagucg gugcUUUU |
| 26 | CD70 sgRNA (E1_T7) | GCUUUGGUCCCAUUGGUCGCguuuuagagcuagaaauagcaaguua aaauaaggcuaguccguuaucaacuugaaaaaguggcaccgagucg gugcUUUU |
| 27 | CD70 sgRNA (E1_T8) | GCCCGCAGGACGCACCCAUAguuuuagagcuagaaauagcaaguua aaauaaggcuaguccguuaucaacuugaaaaaguggcaccgagucg gugcUUUU |
| 28 | CD70 sgRNA (E1_T10) | GUGCAUCCAGCGCUUCGCACguuuuagagcuagaaauagcaaguua aaauaaggcuaguccguuaucaacuugaaaaaguggcaccgagucg gugcUUUU |
| 29 | CD70 sgRNA (E3_T1) | CAGCUACGUAUCCAUCGUGAguuuuagagcuagaaauagcaaguua aaauaaggcuaguccguuaucaacuugaaaaaguggcaccgagucg gugcUUUU |
| 30 | TRAC sgRNA | AGAGCAACAGUGCUGUGGCCguuuuagagcuagaaauagcaaguua aaauaaggcuaguccguuaucaacuugaaaaaguggcaccgagucg gugcUUUU |
| 31 | β2M sgRNA | GCUACUCUCUCUUUCUGGCCguuuuagagcuagaaauagcaaguua aaauaaggcuaguccguuaucaacuugaaaaaguggcaccgagucg gugcUUUU |
| 32 | PD-1 sgRNA | CUGCAGCUUCUCCAACACAUguuuuagagcuagaaauagcaaguua aaauaaggcuaguccguuaucaacuugaaaaaguggcaccgagucg gugcUUUU |
| 33 | CD70 sgRNA (E1_T1) | U*C*A*CCAAGCCCGCGACCAAUguuuuagagcuagaaauagcaag uuaaaauaaggcuaguccguuaucaacuugaaaaaguggcaccgag ucggugcU*U*U*U |
| 34 | CD70 sgRNA (E1_T3) | A*U*C*ACCAAGCCCGCGACCAAguuuuagagcuagaaauagcaag uuaaaauaaggcuaguccguuaucaacuugaaaaaguggcaccgag ucggugcU*U*U*U |

Summary of Sequences

| SEQ ID NO | Description | Sequence |
|---|---|---|
| 35 | CD70 sgRNA (E1_T4) | C*G*G*UGCGGCGCAGGCCCUAUguuuuagagcuagaaauagcaaguuaaaauaaggcuaguccguuaucaacuugaaaaaguggcaccgagucggugcU*U*U*U |
| 36 | CD70 sgRNA (E1_T7) | G*C*U*UUGGUCCCAUUGGUCGCguuuuagagcuagaaauagcaaguuaaaauaaggcuaguccguuaucaacuugaaaaaguggcaccgagucggugcU*U*U*U |
| 37 | CD70 sgRNA (E1_T8) | G*C*C*CGCAGGACGCACCCAUguuuuagagcuagaaauagcaaguuaaaauaaggcuaguccguuaucaacuugaaaaaguggcaccgagucggugcU*U*U*U |
| 38 | CD70 sgRNA (E1_T10) | G*U*G*CAUCCAGCGCUUCGCACguuuuagagcuagaaauagcaaguuaaaauaaggcuaguccguuaucaacuugaaaaaguggcaccgagucggugcU*U*U*U |
| 39 | CD70 sgRNA (E3_T1) | C*A*G*CUACGUAUCCAUCGUGAguuuuagagcuagaaauagcaaguuaaaauaaggcuaguccguuaucaacuugaaaaaguggcaccgagucggugcU*U*U*U |
| 40 | TRAC sgRNA | A*G*A*GCAACAGUGCUGUGGCCguuuuagagcuagaaauagcaaguuaaaauaaggcuaguccguuaucaacuugaaaaaguggcaccgagucggugcU*U*U*U |
| 41 | 132M sgRNA | G*C*U*ACUCUCUCUUUCUGGCCguuuuagagcuagaaauagcaaguuaaaauaaggcuaguccguuaucaacuugaaaaaguggcaccgagucggugcU*U*U*U |
| 42 | PD-1 sgRNA | C*U*G*CAGCUUCUCCAACACAUguuuuagagcuagaaauagcaaguuaaaauaaggcuaguccguuaucaacuugaaaaaguggcaccgagucggugcU*U*U*U |
| 43 | CD70 rAAV (CD70B scFV) with 41BB) | CCTGCAGGCAGCTGCGCGTCGCTCGCTCACTGAGGCCGCCCGGGCGTCGGGCGACCTTTGGTCGCCCGGCCTCAGTGAGCGAGCGAGCGCGCAGAGAGGGAGTGGCCAACTCCATCACTAGGGGTTCCTGCGGCCGCACGCGTGAGATGTAAGGAGCTGCTGTGACTTGCTCAAGGCCTTATATCGAGTAAACGGTAGTGCTGGGGCTTAGACGCAGGTGTTCTGATTTATAGTTCAAAACCTCTATCAATGAGAGAGCAATCTCCTGGTAATGTGATAGATTTCCCAACTTAATGCCAACATACCATAAACCTCCCATTCTGCTAATGCCCAGCCTAAGTTGGGGAGACCACTCCAGATTCCAAGATGTACAGTTTGCTTTGCTGGGCCTTTTTCCCATGCCTGCCTTTACTCTGCCAGAGTTATATTGCTGGGGTTTTGAAGAAGATCCTATTAAATAAAAGAATAAGCAGTATTATTAAGTAGCCCTGCATTTCAGGTTTCCTTGAGTGGCAGGCCAGGCCTGGCCGTGAACGTTCACTGAAATCATGGCCTCTTGGCCAAGATTGATAGCTTGTGCCTGTCCCTGAGTCCCAGTCCATCACGAGCAGCTGGTTTCTAAGATGCTATTTCCCGTATAAAGCATGAGACCGTGACTTGCCAGCCCCACAGAGCCCCGCCCTTGTCCATCACTGGCATCTGGACTCCAGCCTGGGTTGGGGCAAAGAGGGAAATGAGATCATGTCCTAACCCTGATCCTCTTGTCCCACAGATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAGGCTCCGGTGCCCGTCAGTGGGCAGAGCGCACATCGCCCACAGTCCCCGAGAAGTTGGGGGGAGGGGTCGGCAATTGAACCGGTGCCTAGAGAAGGTGGCGCGGGGTAAACTGGGAAAGTGATGTCGTGTACTGGCTCCGCCTTTTTCCCGAGGGTGGGGGAGAACCGTATATAAGTGCAGTAGTCGCCGTGAACGTTCTTTTTCGCAACGGGTTTGCCGCCAGAACACAGGTAAGTGCCGTGTGTGGTTCCCGCGGGCCTGGCCTCTTTACGGGTTATGGCCCTTGCGTGCCTTGAATTACTTCCACTGGCTGCAGTACGTGATTCTTGATCCCGAGCTTCGGGTTGGAAGTGGGTGGGAGAGTTCGAGGCCTTGCGCTTAAGGAGCCCCTTCGCCTCGTGCTTGAGTTGAGGCCTGGCCTGGGCGCTGGGGCCGCCGCGTGCGAATCTGGTGGCACCTTCGCGCCTGTCTCGCTGCTTTCGATAAGTCTCTAGCCATTTAAAATTTTTGATGACCTGCTGCGACGCTTTTTTTCTGGCAAGATAGTCTTGTAAATGCGGGCCAAGATCTGCACACTGGTATTTCGGTTTTGGGGCCGGGCGGCGACGGGGCCCGTGCGTCCCAGCGCACATGTTCGGCGAGGCGGGGCCTGCGAGCGCGGCCACCGAGAATCGGACGGGGGTAGTCTCAAGCTGGCCGGCCTGCTCTGGTGCCTGGCCTCGCGCCGCCGTGTATCGCCCCGCCCTGGGCGGCAAGGCTGGCCCGGTCGGCACCAGTTGCGTGAGCGGAAAGATGGCCGCTTCCCGGCCCTGCTGCAGGGAGCTCAAAATGGAGGACGCGGCGCTCGGGAGAGCGGGCGGGTGAGTCACCCACACAAAGGAAAAGGGCCTTTCCGTCCTCAGCCGTCGCTTCATGTGACTCCACGGAGTACCGGGCGCCGTCCAGGCACCTCGATTAGTTCTCGAGCTTTTGGAGTACGTCGTC |

Summary of Sequences

| SEQ ID NO | Description | Sequence |
|---|---|---|
| | | TTTAGGTTGGGGGGAGGGGTTTTATGCGATGGAGTTTCCCCACACT<br>GAGTGGGTGGAGACTGAAGTTAGGCCAGCTTGGCACTTGATGTAAT<br>TCTCCTTGGAATTTGCCCTTTTTGAGTTTGGATCTTGGTTCATTCT<br>CAAGCCTCAGACAGTGGTTCAAAGTTTTTTCTTCCATTTCAGGTG<br>TCGTGACCACCATGGCGCTTCCGGTGACAGCACTGCTCCTCCCCTT<br>GGCGCTGTTGCTCCACGCAGCAAGGCCGCAGGTCCAGTTGGTGCAA<br>AGCGGGGCGGAGGTGAAAAAACCCGGCGCTTCCGTGAAGGTGTCCT<br>GTAAGGCGTCCGGTTATACGTTCACGAACTACGGGATGAATTGGGT<br>TCGCCAAGCGCCGGGGCAGGGACTGAAATGGATGGGGTGGATAAAT<br>ACCTACACCGGCGAACCTACATACGCCGACGCTTTTAAAGGGCGAG<br>TCACTATGACGCGCGATACCAGATATCCACCGCATACATGGAGCT<br>GTCCCGACTCCGGTCAGACGACACGGCTGTCTACTATTGTGCTCGG<br>GACTATGGCGATTATGGCATGGACTACTGGGGTCAGGGTACGACTG<br>TAACAGTTAGTAGTGGTGGAGGCGGCAGTGGCGGGGGGGAAGCGG<br>AGGAGGGGGTTCTGGTGACATAGTTATGACCCAATCCCCAGATAGT<br>TTGGCGGTTTCTCTGGGCGAGAGGGCAACGATTAATTGTCGCGCAT<br>CAAAGAGCGTTTCAACGAGCGGATATTCTTTTATGCATTGGTACCA<br>GCAAAAACCCGGACAACCGCCGAAGCTGCTGATCTACTTGGCTTCA<br>AATCTTGAGTCTGGGGTGCCGGACCGATTTTCTGGTAGTGGAAGCG<br>GAACTGACTTTACGCTCACGATCAGTTCACTGCAGGCTGAGGATGT<br>AGCGGTCTATTATTGCCAGCACAGTAGAGAAGTCCCCTGGACCTTC<br>GGTCAAGGCACGAAAGTAGAAATTAAAAGTGCTGCTGCCTTTGTCC<br>CGGTATTTCTCCCAGCCAAACCGACCACGACTCCCGCCCCGCGCCC<br>TCCGACACCCGCTCCCACCATCGCCTCTCAACCTCTTAGTCTTCGC<br>CCCGAGGCATGCCGACCCGCCGCCGGGGGTGCTGTTCATACGAGGG<br>GCTTGGACTTCGCTTGTGATATTTACATTTGGGCTCCGTTGGCGGG<br>TACGTGCGGCGTCCTTTTGTTGTCACTCGTTATTACTTTGTATTGT<br>AATCACAGGAATCGCAAACGGGGCAGAAAGAAACTCCTGTATATAT<br>TCAAACAACCATTTATGAGACCAGTACAAACTACTCAAGAGGAAGA<br>TGGCTGTAGCTGCCGATTTCCAGAAGAAGAAGGAGGATGTGAA<br>CTGCGAGTGAAGTTTTCCCGAAGCGCAGACGCTCCGGCATATCAGC<br>AAGGACAGAATCAGCTGTATAACGAACTGAATTTGGGACGCCGCGA<br>GGAGTATGACGTGCTTGATAAACGCCGGGGAGAGACCCGGAAATG<br>GGGGGTAAACCCCGAAGAAAGAATCCCCAAGAAGGACTCTACAATG<br>AACTCCAGAAGGATAAGATGGCGGAGGCCTACTCAGAAATAGGTAT<br>GAAGGGCGAACGACGACGGGGAAAAGGTCACGATGGCCTCTACCAA<br>GGGTTGAGTACGGCAACCAAAGATACGTACGATGCACTGCATATGC<br>AGGCCCTGCCTCCCAGATAATAATAAAATCGCTATCCATCGAAGAT<br>GGATGTGTGTTGGTTTTTTGTGTGTGGAGCAACAAATCTGACTTTG<br>CATGTGCAAACGCCTTCAACAACAGCATTATTCCAGAAGACACCTT<br>CTTCCCCAGCCCAGGTAAGGGCAGCTTTGGTGCCTTCGCAGGCTGT<br>TTCCTTGCTTCAGGAATGGCCAGGTTCTGCCCAGAGCTCTGGTCAA<br>TGATGTCTAAAACTCCTCTGATTGGTGGTCTCGGCCTTATCCATTG<br>CCACCAAAACCCTCTTTTTACTAAGAAACAGTGAGCCTTGTTCTGG<br>CAGTCCAGAGAATGACACGGGAAAAAAGCAGATGAAGAGAAGGTGG<br>CAGGAGAGGGCACGTGGCCCAGCCTCAGTCTCTCCAACTGAGTTCC<br>TGCCTGCCTGCCTTTGCTCAGACTGTTTGCCCCTTACTGCTCTTCT<br>AGGCCTCATTCTAAGCCCCTTCTCCAAGTTGCCTCTCCTTATTTCT<br>CCCTGTCTGCCAAAAAATCTTTCCCAGCTCACTAAGTCAGTCTCAC<br>GCAGTCACTCATTAACCCACCAATCACTGATTGTGCCGGCACATGA<br>ATGCACCAGGTGTTGAAGTGGAGGAATTAAAAAGTCAGATGAGGGG<br>TGTGCCCAGAGGAAGCACCATTCTAGTTGGGGGAGCCCATCTGTCA<br>GCTGGGAAAAGTCCAAATAACTTCAGATTGGAATGTGTTTTAACTC<br>AGGGTTGAGAAAACAGCTACCTTCAGGACAAAAGTCAGGGAAGGGC<br>TCTCTGAAGAAATGCTACTTGAAGATACCAGCCCTACCAAGGGCAG<br>GGAGAGGACCCTATAGAGGCCTGGGACAGGAGCTCAATGAGAAAGG<br>TAACCACGTGCGGACCGAGGCTGCAGCGTCGTCCTCCCTAGGAACC<br>CCTAGTGATGGAGTTGGCCACTCCCTCTGCGCGCTCGCTCGCTC<br>ACTGAGGCCGGGCGACCAAAGGTCGCCCGACGCCCGGGCTTTGCCC<br>GGGCGGCCTCAGTGAGCGAGCGAGCGCGCAGCTGCCTGCAGG |
| 44 | CD70 LHA to RHA CD70B sCFV with 41BB) | GAGATGTAAGGAGCTGCTGTGACTTGCTCAAGGCCTTATATCGAGT<br>AAACGGTAGTGCTGGGGCTTAGACGCAGGTGTTCTGATTTATAGTT<br>CAAAACCTCTATCAATGAGAGAGCAATCTCCTGGTAATGTGATAGA<br>TTTCCCAACTTAATGCCAACATACCATAAACCTCCCATTCTGCTAA<br>TGCCCAGCCTAAGTTGGGGAGACCACTCCAGATTCCAAGATGTACA<br>GTTTGCTTTGCTGGGCCTTTTTCCCATGCCTGCCTTTACTCTGCCA<br>GAGTTATATTGCTGGGGTTTTGAAGAAGATCCTATTAAATAAAGA<br>ATAAGCAGTATTATTAAGTAGCCCTGCATTTCAGGTTTCCTTGAGT<br>GGCAGGCCAGGCCTGGCCGTGAACGTTCACTGAAATCATGGCCTCT<br>TGGCCAAGATTGATAGCTTGTGCCTGTCCCTGAGTCCCAGTCCATC<br>ACGAGCAGCTGGTTTCTAAGATGCTATTTCCCGTATAAAGCATGAG<br>ACCGTGACTTGCCAGCCCCACAGAGCCCCGCCCTTGTCCATCACTG<br>GCATCTGGACTCCAGCCTGGGTTGGGGCAAAGAGGGAAATGAGATC<br>ATGTCCTAACCCTGATCCTCTTGTCCCACAGATATCCAGAACCCTG |

Summary of Sequences

| SEQ ID NO | Description | Sequence |
|---|---|---|
| | | ACCCTGCCGTGTACCAGCTGAGAGACTCTAAATCCAGTGACAAGTC |
| | | TGTCTGCCTATTCACCGATTTTGATTCTCAAACAAATGTGTCACAA |
| | | AGTAAGGATTCTGATGTGTATATCACAGACAAAACTGTGCTAGACA |
| | | TGAGGTCTATGGACTTCAGGCTCCGGTGCCCGTCAGTGGGCAGAGC |
| | | GCACATCGCCCACAGTCCCCGAGAAGTTGGGGGGAGGGGTCGGCAA |
| | | TTGAACCGGTGCCTAGAGAAGGTGGCGCGGGGTAAACTGGGAAAGT |
| | | GATGTCGTGTACTGGCTCCGCCTTTTTCCCGAGGGTGGGGGAGAAC |
| | | CGTATATAAGTGCAGTAGTCGCCGTGAACGTTCTTTTTCGCAACGG |
| | | GTTTGCCGCCAGAACACAGGTAAGTGCCGTGTGTGGTTCCCGCGGG |
| | | CCTGGCCTCTTTACGGGTTATGGCCCTTGCGTGCCTTGAATTACTT |
| | | CCACTGGCTGCAGTACGTGATTCTTGATCCCGAGCTTCGGGTTGGA |
| | | AGTGGGTGGGAGAGTTCGAGGCCTTGCGCTTAAGGAGCCCCTTCGC |
| | | CTCGTGCTTGAGTTGAGGCCTGGCCTGGGCGCTGGGGCCGCCGCGT |
| | | GCGAATCTGGTGGCACCTTCGCGCCTGTCTCGCTGCTTTCGATAAG |
| | | TCTCTAGCCATTTAAAATTTTTGATGACCTGCTGCGACGCTTTTTT |
| | | TCTGGCAAGATAGTCTTGTAAATGCGGGCCAAGATCTGCACACTGG |
| | | TATTTCGGTTTTTGGGGCCGCGGGCGGCGACGGGGCCCGTGCGTCC |
| | | CAGCGCACATGTTCGGCGAGGCGGGGCCTGCGAGCGCGGCCACCGA |
| | | GAATCGGACGGGGGTAGTCTCAAGCTGGCCGGCCTGCTCTGGTGCC |
| | | TGGCCTCGCGCCGCCGTGTATCGCCCCGCCCTGGGCGGCAAGGCTG |
| | | GCCCGGTCGGCACCAGTTGCGTGAGCGGAAAGATGGCCGCTTCCCG |
| | | GCCCTGCTGCAGGGAGCTCAAAATGGAGGACGCGGCGCTCGGGAGA |
| | | GCGGGCGGGTGAGTCACCCACACAAAGGAAAAGGGCCTTTCCGTCC |
| | | TCAGCCGTCGCTTCATGTGACTCCACGGAGTACGGGCGCCGTCCA |
| | | GGCACCTCGATTAGTTCTCGAGCTTTTGGAGTACGTCGTCTTTAGG |
| | | TTGGGGGGAGGGGTTTTATGCGATGGAGTTTCCCCACACTGAGTGG |
| | | GTGGAGACTGAAGTTAGGCCAGCTTGGCACTTGATGTAATTCTCCT |
| | | TGGAATTTGCCCTTTTTGAGTTTGGATCTTGGTTCATTCTCAAGCC |
| | | TCAGACAGTGGTTCAAAGTTTTTTTCTTCCATTTCAGGTGTCGTGA |
| | | CCACCATGGCGCTTCCGGTGACAGCACTGCTCCTCCCCTTGGCGCT |
| | | GTTGCTCCACGCAGCAAGGCCGCAGGTCCAGTTGGTGCAAAGCGGG |
| | | GCGGAGGTGAAAAAACCCGGCGCTTCCGTGAAGGTGTCCTGTAAGG |
| | | CGTCCGGTTATACGTTCACGAACTACGGGATGAATTGGGTTCGCCA |
| | | AGCGCCGGGGCAGGGACTGAAATGGATGGGGTGGATAAATACCTAC |
| | | ACCGGCGAACCTACATACGCCGACGCTTTTAAAGGGCGAGTCACTA |
| | | TGACGCGCGATACCAGCATATCCACCGCATACATGGAGCTGTCCCG |
| | | ACTCCGGTCAGACGACACGGCTGTCTACTATTGTGCTCGGGACTAT |
| | | GGCGATTATGGCATGGACTACTGGGGTCAGGGTACGACTGTAACAG |
| | | TTAGTAGTGGTGGAGGCGGCAGTGGCGGGGGGGGAAGCGGAGGAGG |
| | | GGGTTCTGGTGACATAGTTATGACCCAATCCCCAGATAGTTTGGCG |
| | | GTTTCTCTGGGCGAGAGGGCAACGATTAATTGTCGCGCATCAAAGA |
| | | GCGTTTCAACGAGCGGATATTCTTTTATGCATTGGTACCAGCAAAA |
| | | ACCCGGACAACCGCCGAAGCTGCTGATCTACTTGGCTTCAAATCTT |
| | | GAGTCTGGGGTGCCGGACCGATTTTCTGGTAGTGGAAGCGGAACTG |
| | | ACTTTACGCTCACGATCAGTTCACTGCAGGCTGAGGATGTAGCGGT |
| | | CTATTATTGCCAGCACAGTAGAGAAGTCCCCTGGACCTTCGGTCAA |
| | | GGCACGAAAGTAGAAATTAAAAGTGCTGCTGCCTTTGTCCCGGTAT |
| | | TTCTCCCAGCCAAACCGACCACGACTCCCGCCCCGCGCCCTCCGAC |
| | | ACCCGCTCCCACCATCGCCTCTCAACCTCTTAGTCTTCGCCCCGAG |
| | | GCATGCCGACCCGCCGCCGGGGGTGCTGTTCATACGAGGGGCTTGG |
| | | ACTTCGCTTGTGATATTTACATTTGGGCTCCGTTGGCGGGTACGTG |
| | | CGGCGTCCTTTTGTTGTCACTCGTTATTACTTTGTATTGTAATCAC |
| | | AGGAATCGCAAACGGGCAGAAAGAAACTCCTGTATATATTCAAAC |
| | | AACCATTTATGAGACCAGTACAAACTACTCAAGAGGAAGATGGCTG |
| | | TAGCTGCCGATTTCCAGAAGAAGAAGAAGGAGGATGTGAACTGCGA |
| | | GTGAAGTTTTCCCGAAGCGCAGACGCTCCGGCATATCAGCAAGGAC |
| | | AGAATCAGCTGTATAACGAACTGAATTTGGGACGCCGCGAGGAGTA |
| | | TGACGTGCTTGATAAACGCGGGGGAGAGACCCGGAAATGGGGGGT |
| | | AAACCCCGAAGAAAGAATCCCCAAGAAGGACTCTACAATGAACTCC |
| | | AGAAGGATAAGATGGCGGAGGCCTACTCAGAAATAGGTATGAAGGG |
| | | CGAACGACGACGGGGAAAAGGTCACGATGGCCTCTACCAAGGGTTG |
| | | AGTACGGCAACCAAAGATACGTACGATGCACTGCATATGCAGGCCC |
| | | TGCCTCCCAGATAATAATAAAATCGCTATCCATCGAAGATGGATGT |
| | | GTGTTGGTTTTTGTGTGTGGAGCAACAAATCTGACTTTGCATGTG |
| | | CAAACGCCTTCAACAACAGCATTATTCCAGAAGACACCTTCTTCCC |
| | | CAGCCCAGGTAAGGGCAGCTTTGGTGCCTTCGCAGGCTGTTTCCTT |
| | | GCTTCAGGAATGGCCAGGTTCTGCCCAGAGCTCTGGTCAATGATGT |
| | | CTAAAACTCCTCTGATTGGTGGTCTCGGCCTTATCCATTGCCACCA |
| | | AAACCCTCTTTTTACTAAGAAACAGTGAGCCTTGTTCTGGCAGTCC |
| | | AGAGAATGACACGGGAAAAAAGCAGATGAAGAGAAGGTGGCAGGAG |
| | | AGGGCACGTGGCCCAGCCTCAGTCTCTCCAACTGAGTTCCTGCCTG |
| | | CCTGCCTTTGCTCAGACTGTTTGCCCCTTACTGCTCTTCTAGGCCT |
| | | CATTCTAAGCCCCTTCTCCAAGTTGCCTCTCCTTATTTCTCCCTGT |
| | | CTGCCAAAAAATCTTTCCCAGCTCACTAAGTCAGTCTCACGCAGTC |
| | | ACTCATTAACCCACCAATCACTGATTGTGCCGGCACATGAATGCAC |

Summary of Sequences

| SEQ ID NO | Description | Sequence |
|---|---|---|
| | | CAGGTGTTGAAGTGGAGGAATTAAAAAGTCAGATGAGGGGTGTGCC<br>CAGAGGAAGCACCATTCTAGTTGGGGGAGCCCATCTGTCAGCTGGG<br>AAAAGTCCAATAACTTCAGATTGGAATGTGTTTTAACTCAGGGTT<br>GAGAAAACAGCTACCTTCAGGACAAAAGTCAGGGAAGGGCTCTCTG<br>AAGAAATGCTACTTGAAGATACCAGCCCTACCAAGGGCAGGGAGAG<br>GACCCTATAGAGGCCTGGGACAGGAGCTCAATGAGAAAGG |
| 45 | CD70 CAR nucleotide sequence (CD70B scFV with 41BB) | ATGGCGCTTCCGGTGACAGCACTGCTCCTCCCCTTGGCGCTGTTGC<br>TCCACGCAGCAAGGCCGCAGGTCCAGTTGGTGCAAAGCGGGGCGGA<br>GGTGAAAAAACCCGGCGCTTCCGTGAAGGTGTCCTGTAAGGCGTCC<br>GGTTATACGTTCACGAACTACGGGATGAATTGGGTTCGCCAAGCGC<br>CGGGGCAGGGACTGAAATGGATGGGGTGGATAAATACCTACACCGG<br>CGAACCTACATACGCCGACGCTTTTAAAGGGCGAGTCACTATGACG<br>CGCGATACCAGCATATCCACCGCATACATGGAGCTGTCCCGACTCC<br>GGTCAGACGACACGGCTGTCTACTATTGTGCTCGGGACTATGGCGA<br>TTATGGCATGGACTACTGGGGTCAGGGTACGACTGTAACAGTTAGT<br>AGTGGTGGAGGCGGCAGTGGCGGGGGGGGAAGCGGAGGAGGGGGTT<br>CTGGTGACATAGTTATGACCCAATCCCCAGATAGTTTGGCGGTTTC<br>TCTGGGCGAGAGGGCAACGATTAATTGTCGCGCATCAAAGAGCGTT<br>TCAACGAGCGGATATTCTTTTATGCATTGGTACCAGCAAAAACCCG<br>GACAACCGCCGAAGCTGCTGATCTACTTGGCTTCAAATCTTGAGTC<br>TGGGGTGCCGGACCGATTTTCTGGTAGTGGAAGCGGAACTGACTTT<br>ACGCTCACGATCAGTTCACTGCAGGCTGAGGATGTAGCGGTCTATT<br>ATTGCCAGCACAGTAGAGAAGTCCCCTGGACCTTCGGTCAAGGCAC<br>GAAAGTAGAAATTAAAAGTGCTGCTGCCTTTGTCCCGGTATTTCTC<br>CCAGCCAAACCGACCACGACTCCCGCCCCGCGCCCTCCGACACCCG<br>CTCCCACCATCGCCTCTCAACCTCTTAGTCTTCGCCCCGAGGCATG<br>CCGACCCGCCGCCGGGGTGCTGTTCATACGAGGGGCTTGGACTTC<br>GCTTGTGATATTTACATTTGGGCTCCGTTGGCGGGTACGTGCGGCG<br>TCCTTTTGTTGTCACTCGTTATTACTTTGTATTGTAATCACAGGAA<br>TCGCAAACGGGGCAGAAAGAAACTCCTGTATATATTCAAACAACCA<br>TTTATGAGACCAGTACAAACTACTCAAGAGGAAGATGGCTGTAGCT<br>GCCGATTTCCAGAAGAAGAAGAAGGAGGATGTGAACTGCGAGTGAA<br>GTTTTCCCGAAGCGCAGACGCTCCGGCATATCAGCAAGGACAGAAT<br>CAGCTGTATAACGAACTGAATTTGGGACGCCGCGAGGAGTATGACG<br>TGCTTGATAAACGCCGGGGAGAGACCCGGAAATGGGGGTAAACC<br>CCGAAGAAAGAATCCCCAAGAAGGACTCTACAATGAACTCCAGAAG<br>GATAAGATGGCGGAGGCCTACTCAGAAATAGGTATGAAGGGCGAAC<br>GACGACGGGGAAAAGGTCACGATGGCCTCTACCAAGGGTTGAGTAC<br>GGCAACCAAAGATACGTACGATGCACTGCATATGCAGGCCCTGCCT<br>CCCAGATAA |
| 46 | CD70 CAR amino acid sequence (CD70B scFV with 41BB) | MALPVTALLLPLALLLHAARPQVQLVQSGAEVKKPGASVKVSCKAS<br>GYTFTNYGMNWVRQAPGQGLKWMGWINTYTGEPTYADAFKGRVTMT<br>RDTSISTAYMELSRLRSDDTAVYYCARDYGDYGMDYWGQGTTVTVS<br>SGGGGSGGGGSGGGGSGDIVMTQSPDSLAVSLGERATINCRASKSV<br>STSGYSFMHWYQQKPGQPPKLLIYLASNLESGVPDRFSGSGSGTDF<br>TLTISSLQAEDVAVYYCQHSREVPWTFGQGTKVEIKSAAAFVPVFL<br>PAKPTTTPAPRPPTPAPTIASQPLSLRPEACRPAAGGAVHTRGLDF<br>ACDIYIWAPLAGTCGVLLLSLVITLYCNHRNRKRGRKKLLYIFKQP<br>FMRPVQTTQEEDGCSCRFPEEEGGCELRVKFSRSADAPAYQQGQN<br>QLYNELNLGRREEYDVLDKRRGRDPEMGGKPRRKNPQEGLYNELQK<br>DKMAEAYSEIGMKGERRRGKGHDGLYQGLSTATKDTYDALHMQALP<br>PR |
| 47 | CD70A scFv nucleotide sequence | GATATAGTTATGACCCAATCACCCGATAGTCTTGCGGTAAGCCTGG<br>GGGAGCGAGCAACAATAAACTGTCGGGCATCAAAATCCGTCAGTAC<br>AAGCGGGTATTCATTCATGCACTGGTATCAACAGAAACCCGGTCAG<br>CCACCCAAGCTCCTGATTTATCTTGCGTCTAATCTTGAGTCCGGCG<br>TCCCAGACCGGTTTTCCGGCTCCGGGAGCGGCACGGATTTTACTCT<br>TACTATTTCTAGCCTTCAGGCCGAAGATGTGGCGGTATACTACTGC<br>CAGCATTCAAGGGAAGTTCCTTGGACGTTCGGTCAGGGCACGAAAG<br>TGGAAATTAAAGGCGGGGGGGGATCCGGCGGGGAGGGTCTGGAGG<br>AGGTGGCAGTGGTCAGGTCCAACTGGTGCAGTCCGGGGCAGAGGTA<br>AAAAAACCCGGCGCGTCTGTTAAGGTTTCATGCAAGGCCAGTGGAT<br>ATACTTTCACCAATTACGGAATGAACTGGGTGAGGCAGGCCCCTGG<br>TCAAGGCCTGAAATGGATGGGATGGATAAACACGTACACCGGTGAA<br>CCTACCTATGCCGATGCCTTTAAGGGTCGGGTTACGATGACGAGAG<br>ACACCTCCATATCAACAGCCTACATGGAGCTCAGCAGATTGAGGAG<br>TGACGATACGGCAGTCTATTACTGTGCAAGACTACGGCGATTAT<br>GGCATGGATTACTGGGGCCAGGGCACTACAGTAACCGTTTCCAGC |
| 48 | CD70A scFv amino acid sequence | DIVMTQSPDSLAVSLGERATINC<u>RASKSVSTSGYSFMH</u>WYQQKPGQ<br>PPKLLIYLASNLESGVPDRFSGSGSGTDFTLTISSLQAEDVAVYYC<br>QHSREVPWTFGQGTKVEIK<u>GGGGSGGGGSGGGGSG</u>QVQLVQSGAEV |

| SEQ ID NO | Description | Sequence |
|---|---|---|
| | (linker underlined) | KKPGASVKVSCKASGYTFTNYGMNWVRQAPGQGLKWMGWINTYTGE PTYADAFKGRVTMTRDTSISTAYMELSRLRSDDTAVYYCARDYGDY GMDYWGQGTTVTVSS |
| 49 | CD70B scFv nucleotide sequence | CAGGTCCAGTTGGTGCAAAGCGGGGCGGAGGTGAAAAAACCCGGCG CTTCCGTGAAGGTGTCCTGTAAGGCGTCCGGTTATACGTTCACGAA CTACGGGATGAATTGGGTTCGCCAAGCGCCGGGGCAGGGACTGAAA TGGATGGGGTGGATAAATACCTACACCGGCGAACCTACATACGCCG ACGCTTTTAAAGGGCGAGTCACTATGACGCGCGATACCAGCATATC CACCGCATACATGGAGCTGTCCCGACTCCGGTCAGACGACACGGCT GTCTACTATTGTGCTCGGGACTATGGCGATTATGGCATGGACTACT GGGGTCAGGGTACGACTGTAACAGTTAGTAGTGGTGGAGGCGGCAG TGGCGGGGGGGGAAGCGGAGGAGGGGGTTCTGGTGACATAGTTATG ACCCAATCCCCAGATAGTTTGGCGGTTTCTCTGGGCGAGAGGGCAA CGATTAATTGTCGCGCATCAAAGAGCGTTTCAACGAGCGGATATTC TTTTATGCATTGGTACCAGCAAAAACCCGGACAACCGCCGAAGCTG CTGATCTACTTGGCTTCAAATCTTGAGTCTGGGGTGCCGGACCGAT TTTCTGGTAGTGGAAGCGGAACTGACTTTACGCTCACGATCAGTTC ACTGCAGGCTGAGGATGTAGCGGTCTATTATTGCCAGCACAGTAGA GAAGTCCCCTGGACCTTCGGTCAAGGCACGAAAGTAGAAATTAAA |
| 50 | CD70B scFv amino acid sequence (linker underlined) | QVQLVQSGAEVKKPGASVKVSCKASGYTFTNYGMNWVRQAPGQGLK WMGWINTYTGEPTYADAFKGRVTMTRDTSISTAYMELSRLRSDDTA VYYCARDYGDYGMDYWGQGTTVTVSSGGGGSGGGGSGGGGSGDIVM TQSPDSLAVSLGERATINCRASKSVSTSGYSFMHWYQQKPGQPPKL LIYLASNLESGVPDRFSGSGSGTDFTLTISSLQAEDVAVYYCQHSR EVPWTFGQGTKVEIK |
| 51 | CD70 VH | QVQLVQSGAEVKKPGASVKVSCKASGYTFTNYGMNWVRQAPGQGLK WMGWINTYTGEPTYADAFKGRVTMTRDTSISTAYMELSRLRSDDTA VYYCARDYGDYGMDYWGQGTTVTVSS |
| 52 | CD70 VL | DIVMTQSPDSLAVSLGERATINCRASKSVSTSGYSFMHWYQQKPGQ PPKLLIYLASNLESGVPDRFSGSGSGTDFTLTISSLQAEDVAVYYC QHSREVPWTFGQGTKVEIK |
| 53 | Linker | GGGGSGGGGSGGGGSG |
| 54 | BCMA rAAV | CCTGCAGGCAGCTGCGCGCTCGCTCGCTCACTGAGGCCGCCCGGGC GTCGGGCGACCTTTGGTCGCCCGGCCTCAGTGAGCGAGCGAGCGCG CAGAGAGGGAGTGGCCAACTCCATCACTAGGGGTTCCTGCGGCCGC ACGCGTGAGATGTAAGGAGCTGCTGTGACTTGCTCAAGGCCTTATA TCGAGTAAACGGTAGTGCTGGGGCTTAGACGCAGGTGTTCTGATTT ATAGTTCAAAACCTCTATCAATGAGAGCAATCTCCTGGTAATGT GATAGATTTCCCAACTTAATGCCAACATACCATAAACCTCCCATTC TGCTAATGCCCAGCCTAAGTTGGGGAGACCACTCCAGATTCCAAGA TGTACAGTTTGCTTTGCTGGGCCTTTTTCCCATGCCTGCCTTTACT CTGCCAGAGTTATATTGCTGGGGTTTTGAAGAAGATCCTATTAAAT AAAAGAATAAGCAGTATTATTAAGTAGCCCTGCATTTCAGGTTTCC TTGAGTGGCAGGCCAGGCCTGGCCGTGAACGTTCACTGAAATCATG GCCTCTTGGCCAAGATTGATAGCTTGTGCCTGTCCCTGAGTCCCAG TCCATCACGAGCAGCTGGTTTCTAAGATGCTATTTCCCGTATAAAG CATGAGACCGTGACTTGCCAGCCCCACAGAGCCCCGCCCTTGTCCA TCACTGGCATCTGGACTCCAGCCTGGGTTGGGGCAAAGAGGGAAAT GAGATCATGTCCTAACCCTGATCCTCTTGTCCCACAGATATCCAGA ACCCTGACCCTGCCGTGTACCAGCTGAGAGACTCTAAATCCAGTGA CAAGTCTGTCTGCCTATTCACCGATTTTGATTCTCAAACAAATGTG TCACAAAGTAAGGATTCTGATGTGTATATCACAGACAAAACTGTGC TAGACATGAGGTCTATGGACTTCAGGCTCCGGTGCCCGTCAGTGGG CAGAGCGCACATCGCCCACAGTCCCCGAGAAGTTGGGGGGAGGGGT CGGCAATTGAACCGGTGCCTAGAGAAGGTGGCGCGGGGTAAACTGG GAAAGTGATGTCGTGTACTGGCTCCGCCTTTTTCCCGAGGGTGGGG GAGAACCGTATATAAGTGCAGTAGTCGCCGTGAACGTTCTTTTTCG CAACGGGTTTGCCGCCAGAACACAGGTAAGTGCCGTGTGTGGTTCC CGCGGGCCTGGCCTCTTTACGGGTTATGGCCCTTGCGTGCCTTGAA TTACTTCCACTGGCTGCAGTACGTGATTCTTGATCCCGAGCTTCGG GTTGGAAGTGGGTGGGAGAGTTCGAGGCCTTGCGCTTAAGGAGCCC CTTCGCCTCGTGCTTGAGTTGAGGCCTGGCCTGGGCGCTGGGGCCG CCGCGTGCGAATCTGGTGGCACCTTCGCGCCTGTCTCGCTGCTTTC GATAAGTCTCTAGCCATTTAAAATTTTTGATGACCTGCTGCGACGC TTTTTTTCTGGCAAGATAGTCTTGTAAATGCGGGCCAAGATCTGCA CACTGGTATTTCGGTTTTTGGGGCCGCGGGCGGCGACGGGGCCCGT GCGTCCCAGCGCACATGTTCGGCGAGGCGGGGCCTGCGAGCGCGGC CACCGAGAATCGGACGGGGGTAGTCTCAAGCTGGCCGGCCTGCTCT GGTGCCTGGCCTCGCGCCGCCGTGTATCGCCCCGCCCTGGGCGGCA |

Summary of Sequences

| SEQ ID NO | Description | Sequence |
|---|---|---|
| | | AGGCTGGCCCGGTCGGCACCAGTTGCGTGAGCGGAAAGATGGCCGC |
| | | TTCCCGGCCCTGCTGCAGGGAGCTCAAAATGGAGGACGCGGCGCTC |
| | | GGGAGAGCGGGCGGGTGAGTCACCCACACAAAGGAAAAGGGCCTTT |
| | | CCGTCCTCAGCCGTCGCTTCATGTGACTCCACGGAGTACCGGGCGC |
| | | CGTCCAGGCACCTCGATTAGTTCTCGAGCTTTTGGAGTACGTCGTC |
| | | TTTAGGTTGGGGGGAGGGGTTTTATGCGATGGAGTTTCCCCACACT |
| | | GAGTGGGTGGAGACTGAAGTTAGGCCAGCTTGGCACTTGATGTAAT |
| | | TCTCCTTGGAATTTGCCCTTTTTGAGTTTGGATCTTGGTTCATTCT |
| | | CAAGCCTCAGACAGTGGTTCAAAGTTTTTTTCTTCCATTTCAGGTG |
| | | TCGTGACCACCATGGCGCTTCCGGTGACAGCACTGCTCCTCCCCTT |
| | | GGCGCTGTTGCTCCACGCAGCAAGGCCGCAGGTGCAGCTGGTGCAG |
| | | AGCGGAGCCGAGCTCAAGAAGCCCGGAGCCTCCGTGAAGGTGAGCT |
| | | GCAAGGCCAGCGGCAACACCCTGACCAACTACGTGATCCACTGGGT |
| | | GAGACAAGCCCCCGGCCAAAGGCTGGAGTGGATGGGCTACATCCTG |
| | | CCCTACAACGACCTGACCAAGTACAGCCAGAAGTTCCAGGGCAGGG |
| | | TGACCATCACCAGGGATAAGAGCGCCTCCACCGCCTATATGGAGCT |
| | | GAGCAGCCTGAGGAGCGAGGACACCGCTGTGTACTACTGTACAAGG |
| | | TGGGACTGGGACGGCTTCTTTGACCCCTGGGGCCAGGGCACAACAG |
| | | TGACCGTCAGCAGCGGCGGCGAGGCAGCGGCGGCGGCGGCAGCGG |
| | | CGGAGGCGGAAGCGAAATCGTGATGACCCAGAGCCCCGCCACACTG |
| | | AGCGTGAGCCCTGGCGAGAGGGCCAGCATCTCCTGCAGGGCTAGCC |
| | | AAAGCCTGGTGCACAGCAACGGCAACACCCACCTGCACTGGTACCA |
| | | GCAGAGACCCGGACAGGCTCCCAGGCTGCTGATCTACAGCGTGAGC |
| | | AACAGGTTCTCCGAGGTGCCTGCCAGGTTTAGCGGCAGCGGAAGCG |
| | | GCACCGACTTTACCCTGACCATCAGCAGCGTGGAGTCCGAGGACTT |
| | | CGCCGTGTATTACTGCAGCCAGACCAGCCACATCCCTTACACCTTC |
| | | GGCGGCGGCACCAAGCTGGAGATCAAAAGTGCTGCTGCCTTTGTCC |
| | | CGGTATTTCTCCCAGCCAAACCGACCACGACTCCCGCCCCGCGCCC |
| | | TCCGACACCCGCTCCCACCATCGCCTCTCAACCTCTTAGTCTTCGC |
| | | CCCGAGGCATGCCGACCCGCCGCCGGGGGTGCTGTTCATACGAGGG |
| | | GCTTGGACTTCGCTTGTGATATTTACATTTGGGCTCCGTTGGCGGG |
| | | TACGTGCGGCGTCCTTTTGTTGTCACTCGTTATTACTTTGTATTGT |
| | | AATCACAGGAATCGCAAACGGGGCAGAAAGAAACTCCTGTATATAT |
| | | TCAAACAACCATTTATGAGACCAGTACAAACTACTCAAGAGGAAGA |
| | | TGGCTGTAGCTGCCGATTTCCAGAAGAAGAAGAAGGAGGATGTGAA |
| | | CTGCGAGTGAAGTTTTCCCGAAGCGCAGACGCTCCGGCATATCAGC |
| | | AAGGACAGAATCAGCTGTATAACGAACTGAATTTGGGACGCCGCGA |
| | | GGAGTATGACGTGCTTGATAAACGCCGGGGAGAGACCCGGAAATG |
| | | GGGGGTAAACCCCGAAGAAAGAATCCCCAAGAAGGACTCTACAATG |
| | | AACTCCAGAAGGATAAGATGGCGGAGGCCTACTCAGAAATAGGTAT |
| | | GAAGGGCGAACGACGACGGGGAAAAGGTCACGATGGCCTCTACCAA |
| | | GGGTTGAGTACGGCAACCAAAGATACGTACGATGCACTGCATATGC |
| | | AGGCCCTGCCTCCCAGATAATAATAAAATCGCTATCCATCGAAGAT |
| | | GGATGTGTGTTGGTTTTTTGTGTGTGGAGCAACAAATCTGACTTTG |
| | | CATGTGCAAACGCCTTCAACAACAGCATTATTCCAGAAGACACCTT |
| | | CTTCCCCAGCCCAGGTAAGGGCAGCTTTGGTGCCTTCGCAGGCTGT |
| | | TTCCTTGCTTCAGGAATGGCCAGGTTCTGCCCAGAGCTCTGGTCAA |
| | | TGATGTCTAAAACTCCTCTGATTGGTGGTCTCGGCCTTATCCATTG |
| | | CCACCAAAACCCTCTTTTTACTAAGAAACAGTGAGCCTTGTTCTGG |
| | | CAGTCCAGAGAATGACACGGGAAAAAAGCAGATGAAGAGAAGGTGG |
| | | CAGGAGAGGGCACGTGGCCCAGCCTCAGTCTCTCCAACTGAGTTCC |
| | | TGCCTGCCTGCCTTTGCTCAGACTGTTTGCCCCTTACTGCTCTTCT |
| | | AGGCCTCATTCTAAGCCCCTTCTCCAAGTTGCCTCTCCTTATTTCT |
| | | CCCTGTCTGCCAAAAAATCTTTCCCAGCTCACTAAGTCAGTCTCAC |
| | | GCAGTCACTCATTAACCCACCAATCACTGATTGTGCCGGCACATGA |
| | | ATGCACCAGGTGTTGAAGTGGAGGAATTAAAAAGTCAGATGAGGGG |
| | | TGTGCCCAGAGGAAGCACCATTCTAGTTGGGGGAGCCCATCTGTCA |
| | | GCTGGGAAAAGTCCAAATAACTTCAGATTGGAATGTGTTTTAACTC |
| | | AGGGTTGAGAAAACAGCTACCTTCAGGACAAAAGTCAGGGAAGGGC |
| | | TCTCTGAAGAAATGCTACTTGAAGATACCAGCCCTACCAAGGGCAG |
| | | GGAGAGGACCCTATAGAGGCCTGGGACAGGAGCTCAATGAGAAAGG |
| | | TAACCACGTGCGGACCGAGGCTGCAGCGTCGTCCTCCCTAGGAACC |
| | | CCTAGTGATGGAGTTGGCCACTCCCTCTCTGCGCGCTCGCTCGCTC |
| | | ACTGAGGCCGGGCGACCAAAGGTCGCCCGACGCCCGGGCTTTGCCC |
| | | GGGCGGCCTCAGTGAGCGAGCGAGCGCGCAGCTGCCTGCAGG |
| 55 | BCMA RHA to LHA | GAGATGTAAGGAGCTGCTGTGACTTGCTCAAGGCCTTATATCGAGT |
| | | AAACGGTAGTGCTGGGGCTTAGACGCAGGTGTTCTGATTTATAGTT |
| | | CAAAACCTCTATCAATGAGAGAGCAATCTCCTGGTAATGTGATAGA |
| | | TTTCCCAACTTAATGCCAACATACCATAAACCTCCCATTCTGCTAA |
| | | TGCCCAGCCTAAGTTGGGGAGACCACTCCAGATTCCAAGATGTACA |
| | | GTTTGCTTTGCTGGGCCTTTTTCCCATGCCTGCCTTTACTCTGCCA |
| | | GAGTTATATTGCTGGGGTTTTGAAGAAGATCCTATTAAATAAAGA |
| | | ATAAGCAGTATTATTAAGTAGCCCTGCATTTCAGGTTTCCTTGAGT |
| | | GGCAGGCCAGGCCTGGCCGTGAACGTTCACTGAAATCATGGCCTCT |

Summary of Sequences

| SEQ ID NO | Description | Sequence |
|---|---|---|
| | | TGGCCAAGATTGATAGCTTGTGCCTGTCCCTGAGTCCCAGTCCATC |
| | | ACGAGCAGCTGGTTTCTAAGATGCTATTTCCCGTATAAAGCATGAG |
| | | ACCGTGACTTGCCAGCCCCACAGAGCCCCGCCCTTGTCCATCACTG |
| | | GCATCTGGACTCCAGCCTGGGTTGGGGCAAAGAGGGAAATGAGATC |
| | | ATGTCCTAACCCTGATCCTCTTGTCCCACAGATATCCAGAACCCTG |
| | | ACCCTGCCGTGTACCAGCTGAGAGACTCTAAATCCAGTGACAAGTC |
| | | TGTCTGCCTATTCACCGATTTTGATTCTCAAACAAATGTGTCACAA |
| | | AGTAAGGATTCTGATGTGTATATCACAGACAAAACTGTGCTAGACA |
| | | TGAGGTCTATGGACTTCAGGCTCCGGTGCCCGTCAGTGGGCAGAGC |
| | | GCACATCGCCCACAGTCCCCGAGAAGTTGGGGGGAGGGGTCGGCAA |
| | | TTGAACCGGTGCCTAGAGAAGGTGGCGCGGGGTAAACTGGGAAAGT |
| | | GATGTCGTGTACTGGCTCCGCCTTTTTCCCGAGGGTGGGGGAGAAC |
| | | CGTATATAAGTGCAGTAGTCGCCGTGAACGTTCTTTTTCGCAACGG |
| | | GTTTGCCGCCAGAACACAGGTAAGTGCCGTGTGTGGTTCCCGCGGG |
| | | CCTGGCCTCTTTACGGGTTATGGCCCTTGCGTGCCTTGAATTACTT |
| | | CCACTGGCTGCAGTACGTGATTCTTGATCCCGAGCTTCGGGTTGGA |
| | | AGTGGGTGGGAGAGTTCGAGGCCTTGCGCTTAAGGAGCCCCTTCGC |
| | | CTCGTGCTTGAGTTGAGGCCTGGCCTGGGCGCTGGGGCCGCCGCGT |
| | | GCGAATCTGGTGGCACCTTCGCGCCTGTCTCGCTGCTTTCGATAAG |
| | | TCTCTAGCCATTTAAAATTTTTGATGACCTGCTGCGACGCTTTTTT |
| | | TCTGGCAAGATAGTCTTGTAAATGCGGGCCAAGATCTGCACACTGG |
| | | TATTTCGGTTTTTGGGGCCGCGGGCGGCGACGGGGCCCGTGCGTCC |
| | | CAGCGCACATGTTCGGCGAGGCGGGGCCTGCGAGCGCGGCCACCGA |
| | | GAATCGGACGGGGGTAGTCTCAAGCTGGCCGGCCTGCTCTGGTGCC |
| | | TGGCCTCGCGCCGCCGTGTATCGCCCCGCCCTGGGCGGCAAGGCTG |
| | | GCCCGGTCGGCACCAGTTGCGTGAGCGGAAAGATGGCCGCTTCCCG |
| | | GCCCTGCTGCAGGGAGCTCAAAATGGAGGACGCGGCGCTCGGGAGA |
| | | GCGGGCGGGTGAGTCACCCACACAAAGGAAAAGGGCCTTTCCGTCC |
| | | TCAGCCGTCGCTTCATGTGACTCCACGGAGTACCGGGCGCCGTCCA |
| | | GGCACCTCGATTAGTTCTCGAGCTTTTGGAGTACGTCGTCTTTAGG |
| | | TTGGGGGGAGGGGTTTTATGCGATGGAGTTTCCCCACACTGAGTGG |
| | | GTGGAGACTGAAGTTAGGCCAGCTTGGCACTTGATGTAATTCTCCT |
| | | TGGAATTTGCCCTTTTTGAGTTTGGATCTTGGTTCATTCTCAAGCC |
| | | TCAGACAGTGGTTCAAAGTTTTTTTCTTCCATTTCAGGTGTCGTGA |
| | | CCACCATGGCGCTTCCGGTGACAGCACTGCTCCTCCCCTTGGCGCT |
| | | GTTGCTCCACGCAGCAAGGCCGCAGGTGCAGCTGGTGCAGAGCGGA |
| | | GCCGAGCTCAAGAAGCCCGGAGCCTCCGTGAAGGTGAGCTGCAAGG |
| | | CCAGCGGCAACACCCTGACCAACTACGTGATCCACTGGGTGAGACA |
| | | AGCCCCCGGCCAAAGGCTGGAGTGGATGGGCTACATCCTGCCCTAC |
| | | AACGACCTGACCAAGTACAGCCAGAAGTTCCAGGGCAGGGTGACCA |
| | | TCACCAGGGATAAGAGCGCCTCCACCGCCTATATGGAGCTGAGCAG |
| | | CCTGAGGAGCGAGGACACCGCTGTGTACTACTGTACAAGGTGGGAC |
| | | TGGGACGGCTTCTTTGACCCCTGGGGCCAGGGCACAACAGTGACCG |
| | | TCAGCAGCGGCGGCGGAGGCAGCGGCGGCGGCGGCAGCGGCGGAGG |
| | | CGGAAGCGAAATCGTGATGACCCAGAGCCCCGCCACACTGAGCGTG |
| | | AGCCCTGGCGAGAGGGCCAGCATCTCCTGCAGGGCTAGCAAAGCC |
| | | TGGTGCACAGCAACGGCAACACCCACCTGCACTGGTACCAGCAGAG |
| | | ACCCGGACAGGCTCCCAGGCTGCTGATCTACAGCGTGAGCAACAGG |
| | | TTCTCCGAGGTGCCTGCCAGGTTTAGCGGCAGCGGAAGCGGCACCG |
| | | ACTTTACCCTGACCATCAGCAGCGTGGAGTCCGAGGACTTCGCCGT |
| | | GTATTACTGCAGCCAGACCAGCCACATCCCTTACACCTTCGGCGGC |
| | | GGCACCAAGCTGGAGATCAAAAGTGCTGCTGCCTTTGTCCCGGTAT |
| | | TTCTCCCAGCCAAACCGACCACGACTCCCGCCCCGCGCCCTCCGAC |
| | | ACCCGCTCCCACCATCGCCTCTCAACCTCTTAGTCTTCGCCCCGAG |
| | | GCATGCCGACCCGCCGCCGGGGGTGCTGTTCATACGAGGGGCTTGG |
| | | ACTTCGCTTGTGATATTTACATTTGGGCTCCGTTGGCGGGTACGTG |
| | | CGGCGTCCTTTTGTTGTCACTCGTTATTACTTTGTATTGTAATCAC |
| | | AGGAATCGCAAACGGGGCAGAAAGAAACTCCTGTATATATTCAAAC |
| | | AACCATTTATGAGACCAGTACAAACTACTCAAGAGGAAGATGGCTG |
| | | TAGCTGCCGATTTCCAGAAGAAGAAGAAGGAGGATGTGAACTGCGA |
| | | GTGAAGTTTTCCCGAAGCGCAGACGCTCCGGCATATCAGCAAGGAC |
| | | AGAATCAGCTGTATAACGAACTGAATTTGGGACGCCGCGAGGAGTA |
| | | TGACGTGCTTGATAAACGCCGGGGAGAGACCCGGAAATGGGGGGT |
| | | AAACCCCGAAGAAAGAATCCCCAAGAAGGACTCTACAATGAACTCC |
| | | AGAAGGATAAGATGGCGGAGGCCTACTCAGAAATAGGTATGAAGGG |
| | | CGAACGACGACGGGGAAAAGGTCACGATGGCCTCTACCAAGGGTTG |
| | | AGTACGGCAACCAAAGATACGTACGATGCACTGCATATGCAGGCCC |
| | | TGCCTCCCAGATAATAATAAAATCGCTATCCATCGAAGATGGATGT |
| | | GTGTTGGTTTTTTGTGTGTGGAGCAACAAATCTGACTTTGCATGTG |
| | | CAAACGCCTTCAACAACAGCATTATTCCAGAAGACACCTTCTTCCC |
| | | CAGCCCAGGTAAGGGCAGCTTTGGTGCCTTCGCAGGCTGTTTCCTT |
| | | GCTTCAGGAATGGCCAGGTTCTGCCCAGAGCTCTGGTCAATGATGT |
| | | CTAAAACTCCTCTGATTGGTGGTCTCGGCCTTATCCATTGCCACCA |
| | | AAACCCTCTTTTTACTAAGAAACAGTGAGCCTTGTTCTGGCAGTCC |
| | | AGAGAATGACACGGGAAAAAAGCAGATGAAGAGAAGGTGGCAGGAG |

-continued

| SEQ ID NO | Description | Sequence |
|---|---|---|
| | | AGGGCACGTGGCCCAGCCTCAGTCTCTCCAACTGAGTTCCTGCCTG<br>CCTGCCTTTGCTCAGACTGTTTGCCCCTTACTGCTCTTCTAGGCCT<br>CATTCTAAGCCCCTTCTCCAAGTTGCCTCTCCTTATTTCTCCCTGT<br>CTGCCAAAAAATCTTTCCCAGCTCACTAAGTCAGTCTCACGCAGTC<br>ACTCATTAACCCACCAATCACTGATTGTGCCGGCACATGAATGCAC<br>CAGGTGTTGAAGTGGAGGAATTAAAAAGTCAGATGAGGGGTGTGCC<br>CAGAGGAAGCACCATTCTAGTTGGGGGAGCCCATCTGTCAGCTGGG<br>AAAAGTCCAAATAACTTCAGATTGGAATGTGTTTTAACTCAGGGTT<br>GAGAAAACAGCTACCTTCAGGACAAAAGTCAGGGAAGGGCTCTCTG<br>AAGAAATGCTACTTGAAGATACCAGCCCTACCAAGGGCAGGGAGAG<br>GACCCTATAGAGGCCTGGGACAGGAGCTCAATGAGAAAGG |
| 56 | BCMA CAR nucleotide sequence | ATGGCGCTTCCGGTGACAGCACTGCTCCTCCCCTTGGCGCTGTTGC<br>TCCACGCAGCAAGGCCGCAGGTGCAGCTGGTGCAGAGCGGAGCCGA<br>GCTCAAGAAGCCCGGAGCCTCCGTGAAGGTGAGCTGCAAGGCCAGC<br>GGCAACACCCTGACCAACTACGTGATCCACTGGGTGAGACAAGCCC<br>CCGGCCAAAGGCTGGAGTGGATGGGCTACATCCTGCCCTACAACGA<br>CCTGACCAAGTACAGCCAGAAGTTCCAGGGCAGGGTGACCATCACC<br>AGGGATAAGAGCGCCTCCACCGCCTATATGGAGCTGAGCAGCCTGA<br>GGAGCGAGGACACCGCTGTGTACTACTGTACAAGGTGGGACTGGGA<br>CGGCTTCTTTGACCCCTGGGGCCAGGGCACAACAGTGACCGTCAGC<br>AGCGGCGGCGGAGGCAGCGGCGGCGGCGGCAGCGGCGGAGGCGGAA<br>GCGAAATCGTGATGACCCAGAGCCCCGCCACACTGAGCGTGAGCCC<br>TGGCGAGAGGGCCAGCATCTCCTGCAGGGCTAGCCAAAGCCTGGTG<br>CACAGCAACGGCAACACCCACCTGCACTGGTACCAGCAGAGACCCG<br>GACAGGCTCCCAGGCTGCTGATCTACAGCGTGAGCAACAGGTTCTC<br>CGAGGTGCCTGCCAGGTTTAGCGGCAGCGGAAGCGGCACCGACTTT<br>ACCCTGACCATCAGCAGCGTGGAGTCCGAGGACTTCGCCGTGTATT<br>ACTGCAGCCAGACCAGCCACATCCCTTACACCTTCGGCGGCGGCAC<br>CAAGCTGGAGATCAAAAGTGCTGCTGCCTTTGTCCCGGTATTTCTC<br>CCAGCCAAACCGACCACGACTCCCGCCCCGCGCCCTCCGACACCCG<br>CTCCCACCATCGCCTCTCAACCTCTTAGTCTTCGCCCCGAGGCATG<br>CCGACCCGCCGCCGGGGTGCTGTTCATACGAGGGGCTTGGACTTC<br>GCTTGTGATATTTACATTTGGGCTCCGTTGGCGGGTACGTGCGGCG<br>TCCTTTTGTTGTCACTCGTTATTACTTTGTATTGTAATCACAGGAA<br>TCGCAAACGGGGCAGAAAGAAACTCCTGTATATATTCAAACAACCA<br>TTTATGAGACCAGTACAAACTACTAAGAGGAAGATGGCTGTAGCT<br>GCCGATTTCCAGAAGAAGAAGAAGGAGGATGTGAACTGCGAGTGAA<br>GTTTTCCCGAAGCGCAGACGCTCCGGCATATCAGCAAGGACAGAAT<br>CAGCTGTATAACGAACTGAATTTGGGACGCCGCGAGGAGTATGACG<br>TGCTTGATAAACGCGGGGGAGAGACCCGGAAATGGGGGTAAACC<br>CCGAAGAAAGAATCCCCAAGAAGGACTCTACAATGAACTCCAGAAG<br>GATAAGATGGCGGAGGCCTACTCAGAAATAGGTATGAAGGGCGAAC<br>GACGACGGGGAAAAGGTCACGATGGCCTCTACCAAGGGTTGAGTAC<br>GGCAACCAAAGATACGTACGATGCACTGCATATGCAGGCCCTGCCT<br>CCCAGA |
| 57 | BCMA CAR amino acid sequence | MALPVTALLLPLALLLHAARPQVQLVQSGAELKKPGASVKVSCKAS<br>GNTLTNYVIHWVRQAPGQRLEWMGYILPYNDLTKYSQKFQGRVTIT<br>RDKSASTAYMELSSLRSEDTAVYYCTRWDWDGFFDPWGQGTTVTVS<br>SGGGGSGGGGSGGGGSEIVMTQSPATLSVSPGERASISCRASQSLV<br>HSNGNTHLHWYQQRPGQAPRLLIYSVSNRFSEVPARFSGSGSGTDF<br>TLTISSVESEDFAVYYCSQTSHIPYTFGGGTKLEIKSAAAFVPVFL<br>PAKPTTTPAPRPPTPAPTIASQPLSLRPEACRPAAGGAVHTRGLDF<br>ACDIYIWAPLAGTCGVLLLSLVITLYCNHRNRKRGRKKLLYIFKQP<br>FMRPVQTTQEEDGCSCRFPEEEEGGCELRVKFSRSADAPAYQQGQN<br>QLYNELNLGRREEYDVLDKRRGRDPEMGGKPRRKNPQEGLYNELQK<br>DKMAEAYSEIGMKGERRRGKGHDGLYQGLSTATKDTYDALHMQALP<br>PR |
| 58 | BCMA scFv nucleotide sequence | CAGGTGCAGCTGGTGCAGAGCGGAGCCGAGCTCAAGAAGCCCGGAG<br>CCTCCGTGAAGGTGAGCTGCAAGGCCAGCGGCAACACCCTGACCAA<br>CTACGTGATCCACTGGGTGAGACAAGCCCCCGGCCAAAGGCTGGAG<br>TGGATGGGCTACATCCTGCCCTACAACGACCTGACCAAGTACAGCC<br>AGAAGTTCCAGGGCAGGGTGACCATCACCAGGGATAAGAGCGCCTC<br>CACCGCCTATATGGAGCTGAGCAGCCTGAGGAGCGAGGACACCGCT<br>GTGTACTACTGTACAAGGTGGGACTGGGACGGCTTCTTTGACCCCT<br>GGGGCCAGGGCACAACAGTGACCGTCAGCAGCGGCGGCGGAGGCAG<br>CGGCGGCGGCGGCAGCGGCGGAGGCGGAAGCGAAATCGTGATGACC<br>CAGAGCCCCGCCACACTGAGCGTGAGCCCTGGCGAGAGGGCCAGCA<br>TCTCCTGCAGGGCTAGCCAAAGCCTGGTGCACAGCAACGGCAACAC<br>CCACCTGCACTGGTACCAGCAGAGACCCGGACAGGCTCCCAGGCTG<br>CTGATCTACAGCGTGAGCAACAGGTTCTCCGAGGTGCCTGCCAGGT<br>TTAGCGGCAGCGGAAGCGGCACCGACTTTACCCTGACCATCAGCAG |

-continued

Summary of Sequences

| SEQ ID NO | Description | Sequence |
|---|---|---|
| | | CGTGGAGTCCGAGGACTTCGCCGTGTATTACTGCAGCCAGACCAGC<br>CACATCCCTTACACCTTCGGCGGCGGCACCAAGCTGGAGATCAAA |
| 59 | BCMA scFv amino acid sequence (linker underlined) | QVQLVQSGAELKKPGASVKVSCKASGNTLTNYVIHWVRQAPGQRLE<br>WMGYILPYNDLTKYSQKFQGRVTITRDKSASTAYMELSSLRSEDTA<br>VYYCTRWDWDGFFDPWGQGTTVTVSS<u>GGGGSGGGGSGGGGS</u>EIVMT<br>QSPATLSVSPGERASISCRASQSLVHSNGNTHLHWYQQRPGQAPRL<br>LIYSVSNRFSEVPARFSGSGSGTDFTLTISSVESEDFAVYYCSQTS<br>HIPYTFGGGTKLEIK |
| 60 | BCMA VH | QVQLVQSGAELKKPGASVKVSCKASGNTLTNYVIHWVRQAPGQRLE<br>WMGYILPYNDLTKYSQKFQGRVTITRDKSASTAYMELSSLRSEDTA<br>VYYCTRWDWDGFFDPWGQGTTVTVSS |
| 61 | BCMA VL | EIVMTQSPATLSVSPGERASISCRASQSLVHSNGNTHLHWYQQRPG<br>QAPRLLIYSVSNRFSEVPARFSGSGSGTDFTLTISSVESEDFAVYY<br>CSQTSHIPYTFGGGTKLEIK |
| 62 | CD70 VL CDR1 (Kabat) | RASKSVSTSGYSFMH |
| 63 | CD70 VL CDR1 (Chothia) | <u>SKSVSTSGYSF</u> |
| 64 | CD70 VL CDR2 (Kabat) | LASNLES |
| 65 | CD70 VL CDR2 (Chothia) | LAS |
| 66 | CD70 VL CDR3 (Kabat) | QHSREVPWT |
| 67 | CD70 VL CDR3 (Chothia) | SREVPW |
| 68 | CD70 VH CDR1 (Kabat) | NYGMN |
| 69 | CD70 VH CDR1 (Chothia) | GYTFTNYGMN |
| 70 | CD70 VH CDR2 (Kabat) | WINTYTGEPTYADAFKG |
| 71 | CD70 VH CDR2 (Chothia) | NTYTGE |
| 72 | CD70 VH CDR3 (Kabat) | DYGDYGMDY |
| 73 | CD70 VH CDR3 (Chothia) | CARDYGDYGMDYWG |
| 74 | BCMA VL CDR1 (Kabat) | RASQSLVHSNGNTHLH |
| 75 | BCMA VL CDR1 (Chothia) | RASQSLVHSNGNTHLH |

-continued

| SEQ ID NO | Description | Sequence |
|---|---|---|
| 76 | BCMA VL CDR2 (Kabat) | SVSNR |
| 77 | BCMA VL CDR2 (Chothia) | SVSNR |
| 78 | BCMA VL CDR3 (Kabat) | SQTSHIPYT |
| 79 | BCMA VL CDR3 (Chothia) | SQTSHIPYT |
| 80 | BCMA VH CDR1 (Kabat) | NYVIH |
| 81 | BCMA VH CDR1 (Chothia) | GNTLTNY |
| 82 | BCMA VH CDR2 (Kabat) | YILPYNDLTKYSQKFQG |
| 83 | BCMA VH CDR2 (Chothia) | LPYNDL |
| 84 | BCMA VH CDR3 (Kabat) | WDWDGFFDP |
| 85 | BCMA VH CDR3 (Chothia) | WDWDGFFDP |
| 86 | TRAC target sequence | AGAGCAACAGTGCTGTGGCC |
| 87 | anti-CD33 CAR rAAV | CCTGCAGGCAGCTGCGCGCTCGCTCGCTCACTGAGGCCGCCCGGGC<br>GTCGGGCGACCTTTGGTCGCCCGGCCTCAGTGAGCGAGCGAGCGCG<br>CAGAGAGGGAGTGGCCAACTCCATCACTAGGGGTTCCTGCGGCCGC<br>ACGCGTGAGATGTAAGGAGCTGCTGTGACTTGCTCAAGGCCTTATA<br>TCGAGTAAACGGTAGTGCTGGGGCTTAGACGCAGGTGTTCTGATTT<br>ATAGTTCAAAACCTCTATCAATGAGAGAGCAATCTCCTGGTAATGT<br>GATAGATTTCCCAACTTAATGCCAACATACCATAAACCTCCCATTC<br>TGCTAATGCCCAGCCTAAGTTGGGGAGACCACTCCAGATTCCAAGA<br>TGTACAGTTTGCTTTGCTGGGCCTTTTTCCCATGCCTGCCTTTACT<br>CTGCCAGAGTTATATTGCTGGGGTTTTGAAGAAGATCCTATTAAAT<br>AAAAGAATAAGCAGTATTATTAAGTAGCCCTGCATTTCAGGTTTCC<br>TTGAGTGGCAGGCCAGGCCTGGCCGTGAACGTTCACTGAAATCATG<br>GCCTCTTGGCCAAGATTGATAGCTTGTGCCTGTCCCTGAGTCCCAG<br>TCCATCACGAGCAGCTGGTTTCTAAGATGCTATTTCCCGTATAAAG<br>CATGAGACCGTGACTTGCCAGCCCCACAGAGCCCCGCCCTTGTCCA<br>TCACTGGCATCTGGACTCCAGCCTGGGTTGGGGCAAAGAGGGAAAT<br>GAGATCATGTCCTAACCCTGATCCTCTTGTCCCACAGATATCCAGA<br>ACCCTGACCCTGCCGTGTACCAGCTGAGAGACTCTAAATCCAGTGA<br>CAAGTCTGTCTGCCTATTCACCGATTTTGATTCTCAAACAAATGTG<br>TCACAAAGTAAGGATTCTGATGTGTATATCACAGACAAAACTGTGC<br>TAGACATGAGGTCTATGGACTTCAggctccggtgccgtcagtggg<br>cagagcgcacatcgcccacagtccccgagaagttgggggagggt<br>cggcaattgaaccggtgcctagagaaggtggcgcggggtaaactgg<br>gaaagtgatgtcgtgtactggctccgccttttcccgagggtgggg<br>gagaaccgtatataagtgcagtagtcgccgtgaacgttcttttcg<br>caacgggtttgccgccagaacacaggtaagtgccgtgtgtggttcc<br>cgcgggcctggcctcttacgggttatggcccttgcgtgccttgaa<br>ttacttccactggctgcagtacgtgattcttgatcccgagcttcgg<br>gttggaagtgggtgggagagttcgaggccttgcgcttaaggagccc<br>cttcgcctcgtgcttgagttgaggcctggcctgggcgctgggccg<br>ccgcgtgcgaatctggtggcaccttcgcgcctgtctcgctgctttc |

Summary of Sequences

| SEQ ID NO | Description | Sequence |
|---|---|---|
| | | gataagtctctagccatttaaaattttgatgacctgctgcgacgc |
| | | tttttttctggcaagatagtcttgtaaatgcgggccaagatctgca |
| | | cactggtatttcggttttgggccgcgggcggcgacggggcccgt |
| | | gcgtcccagcgcacatgttcggcgaggcggggcctgcgagcgcggc |
| | | caccgagaatcggacgggggtagtctcaagctggccggcctgctct |
| | | ggtgcctggcctcgcgccgccgtgtatcgccccgccctgggcggca |
| | | aggctggcccggtcggcaccagttgcgtgagcggaaagatggccgc |
| | | ttcccggccctgctgcagggagctcaaaatggaggacgcggcgctc |
| | | gggagagcgggcgggtgagtcacccacacaaaggaaaagggccttt |
| | | ccgtcctcagccgtcgcttcatgtgactccacggagtaccgggcgc |
| | | cgtccaggcacctcgattagttctcgagcttttggagtacgtcgtc |
| | | tttaggttgggggagggttttatgcgatggagtttccccacact |
| | | gagtgggtggagactgaagttaggccagcttggcacttgatgtaat |
| | | ctccttggaatttgcccttttgagtttggatcttggttcattctc |
| | | aagcctcagacagtggttcaaagttttttcttccatttcaggtgt |
| | | cgtgaCCACCATGGCGCTTCCGGTGACAGCACTGCTCCTCCCCTTG |
| | | GCGCTGTTGCTCCACGCAGCAAGGCCGGAAATCGTCCTCACACAAT |
| | | CCCCGGGGAGCCTCGCAGTCAGTCCTGGGGAACGAGTCACTATGAG |
| | | CTGCAAATCCAGTCAGAGTGTTTTTTTCTCAAGTAGCCAGAAGAAC |
| | | TACCTCGCATGGTACCAACAAATACCGGGGCAATCTCCCCGCTTGC |
| | | TTATATACTGGGCAAGTACCCGCGAATCCGGCGTACCGGATCGATT |
| | | CACGGGATCTGGGTCAGGTACTGATTTCACTTTGACTATCAGCTCT |
| | | GTTCAGCCTGAAGATTTGGCAATTTACTACTGTCACCAATACTTGA |
| | | GTAGCCGAACTTTCGGCCAGGGCACGAAGCTCGAAATCAAGGGCGG |
| | | AGGGGGAGGTTCTGGTGGGGCGGTTCTGGCGGTGGAGGAAGCCAA |
| | | GTACAGTTGCAACAGCCAGGGGCGGAGGTCGTAAAACCTGGGGCGT |
| | | CTGTCAAGATGAGCTGTAAAGCAAGTGGATACACCTTCACCTCCTA |
| | | CTATATACATTGGATTAAGCAAACTCCGGGTCAGGGGCTGGAATGG |
| | | GTTGGCGTTATATACCCCGGGAACGATGATATATCATACAACCAAA |
| | | AATTTCAAGGCAAGGCGACTCTGACTGCCGATAAGAGTAGCACAAC |
| | | AGCTTACATGCAGCTTTCTTCCCTGACCAGCGAAGATTCAGCAGTT |
| | | TACTACTGCGCTCGGGAAGTGCGCCTGCGATACTTTGATGTCTGGG |
| | | GTCAAGGAACTACAGTTACTGTATCAAGCAGTGCTGCTGCCTTTGT |
| | | CCCGGTATTTCTCCCAGCCAAACCGACCACGACTCCCGCCCCGCGC |
| | | CCTCCGACACCCGCTCCCACCATCGCCTCTCAACCTCTTAGTCTTC |
| | | GCCCCGAGGCATGCCGACCCGCCGCCGGGGGTGCTGTTCATACGAG |
| | | GGGCTTGGACTTCGCTTGTGATATTTACATTTGGGCTCCGTTGGCG |
| | | GGTACGTGCGGCGTCCTTTTGTTGTCACTCGTTATTACTTTGTATT |
| | | GTAATCACAGGAATCGCAAACGGGGCAGAAAGAAACTTCCTGTATAT |
| | | ATTCAAACAACCATTTATGAGACCAGTACAAACTACTCAAGAGGAA |
| | | GATGGCTGTAGCTGCCGATTTCCAGAAGAAGAAGAAGGAGGATGTG |
| | | AACTGCGAGTGAAGTTTTCCCGAAGCGCAGACGCTCCGGCATATCA |
| | | GCAAGGACAGAATCAGCTGTATAACGAACTGAATTTGGGACGCCGC |
| | | GAGGAGTATGACGTGCTTGATAAACGCCGGGGAGAGACCCGGAAA |
| | | TGGGGGGTAAACCCCGAAGAAAGAATCCCCAAGAAGGACTCTACAA |
| | | TGAACTCCAGAAGGATAAGATGGCGGAGGCCTACTCAGAAATAGGT |
| | | ATGAAGGGCGAACGACGACGGGGAAAAGGTCACGATGGCCTCTACC |
| | | AAGGGTTGAGTACGGCAACCAAAGATACGTACGATGCACTGCATAT |
| | | GCAGGCCCTGCCTCCCAGATAATAATAAAATCGCTATCCATCGAAG |
| | | ATGGATGTGTGTTGGTTTTTTGTGTGTGGAGCAACAAATCTGACTT |
| | | TGCATGTGCAAACGCCTTCAACAACAGCATTATTCCAGAAGACACC |
| | | TTCTTCCCCAGCCCAGGTAAGGGCAGCTTTGGTGCCTTCGCAGGCT |
| | | GTTTCCTTGCTTCAGGAATGGCCAGGTTCTGCCCAGAGCTCTGGTC |
| | | AATGATGTCTAAAACTCCTCTGATTGGTGGTCTCGGCCTTATCCAT |
| | | TGCCACCAAAACCCTCTTTTTACTAAGAAACAGTGAGCCTTGTTCT |
| | | GGCAGTCCAGAGAATGACACGGGAAAAAAGCAGATGAAGAGAAGGT |
| | | GGCAGGAGAGGGCACGTGGCCCAGCCTCAGTCTCTCCAACTGAGTT |
| | | CCTGCCTGCCTGCCTTTGCTCAGACTGTTTGCCCCTTACTGCTCTT |
| | | CTAGGCCTCATTCTAAGCCCCTTCTCCAAGTTGCCTCTCCTTATTT |
| | | CTCCCTGTCTGCCAAAAAATCTTTCCCAGCTCACTAAGTCAGTCTC |
| | | ACGCAGTCACTCATTAACCCACCAATCACTGATTGTGCCGGCACAT |
| | | GAATGCACCAGGTGTTGAAGTGGAGGAATTAAAAAGTCAGATGAGG |
| | | GGTGTGCCCAGAGGAAGCACCATTCTAGTTGGGGGAGCCCATCTGT |
| | | CAGCTGGGAAAAGTCCAAATAACTTCAGATTGGAATGTGTTTTAAC |
| | | TCAGGGTTGAGAAAACAGCTACCTTCAGGACAAAAGTCAGGGAAGG |
| | | GCTCTCTGAAGAAATGCTACTTGAAGATACCAGCCCTACCAAGGGC |
| | | AGGGAGAGGACCCTATAGAGGCCTGGGACAGGAGCTCAATGAGAAA |
| | | GGTAACCACGTGCGGACCGAGGCTGCAGCGTCGTCCTCCCTAGGAA |
| | | CCCCTAGTGATGGAGTTGGCCACTCCCTCTCTGCGCGCTCGCTCGC |
| | | TCACTGAGGCCGGGCGACCAAAAGGTCGCCCGACGCCCGGGCTTTGC |
| | | CCGGGCGGCCCTCAGTGAGCGAGCGAGCGCGCAGCTGCCTGCAGG |

Summary of Sequences

| SEQ ID NO | Description | Sequence |
|---|---|---|
| 88 | signal peptide | MLLLVTSLLLCELPHPAFLLIP |
| 89 | signal peptide | MALPVTALLLPLALLLHAARP |
| 90 | CD8a | FVPVFLPAKPTTTPAPRPPTPAPTIASQPLSLRPEACRPAAGGAVH TRGLDFACDIYIWAPLAGTCGVLLLSLVITLYCNHRNR |
| 91 | CD70 sgRNA (E1_T1) spacer | UCACCAAGCCCGCGACCAAU |
| 92 | CD70 sgRNA (E1_T3) spacer | AUCACCAAGCCCGCGACCAA |
| 93 | CD70 sgRNA (E1_T4) spacer | CGGUGCGGCGCAGGCCCUAU |
| 94 | CD70 sgRNA (E1_T7) spacer | GCUUUGGUCCCAUUGGUCGC |
| 95 | CD70 sgRNA (E1_T8) spacer | GCCCGCAGGACGCACCCAUA |
| 96 | CD70 sgRNA (E1_T10) spacer | GUGCAUCCAGCGCUUCGCAC |
| 97 | CD70 sgRNA (E3_T1) spacer | CAGCUACGUAUCCAUCGUGA |
| 98 | TRAC spacer | AGAGCAACAGUGCUGUGGCC |
| 99 | 32M sgRNA spacer | GCUACUCUCUCUUUCUGGCC |
| 100 | PD-1 sgRNA spacer | CUGCAGCUUCUCCAACACAU |
| 101 | CD70 sgRNA (E1_T3) spacer | U*C*A*CCAAGCCCGCGACCAAU |
| 102 | CD70 sgRNA (E1_T4) spacer | A*U*C*ACCAAGCCCGCGACCAA |
| 103 | CD70 sgRNA (E1_T7) spacer | C*G*G*UGCGGCGCAGGCCCUAU |
| 104 | CD70 sgRNA (E1_T8) spacer | G*C*U*UUGGUCCCAUUGGUCGC |

-continued

Summary of Sequences

| SEQ ID NO | Description | Sequence |
|---|---|---|
| 105 | CD70 sgRNA (E1_T10) spacer | G*C*C*CGCAGGACGCACCCAUA |
| 106 | CD70 sgRNA (E3_T10) spacer | G*U*G*CAUCCAGCGCUUCGCAC |
| 107 | CD70 sgRNA (E1_T3) spacer | C*A*G*CUACGUAUCCAUCGUGA |
| 108 | TRAC spacer | A*G*A*GCAACAGUGCUGUGGCC |
| 109 | β2M sgRNA spacer | G*C*U*ACUCUCUCUUUCUGGCC |
| 110 | PD-1 sgRNA spacer | C*U*G*CAGCUUCUCCAACACAU |
| 111 | CD70 sgRNA (E1_T1) with PAM | TCACCAAGCCCGCGACCAATGGG |
| 112 | CD70 sgRNA (E1_T3) with PAM | ATCACCAAGCCCGCGACCAATGG |
| 113 | CD70 sgRNA (E1_T4) with PAM | CGGTGCGGCGCAGGCCCTATGGG |
| 114 | CD70 sgRNA (E1_T7) with PAM | GCTTTGGTCCCATTGGTCGCGGG |
| 115 | CD70 sgRNA (E1_T8) with PAM | GCCCGCAGGACGCACCCATAGGG |
| 116 | CD70 sgRNA (E1_T10) with PAM | GTGCATCCAGCGCTTCGCACAGG |
| 117 | CD70 sgRNA (E3_T1) with PAM | CAGCTACGTATCCATCGTGATGG |
| 118 | TRAC sgRNA with PAM | AGAGCAACAGTGCTGTGGCCTGG |
| 119 | β2M sgRNA with PAM | GCTACTCTCTCTTTCTGGCCTGG |
| 120 | PD-1 sgRNA with PAM | CTGCAGCTTCTCCAACACATCGG |

Summary of Sequences

| SEQ ID NO | Description | Sequence |
|---|---|---|
| 121 | CD28 nucleotide sequence | TCAAAGCGGAGTAGGTTGTTGCATTCCGATTACATGAATATGACTC<br>CTCGCCGGCCTGGGCCGACAAGAAAACATTACCAACCCTATGCCCC<br>CCCACGAGACTTCGCTGCGTACAGGTCC |
| 122 | TRAC-LHA | GAGATGTAAGGAGCTGCTGTGACTTGCTCAAGGCCTTATATCGAGT<br>AAACGGTAGTGCTGGGGCTTAGACGCAGGTGTTCTGATTTATAGTT<br>CAAAACCTCTATCAATGAGAGAGCAATCTCCTGGTAATGTGATAGA<br>TTTCCCAACTTAATGCCAACATACCATAAACCTCCCATTCTGCTAA<br>TGCCCAGCCTAAGTTGGGGAGACCACTCCAGATTCCAAGATGTACA<br>GTTTGCTTTGCTGGGCCTTTTTCCCATGCCTGCCTTTACTCTGCCA<br>GAGTTATATTGCTGGGGTTTTGAAGAAGATCCTATTAAATAAAAGA<br>ATAAGCAGTATTATTAAGTAGCCCTGCATTTCAGGTTTCCTTGAGT<br>GGCAGGCCAGGCCTGGCCGTGAACGTTCACTGAAATCATGGCCTCT<br>TGGCCAAGATTGATAGCTTGTGCCTGTCCCTGAGTCCCAGTCCATC<br>ACGAGCAGCTGGTTTCTAAGATGCTATTTCCCGTATAAAGCATGAG<br>ACCGTGACTTGCCAGCCCCACAGAGCCCCGCCCTTGTCCATCACTG<br>GCATCTGGACTCCAGCCTGGGTTGGGGCAAAGAGGGAAATGAGATC<br>ATGTCCTAACCCTGATCCTCTTGTCCCACAGATATCCAGAACCCTG<br>ACCCTGCCGTGTACCAGCTGAGAGACTCTAAATCCAGTGACAAGTC<br>TGTCTGCCTATTCACCGATTTTGATTCTCAAACAAATGTGTCACAA<br>AGTAAGGATTCTGATGTGTATATCACAGACAAAACTGTGCTAGACA<br>TGAGGTCTATGGACTTCA |
| 123 | EF1α promoter | GGCTCCGGTGCCCGTCAGTGGGCAGAGCGCACATCGCCCACAGTCC<br>CCGAGAAGTTGGGGGGAGGGGTCGGCAATTGAACCGGTGCCTAGAG<br>AAGGTGGCGCGGGGTAAACTGGGAAAGTGATGTCGTGTACTGGCTC<br>CGCCTTTTTCCCGAGGGTGGGGGAGAACCGTATATAAGTGCAGTAG<br>TCGCCGTGAACGTTCTTTTTCGCAACGGGTTTGCCGCCAGAACACA<br>GGTAAGTGCCGTGTGTGGTTCCCGCGGGCCTGGCCTCTTTACGGGT<br>TATGGCCCTTGCGTGCCTTGAATTACTTCCACTGGCTGCAGTACGT<br>GATTCTTGATCCCGAGCTTCGGGTTGGAAGTGGGTGGGAGAGTTCG<br>AGGCCTTGCGCTTAAGGAGCCCCTTCGCCTCGTGCTTGAGTTGAGG<br>CCTGGCCTGGGCGCTGGGGCCGCCGCGTGCGAATCTGGTGGCACCT<br>TCGCGCCTGTCTCGCTGCTTTCGATAAGTCTCTAGCCATTTAAAAT<br>TTTTGATGACCTGCTGCGACGCTTTTTTTTCTGGCAAGATAGTCTTG<br>TAAATGCGGGCCAAGATCTGCACACTGGTATTTCGGTTTTTGGGGC<br>CGCGGGCGGCGACGGGGCCCGTGCGTCCCAGCGCACATGTTCGGCG<br>AGGCGGGGCCTGCGAGCGCGGCCACCGAGAATCGGACGGGGGTAGT<br>CTCAAGCTGGCCGGCCTGCTCTGGTGCCTGGCCTCGCGCCGCCGTG<br>TATCGCCCCGCCCTGGGCGGCAAGGCTGGCCCGGTCGGCACCAGTT<br>GCGTGAGCGGAAAGATGGCCGCTTCCCGGCCCTGCTGCAGGGAGCT<br>CAAAATGGAGGACGCGGCGCTCGGGAGAGCGGGCGGGTGAGTCACC<br>CACACAAAGGAAAAGGGCCTTTCCGTCCTCAGCCGTCGCTTCATGT<br>GACTCCACGGAGTACCGGGCGCCGTCCAGGCACCTCGATTAGTTCT<br>CGAGCTTTTGGAGTACGTCGTCTTTAGGTTGGGGGGAGGGGTTTTA<br>TGCGATGGAGTTTCCCCACACTGAGTGGGTGGAGACTGAAGTTAGG<br>CCAGCTTGGCACTTGATGTAATTCTCCTTGGAATTTGCCCTTTTTG<br>AGTTTGGATCTTGGTTCATTCTCAAGCCTCAGACAGTGGTTCAAAG<br>TTTTTTTCTTCCATTTCAGGTGTCGTGA |
| 124 | Synthetic poly(A) signal | AATAAAATCGCTATCCATCGAAGATGGATGTGTGTTGGTTTTTTGT<br>GTG |
| 125 | TRAC-RHA | TGGAGCAACAAATCTGACTTTGCATGTGCAAACGCCTTCAACAACA<br>GCATTATTCCAGAAGACACCTTCTTCCCCAGCCCAGGTAAGGGCAG<br>CTTTGGTGCCTTCGCAGGCTGTTTCCTTGCTTCAGGAATGGCCAGG<br>TTCTGCCCAGAGCTCTGGTCAATGATGTCTAAAACTCCTCTGATTG<br>GTGGTCTCGGCCTTATCCATTGCCACCAAAACCCTCTTTTTACTAA<br>GAAACAGTGAGCCTTGTTCTGGCAGTCCAGAGAATGACACGGGAAA<br>AAAGCAGATGAAGAGAAGGTGGCAGGAGAGGGCACGTGGCCCAGCC<br>TCAGTCTCTCCAACTGAGTTCCTGCCTGCCTGCCTTTGCTCAGACT<br>GTTTGCCCCTTACTGCTCTTCTAGGCCTCATTCTAAGCCCCTTCTC<br>CAAGTTGCCTCTCCTTATTTCTCCCTGTCTGCCAAAAAATCTTTCC<br>CAGCTCACTAAGTCAGTCTCACGCAGTCACTCATTAACCCACCAAT<br>CACTGATTGTGCCGGCACATGAATGCACCAGGTGTTGAAGTGGAGG<br>AATTAAAAAGTCAGATGAGGGGTGTGCCCAGAGGAAGCACCATTCT<br>AGTTGGGGGAGCCCATCTGTCAGCTGGGAAAAGTCCAAATAACTTC<br>AGATTGGAATGTGTTTTAACTCAGGGTTGAGAAAACAGCTACCTTC<br>AGGACAAAAGTCAGGGAAGGGCTCTCTGAAGAAATGCTACTTGAAG<br>ATACCAGCCCCTACCAAGGGCAGGGAGAGGACCCTATAGAGGCCTGG<br>GACAGGAGCTCAATGAGAAAGG |

-continued

Summary of Sequences

| SEQ ID NO | Description | Sequence |
|---|---|---|
| 126 | CD8a transmembrane | IYIWAPLAGTCGVLLLSLVITLY |
| 127 | CD70 forward primer | TCGTCGGCAGCGTCAGATGTGTATAAGAGACAGcccaacttttcca tctcaactcaccccaagtg |
| 128 | CD70 reverse primer | GTCTCGTGGGCTCGGAGATGTGTATAAGAGACAGccctcctgcgc tagcgga |
| 129 | CD70 Indel | CACACCACGAGGCAGATCACCAAGCCCGCG-CAATGGGACCAAAGC AGCCCGCAGGACG |
| 130 | CD70 Indel | CACACCACGAGGCAGATCACCAAGCCCGCGAACCAATGGGACCAAA GCAGCCCGCAGGACG |
| 131 | CD70 Indel | CACACCACGAGGCAGATC-----------ACCAATGGGACCAAAG CAGCCCGCAGGACG |
| 132 | CD70 Indel | CACACCACGAGGCAGATCACCAAGCCCGCG-CCAATGGGACCAAAG CAGCCCGCAGGACG |
| 133 | CD70 Indel | CACACCACGAGGCAGATCACCAAGCCCGC-ACCAATGGGACCAAAG CAGCCCGCAGGACG |
| 134 | CD70 Indel | CACACCACGAGGCAGATCACCA------------------------AGCCCGCAGGACG |
| 135 | Anti-CD33 CAR Donor LHA to RHA 41BB costim. | GAGATGTAAGGAGCTGCTGTGACTTGCTCAAGGCCTTATATCGAGT AAACGGTAGTGCTGGGGCTTAGACGCAGGTGTTCTGATTTATAGTT CAAAACCTCTATCAATGAGAGAGCAATCTCCTGGTAATGTGATAGA TTTCCCAACTTAATGCCAACATACCATAAACCTCCCATTCTGCTAA TGCCCAGCCTAAGTTGGGGAGACCACTCCAGATTCCAAGATGTACA GTTTGCTTTGCTGGGCCTTTTTCCCATGCCTGCCTTTACTCTGCCA GAGTTATATTGCTGGGGTTTTGAAGAAGATCCTATTAAATAAAAGA ATAAGCAGTATTATTAAGTAGCCCTGCATTTCAGGTTTCCTTGAGT GGCAGGCCAGGCCTGGCCGTGAACGTTCACTGAAATCATGGCCTCT TGGCCAAGATTGATAGCTTGTGCCTGTCCCTGAGTCCCAGTCCATC ACGAGCAGCTGGTTTCTAAGATGCTATTTCCCGTATAAAGCATGAG ACCGTGACTTGCCAGCCCCACAGAGCCCCGCCCTTGTCCATCACTG GCATCTGGACTCCAGCCTGGGTTGGGGCAAAGAGGGAAATGAGATC ATGTCCTAACCCTGATCCTCTTGTCCCACAGATATCCAGAACCCTG ACCCTGCCGTGTACCAGCTGAGAGACTCTAAATCCAGTGACAAGTC TGTCTGCCTATTCACCGATTTTGATTCTCAAACAAATGTGTCACAA AGTAAGGATTCTGATGTGTATATCACAGACAAAACTGTGCTAGACA TGAGGTCTATGGACTTCAggctccggtgcccgtcagtgggcagagc gcacatcgcccacagtccccgagaagttgggggagggtcggcaa ttgaaccggtgcctagagaaggtggcgcggggtaaactgggaaagt gatgtcgtgtactggctccgcctttttcccgagggtgggggagaac cgtatataagtgcagtagtcgccgtgaacgttcttttttcgcaacgg gtttgccgccagaacacaggtaagtgccgtgtgtggttcccgcggg cctggcctctttacgggttatggcccttgcgtgccttgaattactt ccactggctgcagtacgtgattcttgatcccgagcttcgggaggaa gtgggtgggagagttcgaggccttgcgcttaaggagcccccttcgcc tcgtgcttgagttgaggcctggcctgggcgctggggccgccgcgtg cgaatctggtggcaccttcgcgcctgtctcgctgctttcgataagt ctctagccatttaaaatttttgatgacctgctgcgacgcattatct ggcaagatagtcttgtaaatgcgggccaagatctgcacactggtat ttcggatttggggccgcggcggcgacggggcccgtgcgtcccagc gcacatgttcggcgaggcggggcctgcgagcgcggccaccgagaat cggacggggtagtctcaagctggccggcctgctctggtgcctggc ctcgcgccgccgtgtatcgccccgccctgggcggcaaggctggccc ggtcggcaccagttgcgtgagcggaaagatggccgcttcccggccc tgctgcaggagctcaaaatggaggacgcggcgctcgggagagcgg gcgggtgagtcaccacacaaaggaaaagggccatccgtcctcagc cgtcgcttcatgtgactccacggagtaccgggcgccgtccaggcac ctcgattagttctcgagcttttggagtacgtcgtctttaggttggg gggagggttttatgcgatggagttttcccacactgagtgggtgga gactgaagttaggccagcttggcacttgatgtaattctccaggaat ttgccatatgagtaggatcttggttcattctcaagcctcagacagt ggttcaaagttttttttcttccatttcaggtgtcgtgaCCACCATGG CGCTTCCGGTGACAGCACTGCTCCTCCCCTTGGCGCTGTTGCTCCA CGCAGCAAGGCCGGAAATCGTCCTCACACAATCCCCGGGGAGCCTC |

Summary of Sequences

| SEQ ID NO | Description | Sequence |
|---|---|---|
| | | GCAGTCAGTCCTGGGGAACGAGTCACTATGAGCTGCAAATCCAGTC
AGAGTGTTTTTTTCTCAAGTAGCCAGAAGAACTACCTCGCATGGTA
CCAACAAATACCGGGGCAATCTCCCCGCTTGCTTATATACTGGGCA
AGTACCCGCGAATCCGGCGTACCGGATCGATTCACGGGATCTGGGT
CAGGTACTGATTTCACTTTGACTATCAGCTCTGTTCAGCCTGAAGA
TTTGGCAATTTACTACTGTCACCAATACTTGAGTAGCCGAACTTTC
GGCCAGGGCACGAAGCTCGAAATCAAGGGCGGAGGGGAGGTTCTG
GTGGGGGCGGTTCTGGCGGTGGAGGAAGCCAAGTACAGTTGCAACA
GCCAGGGGCGGAGGTCGTAAAACCTGGGGCGTCTGTCAAGATGAGC
TGTAAAGCAAGTGGATACACCTTCACCTCCTACTATATACATTGGA
TTAAGCAAACTCCGGGTCAGGGGCTGGAATGGGTTGGCGTTATATA
CCCCGGGAACGATGATATATCATACAACCAAAAATTTCAAGGCAAG
GCGACTCTGACTGCCGATAAGAGTAGCACAACAGCTTACATGCAGC
TTTCTTCCCTGACCAGCGAAGATTCAGCAGTTTACTACTGCGCTCG
GGAAGTGCGCCTGCGATACTTTGATGTCTGGGGTCAAGGAACTACA
GTTACTGTATCAAGCAGTGCTGCTGCCTTTGTCCCGGTATTTCTCC
CAGCCAAACCGACCACGACTCCCGCCCCGCGCCCTCCGACACCCGC
TCCCACCATCGCCTCTCAACCTCTTAGTCTTCGCCCCGAGGCATGC
CGACCCGCCGCCGGGGGTGCTGTTCATACGAGGGGCTTGGACTTCG
CTTGTGATATTTACATTTGGGCTCCGTTGGCGGGTACGTGCGGCGT
CCTTTTGTTGTCACTCGTTATTACTTTGTATTGTAATCACAGGAAT
CGCAAACGGGGCAGAAAGAAACTCCTGTATATATTCAAACAACCAT
TTATGAGACCAGTACAAACTACTCAAGAGGAAGATGGCTGTAGCTG
CCGATTTCCAGAAGAAGAAGGAGGATGTGAACTGCGAGTGAAG
TTTTCCCGAAGCGCAGACGCTCCGGCATATCAGCAAGGACAGAATC
AGCTGTATAACGAACTGAATTTGGGACGCCGCGAGGAGTATGACGT
GCTTGATAAACGCCGGGGAGAGACCCGGAAATGGGGGTAAACCC
CGAAGAAAGAATCCCCAAGAAGGACTCTACAATGAACTCCAGAAGG
ATAAGATGGCGGAGGCCTACTCAGAAATAGGTATGAAGGGCAACG
ACGACGGGGAAAAGGTCACGATGGCCTCTACCAAGGGTTGAGTACG
GCAACCAAAGATACGTACGATGCACTGCATATGCAGGCCCTGCCTC
CCAGATAATAATAAAATCGCTATCCATCGAAGATGGATGTGTGTTG
GTTTTTTGTGTGTGGAGCAACAAATCTGACTTTGCATGTGCAAACG
CCTTCAACAACAGCATTATTCCAGAAGACACCTTCTTCCCCAGCCC
AGGTAAGGGCAGCTTTGGTGCCTTCGCAGGCTGTTTCCTTGCTTCA
GGAATGGCCAGGTTCTGCCCAGAGCTCTGGTCAATGATGTCTAAAA
CTCCTCTGATTGGTGGTCTCGGCCTTATCCATTGCCACCAAAACCC
TCTTTTTACTAAGAAACAGTGAGCCTTGTTCTGGCAGTCCAGAGAA
TGACACGGCCAAAAAAGCAGATGAAGAGAAGGTGGCAGGAGAGGGCA
CGTGGCCCAGCCTCAGTCTCTCCAACTGAGTTCCTGCCTGCCTGCC
TTTGCTCAGACTGTTTGCCCCTTACTGCTCTTCTAGGCCTCATTCT
AAGCCCCTTCTCCAAGTTGCCTCTCCTTATTTCTCCCTGTCTGCCA
AAAAATCTTTCCCAGCTCACTAAGTCAGTCTCACGCAGTCACTCAT
TAACCCACCAATCACTGATTGTGCCGGCACATGAATGCACCAGGTG
TTGAAGTGGAGGAATTAAAAAGTCAGATGAGGGGTGTGCCCAGAGG
AAGCACCATTCTAGTTGGGGGAGCCCATCTGTCAGCTGGGAAAAGT
CCAAATAACTTCAGATTGGAATGTGTTTTAACTCAGGGTTGAGAAA
ACAGCTACCTTCAGGACAAAAGTCAGGGAAGGGCTCTCTGAAGAAA
TGCTACTTGAAGATACCAGCCCTACCAAGGGCAGGGAGAGGACCCT
ATAGAGGCCTGGGACAGGAGCTCAATGAGAAAGG |
| 136 | Anti-CD33 CAR 41BB costim | CCACCATGGCGCTTCCGGTGACAGCACTGCTCCTCCCCTTGGCGCT
GTTGCTCCACGCAGCAAGGCCGGAAATCGTCCTCACACAATCCCCG
GGGAGCCTCGCAGTCAGTCCTGGGGAACGAGTCACTATGAGCTGCA
AATCCAGTCAGAGTGTTTTTTTCTCAAGTAGCCAGAAGAACTACCT
CGCATGGTACCAACAAATACCGGGGCAATCTCCCCGCTTGCTTATA
TACTGGGCAAGTACCCGCGAATCCGGCGTACCGGATCGATTCACGG
GATCTGGGTCAGGTACTGATTTCACTTTGACTATCAGCTCTGTTCA
GCCTGAAGATTTGGCAATTTACTACTGTCACCAATACTTGAGTAGC
CGAACTTTCGGCCAGGGCACGAAGCTCGAAATCAAGGGCGGAGGGG
AGGTTCTGGTGGGGGCGGTTCTGGCGGTGGAGGAAGCCAAGTACA
GTTGCAACAGCCAGGGGCGGAGGTCGTAAAACCTGGGGCGTCTGTC
AAGATGAGCTGTAAAGCAAGTGGATACACCTTCACCTCCTACTATA
TACATTGGATTAAGCAAACTCCGGGTCAGGGGCTGGAATGGGTTGG
CGTTATATACCCCGGGAACGATGATATATCATACAACCAAAAATTT
CAAGGCAAGGCGACTCTGACTGCCGATAAGAGTAGCACAACAGCTT
ACATGCAGCTTTCTTCCCTGACCAGCGAAGATTCAGCAGTTTACTA
CTGCGCTCGGGAAGTGCGCCTGCGATACTTTGATGTCTGGGGTCAA
GGAACTACAGTTACTGTATCAAGCAGTGCTGCTGCCTTTGTCCCGG
TATTTCTCCCAGCCAAACCGACCACGACTCCCGCCCCGCGCCCTCC
GACACCCGCTCCCACCATCGCCTCTCAACCTCTTAGTCTTCGCCCC
GAGGCATGCCGACCCGCCGCCGGGGGTGCTGTTCATACGAGGGGCT
TGGACTTCGCTTGTGATATTTACATTTGGGCTCCGTTGGCGGGTAC
GTGCGGCGTCCTTTTGTTGTCACTCGTTATTACTTTGTATTGTAAT
CACAGGAATCGCAAACGGGGCAGAAAGAAACTCCTGTATATATTCA |

Summary of Sequences

| SEQ ID NO | Description | Sequence |
|---|---|---|
| | | AACAACCATTTATGAGACCAGTACAAACTACTCAAGAGGAAGATGG CTGTAGCTGCCGATTTCCAGAAGAAGAAGAAGGAGGATGTGAACTG CGAGTGAAGTTTTCCCGAAGCGCAGACGCTCCGGCATATCAGCAAG GACAGAATCAGCTGTATAACGAACTGAATTTGGGACGCCGCGAGGA GTATGACGTGCTTGATAAACGCCGGGGGAGAGACCCGGAAATGGGG GGTAAACCCCGAAGAAAGAATCCCCAAGAAGGACTCTACAATGAAC TCCAGAAGGATAAGATGGCGGAGGCCTACTCAGAAATAGGTATGAA GGGCGAACGACGACGGGGAAAAGGTCACGATGGCCTCTACCAAGGG TTGAGTACGGCAACCAAAGATACGTACGATGCACTGCATATGCAGG CCCTGCCTCCCAGATAATAATAAAATCGCTATCCATCGAAGATGGA TGTGTGTTGGTTTTTTGTGTG |
| 137 | Anti-CD33 scFv Linker underlined | EIVLTQSPGSLAVSPGERVTMSCKSSQSVFFSSSQKNYLAWYQQIP GQSPRLLIYWASTRESGVPDRFTGSGSGTDFTLTISSVQPEDLAIY YCHQYLSSRTFGQGTKLEIK<u>GGGGSGGGGSGGGGS</u>QVQLQQPGAE VVKPGASVKMSCKASGYTFTSYYIHWIKQTPGQGLEWVGVIYPGND DISYNQKFQGKATLTADKSSTTAYMQLSSLTSEDSAVYYCAREVRL RYFDVWGQGTTVTVSS |
| 138 | Anti-CD33 scFv | GAAATCGTCCTCACACAATCCCCGGGGAGCCTCGCAGTCAGTCCTG GGGAACGAGTCACTATGAGCTGCAAATCCAGTCAGAGTGTTTTTTT CTCAAGTAGCCAGAAGAACTACCTCGCATGGTACCAACAAATACCG GGGCAATCTCCCCGCTTGCTTATATACTGGGCAAGTACCCGCGAAT CCGGCGTACCGGATCGATTCACGGGATCTGGGTCAGGTACTGATTT CACTTTGACTATCAGCTCTGTTCAGCCTGAAGATTTGGCAATTTAC TACTGTCACCAATACTTGAGTAGCCGAACTTTCGGCCAGGGCACGA AGCTCGAAATCAAGGGCGGAGGGGGAGGTTCTGGTGGGGCGGTTC TGGCGGTGGAGGAAGCCAAGTACAGTTGCAACAGCCAGGGGCGGAG GTCGTAAAACCTGGGGCGTCTGTCAAGATGAGCTGTAAAGCAAGTG GATACACCTTCACCTCCTACTATATACATTGGATTAAGCAAACTCC GGGTCAGGGGCTGGAATGGGTTGGCGTTATATACCCCGGGAACGAT GATATATCATACAACCAAAAATTTCAAGGCAAGGCGACTCTGACTG CCGATAAGAGTAGCACAACAGCTTACATGCAGCTTTCTTCCCTGAC CAGCGAAGATTCAGCGTTTACTACTGCGCTCGGGAAGTGCGCCTG CGATACTTTGATGTCTGGGGTCAAGGAACTACAGTTACTGTATCAA GC |
| 139 | Anti-CD33 CAR 41BB costim. | MALPVTALLLPLALLLHAARPEIVLTQSPGSLAVSPGERVTMSCKS SQSVFFSSSQKNYLAWYQQIPGQSPRLLIYWASTRESGVPDRFTGS GSGTDFTLTISSVQPEDLAIYYCHQYLSSRTFGQGTKLEIKGGGGG SGGGGSGGGGSQVQLQQPGAEVVKPGASVKMSCKASGYTFTSYYIH WIKQTPGQGLEWVGVIYPGNDDISYNQKFQGKATLTADKSSTTAYM QLSSLTSEDSAVYYCAREVRLRYFDVWGQGTTVTVSSSAAAFVPVF LPAKPTTTPAPRPPTPAPTIASQPLSLRPEACRPAAGGAVHTRGLD FACDIYIWAPLAGTCGVLLLSLVITLYCNHRNRKRGRKKLLYIFKQ PFMRPVQTTQEEDGCSCRFPEEEEGGCELRVKFSRSADAPAYQQGQ NQLYNELNLGRREEYDVLDKRRGRDPEMGGKPRRKNPQEGLYNELQ KDKMAEAYSEIGMKGERRRGKHDGLYQGLSTATKDTYDALHMQAL PPR |
| 140 | anti-CD33 antibody VH CDRs underlined and in bold | QVQLQQPGAEVVKPGASVKMSCKASGYTFT<u>SYYIH</u>WIKQTPGQGLE WVG<u>VIYPGNDDISYNQKFQG</u>KATLTADKSSTTAYMQLSSLTSEDSA VYYCAR<u>EVRLRYFDV</u>WGQGTTVTVSS |
| 141 | anti-CD33 antibody VL CDRs underlined and in bold | EIVLTQSPGSLAVSPGERVTMSC<u>KSSQSVFFSSSQKNYLA</u>WYQQIP GQSPRLLIY<u>WASTRES</u>GVPDRFTGSGSGTDFTLTISSVQPEDLAIY YC<u>HQYLSSRT</u>FGQGTKLEIK |
| 142 | anti-CD33 antibody VH CDR1 (Kabat) | <u>SYYIH</u> |
| 143 | anti-CD33 antibody VH CDR2 (Kabat) | <u>VIYPGNDDISYNQKFQG</u> |

| | | |
|---|---|---|
| SEQ ID NO | Description | Sequence |
| 144 | anti-CD33 antibody VH CDR3 (Kabat) | EVRLRYFDV |
| 145 | anti-CD33 antibody VL CDR1 (Kabat & Chothia) | KSSQSVFFSSSQKNYLA |
| 146 | anti-CD33 antibody VL CDR2 (Kabat & Chothia | WASTRES |
| 147 | anti-CD33 antibody VL CDR3 (Kabat & Chothia) | HQYLSSRT |
| 148 | Anti-CD19 CAR CD8[tm]-CD28[co-stimulatory domain]-CD3z) | ATGCTTCTTTTGGTTACGTCTCTGTTGCTTTGCGAACTTCCTCATC CAGCGTTCTTGCTGATCCCCGATATTCAGATGACTCAGACCACCAG TAGCTTGTCTGCCTCACTGGGAGACCGAGTAACAATCTCCTGCAGG GCAAGTCAAGACATTAGCAAATACCTCAATTGGTACCAGCAGAAGC CCGACGGAACGGTAAAACTCCTCATCTATCATACGTCAAGGTTGCA TTCCGGAGTACCGTCACGATTTTCAGGTTCTGGGAGCGGAACTGAC TATTCCTTGACTATTTCAAACCTCGAGCAGGAGGACATTGCGACAT ATTTTTGTCAACAAGGTAATACCCTCCCTTACACTTTCGGAGGAGG AACCAAACTCGAAATTACCGGGTCCACCAGTGGCTCTGGGAAGCCT GGCAGTGGAGAAGGTTCCACTAAAGGCGAGGTGAAGCTCCAGGAGA GCGGCCCCGGTCTCGTTGCCCCCAGTCAAAGCCTCTCTGTAACGTG CACAGTGAGTGGTGTATCATTGCCTGATTATGGCGTCTCCTGGATA AGGCAGCCCCCGCGAAAGGGTCTTGAATGGCTTGGGGTAATATGGG GCTCAGAGACAACGTATTATAACTCCGCTCTCAAAAGTCGCTTGAC GATAATAAAAGATAACTCCAAGAGTCAAGTTTTCCTTAAAATGAAC AGTTTGCAGACTGACGATACCGCTATATATTATTGTGCTAAACATT ATTACTACGGCGGTAGTTACGCGATGGATTATTGGGGGCAGGGGAC TTCTGTCACAGTCAGTAGTGCTGCTGCCTTTGTCCCGGTATTCTC CCAGCCAAACCGACCACGACTCCCGCCCCGCGCCCTCCGACACCCG CTCCCACCATCGCCTCTCAACCTCTTAGTCTTCGCCCCGAGGCATG CCGACCCGCCGCCGGGGTGCTGTTCATACGAGGGGCTTGGACTTC GCTTGTGATATTTACATTTGGGCTCCGTTGGCGGGTACGTGCGGCG TCCTTTTGTTGTCACTCGTTATTACTTTGTATTGTAATCACAGGAA TCGCTCAAAGCGGAGTAGGTTGTTGCATTCCGATTACATGAATATG ACTCCTCGCCGGCCTGGGCCGACAAGAAAACATTACCAACCCTATG CCCCCCCACGAGACTTCGCTGCGTACAGGTCCCGAGTGAAGTTTTC CCGAAGCGCAGACGCTCCGGCATATCAGCAAGGACAGAATCAGCTG TATAACGAACTGAATTTGGGACGCCGCGAGGAGTATGACGTGCTTG ATAAACGCCGGGGAGAGACCCGGAAATGGGGGGTAAACCCCGAAG AAAGAATCCCCAAGAAGGACTCTACAATGAACTCCAGAAGGATAAG ATGGCGGAGGCCTACTCAGAAATAGGTATGAAGGGCGAACGACGAC GGGGAAAAGGTCACGATGGCCTCTACCAAGGGTTGAGTACGGCAAC CAAAGATACGTACGATGCACTGCATATGCAGGCCCTGCCTCCCAGA |
| 149 | Anti-CD19 CAR CD8[tm]-CD28[co-stimulatory domain]-CD3z) Amino Acid | MLLLVTSLLLCELPHPAFLLIPDIQMTQTTSSLSASLGDRVTISCR ASQDISKYLNWYQQKPDGTVKLLIYHTSRLHSGVPSRFSGSGSGTD YSLTISNLEQEDIATYFCQQGNTLPYTFGGGTKLEITGSTSGSGKP GSGEGSTKGEVKLQESGPGLVAPSQSLSVTCTVSGVSLPDYGVSWI RQPPRKGLEWLGVIWGSETTYYNSALKSRLTIIKDNSKSQVFLKMN SLQTDDTAIYYCAKHYYYGGSYAMDYWGQGTSVTVSSAAAFVPVFL PAKPTTTPAPRPPTPAPTIASQPLSLRPEACRPAAGGAVHTRGLDF ACDIYIWAPLAGTCGVLLLSLVITLYCNHRNRSKRSRLLHSDYMNM TPRRPGPTRKHYQPYAPPRDFAAYRSRVKFSRSADAPAYQQGQNQL YNELNLGRREEYDVLDKRRGRDPEMGGKPRRKNPQEGLYNELQKDK MAEAYSEIGMKGERRRGKGHDGLYQGLSTATKDTYDALHMQALPPR |
| 150 | Anti-CD19 scFv | GATATTCAGATGACTCAGACCACCAGTAGCTTGTCTGCCTCACTGG GAGACCGAGTAACAATCTCCTGCAGGGCAAGTCAAGACATTAGCAA ATACCTCAATTGGTACCAGCAGAAGCCCGACGGAACGGTAAAACTC CTCATCTATCATACGTCAAGGTTGCATTCCGGAGTACCGTCACGAT TTTCAGGTTCTGGGAGCGGAACTGACTATTCCTTGACTATTTCAAA |

Summary of Sequences

| SEQ ID NO | Description | Sequence |
|---|---|---|
| | | CCTCGAGCAGGAGGACATTGCGACATATTTTTGTCAACAAGGTAAT<br>ACCCTCCCTTACACTTTCGGAGGAGGAACCAAACTCGAAATTACCG<br>GGTCCACCAGTGGCTCTGGGAAGCCTGGCAGTGGAGAAGGTTCCAC<br>TAAAGGCGAGGTGAAGCTCCAGGAGAGCGGCCCCGGTCTCGTTGCC<br>CCCAGTCAAAGCCTCTCTGTAACGTGCACAGTGAGTGGTGTATCAT<br>TGCCTGATTATGGCGTCTCCTGGATAAGGCAGCCCCGCGAAAGGG<br>TCTTGAATGGCTTGGGGTAATATGGGGCTCAGAGACAACGTATTAT<br>AACTCCGCTCTCAAAAGTCGCTTGACGATAATAAAAGATAACTCCA<br>AGAGTCAAGTTTTCCTTAAAATGAACAGTTTGCAGACTGACGATAC<br>CGCTATATATTATTGTGCTAAACATTATTACTACGGCGGTAGTTAC<br>GCGATGGATTATTGGGGGCAGGGGACTTCTGTCACAGTCAGTAGT |
| 151 | CD19 scFv amino acid sequence Linker underlined | DIQMTQTTSSLSASLGDRVTISCRASQDISKYLNWYQQKPDGTVKL<br>LIYHTSRLHSGVPSRFSGSGSGTDYSLTISNLEQEDIATYFCQQGN<br>TLPYTFGGGTKLEIT<u>GSTSGSGKPGSGEGSTKG</u>EVKLQESGPGLVA<br>PSQSLSVTCTVSGVSLPDYGVSWIRQPPRKGLEWLGVIWGSETTYY<br>NSALKSRLTIIKDNSKSQVFLKMNSLQTDDTAIYYCAKHYYYGGSY<br>AMDYWGQGTSVTVSS |
| 152 | Anti-CD19 VH | EVKLQESGPGLVAPSQSLSVTCTVSGVSLPDYGVSWIRQPPRKGLE<br>WLGVIWGSETTYYNSALKSRLTIIKDNSKSQVFLKMNSLQTDDTAI<br>YYCAKHYYYGGSYAMDYWGQGTSVTVSS |
| 153 | Anti-CD19 VL | DIQMTQTTSSLSASLGDRVTISCRASQDISKYLNWYQQKPDGTVKL<br>LIYHTSRLHSGVPSRFSGSGSGTDYSLTISNLEQEDIATYFCQQGN<br>TLPYTFGGGTKLEIT |
| 154 | Anti-CD19 scFv linker | GSTSGSGKPGSGEGSTKG |
| 155 | anti-CD19 CAR rAAV | CCTGCAGGCAGCTGCGCGCTCGCTCGCTCACTGAGGCCGCCCGGGC<br>GTCGGGCGACCTTTGGTCGCCCGGCCTCAGTGAGCGAGCGAGCGCG<br>CAGAGAGGGAGTGGCCAACTCCATCACTAGGGGTTCCTGCGGCCGC<br>ACGCGTGAGATGTAAGGAGCTGCTGTGACTTGCTCAAGGCCTTATA<br>TCGAGTAAACGGTAGTGCTGGGGCTTAGACGCAGGTGTTCTGATTT<br>ATAGTTCAAAACCTCTATCAATGAGAGAGCAATCTCCTGGTAATGT<br>GATAGATTTCCCAACTTAATGCCAACATACCATAAACCTCCCATTC<br>TGCTAATGCCCAGCCTAAGTTGGGGAGACCACTCCAGATTCCAAGA<br>TGTACAGTTTGCTTTGCTGGGCTTTTTCCCATGCCTGCCTTTACT<br>CTGCCAGAGTTATATTGCTGGGGTTTTGAAGAAGATCCTATTAAAT<br>AAAAGAATAAGCAGTATTATTAAGTAGCCCTGCATTTCAGGTTTCC<br>TTGAGTGGCAGGCCAGGCCTGGCCGTGAACGTTCACTGAAATCATG<br>GCCTCTTGGCCAAGATTGATAGCTTGTGCCTGTCCCTGAGTCCCAG<br>TCCATCACGAGCAGCTGGTTTCTAAGATGCTATTTCCCGTATAAAG<br>CATGAGACCGTGACTTGCCAGCCCCACAGAGCCCCGCCCTTGTCCA<br>TCACTGGCATCTGGACTCCAGCCTGGGTTGGGGCAAAGAGGGAAAT<br>GAGATCATGTCCTAACCCTGATCCTCTTGTCCCACAGATATCCAGA<br>ACCCTGACCCTGCCGTGTACCAGCTGAGAGACTCTAAATCCAGTGA<br>CAAGTCTGTCTGCCTATTCACCGATTTTGATTCTCAAACAAATGTG<br>TCACAAAGTAAGGATTCTGATGTGTATATCACAGACAAAACTGTGC<br>TAGACATGAGGTCTATGGACTTCAGGCTCCGGTGCCCGTCAGTGGG<br>CAGAGCGCACATCGCCCACAGTCCCCGAGAAGTTGGGGGGAGGGGT<br>CGGCAATTGAACCGGTGCCTAGAGAAGGTGGCGCGGGGTAAACTGG<br>GAAAGTGATGTCGTGTACTGGCTCCGCCTTTTTCCCGAGGGTGGGG<br>GAGAACCGTATATAAGTGCAGTAGTCGCCGTGAACGTTCTTTTTCG<br>CAACGGGTTTGCCGCCAGAACACAGGTAAGTGCCGTGTGTGGTTCC<br>CGCGGGCCTGGCCTCTTTACGGGTTATGGCCCTTGCGTGCCTTGAA<br>TTACTTCCACTGGCTGCAGTACGTGATTCTTGATCCCGAGCTTCGG<br>GTTGGAAGTGGGTGGGAGAGTTCGAGGCCTTGCGCTTAAGGAGCCC<br>CTTCGCCTCGTGCTTGAGTTGAGGCCTGGCCTGGGCGCTGGGGCCG<br>CCGCGTGCGAATCTGGTGGCACCTTCGCGCCTGTCTCGCTGCTTTC<br>GATAAGTCTCTAGCCATTTAAAATTTTTGATGACCTGCTGCGACGC<br>TTTTTTTCTGGCAAGATAGTCTTGTAAATGCGGGCCAAGATCTGCA<br>CACTGGTATTTCGGTTTTTGGGGCCGCGGGCGGCGACGGGGCCCGT<br>GCGTCCCAGCGCACATGTTCGGCGAGGCGGGGCCTGCGAGCGCGGC<br>CACCGAGAATCGGACGGGGGTAGTCTCAAGCTGGCCGGCCTGCTCT<br>GGTGCCTGGCCTCGCGCCGCCGTGTATCGCCCCGCCCTGGGCGGCA<br>AGGCTGGCCCGGTCGGCACCAGTTGCGTGAGCGGAAAGATGGCCGC<br>TTCCCGGCCCTGCTGCAGGGAGCTCAAAATGGAGGACGCGGCGCTC<br>GGGAGAGCGGGCGGGTGAGTCACCCACACAAAGGAAAAGGGCCTTT<br>CCGTCCTCAGCCGTCGCTTCATGTGACTCCACGGAGTACCGGGCGC<br>CGTCCAGGCACCTCGATTAGTTCTCGAGCTTTTGGAGTACGTCGTC<br>TTTAGGTTGGGGGGAGGGGTTTTATGCGATGGAGTTTCCCCACACT<br>GAGTGGGTGGAGACTGAAGTTAGGCCAGCTTGGCACTTGATGTAAT<br>TCTCCTTGGAATTTGCCCTTTTTGAGTTTGGATCTTGGTTCATTCT |

Summary of Sequences

| SEQ ID NO | Description | Sequence |
|---|---|---|
| | | CAAGCCTCAGACAGTGGTTCAAAGTTTTTTTCTTCCATTTCAGGTG<br>TCGTGACCACCATGCTTCTTTTGGTTACGTCTCTGTTGCTTTGCGA<br>ACTTCCTCATCCAGCGTTCTTGCTGATCCCCGATATTCAGATGACT<br>CAGACCACCAGTAGCTTGTCTGCCTCACTGGGAGACCGAGTAACAA<br>TCTCCTGCAGGGCAAGTCAAGACATTAGCAAATACCTCAATTGGTA<br>CCAGCAGAAGCCCGACGGAACGGTAAAACTCCTCATCTATCATACG<br>TCAAGGTTGCATTCCGGAGTACCGTCACGATTTTCAGGTTCTGGGA<br>GCGGAACTGACTATTCCTTGACTATTTCAAACCTCGAGCAGGAGGA<br>CATTGCGACATATTTTTGTCAACAAGGTAATACCCTCCCTTACACT<br>TTCGGAGGAGGAACCAAACTCGAAATTACCGGGTCCACCAGTGGCT<br>CTGGGAAGCCTGGCAGTGGAGAAGGTTCCACTAAAGGCGAGGTGAA<br>GCTCCAGGAGAGCGGCCCCGGTCTCGTTGCCCCCAGTCAAAGCCTC<br>TCTGTAACGTGCACAGTGAGTGGTGTATCATTGCCTGATTATGGCG<br>TCTCCTGGATAAGGCAGCCCCCGCGAAAGGGTCTTGAATGGCTTGG<br>GGTAATATGGGCTCAGAGACAACGTATTATAACTCCGCTCTCAAA<br>AGTCGCTTGACGATAATAAAAGATAACTCCAAGAGTCAAGTTTTCC<br>TTAAAATGAACAGTTTGCAGACTGACGATACCGCTATATATTATTG<br>TGCTAAACATTATTACTACGGCGGTAGTTACGCGATGGATTATTGG<br>GGGCAGGGGACTTCTGTCACAGTCAGTAGTGCTGCTGCCTTTGTCC<br>CGGTATTTCTCCCAGCCAAACCGACCACGACTCCCGCCCCGCGCCC<br>TCCGACACCCGCTCCCACCATCGCCTCTCAACCTCTTAGTCTTCGC<br>CCCGAGGCATGCCGACCCGCCGCCGGGGGTGCTGTTCATACGAGGG<br>GCTTGGACTTCGCTTGTGATATTTACATTTGGGCTCCGTTGGCGGG<br>TACGTGCGGCGTCCTTTTGTTGTCACTCGTTATTACTTTGTATTGT<br>AATCACAGGAATCGCTCAAAGCGGAGTAGGTTGTTGCATTCCGATT<br>ACATGAATATGACTCCTCGCCGGCCTGGGCCGACAAGAAAACATTA<br>CCAACCCTATGCCCCCCACGAGACTTCGCTGCGTACAGGTCCCGA<br>GTGAAGTTTTCCCGAAGCGCAGACGCTCCGGCATATCAGCAAGGAC<br>AGAATCAGCTGTATAACGAACTGAATTTGGGACGCCGCGAGGAGTA<br>TGACGTGCTTGATAAACGCCGGGGAGAGACCCGGAAATGGGGGGT<br>AAACCCCGAAGAAAGAATCCCCAAGAAGGACTCTACAATGAACTCC<br>AGAAGGATAAGATGGCGGAGGCCTACTCAGAAATAGGTATGAAGGG<br>CGAACGACGACGGGGAAAAGGTCACGATGGCCTCTACCAAGGGTTG<br>AGTACGGCAACCAAAGATACGTACGATGCACTGCATATGCAGGCCC<br>TGCCTCCCAGATAATAATAAAATCGCTATCCATCGAAGATGGATGT<br>GTGTTGGTTTTTGTGTGTGGAGCAACAAATCTGACTTTGCATGTG<br>CAAACGCCTTCAACAACAGCATTATTCCAGAAGACACCTTCTTCCC<br>CAGCCCAGGTAAGGGCAGCTTTGGTGCCTTCGCAGGCTGTTTCCTT<br>GCTTCAGGAATGGCCAGGTTCTGCCCAGAGCTCTGGTCAATGATGT<br>CTAAAACTCCTCTGATTGGTGGTCTCGGCCTTATCCATTGCCACCA<br>AAACCCTCTTTTTACTAAGAAACAGTGAGCCTTGTTCTGGCAGTCC<br>AGAGAATGACACGGGAAAAAAGCAGATGAAGAGAAGGTGGCAGGAG<br>AGGGCACGTGGCCCAGCCTCAGTCTCTCCAACTGAGTTCCTGCCTG<br>CCTGCCTTTGCTCAGACTGTTTGCCCCTTACTGCTCTTCTAGGCCT<br>CATTCTAAGCCCCTTCTCCAAGTTGCCTCTCCTTATTTCTCCCTGT<br>CTGCCAAAAAATCTTTCCCAGCTCACTAAGTCAGTCTCACGCAGTC<br>ACTCATTAACCCACCAATCACTGATTGTGCCGGCACATGAATGCAC<br>CAGGTGTTGAAGTGGAGGAATTAAAAAGTCAGATGAGGGGTGTGCC<br>CAGAGGAAGCACCATTCTAGTTGGGGGAGCCCATCTGTCAGCTGGG<br>AAAAGTCCAAATAACTTCAGATTGGAATGTGTTTAACTCAGGGTT<br>GAGAAAACAGCTACCTTCAGGACAAAAGTCAGGGAAGGGCTCTCTG<br>AAGAAATGCTACTTGAAGATACCAGCCCTACCAAGGGCAGGGAGAG<br>GACCCTATAGAGGCCTGGGACAGGAGCTCAATGAGAAAGGTAACCA<br>CGTGCGGACCGAGGCTGCAGCGTCGTCCTCCCTAGGAACCCCTAGT<br>GATGGAGTTGGCCACTCCCTCTCTGCGCGCTCGCTCGCTCACTGAG<br>GCCGGGCGACCAAAGGTCGCCCGACGCCCGGGCTTTGCCCGGGCGG<br>CCTCAGTGAGCGAGCGAGCGCGCAGCTGCCTGCAGG |
| 156 | Anti-CD19 CAR LHA to RHA | GAGATGTAAGGAGCTGCTGTGACTTGCTCAAGGCCTTATATCGAGT<br>AAACGGTAGTGCTGGGGCTTAGACGCAGGTGTTCTGATTTATAGTT<br>CAAAACCTCTATCAATGAGAGAGCAATCTCCTGGTAATGTGATAGA<br>TTTCCCAACTTAATGCCAACATACCATAAACCTCCCATTCTGCTAA<br>TGCCCAGCCTAAGTTGGGGAGACCACTCCAGATTCCAAGATGTACA<br>GTTTGCTTTGCTGGGCCTTTTTCCCATGCCTGCCTTTACTCTGCCA<br>GAGTTATATTGCTGGGGTTTTGAAGAAGATCCTATTAAATAAAAGA<br>ATAAGCAGTATTATTAAGTAGCCCTGCATTTCAGGTTTCCTTGAGT<br>GGCAGGCCAGGCCTGGCCGTGAACGTTCACTGAAATCATGGCCTCT<br>TGGCCAAGATTGATAGCTTGTGCCTGTCCCTGAGTCCCAGTCCATC<br>ACGAGCAGCTGGTTTCTAAGATGCTATTTCCCGTATAAAGCATGAG<br>ACCGTGACTTGCCAGCCCCACAGAGCCCCGCCCTTGTCCATCACTG<br>GCATCTGGACTCCAGCCTGGGTTGGGGCAAAGAGGGAAATGAGATC<br>ATGTCCTAACCCTGATCCTCTTGTCCCACAGATATCCAGAACCCTG<br>ACCCTGCCGTGTACCAGCTGAGAGACTCTAAATCCAGTGACAAGTC<br>TGTCTGCCTATTCACCGATTTTGATTCTCAAACAAATGTGTCACAA<br>AGTAAGGATTCTGATGTGTATATCACAGACAAAACTGTGCTAGACA |

Summary of Sequences

| SEQ ID NO | Description | Sequence |
|---|---|---|
| | | TGAGGTCTATGGACTTCAGGCTCCGGTGCCCGTCAGTGGGCAGAGC |
| | | GCACATCGCCCACAGTCCCCGAGAAGTTGGGGGGAGGGGTCGGCAA |
| | | TTGAACCGGTGCCTAGAGAAGGTGGCGCGGGGTAAACTGGGAAAGT |
| | | GATGTCGTGTACTGGCTCCGCCTTTTTCCCGAGGGTGGGGGAGAAC |
| | | CGTATATAAGTGCAGTAGTCGCCGTGAACGTTCTTTTTCGCAACGG |
| | | GTTTGCCGCCAGAACACAGGTAAGTGCCGTGTGTGGTTCCCGCGGG |
| | | CCTGGCCTCTTTACGGGTTATGGCCCTTGCGTGCCTTGAATTACTT |
| | | CCACTGGCTGCAGTACGTGATTCTTGATCCCGAGCTTCGGGTTGGA |
| | | AGTGGGTGGGAGAGTTCGAGGCCTTGCGCTTAAGGAGCCCCTTCGC |
| | | CTCGTGCTTGAGTTGAGGCCTGGCCTGGGCGCTGGGGCCGCCGCGT |
| | | GCGAATCTGGTGGCACCTTCGCGCCTGTCTCGCTGCTTTCGATAAG |
| | | TCTCTAGCCATTTAAAATTTTTGATGACCTGCTGCGACGCTTTTTT |
| | | TCTGGCAAGATAGTCTTGTAAATGCGGGCCAAGATCTGCACACTGG |
| | | TATTTCGGTTTTTGGGGCCGCGGGCGGCGACGGGGCCCGTGCGTCC |
| | | CAGCGCACATGTTCGGCGAGGCGGGGCCTGCGAGCGCGGCCACCGA |
| | | GAATCGGACGGGGGTAGTCTCAAGCTGGCCGGCCTGCTCTGGTGCC |
| | | TGGCCTCGCGCCGCCGTGTATCGCCCCGCCCTGGGCGGCAAGGCTG |
| | | GCCCGGTCGGCACCAGTTGCGTGAGCGGAAAGATGGCCGCTTCCCG |
| | | GCCCTGCTGCAGGGAGCTCAAAATGGAGGACGCGGCGCTCGGGAGA |
| | | GCGGGCGGGTGAGTCACCCACACAAAGGAAAAGGGCCTTTCCGTCC |
| | | TCAGCCGTCGCTTCATGTGACTCCACGGAGTACCGGGCGCCGTCCA |
| | | GGCACCTCGATTAGTTCTCGAGCTTTTGGAGTACGTCGTCTTTAGG |
| | | TTGGGGGGAGGGGTTTTATGCGATGGAGTTTCCCCACACTGAGTGG |
| | | GTGGAGACTGAAGTTAGGCCAGCTTGGCACTTGATGTAATTCTCCT |
| | | TGGAATTTGCCCTTTTTGAGTTTGGATCTTGGTTCATTCTCAAGCC |
| | | TCAGACAGTGGTTCAAAGTTTTTTTCTTCCATTTCAGGTGTCGTGA |
| | | CCACCATGCTTCTTTTGGTTACGTCTCTGTTGCTTTGCGAACTTCC |
| | | TCATCCAGCGTTCTTGCTGATCCCGATATTCAGATGACTCAGACC |
| | | ACCAGTAGCTTGTCTGCCTCACTGGGAGACCGAGTAACAATCTCCT |
| | | GCAGGGCAAGTCAAGACATTAGCAAATACCTCAATTGGTACCAGCA |
| | | GAAGCCCGACGGAACGGTAAAACTCCTCATCTATCATACGTCAAGG |
| | | TTGCATTCCGGAGTACCGTCACGATTTTCAGGTTCTGGGAGCGGAA |
| | | CTGACTATTCCTTGACTATTTCAAACCTCGAGCAGGAGGACATTGC |
| | | GACATATTTTTGTCAACAAGGTAATACCCTCCCTTACACTTTCGGA |
| | | GGAGGAACCAAACTCGAAATTACCGGGTCCACCAGTGGCTCTGGGA |
| | | AGCCTGGCAGTGGAGAAGGTTCCACTAAAGGCGAGGTGAAGCTCCA |
| | | GGAGAGCGGCCCCGGTCTCGTTGCCCCCAGTCAAAGCCTCTCTGTA |
| | | ACGTGCACAGTGAGTGGTGTATCATTGCCTGATTATGGCGTCTCCT |
| | | GGATAAGGCAGCCCCCGCGAAAGGGTCTTGAATGGCTTGGGGTAAT |
| | | ATGGGGCTCAGAGACAACGTATTATAACTCCGCTCTCAAAAGTCGC |
| | | TTGACGATAATAAAAGATAACTCCAAGAGTCAAGTTTTCCTTAAAA |
| | | TGAACAGTTTGCAGACTGACGATACCGCTATATATTATTGTGCTAA |
| | | ACATTATTACTACGGCGGTAGTTACGCGATGGATTATTGGGGGCAG |
| | | GGGACTTCTGTCACAGTCAGTAGTGCTGCTGCCTTTGTCCCGGTAT |
| | | TTCTCCCAGCCAAACCGACCACGACTCCCGCCCCGCGCCCTCCGAC |
| | | ACCCGCTCCCACCATCGCCTCTCAACCTCTTAGTCTTCGCCCCGAG |
| | | GCATGCCGACCCGCCGCCGGGGGTGCTGTTCATACGAGGGGCTTGG |
| | | ACTTCGCTTGTGATATTTACATTTGGGCTCCGTTGGCGGGTACGTG |
| | | CGGCGTCCTTTTGTTGTCACTCGTTATTACTTTGTATTGTAATCAC |
| | | AGGAATCGCTCAAAGCGGAGTAGGTTGTTGCATTCCGATTACATGA |
| | | ATATGACTCCTCGCCGGCCTGGGCCGACAAGAAAACATTACCAACC |
| | | CTATGCCCCCCACGAGACTTCGCTGCGTACAGGTCCCGAGTGAAG |
| | | TTTTCCCGAAGCGCAGACGCTCCGGCATATCAGCAAGGACAGAATC |
| | | AGCTGTATAACGAACTGAATTTGGGACGCCGCGAGGAGTATGACGT |
| | | GCTTGATAAACGCCGGGGAGAGACCCGGAAATGGGGGGTAAACCC |
| | | CGAAGAAAGAATCCCCAAGAAGGACTCTACAATGAACTCCAGAAGG |
| | | ATAAGATGGCGGAGGCCTACTCAGAAATAGGTATGAAGGGCGAACG |
| | | ACGACGGGGAAAAGGTCACGATGGCCTCTACCAAGGGTTGAGTACG |
| | | GCAACCAAAGATACGTACGATGCACTGCATATGCAGGCCCTGCCTC |
| | | CCAGATAATAATAAAATCGCTATCCATCGAAGATGGATGTGTGTTG |
| | | GTTTTTTGTGTGTGGAGCAACAAATCTGACTTTGCATGTGCAAACG |
| | | CCTTCAACAACAGCATTATTCCAGAAGACACCTTCTTCCCCAGCCC |
| | | AGGTAAGGGCAGCTTTGGTGCCTTCGCAGGCTGTTTCCTTGCTTCA |
| | | GGAATGGCCAGGTTCTGCCCAGAGCTCTGGTCAATGATGTCTAAAA |
| | | CTCCTCTGATTGGTGGTCTCGGCCTTATCCATTGCCACCAAAACCC |
| | | TCTTTTTACTAAGAAACAGTGAGCCTTGTTCTGGCAGTCCAGAGAA |
| | | TGACACGGGAAAAAAGCAGATGAAGAGAAGGTGGCAGGAGAGGGCA |
| | | CGTGGCCCAGCCTCAGTCTCTCCAACTGAGTTCCTGCCTGCCTGCC |
| | | TTTGCTCAGACTGTTTGCCCCTTACTGCTCTTCTAGGCCTCATTCT |
| | | AAGCCCCTTCTCCAAGTTGCCTCTCCTTATTTCTCCCTGTCTGCCA |
| | | AAAAATCTTTCCCAGCTCACTAAGTCAGTCTCACGCAGTCACTCAT |
| | | TAACCCACCAATCACTGATTGTGCCGGACATGAATGCACCAGGTG |
| | | TTGAAGTGGAGGAATTAAAAAGTCAGATGAGGGGTGTGCCCAGAGG |
| | | AAGCACCATTCTAGTTGGGGGAGCCCATCTGTCAGCTGGGAAAAGT |
| | | CCAAATAACTTCAGATTGGAATGTGTTTTAACTCAGGGTTGAGAAA |

-continued

| | | Summary of Sequences |
|---|---|---|
| SEQ ID NO | Description | Sequence |
| | | ACAGCTACCTTCAGGACAAAAGTCAGGGAAGGGCTCTCTGAAGAAA |
| | | TGCTACTTGAAGATACCAGCCCTACCAAGGGCAGGGAGAGGACCCT |
| | | ATAGAGGCCTGGGACAGGAGCTCAATGAGAAAGG |
| 157 | CD70 sgRNA (E1_T1) | TCACCAAGCCCGCGACCAAT |
| 158 | CD70 sgRNA (E1_T3) | ATCACCAAGCCCGCGACCAA |
| 159 | CD70 sgRNA (E1_T4) | CGGTGCGGCGCAGGCCCTAT |
| 160 | CD70 sgRNA (E1_T7) | GCTTTGGTCCCATTGGTCGC |
| 161 | CD70 sgRNA (E1_T8) | GCCCGCAGGACGCACCCATA |
| 162 | CD70 sgRNA (E1_T10) | GTGCATCCAGCGCTTCGCAC |
| 163 | CD70 sgRNA (E3_T1) | CAGCTACGTATCCATCGTGA |
| 164 | β2M sgRNA | GCTACTCTCTCTTTCTGGCC |
| 165 | PD-1 sgRNA | CTGCAGCTTCTCCAACACAT |
| 166 | anti-CD19 VL CDR1 (Kabat) | RASQDISKYLN |
| 167 | anti-CD19 VL CDR2 (Kabat) | HTSRLHS |
| 168 | anti-CD19 VL CDR3 (Kabat) | QQGNTLPYT |
| 169 | anti-CD19 VH CDR1 (Kabat) | DYGVS |
| 170 | anti-CD19 VH CDR2 (Kabat) | VIWGSETTYYNSALKS |
| 171 | anti-CD19 VH CDR3 (Kabat) | HYYYGGSYAMDY |
| 172 | anti-CD19 VL CDR1 (Chothia) | RASQDISKYLN |
| 173 | anti-CD19 VL CDR2 (Chothia) | HTSRLHS |
| 174 | anti-CD19 VL CDR3 (Chothia) | QQGNTLPYT |
| 175 | anti-CD19 VH CDR1 (Chothia) | GVSLPDY |

-continued

Summary of Sequences

| SEQ ID NO | Description | Sequence |
|---|---|---|
| 176 | anti-CD19 VH CDR2 (Chothia) | WGSET |
| 177 | anti-CD19 VH CDR3 (Chothia) | HYYYGGSYAMDY |
| 178 | anti-CD33 VH CDR1 (Chothia) | GYTFTSY |
| 179 | anti-CD33 VH CDR2 (Chothia) | YPGNDD |
| 180 | anti-CD33 VH CDR3 (Chothia) | EVRLRYFDV |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A population of engineered T cells, wherein the engineered T cells comprise:
   (i) a disrupted TRAC gene;
   (ii) a disrupted βl2M gene;
   (iii) a disrupted CD70 gene; and
   (iv) a nucleic acid encoding a CAR that binds CD70; wherein the CAR that binds CD70 comprises the amino acid sequence of SEQ ID NO: 46.

2. The population of cells of claim 1, wherein the nucleic acid encoding the CAR is inserted in the disrupted TRAC gene.

3. The population of cells of claim 1, wherein the nucleic acid encoding the CAR that binds CD70 comprises the nucleotide sequence of SEQ ID NO:45.

4. The population of cells of claim 1, wherein the disrupted TRAC gene comprises a deletion comprising SEQ ID NO:86.

5. The population of cells of claim 4, wherein the disrupted TRAC gene comprises the nucleotide sequence of SEQ ID NO: 44.

6. The population of cells of claim 1, wherein the disrupted β2M gene comprises at least one nucleotide sequence of any one of SEQ ID NOs:9-14.

7. The population of cells of claim 1, wherein the disrupted CD70 gene comprises at least one nucleotide sequence of any one of SEQ ID NOs:129-134.

8. The population of cells of claim 1, wherein at least 90% of the engineered T cells do not express a detectable level of a TCR surface protein.

9. The population of cells of claim 1, wherein the engineered cells are human T cells.

10. The population of cells of claim 9, wherein the human T cells are derived from one or more donors.

11. The population of cells of claim 1, wherein the disrupted TRAC gene comprises the nucleotide sequence of SEQ ID NO: 44, wherein the disrupted β2M gene comprises at least one nucleotide sequence of any one of SEQ ID NOs:9-14; wherein the disrupted CD70 gene comprises at least one nucleotide sequence of any one of SEQ ID NOs: 129-134; and wherein the engineered T cells express the CAR that binds CD70, the CAR comprising the amino acid sequence of SEQ ID NO:46.

12. The population of cells of claim 11, wherein at least 90% of the engineered T cells do not express a detectable level of a TCR surface protein.

13. The population of cells of claim 12, wherein the engineered cells are human T cells.

14. The population of cells of claim 13, wherein the human T cells are derived from one or more donors.

* * * * *

SEQUENCE LISTING

<160> NUMBER OF SEQ ID NOS: 180

<210> SEQ ID NO 1
<211> LENGTH: 19
<212> TYPE: DNA
<213> ORGANISM: Artificial Sequence
<220> FEATURE:
<223> OTHER INFORMATION: Synthetic: TRAC Indel

<400> SEQUENCE: 1
aagagcaaca aatctgact        19

<210> SEQ ID NO 2
<211> LENGTH: 58
<212> TYPE: DNA
<213> ORGANISM: Artificial Sequence
<220> FEATURE:
<223> OTHER INFORMATION: Synthetic: TRAC Indel

<400> SEQUENCE: 2
aagagcaaca gtgctgtgcc tggagcaaca aatctgacta agagcaacaa atctgact        58

<210> SEQ ID NO 3
<211> LENGTH: 52
<212> TYPE: DNA
<213> ORGANISM: Artificial Sequence

```
<220> FEATURE:
<223> OTHER INFORMATION: Synthetic: TRAC Indel

<400> SEQUENCE: 3
aagagcaaca gtgctggagc aacaaatctg actaagagca acaaatctga ct          52

<210> SEQ ID NO 4
<211> LENGTH: 53
<212> TYPE: DNA
<213> ORGANISM: Artificial Sequence
<220> FEATURE:
<223> OTHER INFORMATION: Synthetic: TRAC Indel

<400> SEQUENCE: 4
aagagcaaca gtgcctggag caacaaatct gactaagagc aacaaatctg act         53

<210> SEQ ID NO 5
<211> LENGTH: 38
<212> TYPE: DNA
<213> ORGANISM: Artificial Sequence
<220> FEATURE:
<223> OTHER INFORMATION: Synthetic: TRAC Indel

<400> SEQUENCE: 5
aagagcaaca gtgctgacta agagcaacaa atctgact                          38

<210> SEQ ID NO 6
<211> LENGTH: 60
<212> TYPE: DNA
<213> ORGANISM: Artificial Sequence
<220> FEATURE:
<223> OTHER INFORMATION: Synthetic: TRAC Indel

<400> SEQUENCE: 6
aagagcaaca gtgctgtggg cctggagcaa caaatctgac taagagcaac aaatctgact  60

<210> SEQ ID NO 7
<211> LENGTH: 57
<212> TYPE: DNA
<213> ORGANISM: Artificial Sequence
<220> FEATURE:
<223> OTHER INFORMATION: Synthetic: TRAC Indel

<400> SEQUENCE: 7
aagagcaaca gtgctggcct ggagcaacaa atctgactaa gagcaacaaa tctgact     57

<210> SEQ ID NO 8
<211> LENGTH: 60
<212> TYPE: DNA
<213> ORGANISM: Artificial Sequence
<220> FEATURE:
<223> OTHER INFORMATION: Synthetic: TRAC Indel

<400> SEQUENCE: 8
aagagcaaca gtgctgtgtg cctggagcaa caaatctgac taagagcaac aaatctgact  60

<210> SEQ ID NO 9
<211> LENGTH: 79
<212> TYPE: DNA
<213> ORGANISM: Artificial Sequence
<220> FEATURE:
<223> OTHER INFORMATION: Synthetic: B2M Indel

<400> SEQUENCE: 9
cgtggcctta gctgtgctcg cgctactctc tctttctgcc tggaggctat ccagcgtgag  60
```

```
                                                            79
tctctcctac cctcccgct <210> SEQ ID NO 10
<211> LENGTH: 78
<212> TYPE: DNA
<213> ORGANISM: Artificial Sequence
<220> FEATURE:
<223> OTHER INFORMATION: Synthetic: B2M Indel

<400> SEQUENCE: 10
cgtggcctta gctgtgctcg cgctactctc tctttcgcct ggaggctatc cagcgtgagt    60
ctctcctacc ctcccgct                                                  78

<210> SEQ ID NO 11
<211> LENGTH: 75
<212> TYPE: DNA
<213> ORGANISM: Artificial Sequence
<220> FEATURE:
<223> OTHER INFORMATION: Synthetic: B2M Indel

<400> SEQUENCE: 11
cgtggcctta gctgtgctcg cgctactctc tctttctgga ggctatccag cgtgagtctc    60
tcctaccctc ccgct                                                     75

<210> SEQ ID NO 12
<211> LENGTH: 84
<212> TYPE: DNA
<213> ORGANISM: Artificial Sequence
<220> FEATURE:
<223> OTHER INFORMATION: Synthetic: B2M Indel

<400> SEQUENCE: 12
cgtggcctta gctgtgctcg cgctactctc tctttctgga tagcctggag gctatccagc    60
gtgagtctct cctaccctcc cgct                                           84

<210> SEQ ID NO 13
<211> LENGTH: 55
<212> TYPE: DNA
<213> ORGANISM: Artificial Sequence
<220> FEATURE:
<223> OTHER INFORMATION: Synthetic: B2M Indel

<400> SEQUENCE: 13
cgtggcctta gctgtgctcg cgctatccag cgtgagtctc tcctaccctc ccgct         55

<210> SEQ ID NO 14
<211> LENGTH: 82
<212> TYPE: DNA
<213> ORGANISM: Artificial Sequence
<220> FEATURE:
<223> OTHER INFORMATION: Synthetic: B2M Indel

<400> SEQUENCE: 14
cgtggcctta gctgtgctcg cgctactctc tctttctgtg gcctggaggc tatccagcgt    60
gagtctctcc taccctcccg ct                                             82

<210> SEQ ID NO 15
<211> LENGTH: 100
<212> TYPE: RNA
<213> ORGANISM: Artificial Sequence
<220> FEATURE:
<223> OTHER INFORMATION: Synthetic: sgRNA
<220> FEATURE:
<221> NAME/KEY: misc_feature
```

<222> LOCATION: (1)..(20)
<223> OTHER INFORMATION: n is a, c, g, or u

<400> SEQUENCE: 15
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 16
<211> LENGTH: 96
<212> TYPE: RNA
<213> ORGANISM: Artificial Sequence
<220> FEATURE:
<223> OTHER INFORMATION: Synthetic: sgRNA
<220> FEATURE:
<221> NAME/KEY: misc_feature
<222> LOCATION: (1)..(20)
<223> OTHER INFORMATION: n is a, c, g, or u

<400> SEQUENCE: 16
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 17
<211> LENGTH: 114
<212> TYPE: RNA
<213> ORGANISM: Artificial Sequence
<220> FEATURE:
<223> OTHER INFORMATION: Synthetic: sgRNA
<220> FEATURE:
<221> NAME/KEY: misc_feature
<222> LOCATION: (1)..(30)
<223> OTHER INFORMATION: n is a, c, g, or u
<220> FEATURE:
<221> NAME/KEY: misc_feature
<222> LOCATION: (18)..(30)
<223> OTHER INFORMATION: n may be present or absent
<220> FEATURE:
<221> NAME/KEY: misc_feature
<222> LOCATION: (108)..(114)
<223> OTHER INFORMATION: u may be present or absent

<400> SEQUENCE: 17 nnnnnnnnn nnnnnnnnnn nnnnnnnnnn guuuuagagc uagaaauagc aaguuaaaau    60
aaggcuaguc cguuaucaac uugaaaaagu ggcaccgagu cggugcuuuu uuuu         114

<210> SEQ ID NO 18
<211> LENGTH: 126
<212> TYPE: DNA
<213> ORGANISM: Artificial Sequence
<220> FEATURE:
<223> OTHER INFORMATION: Synthetic: 4-1BB nucleotide sequence

<400> SEQUENCE: 18
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 19
<211> LENGTH: 42
<212> TYPE: PRT
<213> ORGANISM: Artificial Sequence
<220> FEATURE:
<223> OTHER INFORMATION: Synthetic: 4-1BB amino acid sequence

<400> SEQUENCE: 19

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 20
<211> LENGTH: 40
<212> TYPE: PRT
<213> ORGANISM: Artificial Sequence
<220> FEATURE:
<223> OTHER INFORMATION: Synthetic: CD28 amino acid sequence

<400> SEQUENCE: 20

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

```
<210> SEQ ID NO 21
<211> LENGTH: 336
<212> TYPE: DNA
<213> ORGANISM: Artificial Sequence
<220> FEATURE:
<223> OTHER INFORMATION: Synthetic: CD3-z nucleotide sequence

<400> SEQUENCE: 21
cgagtgaagt tttcccgaag cgcagacgct ccggcatatc agcaaggaca gaatcagctg      60
tataacgaac tgaatttggg acgccgcgag gagtatgacg tgcttgataa acgccggggg     120
agagacccgg aaatgggggg taaaccccga agaaagaatc cccagaagg actctacaat     180 gaactccaga aggataagat ggcggaggcc tactcagaaa taggtatgaa gggcgaacga     240
cgacggggaa aaggtcacga tggcctctac caagggttga gtacggcaac caaagatacg     300
tacgatgcac tgcatatgca ggccctgcct cccaga                              336
```

```
<210> SEQ ID NO 22
<211> LENGTH: 112
<212> TYPE: PRT
<213> ORGANISM: Artificial Sequence
<220> FEATURE:
<223> OTHER INFORMATION: Synthetic: CD3-z amino acid sequence

<400> SEQUENCE: 22

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
```

<210> SEQ ID NO 23
<211> LENGTH: 100
<212> TYPE: RNA
<213> ORGANISM: Artificial Sequence
<220> FEATURE:
<223> OTHER INFORMATION: Synthetic: CD70 sgRNA (E1_T1)

<400> SEQUENCE: 23
ucaccaagcc cgcgaccaau guuuuagagc uagaaauagc aaguuaaaau aaggcuaguc    60
cguuaucaac uugaaaaagu ggcaccgagu cggugcuuuu                         100

<210> SEQ ID NO 24
<211> LENGTH: 100
<212> TYPE: RNA
<213> ORGANISM: Artificial Sequence
<220> FEATURE:
<223> OTHER INFORMATION: Synthetic: CD70 sgRNA (E1_T3)

<400> SEQUENCE: 24
aucaccaagc ccgcgaccaa guuuuagagc uagaaauagc aaguuaaaau aaggcuaguc    60
cguuaucaac uugaaaaagu ggcaccgagu cggugcuuuu                         100

<210> SEQ ID NO 25
<211> LENGTH: 100
<212> TYPE: RNA
<213> ORGANISM: Artificial Sequence
<220> FEATURE:
<223> OTHER INFORMATION: Synthetic: CD70 sgRNA (E1_T4)

<400> SEQUENCE: 25
cggugcggcg caggcccuau guuuuagagc uagaaauagc aaguuaaaau aaggcuaguc    60
cguuaucaac uugaaaaagu ggcaccgagu cggugcuuuu                         100

<210> SEQ ID NO 26
<211> LENGTH: 100
<212> TYPE: RNA
<213> ORGANISM: Artificial Sequence
<220> FEATURE:
<223> OTHER INFORMATION: Synthetic: CD70 sgRNA (E1_T7)

<400> SEQUENCE: 26
gcuuuggucc cauuggucgc guuuuagagc uagaaauagc aaguuaaaau aaggcuaguc    60
cguuaucaac uugaaaaagu ggcaccgagu cggugcuuuu                         100

<210> SEQ ID NO 27
<211> LENGTH: 100
<212> TYPE: RNA
<213> ORGANISM: Artificial Sequence
<220> FEATURE:
<223> OTHER INFORMATION: Synthetic: CD70 sgRNA (E1_T8)

<400> SEQUENCE: 27
gcccgcagga cgcacccaua guuuuagagc uagaaauagc aaguuaaaau aaggcuaguc    60
cguuaucaac uugaaaaagu ggcaccgagu cggugcuuuu                         100

<210> SEQ ID NO 28
<211> LENGTH: 100
<212> TYPE: RNA
<213> ORGANISM: Artificial Sequence
<220> FEATURE:
<223> OTHER INFORMATION: Synthetic: CD70 sgRNA (E1_T10)

```
<400> SEQUENCE: 28
gugcauccag cgcuucgcac guuuuagagc uagaaauagc aaguuaaaau aaggcuaguc    60
cguuaucaac uugaaaaagu ggcaccgagu cggugcuuuu                        100

<210> SEQ ID NO 29
<211> LENGTH: 100
<212> TYPE: RNA
<213> ORGANISM: Artificial Sequence
<220> FEATURE:
<223> OTHER INFORMATION: Synthetic: CD70 sgRNA (E3_T1)

<400> SEQUENCE: 29
cagcuacgua uccaucguga guuuuagagc uagaaauagc aaguuaaaau aaggcuaguc    60
cguuaucaac uugaaaaagu ggcaccgagu cggugcuuuu                        100

<210> SEQ ID NO 30
<211> LENGTH: 100
<212> TYPE: RNA
<213> ORGANISM: Artificial Sequence
<220> FEATURE:
<223> OTHER INFORMATION: Synthetic: TRAC sgRNA

<400> SEQUENCE: 30
agagcaacag ugcuguggcc guuuuagagc uagaaauagc aaguuaaaau aaggcuaguc    60
cguuaucaac uugaaaaagu ggcaccgagu cggugcuuuu                        100

<210> SEQ ID NO 31
<211> LENGTH: 100
<212> TYPE: RNA
<213> ORGANISM: Artificial Sequence
<220> FEATURE:
<223> OTHER INFORMATION: Synthetic: b2M sgRNA

<400> SEQUENCE: 31
gcuacucucu cuuucuggcc guuuuagagc uagaaauagc aaguuaaaau aaggcuaguc    60
cguuaucaac uugaaaaagu ggcaccgagu cggugcuuuu                        100

<210> SEQ ID NO 32
<211> LENGTH: 100
<212> TYPE: RNA
<213> ORGANISM: Artificial Sequence
<220> FEATURE:
<223> OTHER INFORMATION: Synthetic: PD-1 sgRNA

<400> SEQUENCE: 32
cugcagcuuc uccaacacau guuuuagagc uagaaauagc aaguuaaaau aaggcuaguc    60
cguuaucaac uugaaaaagu ggcaccgagu cggugcuuuu                        100

<210> SEQ ID NO 33
<211> LENGTH: 100
<212> TYPE: RNA
<213> ORGANISM: Artificial Sequence
<220> FEATURE:
<223> OTHER INFORMATION: Synthetic: CD70 sgRNA (E1_T1)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate
```

```
<400> SEQUENCE: 33
ucaccaagcc cgcgaccaau guuuuagagc uagaaauagc aaguuaaaau aaggcuaguc    60
cguuaucaac uugaaaaagu ggcaccgagu cggugcuuuu                         100

<210> SEQ ID NO 34
<211> LENGTH: 100
<212> TYPE: RNA
<213> ORGANISM: Artificial Sequence
<220> FEATURE:
<223> OTHER INFORMATION: Synthetic: CD70 sgRNA (E1_T3)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 34
aucaccaagc ccgcgaccaa guuuuagagc uagaaauagc aaguuaaaau aaggcuaguc    60
cguuaucaac uugaaaaagu ggcaccgagu cggugcuuuu                         100

<210> SEQ ID NO 35
<211> LENGTH: 100
<212> TYPE: RNA
<213> ORGANISM: Artificial Sequence
<220> FEATURE:
<223> OTHER INFORMATION: Synthetic: CD70 sgRNA (E1_T4)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 35
cggugcggcg caggcccuau guuuuagagc uagaaauagc aaguuaaaau aaggcuaguc    60
cguuaucaac uugaaaaagu ggcaccgagu cggugcuuuu                         100

<210> SEQ ID NO 36
<211> LENGTH: 100
<212> TYPE: RNA
<213> ORGANISM: Artificial Sequence
<220> FEATURE:
<223> OTHER INFORMATION: Synthetic: CD70 sgRNA (E1_T7)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 36 gcuuggucc cauuggucgc guuuuagagc uagaaauagc aaguuaaaau aaggcuaguc    60
cguuaucaac uugaaaaagu ggcaccgagu cggugcuuuu                         100

<210> SEQ ID NO 37
<211> LENGTH: 100
<212> TYPE: RNA
<213> ORGANISM: Artificial Sequence
<220> FEATURE:
<223> OTHER INFORMATION: Synthetic: CD70 sgRNA (E1_T8)
```

```
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 37
gcccgcagga cgcacccaua guuuuagagc uagaaauagc aaguuaaaau aaggcuaguc    60
cguuaucaac uugaaaaagu ggcaccgagu cggugcuuuu                        100

<210> SEQ ID NO 38
<211> LENGTH: 100
<212> TYPE: RNA
<213> ORGANISM: Artificial Sequence
<220> FEATURE:
<223> OTHER INFORMATION: Synthetic: CD70 sgRNA (E1_T10)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 38
gugcauccag cgcuucgcac guuuuagagc uagaaauagc aaguuaaaau aaggcuaguc    60
cguuaucaac uugaaaaagu ggcaccgagu cggugcuuuu                        100

<210> SEQ ID NO 39
<211> LENGTH: 100
<212> TYPE: RNA
<213> ORGANISM: Artificial Sequence
<220> FEATURE:
<223> OTHER INFORMATION: Synthetic: CD70 sgRNA (E3_T1)
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 39
cagcuacgua uccaucguga guuuuagagc uagaaauagc aaguuaaaau aaggcuaguc    60
cguuaucaac uugaaaaagu ggcaccgagu cggugcuuuu                        100

<210> SEQ ID NO 40
<211> LENGTH: 100
<212> TYPE: RNA
<213> ORGANISM: Artificial Sequence
<220> FEATURE:
<223> OTHER INFORMATION: Synthetic: TRAC sgRNA
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 40
agagcaacag ugcuguggcc guuuuagagc uagaaauagc aaguuaaaau aaggcuaguc    60
```

```
cguuaucaac uugaaaaagu ggcaccgagu cggugcuuuu            100

<210> SEQ ID NO 41
<211> LENGTH: 100
<212> TYPE: RNA
<213> ORGANISM: Artificial Sequence
<220> FEATURE:
<223> OTHER INFORMATION: Synthetic: b2M sgRNA
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 41
gcuacucucu cuuucuggcc guuuuagagc uagaaauagc aaguuaaaau aaggcuaguc    60
cguuaucaac uugaaaaagu ggcaccgagu cggugcuuuu           100

<210> SEQ ID NO 42
<211> LENGTH: 100
<212> TYPE: RNA
<213> ORGANISM: Artificial Sequence
<220> FEATURE:
<223> OTHER INFORMATION: Synthetic: PD-1 sgRNA
<220> FEATURE:
<221> NAME/KEY: modified_base
<222> LOCATION: (1)..(3)
<223> OTHER INFORMATION: 2'-O-methyl phosphorothioate
<220> FEATURE:
<221> NAME/KEY: modified_base
<222> LOCATION: (97)..(99)
<223> OTHER INFORMATION: 2'-O-methyl phosphorothioate

<400> SEQUENCE: 42
cugcagcuuc uccaacacau guuuuagagc uagaaauagc aaguuaaaau aaggcuaguc    60
cguuaucaac uugaaaaagu ggcaccgagu cggugcuuuu           100

<210> SEQ ID NO 43
<211> LENGTH: 4688
<212> TYPE: DNA
<213> ORGANISM: Artificial Sequence
<220> FEATURE:
<223> OTHER INFORMATION: Synthetic: CD70 rAAV  (CD70B scFV with 41BB)

<400> SEQUENCE: 43
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact   120 agggggttcct gcggccgcac gcgtgagatg taaggagctg ctgtgacttg ctcaaggcct   180
tatatcgagt aaacggtagt gctggggctt agacgcaggt gttctgattt atagttcaaa   240
acctctatca atgagagagc aatctcctgg taatgtgata gatttcccaa cttaatgcca   300
acataccata aacctcccat tctgctaatg cccagcctaa gttggggaga ccactccaga   360
ttccaagatg tacagtttgc tttgctgggc cttttttccca tgcctgcctt tactctgcca   420
gagttatatt gctggggttt tgaagaagat cctattaaat aaaagaataa gcagtattat   480
taagtagccc tgcatttcag gtttccttga gtggcaggcc aggcctggcc gtgaacgttc   540
actgaaatca tggcctcttg gccaagatta tagcttgtg cctgtccctg agtcccagtc   600
catcacgagc agctggtttc taagatgcta tttcccgtat aaagcatgag accgtgactt   660
gccagcccca cagagcccg cccttgtcca tcactggcat ctggactcca gctgggttg   720
```

```
gggcaaagag ggaaatgaga tcatgtccta accctgatcc tcttgtccca cagatatcca      780
gaaccctgac cctgccgtgt accagctgag agactctaaa tccagtgaca agtctgtctg      840
cctattcacc gattttgatt ctcaaacaaa tgtgtcacaa agtaaggatt ctgatgtgta      900
tatcacagac aaaactgtgc tagacatgag gtctatggac ttcaggctcc ggtgcccgtc      960
agtgggcaga gcgcacatcg cccacagtcc ccgagaagtt gggggagggg tcggcaatt     1020
gaaccggtgc ctagagaagg tggcgcgggg taaactggga aagtgatgtc gtgtactggc     1080
tccgcctttt tcccgagggt ggggagaac cgtatataag tgcagtagtc gccgtgaacg      1140
ttcttttcg caacgggttt gccgccagaa cacaggtaag tgccgtgtgt ggttcccgcg     1200
ggcctggcct ctttacgggt tatggccctt gcgtgccttg aattacttcc actggctgca     1260
gtacgtgatt cttgatcccg agcttcgggt tggaagtggg tgggagagtt cgaggccttg     1320
cgcttaagga gcccctttcgc ctcgtgcttg agttgaggcc tggcctgggc gctggggccg     1380
ccgcgtgcga atctggtggc accttcgcgc ctgtctcgct gctttcgata agtctctagc     1440
catttaaaat ttttgatgac ctgctgcgac gcttttttc tggcaagata gtcttgtaaa     1500
tgcgggccaa gatctgcaca ctggtatttc ggttttgg gccgcgggcg gcgacggggc     1560
ccgtgcgtcc cagcgcacat gttcggcgag gcggggcctg cgagcgcggc caccgagaat     1620
cggacggggg tagtctcaag ctggccggcc tgctctggtg cctggcctcg cgccgccgtg     1680
tatcgccccg ccctgggcgg caaggctggc ccggtcggca ccagttgcgt gagcggaaag     1740
atggccgctt cccggccctg ctgcaggag ctcaaaatgg aggacgcggc gctcgggaga     1800
gcgggcgggt gagtcaccca cacaaaggaa aagggccttt ccgtcctcag ccgtcgcttc     1860
atgtgactcc acgagtacc gggcgccgtc caggcacctc gattagttct cgagcttttg     1920
gagtacgtcg tctttaggtt ggggggaggg gttttatgcg atggagtttc cccacactga     1980
gtgggtggag actgaagtta ggccagcttg gcacttgatg taattctcct tggaatttgc     2040
cctttttgag tttggatctt ggttcattct caagcctcag acagtggttc aaagtttttt     2100
tcttccattt caggtgtcgt gaccaccatg gcgcttccgg tgacagcact gctcctcccc     2160
ttggcgctgt tgctccacgc agcaaggccg caggtccagt tggtgcaaag cggggcggag     2220
gtgaaaaaac ccggcgcttc cgtgaaggtg tcctgtaagg cgtccggtta tacgttcacg     2280
aactacggga tgaattgggt tcgccaagcg ccggggcagg gactgaaatg gatggggtgg     2340
ataaatacct acaccggcga acctacatac gccgacgctt ttaaagggcg agtcactatg     2400
acgcgcgata ccagcatatc caccgcatac atggagctgt cccgactccg gtcagacgac     2460
acggctgtct actattgtgc tcgggactat ggcgattatg catggactca ctggggtcag     2520
ggtacgactg taacagttag tagtggtgga ggcggcagtg gcgggggggg aagcggagga     2580
gggggttctg gtgacatagt tatgacccaa tccccagata gtttggcggt ttctctgggc     2640
gagagggcaa cgattaattg tcgcgcatca aagagcgttt caacgagcgg atattctttt     2700
atgcattggt accagcaaaa acccggacaa ccgccgaagc tgctgatcta cttggcttca     2760
aatcttgagt ctggggtgcc ggaccgattt tctggtagtg gaagcggaac tgactttacg     2820
ctcacgatca gttcactgca ggctgaggat gtagcggtct attattgcca gcacagtaga     2880
gaagtcccct ggaccttcgg tcaaggcacg aaagtagaaa ttaaaagtgc tgctgccttt     2940
gtcccggtat ttctcccagc caaaccgacc acgactcccg cccgcgccc tccgacaccc     3000
gctcccacca tcgcctctca acctcttagt cttcgccccg aggcatgccg accgccgcc     3060
```

```
ggggggtgctg ttcatacgag gggcttggac ttcgcttgtg atatttacat ttgggctccg    3120
ttggcgggta cgtgcggcgt cctttttgttg tcactcgtta ttactttgta ttgtaatcac    3180
aggaatcgca acggggcag aaagaaactc ctgtatatat tcaaacaacc atttatgaga     3240
ccagtacaaa ctactcaaga ggaagatggc tgtagctgcc gatttccaga agaagaagaa    3300
ggaggatgtg aactgcgagt gaagttttcc cgaagcgcag acgctccggc atatcagcaa    3360
ggacagaatc agctgtataa cgaactgaat ttgggacgcc gcgaggagta tgacgtgctt    3420
gataaacgcc gggggagaga cccggaaatg gggggtaaac cccgaagaaa gaatccccaa    3480
gaaggactct acaatgaact ccagaaggat aagatggcgg aggcctactc agaaataggt    3540
atgaagggcg aacgacgacg gggaaaaggt cacgatggcc tctaccaagg gttgagtacg    3600
gcaaccaaag atacgtacga tgcactgcat atgcaggccc tgcctcccag ataataataa    3660
aatcgctatc catcgaagat ggatgtgtgt tggttttttg tgtgtggagc aacaaatctg    3720
actttgcatg tgcaaacgcc ttcaacaaca gcattattcc agaagacacc ttcttcccca    3780
gcccaggtaa gggcagcttt ggtgccttcg caggctgttt ccttgcttca ggaatggcca    3840
ggttctgccc agagctctgg tcaatgatgt ctaaaactcc tctgattggt ggtctcggcc    3900
ttatccattg ccaccaaaac cctcttttta ctaagaaaca gtgagccttg ttctggcagt    3960
ccagagaatg acacgggaaa aaagcagatg aagagaaggt ggcaggagag ggcacgtggc    4020
ccagcctcag tctctccaac tgagttcctg cctgcctgcc tttgctcaga ctgtttgccc    4080
cttactgctc ttctaggcct cattctaagc cccttctcca agttgcctct ccttatttct    4140
ccctgtctgc caaaaaatct ttcccagctc actaagtcag tctcacgcag tcactcatta    4200
acccaccaat cactgattgt gccggcacat gaatgcacca ggtgttgaag tggaggaatt    4260
aaaaagtcag atgaggggtg tgcccagagg aagcaccatt ctagttgggg gagcccatct    4320
gtcagctggg aaaagtccaa ataacttcag attggaatgt gttttaactc agggttgaga    4380
aaacagctac cttcaggaca aaagtcaggg aagggctctc tgaagaaatg ctacttgaag    4440
ataccagccc taccaagggc agggagagga ccctatagag gcctgggaca ggagctcaat    4500
gagaaaggta accacgtgcg gaccgaggct gcagcgtcgt cctccctagg aaccccctagt    4560 gatggagttg gccactccct ctctgcgcgc tcgctcgctc actgaggccg gcgaccaaa     4620 ggtcgcccga cgcccgggct ttgcccgggc ggcctcagtg agcgagcgag cgcgcagctg    4680
cctgcagg                                                             4688
```

<210> SEQ ID NO 44
<211> LENGTH: 4364
<212> TYPE: DNA
<213> ORGANISM: Artificial Sequence
<220> FEATURE:
<223> OTHER INFORMATION: Synthetic: CD70 LHA to RHA  (CD70B scFV with 41BB)

<400> SEQUENCE: 44

```
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg    240
ctgggccttt ttcccatgcc tgcctttact ctgccagagt tatattgctg ggttttgaa     300 gaagatccta ttaaataaaa gaataagcag tattattaag tagccctgca tttcaggttt    360
```

| | |
|---|---|
| ccttgagtgg caggccaggc ctggccgtga acgttcactg aaatcatggc ctcttggcca | 420 |
| agattgatag cttgtgcctg tccctgagtc ccagtccatc acgagcagct ggtttctaag | 480 |
| atgctatttc ccgtataaag catgagaccg tgacttgcca gccccacaga gccccgccct | 540 |
| tgtccatcac tggcatctgg actccagcct gggttgggc aaagagggaa atgagatcat | 600 |
| gtcctaaccc tgatcctctt gtcccacaga tatccagaac cctgaccctg ccgtgtacca | 660 |
| gctgagagac tctaaatcca gtgacaagtc tgtctgccta ttcaccgatt ttgattctca | 720 |
| aacaaatgtg tcacaaagta aggattctga tgtgtatatc acagacaaaa ctgtgctaga | 780 |
| catgaggtct atggacttca ggctccggtg cccgtcagtg ggcagagcgc acatcgccca | 840 |
| cagtccccga gaagttgggg ggagggggtcg gcaattgaac cggtgcctag agaaggtggc | 900 |
| gcggggtaaa ctgggaaagt gatgtcgtgt actggctccg ccttttttccc gagggtgggg | 960 |
| gagaaccgta tataagtgca gtagtcgccg tgaacgttct ttttcgcaac gggtttgccg | 1020 |
| ccagaacaca ggtaagtgcc gtgtgtggtt cccgcgggcc tggcctcttt acgggttatg | 1080 |
| gcccttgcgt gccttgaatt acttccactg gctgcagtac gtgattcttg atcccgagct | 1140 |
| tcgggttgga agtgggtggg agagttcgag gccttgcgct taaggagccc cttcgcctcg | 1200 |
| tgcttgagtt gaggcctggc ctgggcgctg gggccgccgc gtgcgaatct ggtggcacct | 1260 |
| tcgcgcctgt ctcgctgctt tcgataagtc tctagccatt taaaattttt gatgacctgc | 1320 |
| tgcgacgctt tttttctggc aagatagtct tgtaaatgcg ggccaagatc tgcacactgg | 1380 |
| tatttcggtt tttggggccg cgggcggcga cggggcccgt gcgtcccagc gcacatgttc | 1440 |
| ggcgaggcgg ggcctgcgag cgcggccacc gagaatcgga cggggtagt ctcaagctgg | 1500 |
| ccggcctgct ctggtgcctg gcctcgcgcc gccgtgtatc gcccgccct gggcggcaag | 1560 |
| gctggccgg tcgcaccag ttgcgtgagc ggaaagatgg ccgcttcccg gccctgctgc | 1620 |
| agggagctca aaatggagga cgcggcgctc gggagagcgg gcgggtgagt cacccacaca | 1680 |
| aaggaaaagg gcctttccgt cctcagccgt cgcttcatgt gactccacgg agtaccgggc | 1740 |
| gccgtccagg cacctcgatt agttctcgag cttttggagt acgtcgtctt taggttgggg | 1800 |
| ggagggtttt tatgcgatgg agtttccca cactgagtgg gtggagactg aagttaggcc | 1860 |
| agcttggcac ttgatgtaat tctccttgga atttgccctt tttgagtttg atcttggtt | 1920 |
| cattctcaag cctcagacag tggttcaaag ttttttttctt ccatttcagg tgtcgtgacc | 1980 |
| accatggcgc ttccggtgac agcactgctc ctcccccttgg cgctgttgct ccacgcagca | 2040 |
| aggccgcagg tccagttggt gcaaagcggg gcggaggtga aaaacccggg cgcttccgtg | 2100 |
| aaggtgtcct gtaaggcgtc cggttatacg ttcacgaact acgggatgaa ttgggttcgc | 2160 |
| caagcgccgg ggcagggact gaaatggatg ggtggataa ataccacac ggcgaacct | 2220 |
| acatacgccg acgctttta agggcgagtc actatgacgc gcgataccag catatccacc | 2280 |
| gcatacatgg agctgtcccg actccggtca gacgacacgg ctgtctacta ttgtgctcgg | 2340 |
| gactatggcg attatggcat ggactactgg ggtcaggta cgactgtaac agttagtagt | 2400 |
| ggtggaggcg gcagtggcgg ggggggaagc ggaggagggg gttctggtga catagttatg | 2460 |
| acccaatccc cagatagttt ggcggttct ctgggcgaga gggcaacgat taattgtcgc | 2520 |
| gcatcaaaga gcgtttcaac gagcggatat tcttttatgc attggtacca gcaaaaaccc | 2580 |
| ggacaaccgc cgaagctgct gatctacttg gcttcaaatc ttgagtctgg ggtgccggac | 2640 |
| cgattttctg gtagtggaag cggaactgac tttacgctca cgatcagttc actgcaggct | 2700 |
| gaggatgtag cggtctatta ttgccagcac agtagagaag tcccctggac cttcggtcaa | 2760 |

```
ggcacgaaag tagaaattaa aagtgctgct gcctttgtcc cggtatttct cccagccaaa    2820
ccgaccacga ctcccgcccc gcgccctccg acacccgctc ccaccatcgc ctctcaacct    2880
cttagtcttc gccccgaggc atgccgaccc gccgccgggg gtgctgttca tacgaggggc    2940
ttggacttcg cttgtgatat ttacatttgg gctccgttgg cgggtacgtg cggcgtcctt    3000
ttgttgtcac tcgttattac tttgtattgt aatcacagga atcgcaaacg gggcagaaag    3060
aaactcctgt atatattcaa acaaccattt atgagaccag tacaaactac tcaagaggaa    3120
gatggctgta gctgccgatt ccagaagaa gaagaaggag gatgtgaact gcgagtgaag    3180
ttttcccgaa gcgcagacgc tccggcatat cagcaaggac agaatcagct gtataacgaa    3240
ctgaatttgg gacgccgcga ggagtatgac gtgcttgata acgccgggg gagagacccg    3300 gaaatggggg gtaaacccccg aagaaagaat ccccaagaag gactctacaa tgaactccag    3360
aaggataaga tggcggaggc ctactcagaa ataggtatga agggcgaacg acgacgggga    3420
aaaggtcacg atgcctcta ccaagggttg agtacggcaa ccaaagatac gtacgatgca    3480
ctgcatatgc aggccctgcc tcccagataa taataaaatc gctatccatc gaagatggat    3540
gtgtgttggt ttttttgtgtg tggagcaaca aatctgactt tgcatgtgca aacgccttca    3600
acaacagcat tattccagaa gacaccttct tccccagccc aggtaagggc agctttggtg    3660
ccttcgcagg ctgtttcctt gcttcaggaa tggccaggtt ctgcccagag ctctggtcaa    3720
tgatgtctaa aactcctctg attggtggtc tcggccttat ccattgccac caaaaccctc    3780
tttttactaa gaaacagtga gccttgttct ggcagtccag agaatgacac gggaaaaaag    3840
cagatgaaga gaaggtggca ggagagggca cgtggcccag cctcagtctc tccaactgag    3900
ttcctgcctg cctgccttg ctcagactgt ttgcccctta ctgctcttct aggcctcatt    3960 ctaagccct tctccaagtt gcctctcctt atttctccct gtctgccaaa aaatctttcc    4020
cagctcacta agtcagtctc acgcagtcac tcattaaccc accaatcact gattgtgccg    4080
gcacatgaat gcaccaggtg ttgaagtgga ggaattaaaa agtcagatga ggggtgtgcc    4140
cagaggaagc accattctag ttgggggagc ccatctgtca gctggaaaaa gtccaaataa    4200
cttcagattg gaatgtgttt taactcaggg ttgagaaaac agctaccttc aggacaaaag    4260
tcagggaagg gctctctgaa gaaatgctac ttgaagatac cagccctacc aagggcaggg    4320
agaggaccct atagaggcct gggacaggag ctcaatgaga aagg                    4364
```

<210> SEQ ID NO 45
<211> LENGTH: 1527
<212> TYPE: DNA
<213> ORGANISM: Artificial Sequence
<220> FEATURE:
<223> OTHER INFORMATION: Synthetic: CD70 CAR nucleotide sequence (CD70B scFV with 41BB)

<400> SEQUENCE: 45

```
atggcgcttc cggtgacagc actgctcctc cccttggcgc tgttgctcca cgcagcaagg     60
ccgcaggtcc agttggtgca aagcggggcg gaggtgaaaa acccggcgc ttccgtgaag    120 gtgtcctgta aggcgtccgg ttatacgttc acgaactacg gatgaattg gttcgccaa     180 gcgccgggc agggactgaa atggatgggg tggataaata cctacaccgg cgaacctaca    240
tacgccgacg ctttaaagg gcgagtcact atgacgcgcg ataccagcat atccaccgca    300
tacatggagc tgtcccgact ccggtcagac gacacggctg tctactattg tgctcggac    360 tatggcgatt atggcatgga ctactggggt cagggtacga ctgtaacagt tagtagtggt    420
```

```
ggaggcggca gtggcggggg gggaagcgga ggaggggggtt ctggtgacat agttatgacc    480
caatccccag atagtttggc ggtttctctg ggcgagaggg caacgattaa ttgtcgcgca    540
tcaaagagcg tttcaacgag cggatattct tttatgcatt ggtaccagca aaaacccgga    600
caaccgccga agctgctgat ctacttggct tcaaatcttg agtctggggt gccggaccga    660
ttttctggta gtggaagcgg aactgacttt acgctcacga tcagttcact gcaggctgag    720
gatgtagcgg tctattattg ccagcacagt agagaagtcc cctggacctt cggtcaaggc    780
acgaaagtag aaattaaaag tgctgctgcc tttgtcccgg tatttctccc agccaaaccg    840
accacgactc ccgccccgcg ccctccgaca cccgctccca ccatcgcctc tcaacctctt    900
agtcttcgcc ccgaggcatg ccgacccgcc gccgggggtg ctgttcatac gagggcttg    960 gacttcgctt gtgatattta catttgggct ccgttggcgg gtacgtgcgg cgtcctttg   1020 ttgtcactcg ttattacttt gtattgtaat cacaggaatc gcaacggggg cagaaagaaa   1080
ctcctgtata tattcaaaca accatttatg agaccagtac aaactactca agaggaagat   1140
ggctgtagct gccgatttcc agaagaagaa gaaggaggat gtgaactgcg agtgaagttt   1200
tcccgaagcg cagacgctcc ggcatatcag caaggacaga atcagctgta taacgaactg   1260
aatttgggac gccgcgagga gtatgacgtg cttgataaac gccgggggag agacccggaa   1320 atgggggta aaccccgaag aaagaatccc caagaaggac tctacaatga actccagaag   1380
gataagatgg cggaggccta ctcagaaata ggtatgaagg gcgaacgacg acggggaaaa   1440
ggtcacgatg gcctctacca agggttgagt acggcaacca agatacgta cgatgcactg   1500 catatgcagg ccctgcctcc cagataa                                       1527
```

<210> SEQ ID NO 46
<211> LENGTH: 508
<212> TYPE: PRT
<213> ORGANISM: Artificial Sequence
<220> FEATURE:
<223> OTHER INFORMATION: Synthetic: CD70 CAR amino acid sequence (CD70B scFV with 41BB)

<400> SEQUENCE: 46

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Asn Tyr Gly Met Asn Trp Val Arg Gln Ala Pro Gly Gln
    50                  55                  60

Gly Leu Lys Trp Met Gly Trp Ile Asn Thr Tyr Thr Gly Glu Pro Thr
65                  70                  75                  80

Tyr Ala Asp Ala Phe Lys Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp Tyr Gly Asp Tyr Gly Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Gly Asp Ile Val Met Thr
145                 150                 155                 160
```

Gln Ser Pro Asp Ser Leu Ala Val Ser Leu Gly Glu Arg Ala Thr Ile
            165                 170                 175

Asn Cys Arg Ala Ser Lys Ser Val Ser Thr Ser Gly Tyr Ser Phe Met
        180                 185                 190

His Trp Tyr Gln Gln Lys Pro Gly Gln Pro Pro Lys Leu Leu Ile Tyr
    195                 200                 205

Leu Ala Ser Asn Leu Glu Ser Gly Val Pro Asp Arg Phe Ser Gly Ser
210                 215                 220

Gly Ser Gly Thr Asp Phe Thr Leu Thr Ile Ser Ser Leu Gln Ala Glu
225                 230                 235                 240

Asp Val Ala Val Tyr Tyr Cys Gln His Ser Arg Glu Val Pro Trp Thr
                245                 250                 255

Phe Gly Gln Gly Thr Lys Val Glu Ile Lys Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 47
<211> LENGTH: 735
<212> TYPE: DNA
<213> ORGANISM: Artificial Sequence
<220> FEATURE:
<223> OTHER INFORMATION: Synthetic: CD70A scFv nucleotide sequence

<400> SEQUENCE: 47
gatatagtta tgacccaatc acccgatagt cttgcggtaa gcctgggggga gcgagcaaca    60

```
ataaactgtc gggcatcaaa atccgtcagt acaagcgggt attcattcat gcactggtat   120
caacagaaac ccggtcagcc acccaagctc ctgatttatc ttgcgtctaa tcttgagtcc   180
ggcgtcccag accggttttc cggctccggg agcggcacgg attttactct tactatttct   240
agccttcagg ccgaagatgt ggcggtatac tactgccagc attcaaggga agttccttgg   300
acgttcggtc agggcacgaa agtggaaatt aaaggcgggg ggggatccgg cggggagggg   360
tctggaggag gtggcagtgg tcaggtccaa ctggtgcagt ccggggcaga ggtaaaaaaa   420
cccggcgcgt ctgttaaggt ttcatgcaag gccagtggat atactttcac caattacgga   480
atgaactggg tgaggcaggc ccctggtcaa ggcctgaaat ggatgggatg gataaacacg   540
tacaccggtg aacctaccta tgccgatgcc tttaagggtc gggttacgat gacgagagac   600
acctccatat caacagccta catggagctc agcagattga ggagtgacga tacggcagtc   660
tattactgtg caagagacta cggcgattat ggcatggatt actggggcca gggcactaca   720
gtaaccgttt ccagc                                                    735
```

<210> SEQ ID NO 48
<211> LENGTH: 245
<212> TYPE: PRT
<213> ORGANISM: Artificial Sequence
<220> FEATURE:
<223> OTHER INFORMATION: Synthetic: CD70A scFv amino acid sequence

<400> SEQUENCE: 48

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Gly
            100                 105                 110

Gly Gly Gly Ser Gly Gly Gly Gly Ser Gly Gly Gly Gly Ser Gly Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Asn Tyr Gly
145                 150                 155                 160

Met Asn Trp Val Arg Gln Ala Pro Gly Gln Gly Leu Lys Trp Met Gly
                165                 170                 175

Trp Ile Asn Thr Tyr Thr Gly Glu Pro Thr Tyr Ala Asp Ala Phe Lys
            180                 185                 190

Gly Arg Val Thr Met Thr Arg Asp Thr Ser Ile Ser Thr Ala Tyr Met
        195                 200                 205

Glu Leu Ser Arg Leu Arg Ser Asp Asp Thr Ala Val Tyr Tyr Cys Ala
    210                 215                 220

Arg Asp Tyr Gly Asp Tyr Gly Met Asp Tyr Trp Gly Gln Gly Thr Thr
225                 230                 235                 240
```

Val Thr Val Ser Ser
            245

<210> SEQ ID NO 49
<211> LENGTH: 735
<212> TYPE: DNA
<213> ORGANISM: Artificial Sequence
<220> FEATURE:
<223> OTHER INFORMATION: Synthetic: CD70B scFv nucleotide sequence

<400> SEQUENCE: 49

```
caggtccagt tggtgcaaag cggggcggag gtgaaaaaac ccggcgcttc cgtgaaggtg     60
tcctgtaagg cgtccggtta tacgttcacg aactacggga tgaattgggt tcgccaagcg    120
ccggggcagg gactgaaatg gatggggtgg ataaatacct acaccggcga acctacatac    180
gccgacgctt ttaaagggcg agtcactatg acgcgcgata ccagcatatc caccgcatac    240
atggagctgt cccgactccg gtcagacgac acggctgtct actattgtgc tcgggactat    300
ggcgattatg gcatggacta ctggggtcag ggtacgactg taacagttag tagtggtgga    360
ggcggcagtg gcggggggg aagcggagga ggggttctg gtgacatagt tatgacccaa    420
tccccagata gtttggcggt ttctctgggc gagagggcaa cgattaattg tcgcgcatca    480
aagagcgttt caacgagcgg atattctttt atgcattggt accagcaaaa acccggacaa    540
ccgccgaagc tgctgatcta cttggcttca aatcttgagt ctgggggtgcc ggaccgattt    600
tctggtagtg gaagcggaac tgactttacg ctcacgatca gttcactgca ggctgaggat    660
gtagcggtct attattgcca gcacagtaga gaagtcccct ggaccttcgg tcaaggcacg    720
aaagtagaaa ttaaa                                                      735
```

<210> SEQ ID NO 50
<211> LENGTH: 245
<212> TYPE: PRT
<213> ORGANISM: Artificial Sequence
<220> FEATURE:
<223> OTHER INFORMATION: Synthetic: CD70B scFv amino acid sequence

<400> SEQUENCE: 50

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Gly Asp Ile Val Met Thr Gln Ser Pro Asp Ser
    130                 135                 140

Leu Ala Val Ser Leu Gly Glu Arg Ala Thr Ile Asn Cys Arg Ala Ser
145                 150                 155                 160

```
Lys Ser Val Ser Thr Ser Gly Tyr Ser Phe Met His Trp Tyr Gln Gln
                165                 170                 175

Lys Pro Gly Gln Pro Pro Lys Leu Leu Ile Tyr Leu Ala Ser Asn Leu
            180                 185                 190

Glu Ser Gly Val Pro Asp Arg Phe Ser Gly Ser Gly Ser Gly Thr Asp
        195                 200                 205

Phe Thr Leu Thr Ile Ser Ser Leu Gln Ala Glu Asp Val Ala Val Tyr
    210                 215                 220

Tyr Cys Gln His Ser Arg Glu Val Pro Trp Thr Phe Gly Gln Gly Thr
225                 230                 235                 240

Lys Val Glu Ile Lys
            245

<210> SEQ ID NO 51
<211> LENGTH: 118
<212> TYPE: PRT
<213> ORGANISM: Artificial Sequence
<220> FEATURE:
<223> OTHER INFORMATION: Synthetic: CD70 VH

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 52
<211> LENGTH: 111
<212> TYPE: PRT
<213> ORGANISM: Artificial Sequence
<220> FEATURE:
<223> OTHER INFORMATION: Synthetic: CD70 VL

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95
```

Glu Val Pro Trp Thr Phe Gly Gln Gly Thr Lys Val Glu Ile Lys
            100                 105                 110

<210> SEQ ID NO 53
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 53

Gly Gly Gly Gly Ser Gly Gly Gly Gly Ser Gly Gly Gly Gly Ser Gly
1               5                   10                  15

<210> SEQ ID NO 54
<211> LENGTH: 4688
<212> TYPE: DNA
<213> ORGANISM: Artificial Sequence
<220> FEATURE:
<223> OTHER INFORMATION: Synthetic: BCMA rAAV

<400> SEQUENCE: 54
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgagatg taaggagctg ctgtgacttg ctcaaggcct    180
tatatcgagt aaacggtagt gctggggctt agacgcaggt gttctgattt atagttcaaa    240
acctctatca atgagagagc aatcctctgg taatgtgata gatttcccaa cttaatgcca    300
acataccata aacctcccat tctgctaatg cccagcctaa gttggggaga ccactccaga    360
ttccaagatg tacagtttgc tttgctgggc ctttttccca tgcctgcctt tactctgcca    420
gagttatatt gctggggttt tgaagaagat cctattaaat aaaagaataa gcagtattat    480
taagtagccc tgcatttcag gtttccttga gtggcaggcc aggcctggcc gtgaacgttc    540
actgaaatca tggcctcttg gccaagattg atagcttgtg cctgtccctg agtcccagtc    600
catcacgagc agctggtttc taagatgcta tttcccgtat aaagcatgag accgtgactt    660
gccagcccca cagagccccg cccttgtcca tcactggcat ctggactcca gcctgggttg    720
gggcaaagag ggaaatgaga tcatgtccta accctgatcc tcttgtccca cagatatcca    780
gaaccctgac cctgccgtgt accagctgag agactctaaa tccagtgaca gtctgtctg     840 cctattcacc gattttgatt ctcaaacaaa tgtgtcacaa gtaaggatt ctgatgtgta    900 tatcacagac aaaactgtgc tagacatgag gtctatggca ttcaggctcc ggtgccgtc    960 agtgggcaga gcgcacatcg cccacagtcc ccgagaagtt gggggagggg tcggcaatt    1020 gaaccggtgc ctagagaagg tggcgcgggg taaactggga aagtgatgtc gtgtactggc   1080
tccgcctttt tcccgagggt gggggagaac cgtatataag tgcagtagtc gccgtgaacg   1140 ttcttttttcg caacgggttt gccgccagaa cacaggtaag tgccgtgtgt ggttcccgcg   1200
ggcctggcct ctttacgggt tatggccctt gcgtgccttg aattacttcc actggctgca   1260
gtacgtgatt cttgatcccg agcttcgggt tggaagtggg tgggagagtt cgaggccttg   1320
cgcttaagga gccccttcgc ctcgtgcttg agttgaggcc tggcctgggc gctggggccg   1380
ccgcgtgcga atctggtggc accttcgcgc ctgtctcgct gctttcgata agtctctagc   1440
catttaaaat ttttgatgac ctgctgcgac gctttttttc tggcaagata gtcttgtaaa   1500
tgcgggccaa gatctgcaca ctggtatttc ggttttttggg gccgcgggcg cgacggggc    1560

```
ccgtgcgtcc cagcgcacat gttcggcgag gcggggcctg cgagcgcggc caccgagaat    1620
cggacggggg tagtctcaag ctggccggcc tgctctggtg cctggcctcg cgccgccgtg    1680
tatcgccccg ccctgggcgg caaggctggc ccggtcggca ccagttgcgt gagcggaaag    1740
atggccgctt cccggccctg ctgcagggag ctcaaaatgg aggacgcggc gctcgggaga    1800
gcggcgggt gagtcaccca cacaaaggaa aagggccttt ccgtcctcag ccgtcgcttc     1860
atgtgactcc acggagtacc gggcgccgtc caggcacctc gattagttct cgagcttttg    1920
gagtacgtcg tctttaggtt gggggggaggg gttttatgcg atggagtttc cccacactga   1980
gtgggtggag actgaagtta ggccagcttg gcacttgatg taattctcct tggaatttgc    2040
cctttttgag tttggatctt ggttcattct caagcctcag acagtggttc aaagtttttt    2100
tcttccattt caggtgtcgt gaccaccatg gcgcttccgg tgacagcact gctcctcccc    2160
ttggcgctgt tgctccacgc agcaaggccg caggtgcagc tggtgcagag cggagccgag    2220
ctcaagaagc ccggagcctc cgtgaaggtg agctgcaagg ccagcggcaa caccctgacc    2280
aactacgtga tccactgggt gagacaagcc cccggccaaa ggctgagtg gatgggctac     2340
atcctgccct acaacgacct gaccaagtac agccagaagt tccagggcag ggtgaccatc    2400
accagggata gagcgcctc caccgcctat atggagctga gcagcctgag gagcgaggac     2460
accgctgtgt actactgtac aaggtgggac tgggacggct tctttgaccc ctggggccag    2520
ggcacaacag tgaccgtcag cagcggcggc ggaggcagcg gcggcggcgg cagcggcgga    2580
ggcggaagcg aaatcgtgat gacccagagc cccgccacac tgagcgtgag ccctggcgag    2640
agggccagca tctcctgcag ggctagccaa agcctggtgc acagcaacgg caacaccccac  2700
ctgcactggt accagcagag acccggacag gctcccaggc tgctgatcta cagcgtgagc    2760
aacaggttct ccgaggtgcc tgccaggttt agcggcagcg gaagcggcac cgactttacc    2820
ctgaccatca gcagcgtgga gtccgaggac ttcgccgtgt attactgcag ccagaccagc    2880
cacatccctt acaccttcgg cggcggcacc aagctggaga tcaaaagtgc tgctgccttt    2940
gtcccggtat ttctcccagc caaaccgacc acgactcccg cccccgcgcc tccgacaccc    3000
gctcccacca tcgcctctca acctcttagt cttcgccccg aggcatgccg acccgccgcc    3060
gggggtgctg ttcatacgag gggcttggac ttcgcttgtg atatttacat ttgggctccg    3120
ttggcgggta cgtgcggcgt ccttttgttg tcactcgtta ttactttgta ttgtaatcac    3180
aggaatcgca acgggcag aaagaaactc ctgtatatat tcaaacaacc atttatgaga     3240
ccagtacaaa ctactcaaga ggaagatggc tgtagctgcc gatttccaga agaagaagaa    3300
ggaggatgtg aactgcgagt gaagttttcc cgaagcgcag acgctccggc atatcagcaa    3360
ggacagaatc agctgtataa cgaactgaat ttggacgcc gcgaggagta tgacgtgctt     3420
gataaacgcc gggggagaga cccggaaatg gggggtaaac cccgaagaaa gaatccccaa    3480
gaaggactct acaatgaact ccagaaggat aagatggcgg aggcctactc agaaataggt    3540
atgaagggcg aacgacgacg gggaaaaggt cacgatggcc tctaccaagg gttgagtacg    3600
gcaaccaaag atacgtacga tgcactgcat atgcaggccc tgcctcccag ataataataa    3660
aatcgctatc catcgaagat ggatgtgtgt tggttttttg tgtgtggagc aacaaatctg    3720
actttgcatg tgcaaacgcc ttcaacaaca gcattattcc agaagacacc ttcttcccca    3780
gcccaggtaa gggcagcttt ggtgccttcg caggctgttt ccttgcttca ggaatggcca    3840
ggttctgccc agagctctgg tcaatgatgt ctaaaactcc tctgattggt ggtctcggcc    3900
ttatccattg ccaccaaaac cctctttta ctaagaaaca gtgagccttg ttctggcagt     3960
```

```
ccagagaatg acacgggaaa aaagcagatg aagagaaggt ggcaggagag ggcacgtggc    4020
ccagcctcag tctctccaac tgagttcctg cctgcctgcc tttgctcaga ctgtttgccc    4080
cttactgctc ttctaggcct cattctaagc cccttctcca agttgcctct ccttatttct    4140
ccctgtctgc caaaaatct ttcccagctc actaagtcag tctcacgcag tcactcatta    4200
acccaccaat cactgattgt gccggcacat gaatgcacca ggtgttgaag tggaggaatt    4260
aaaaagtcag atgaggggtg tgcccagagg aagcaccatt ctagttgggg gagcccatct    4320
gtcagctggg aaaagtccaa ataacttcag attggaatgt gttttaactc agggttgaga    4380
aaacagctac cttcaggaca aaagtcaggg aagggctctc tgaagaaatg ctacttgaag    4440
ataccagccc taccaagggc agggagagga ccctatagag gcctgggaca ggagctcaat    4500
gagaaaggta accacgtgcg gaccgaggct gcagcgtcgt cctccctagg aaccccctagt   4560 gatggagttg gccactccct ctctgcgcgc tcgctcgctc actgaggccg ggcgaccaaa    4620
ggtcgcccga cgcccgggct ttgcccgggc ggcctcagtg agcgagcgag cgcgcagctg    4680
cctgcagg                                                            4688

<210> SEQ ID NO 55
<211> LENGTH: 4364
<212> TYPE: DNA
<213> ORGANISM: Artificial Sequence
<220> FEATURE:
<223> OTHER INFORMATION: Synthetic: BCMA  RHA to LHA

<400> SEQUENCE: 55
gagatgtaag gagctgctgt gacttgctca aggccttata tcgagtaaac ggtagtgctg      60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg gggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg ccttttctcc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
```

```
tcgcgcctgt ctcgctgctt tcgataagtc tctagccatt taaaatttt gatgacctgc      1320 tgcgacgctt tttttctggc aagatagtct tgtaaatgcg ggccaagatc tgcacactgg      1380
tatttcggtt tttggggccg cgggcggcga cggggcccgt gcgtcccagc gcacatgttc      1440
ggcgaggcgg ggcctgcgag cgcggccacc gagaatcgga cggggggtagt ctcaagctgg      1500 ccggcctgct ctggtgcctg gcctcgcgcc gccgtgtatc gccccgccct gggcggcaag      1560
gctggcccgg tcgcaccag ttgcgtgagc ggaaagatgg ccgcttcccg gccctgctgc      1620
agggagctca aaatggagga cgcggcgctc gggagagcgg gcgggtgagt cacccacaca      1680
aaggaaaagg gcctttccgt cctcagccgt cgcttcatgt gactccacgg agtaccgggc      1740
gccgtccagg cacctcgatt agttctcgag cttttggagt acgtcgtctt taggttgggg      1800
ggaggggttt tatgcgatgg agtttcccca cactgagtgg gtggagactg aagttaggcc      1860
agcttggcac ttgatgtaat tctccttgga atttgcccct tttgagtttg gatcttggtt      1920
cattctcaag cctcagacag tggttcaaag ttttttttctt ccatttcagg tgtcgtgacc      1980
accatggcgc ttccggtgac agcactgctc ctccccttgg cgctgttgct ccacgcagca      2040
aggccgcagg tgcagctggt gcagagcgga gccgagctca agaagcccgg agcctccgtg      2100
aaggtgagct gcaaggccag cggcaacacc ctgaccaact acgtgatcca ctgggtgaga      2160
caagcccccg gccaaaggct ggagtggatg ggctacatcc tgccctacaa cgacctgacc      2220
aagtacagcc agaagttcca gggcagggtg accatcacca gggataagag cgcctccacc      2280
gcctatatgg agctgagcag cctgaggagc gaggacaccg ctgtgtacta ctgtacaagg      2340
tgggactggg acgccttctt tgaccctgg gccagggca aacagtgac cgtcagcagc      2400 ggcggcggag gcagcggcgg cggcggcagc ggcggaggcg gaagcgaaat cgtgatgacc      2460
cagagccccg ccacactgag cgtgagccct ggcgagaggg ccagcatctc ctgcagggct      2520
agccaaagcc tggtgcacag caacggcaac acccacctgc actggtacca gcagagaccc      2580
ggacaggctc ccaggctgct gatctacagc gtgagcaaca ggttctccga ggtgcctgcc      2640
aggtttagcg gcagcggaag cggcaccgac tttaccctga ccatcagcag cgtggagtcc      2700
gaggacttcg ccgtgtatta ctgcagccag accagccaca tcccttacac cttcggcggc      2760
ggcaccaagc tggagatcaa aagtgctgct gcctttgtcc cggtatttct cccagccaaa      2820
ccgaccacga ctcccgccc cgcgcctccg cacccgctc ccaccatcgc ctctcaacct      2880
cttagtcttc gccccgaggc atgccgaccc gccgccgggg gtgctgttca tacgaggggc      2940
ttggacttcg cttgtgatat ttacatttgg gctccgttgg cgggtacgtg cggcgtcctt      3000
ttgttgtcac tcgttattac tttgtattgt aatcacagga atcgcaaacg gggcagaaag      3060
aaactcctgt atatattcaa acaaccattt atgagaccag tacaaactac tcaagaggaa      3120
gatggctgta gctgccgatt tccagaagaa gaagaaggag gatgtgaact gcgagtgaag      3180
tttccccgaa gcgcagacgc tccggcatat cagcaaggac agaatcagct gtataacgaa      3240
ctgaatttgg gacgccgcga ggagtatgac gtgcttgata acgccgggg gagagacccg      3300 gaaatggggg gtaaaccccg aagaaagaat ccccaagaag gactctacaa tgaactccag      3360
aaggataaga tggcggaggc ctactcagaa ataggtatga agcgcaacg acgacgggga      3420 aaaggtcacg atggcctcta ccaagggttg agtacggcaa ccaaagatac gtacgatgca      3480
ctgcatatgc aggccctgcc tcccagataa taataaaatc gctatccatc gaagatggat      3540
gtgtgttggt ttttgtgtg tggagcaaca aatctgactt tgcatgtgca aacgccttca      3600
acaacagcat tattccagaa gacaccttct tcccccagccc aggtaagggc agctttggtg      3660
```

| | | |
|---|---|---|
| ccttcgcagg ctgtttcctt gcttcaggaa tggccaggtt ctgcccagag ctctggtcaa | 3720 | |
| tgatgtctaa aactcctctg attggtggtc tcggccttat ccattgccac caaaaccctc | 3780 | |
| tttttactaa gaaacagtga gccttgttct ggcagtccag agaatgacac gggaaaaaag | 3840 | |
| cagatgaaga gaaggtggca ggagagggca cgtggcccag cctcagtctc tccaactgag | 3900 | |
| ttcctgcctg cctgcctttg ctcagactgt ttgcccctta ctgctcttct aggcctcatt | 3960 | |
| ctaagcccct tctccaagtt gcctctcctt atttctccct gtctgccaaa aaatctttcc | 4020 | |
| cagctcacta agtcagtctc acgcagtcac tcattaaccc accaatcact gattgtgccg | 4080 | |
| gcacatgaat gcaccaggtg ttgaagtgga ggaattaaaa agtcagatga ggggtgtgcc | 4140 | |
| cagaggaagc accattctag ttgggggagc ccatctgtca gctgggaaaa gtccaaataa | 4200 | |
| cttcagattg gaatgtgttt taactcaggg ttgagaaaac agctaccttc aggacaaaag | 4260 | |
| tcagggaagg gctctctgaa gaaatgctac ttgaagatac cagccctacc aagggcaggg | 4320 | |
| agaggaccct atagaggcct gggacaggag ctcaatgaga aagg | 4364 | |

<210> SEQ ID NO 56
<211> LENGTH: 1524
<212> TYPE: DNA
<213> ORGANISM: Artificial Sequence
<220> FEATURE:
<223> OTHER INFORMATION: Synthetic: BCMA CAR nucleotide sequence

<400> SEQUENCE: 56

| | | |
|---|---|---|
| atggcgcttc cggtgacagc actgctcctc cccttggcgc tgttgctcca cgcagcaagg | 60 | |
| ccgcaggtgc agctggtgca gagcggagcc gagctcaaga agcccggagc ctccgtgaag | 120 | |
| gtgagctgca aggccagcgg caacaccctg accaactacg tgatccactg ggtgagacaa | 180 | |
| gcccccggcc aaaggctgga gtggatgggc tacatcctgc cctacaacga cctgaccaag | 240 | |
| tacagccaga gttccagggg cagggtgacc atcaccaggg ataagagcgc ctccaccgcc | 300 | |
| tatatggagc tgagcagcct gaggagcgag gacaccgctg tgtactactg tacaaggtgg | 360 | |
| gactgggacg gcttctttga ccccctgggg cagggcacaa cagtgaccgt cagcagcggc | 420 | |
| ggcggaggca gcggcggcgg cggcagcggc ggaggcggaa gcgaaatcgt gatgacccag | 480 | |
| agccccgcca cactgagcgt gagccctggc gagagggcca gcatctcctg cagggctagc | 540 | |
| caaagcctgg tgcacagcaa cggcaacacc cacctgcact ggtaccagca gagacccgga | 600 | |
| caggctccca ggctgctgat ctacagcgtg agcaacaggt tctccgaggt gcctgccagg | 660 | |
| tttagcggca gcgaagcggg caccgacttt accctgacca tcagcagcgt ggagtccgag | 720 | |
| gacttcgccg tgtattactg cagccagacc agccacatcc cttacacctt cggcggcggc | 780 | |
| accaagctgg agatcaaaag tgctgctgcc tttgtcccgg tatttctccc agccaaaccg | 840 | |
| accacgactc ccgccccgcg ccctccgaca cccgctccca ccatcgcctc tcaacctctt | 900 | |
| agtcttcgcc ccgaggcatg ccgacccgcc gccggggtg ctgttcatac gaggggcttg | 960 | |
| gacttcgctt gtgatattta catttgggct ccgttggcgg gtacgtgcgg cgtccttttg | 1020 | |
| ttgtcactcg ttattacttt gtattgtaat cacaggaatc gcaaacgggg cagaagagaaa | 1080 | |
| ctcctgtata tattcaaaca accatttatg agaccagtac aaaactactca agaggaagat | 1140 | |
| ggctgtagct gccgatttcc agaagaagaa gaaggaggat gtgaactgcg agtgaagttt | 1200 | |
| tcccgaagcg cagacgctcc ggcatatcag caaggacaga atcagctgta taacgaactg | 1260 | |
| aatttgggac gccgcgagga gtatgacgtg cttgataaac gccgggggag agacccggaa | 1320 | |

-continued

```
atgggggta   aaccccgaag   aaagaatccc   caagaaggac   tctacaatga   actccagaag    1380
gataagatgg  cggaggccta   ctcagaaata   ggtatgaagg   gcgaacgacg   acggggaaaa    1440
ggtcacgatg  gcctctacca   agggttgagt   acggcaacca   aagatacgta   cgatgcactg    1500
catatgcagg  ccctgcctcc   caga                                                1524
```

<210> SEQ ID NO 57
<211> LENGTH: 508
<212> TYPE: PRT
<213> ORGANISM: Artificial Sequence
<220> FEATURE:
<223> OTHER INFORMATION: Synthetic: BCMA CAR amino acid sequence

<400> SEQUENCE: 57

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Leu
            20                  25                  30

Lys Lys Pro Gly Ala Ser Val Lys Val Ser Cys Lys Ala Ser Gly Asn
        35                  40                  45

Thr Leu Thr Asn Tyr Val Ile His Trp Val Arg Gln Ala Pro Gly Gln
    50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
                85                  90                  95

Ala Ser Thr Ala Tyr Met Glu Leu Ser Ser Leu Arg Ser Glu Asp Thr
            100                 105                 110

Ala Val Tyr Tyr Cys Thr Arg Trp Asp Trp Asp Gly Phe Phe Asp Pro
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Glu Ile Val Met Thr Gln
145                 150                 155                 160

Ser Pro Ala Thr Leu Ser Val Ser Pro Gly Glu Arg Ala Ser Ile Ser
                165                 170                 175

Cys Arg Ala Ser Gln Ser Leu Val His Ser Asn Gly Asn Thr His Leu
            180                 185                 190

His Trp Tyr Gln Gln Arg Pro Gly Gln Ala Pro Arg Leu Leu Ile Tyr
        195                 200                 205

Ser Val Ser Asn Arg Phe Ser Glu Val Pro Ala Arg Phe Ser Gly Ser
    210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr His Ile Pro Tyr Thr
                245                 250                 255

Phe Gly Gly Gly Thr Lys Leu Glu Ile Lys Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
```

```
              325                 330                 335
Gly Val Leu Leu Leu Ser Leu Val Ile Thr Leu Tyr Cys Asn His Arg
                340                 345                 350

Asn Arg Lys Arg Gly Arg Lys Lys Leu Leu Tyr Ile Phe Lys Gln Pro
            355                 360                 365

Phe Met Arg Pro Val Gln Thr Thr Gln Glu Glu Asp Gly Cys Ser Cys
370                 375                 380

Arg Phe Pro Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 58
<211> LENGTH: 735
<212> TYPE: DNA
<213> ORGANISM: Artificial Sequence
<220> FEATURE:
<223> OTHER INFORMATION: Synthetic: BCMA scFv nucleotide sequence

<400> SEQUENCE: 58
caggtgcagc tggtgcagag cggagccgag ctcaagaagc ccggagcctc cgtgaaggtg      60
agctgcaagg ccagcggcaa caccctgacc aactacgtga tccactgggt gagacaagcc     120
cccggccaaa ggctggagtg gatgggctac atcctgccct acaacgacct gaccaagtac     180
agccagaagt tccagggcag ggtgaccatc accagggata agagcgcctc caccgcctat     240
atggagctga gcagcctgag gagcgaggac accgctgtgt actactgtac aaggtgggac     300
tgggacggct tctttgaccc ctggggccag ggcacaacag tgaccgtcag cagcggcggc     360
ggaggcagcg gcggcggcgg cagcggcgga ggcggaagcg aaatcgtgat gacccagagc     420
cccgccacac tgagcgtgag ccctggcgag agggccagca tctcctgcag ggctagccaa     480
agcctggtgc acagcaacgg caacacccac ctgcactggt accagcagag acccggacag     540
gctcccaggc tgctgatcta cagcgtgagc aacaggttct ccgaggtgcc tgccaggttt     600
agcggcagcg gaagcggcac cgactttacc ctgaccatca gcagcgtgga gtccgaggac     660
ttcgccgtgt attactgcag ccagaccagc cacatccctt acaccttcgg cggcggcacc     720
aagctggaga tcaaa                                                     735

<210> SEQ ID NO 59
<211> LENGTH: 245
<212> TYPE: PRT
<213> ORGANISM: Artificial Sequence
<220> FEATURE:
<223> OTHER INFORMATION: Synthetic: BCMA scFv amino acid sequence
```

<400> SEQUENCE: 59

```
Gln Val Gln Leu Val Gln Ser Gly Ala Glu Leu Lys Lys Pro Gly Ala
1               5                   10                  15
Ser Val Lys Val Ser Cys Lys Ala Ser Gly Asn Thr Leu Thr Asn Tyr
                20                  25                  30
Val Ile His Trp Val Arg Gln Ala Pro Gly Gln Arg Leu Glu Trp Met
            35                  40                  45
Gly Tyr Ile Leu Pro Tyr Asn Asp Leu Thr Lys Tyr Ser Gln Lys Phe
        50                  55                  60
Gln Gly Arg Val Thr Ile Thr Arg Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Trp Asp Trp Asp Gly Phe Phe Asp Pro Trp Gly Gln Gly Thr
            100                 105                 110
Thr Val Thr Val Ser Ser Gly Gly Gly Ser Gly Gly Gly Gly Ser
        115                 120                 125
Gly Gly Gly Gly Ser Glu Ile Val Met Thr Gln Ser Pro Ala Thr Leu
130                 135                 140
Ser Val Ser Pro Gly Glu Arg Ala Ser Ile Ser Cys Arg Ala Ser Gln
145                 150                 155                 160
Ser Leu Val His Ser Asn Gly Asn Thr His Leu His Trp Tyr Gln Gln
                165                 170                 175
Arg Pro Gly Gln Ala Pro Arg Leu Leu Ile Tyr Ser Val Ser Asn Arg
            180                 185                 190
Phe Ser Glu Val Pro Ala Arg Phe Ser Gly Ser Gly Ser Gly Thr Asp
        195                 200                 205
Phe Thr Leu Thr Ile Ser Ser Val Glu Ser Glu Asp Phe Ala Val Tyr
    210                 215                 220
Tyr Cys Ser Gln Thr Ser His Ile Pro Tyr Thr Phe Gly Gly Gly Thr
225                 230                 235                 240
Lys Leu Glu Ile Lys
                245
```

<210> SEQ ID NO 60
<211> LENGTH: 118
<212> TYPE: PRT
<213> ORGANISM: Artificial Sequence
<220> FEATURE:
<223> OTHER INFORMATION: Synthetic: BCMA VH

<400> SEQUENCE: 60

```
Gln Val Gln Leu Val Gln Ser Gly Ala Glu Leu Lys Lys Pro Gly Ala
1               5                   10                  15
Ser Val Lys Val Ser Cys Lys Ala Ser Gly Asn Thr Leu Thr Asn Tyr
                20                  25                  30
Val Ile His Trp Val Arg Gln Ala Pro Gly Gln Arg Leu Glu Trp Met
            35                  40                  45
Gly Tyr Ile Leu Pro Tyr Asn Asp Leu Thr Lys Tyr Ser Gln Lys Phe
        50                  55                  60
Gln Gly Arg Val Thr Ile Thr Arg Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Trp Asp Trp Asp Gly Phe Phe Asp Pro Trp Gly Gln Gly Thr
```

Thr Val Thr Val Ser Ser
      115

<210> SEQ ID NO 61
<211> LENGTH: 112
<212> TYPE: PRT
<213> ORGANISM: Artificial Sequence
<220> FEATURE:
<223> OTHER INFORMATION: Synthetic: BCMA VL

<400> SEQUENCE: 61

Glu Ile Val Met Thr Gln Ser Pro Ala Thr Leu Ser Val Ser Pro Gly
1               5                   10                  15

Glu Arg Ala Ser Ile Ser Cys Arg Ala Ser Gln Ser Leu Val His Ser
            20                  25                  30

Asn Gly Asn Thr His Leu His Trp Tyr Gln Gln Arg Pro Gly Gln Ala
        35                  40                  45

Pro Arg Leu Leu Ile Tyr Ser Val Ser Asn Arg Phe Ser Glu Val Pro
    50                  55                  60

Ala Arg Phe Ser Gly Ser Gly Ser Gly Thr Asp Phe Thr Leu Thr Ile
65                  70                  75                  80

Ser Ser Val Glu Ser Glu Asp Phe Ala Val Tyr Tyr Cys Ser Gln Thr
                85                  90                  95

Ser His Ile Pro Tyr Thr Phe Gly Gly Gly Thr Lys Leu Glu Ile Lys
            100                 105                 110

<210> SEQ ID NO 62
<211> LENGTH: 15
<212> TYPE: PRT
<213> ORGANISM: Artificial Sequence
<220> FEATURE:
<223> OTHER INFORMATION: Synthetic: CD70 VL CDR1 (Kabat)

<400> SEQUENCE: 62

Arg Ala Ser Lys Ser Val Ser Thr Ser Gly Tyr Ser Phe Met His
1               5                   10                  15

<210> SEQ ID NO 63
<211> LENGTH: 11
<212> TYPE: PRT
<213> ORGANISM: Artificial Sequence
<220> FEATURE:
<223> OTHER INFORMATION: Synthetic: CD70 VL CDR1 (Chothia)

<400> SEQUENCE: 63

Ser Lys Ser Val Ser Thr Ser Gly Tyr Ser Phe
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic: CD70 VL CDR2 (Kabat)

<400> SEQUENCE: 64

Leu Ala Ser Asn Leu Glu Ser
1               5

<210> SEQ ID NO 65
<211> LENGTH: 3
<212> TYPE: PRT

<213> ORGANISM: Artificial Sequence
<220> FEATURE:
<223> OTHER INFORMATION: Synthetic: CD70 VL CDR2 (Chothia)

<400> SEQUENCE: 65

Leu Ala Ser
1

<210> SEQ ID NO 66
<211> LENGTH: 9
<212> TYPE: PRT
<213> ORGANISM: Artificial Sequence
<220> FEATURE:
<223> OTHER INFORMATION: Synthetic: CD70 VL CDR3 (Kabat)

<400> SEQUENCE: 66

Gln His Ser Arg Glu Val Pro Trp Thr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic: CD70 VL CDR3 (Chothia)

<400> SEQUENCE: 67

Ser Arg Glu Val Pro Trp
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic: CD70 VH CDR1 (Kabat)

<400> SEQUENCE: 68

Asn Tyr Gly Met Asn
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic: CD70 VH CDR1 (Chothia)

<400> SEQUENCE: 69

Gly Tyr Thr Phe Thr Asn Tyr Gly Met Asn
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Synthetic: CD70 VH CDR2 (Kabat)

<400> SEQUENCE: 70

Trp Ile Asn Thr Tyr Thr Gly Glu Pro Thr Tyr Ala Asp Ala Phe Lys
1               5                   10                  15

Gly

<210> SEQ ID NO 71
<211> LENGTH: 6

```
<212> TYPE: PRT
<213> ORGANISM: Artificial Sequence
<220> FEATURE:
<223> OTHER INFORMATION: Synthetic: CD70 VH CDR2 (Chothia)

<400> SEQUENCE: 71

Asn Thr Tyr Thr Gly Glu
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic: CD70 VH CDR3 (Kabat)

<400> SEQUENCE: 72

Asp Tyr Gly Asp Tyr Gly Met Asp Tyr
1               5

<210> SEQ ID NO 73
<211> LENGTH: 14
<212> TYPE: PRT
<213> ORGANISM: Artificial Sequence
<220> FEATURE:
<223> OTHER INFORMATION: Synthetic: CD70 VH CDR3 (Chothia)

<400> SEQUENCE: 73

Cys Ala Arg Asp Tyr Gly Asp Tyr Gly Met Asp Tyr Trp Gly
1               5                   10

<210> SEQ ID NO 74
<211> LENGTH: 16
<212> TYPE: PRT
<213> ORGANISM: Artificial Sequence
<220> FEATURE:
<223> OTHER INFORMATION: Synthetic: BCMA VL CDR1 (Kabat)

<400> SEQUENCE: 74

Arg Ala Ser Gln Ser Leu Val His Ser Asn Gly Asn Thr His Leu His
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic: BCMA VL CDR1 (Chothia)

<400> SEQUENCE: 75

Arg Ala Ser Gln Ser Leu Val His Ser Asn Gly Asn Thr His Leu His
1               5                   10                  15

<210> SEQ ID NO 76
<211> LENGTH: 5
<212> TYPE: PRT
<213> ORGANISM: Artificial Sequence
<220> FEATURE:
<223> OTHER INFORMATION: Synthetic: BCMA VL CDR2 (Kabat)

<400> SEQUENCE: 76

Ser Val Ser Asn Arg
1               5

<210> SEQ ID NO 77
<211> LENGTH: 5
<212> TYPE: PRT
```

```
<213> ORGANISM: Artificial Sequence
<220> FEATURE:
<223> OTHER INFORMATION: Synthetic: BCMA VL CDR2 (Chothia)

<400> SEQUENCE: 77

Ser Val Ser Asn Arg
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic: BCMA VL CDR3 (Kabat)

<400> SEQUENCE: 78

Ser Gln Thr Ser His Ile Pro Tyr Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic: BCMA VL CDR3 (Chothia)

<400> SEQUENCE: 79

Ser Gln Thr Ser His Ile Pro Tyr Thr
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic: BCMA VH CDR1 (Kabat)

<400> SEQUENCE: 80

Asn Tyr Val Ile His
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic: BCMA VH CDR1 (Chothia)

<400> SEQUENCE: 81

Gly Asn Thr Leu Thr Asn Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: Synthetic: BCMA VH CDR2 (Kabat)

<400> SEQUENCE: 82

Tyr Ile Leu Pro Tyr Asn Asp Leu Thr Lys Tyr Ser Gln Lys Phe Gln
1               5                   10                  15

Gly

<210> SEQ ID NO 83
<211> LENGTH: 6
```

```
<212> TYPE: PRT
<213> ORGANISM: Artificial Sequence
<220> FEATURE:
<223> OTHER INFORMATION: Synthetic: BCMA VH CDR2 (Chothia)

<400> SEQUENCE: 83

Leu Pro Tyr Asn Asp Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic: BCMA VH CDR3 (Kabat)

<400> SEQUENCE: 84

Trp Asp Trp Asp Gly Phe Phe Asp Pro
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic: BCMA VH CDR3 (Chothia)

<400> SEQUENCE: 85

Trp Asp Trp Asp Gly Phe Phe Asp Pro
1               5

<210> SEQ ID NO 86
<211> LENGTH: 20
<212> TYPE: DNA
<213> ORGANISM: Artificial Sequence
<220> FEATURE:
<223> OTHER INFORMATION: Synthetic: TRAC target sequence

<400> SEQUENCE: 86
agagcaacag tgctgtggcc                                              20

<210> SEQ ID NO 87
<211> LENGTH: 4691
<212> TYPE: DNA
<213> ORGANISM: Artificial Sequence
<220> FEATURE:
<223> OTHER INFORMATION: Synthetic: anti-CD33 CAR rAAV

<400> SEQUENCE: 87
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120 agggggttcct gcggccgcac gcgtgagatg taaggagctg ctgtgacttg ctcaaggcct     180
tatatcgagt aaacggtagt gctgggcttt agacgcaggt gttctgattt atagttcaaa     240
acctctatca atgagagagc aatctcctgg taatgtgata gatttcccaa cttaatgcca     300
acataccata aacctcccat tctgctaatg cccagcctaa gttggggaga ccactccaga     360
ttccaagatg tacagtttgc tttgctgggc ttttttccca tgcctgcctt tactctgcca     420
gagttatatt gctggggttt tgaagaagat cctattaaat aaaagaataa gcagtattat     480
taagtagccc tgcatttcag gtttccttga gtggcaggcc aggcctggcc gtgaacgttc     540
actgaaatca tggcctcttg gccaagattg atagcttgtg cctgtccctg agtcccagtc     600
catcacgagc agctggtttc taagatgcta tttcccgtat aaagcatgag accgtgactt     660
```

```
gccagcccca cagagcccg cccttgtcca tcactggcat ctggactcca gcctgggttg    720
gggcaaagag ggaaatgaga tcatgtccta accctgatcc tcttgtccca cagatatcca    780
gaaccctgac cctgccgtgt accagctgag agactctaaa tccagtgaca agtctgtctg    840
cctattcacc gattttgatt ctcaaacaaa tgtgtcacaa agtaaggatt ctgatgtgta    900
tatcacagac aaaactgtgc tagacatgag gtctatggac ttcaggctcc ggtgcccgtc    960
agtgggcaga gcgcacatcg cccacagtcc ccgagaagtt ggggggaggg gtcggcaatt   1020
gaaccggtgc ctagagaagg tggcgcgggg taaactggga aagtgatgtc gtgtactggc   1080
tccgcctttt tcccgagggt gggggagaac cgtatataag tgcagtagtc gccgtgaacg   1140
ttcttttccg caacgggttt gccgccagaa cacaggtaag tgccgtgtgt ggttcccgcg   1200
ggcctggcct ctttacgggt tatggccctt gcgtgccttg aattacttcc actggctgca   1260
gtacgtgatt cttgatcccg agcttcgggt tggaagtggg tgggagagtt cgaggccttg   1320
cgcttaagga gccccttcgc ctcgtgcttg agttgaggcc tggcctgggc gctggggccg   1380
ccgcgtgcga atctggtggc accttcgcgc ctgtctcgct gctttcgata agtctctagc   1440
catttaaaat ttttgatgac ctgctgcgac gcttttttc tggcaagata gtcttgtaaa   1500
tgcgggccaa gatctgcaca ctggtatttc ggttttggg gccgcgggcg cgacggggc    1560 ccgtgcgtcc cagcgcacat gttcggcgag gcggggcctg cgagcgcggc caccgagaat   1620 cggacgggg tagtctcaag ctggccggcc tgctctggtg cctggcctcg cgccgccgtg    1680
tatcgccccg ccctgggcgg caaggctggc ccggtcggca ccagttgcgt gagcggaaag   1740
atggccgctt cccggccctg ctgcagggag ctcaaaatgg aggacgcggc gctcgggaga   1800
gcgggcgggt gagtcaccca cacaaaggaa aagggccttt ccgtcctcag ccgtcgcttc   1860
atgtgactcc acggagtacc gggcgccgtc caggcacctc gattagttct cgagcttttg   1920
gagtacgtcg tctttaggtt gggggagg gttttatgcg atggagtttc cccacactga    1980
gtgggtggag actgaagtta ggccagcttg gcacttgatg taattctcct tggaatttgc   2040 ccttttgag tttggatctt ggttcattct caagcctcag acagtggttc aaagttttt    2100 tcttccattt caggtgtcgt gaccaccatg gcgcttccgg tgacagcact gctcctcccc   2160
ttggcgctgt tgctccacgc agcaaggccg gaaatcgtcc tcacacaatc cccggggagc   2220
ctcgcagtca gtcctgggga acgagtcact atgagctgca aatccagtca gagtgttttt   2280
ttctcaagta gccagaagaa ctacctcgca tggtaccaac aaataccggg gcaatctccc   2340
cgcttgctta tatactgggc aagtacccgc gaatccggcg taccggatcg attcacggga   2400
tctgggtcag gtactgattt cactttgact atcagctctg ttcagcctga agatttggca   2460
atttactact gtcaccaata cttgagtagc cgaactttcg gccagggcac gaagctcgaa   2520
atcaagggcg gaggggagg ttctggtggg ggcggttctg gcggtggagg aagccaagta    2580
cagttgcaac agccagggc ggaggtcgta aaacctgggg cgtctgtcaa gatgagctgt    2640
aaagcaagtg gatacacctt cacctcctac tatatacatt ggattaagca aactccgggt   2700 cagggctgg aatgggttgg cgttatatac cccgggaacg atgatatatc atacaaccaa    2760
aaatttcaag gcaaggcgac tctgactgcc gataagagta gcacaacagc ttacatgcag   2820 cttttcttccc tgaccagcga agattcagca gtttactact gcgctcggga agtgcgcctg   2880
cgatactttg atgtctgggg tcaaggaact acagttactg tatcaagcag tgctgctgcc   2940
tttgtcccgg tatttctccc agccaaaccg accacgactc ccgccccgcg ccctccgaca   3000
```

| | |
|---|---|
| cccgctccca ccatcgcctc tcaacctctt agtcttcgcc ccgaggcatg ccgacccgcc | 3060 |
| gccggggtg ctgttcatac gaggggcttg gacttcgctt gtgatattta catttgggct | 3120 |
| ccgttggcgg gtacgtgcgg cgtccttttg ttgtcactcg ttattacttt gtattgtaat | 3180 |
| cacaggaatc gcaaacgggg cagaaagaaa ctcctgtata tattcaaaca accatttatg | 3240 |
| agaccagtac aaactactca agaggaagat ggctgtagct gccgatttcc agaagaagaa | 3300 |
| gaaggaggat gtgaactgcg agtgaagttt tcccgaagcg cagacgctcc ggcatatcag | 3360 |
| caaggacaga atcagctgta taacgaactg aatttgggac gccgcgagga gtatgacgtg | 3420 |
| cttgataaac gccgggggag agacccggaa atgggggggta accccgaag aaagaatccc | 3480 |
| caagaaggac tctacaatga actccagaag gataagatgg cggaggccta ctcagaaata | 3540 |
| ggtatgaagg cgaacgacg acggggaaaa ggtcacgatg gcctctacca agggttgagt | 3600 |
| acggcaacca agatacgta cgatgcactg catatgcagg ccctgcctcc cagataataa | 3660 |
| taaaatcgct atccatcgaa gatggatgtg tgttggtttt ttgtgtgtgg agcaacaaat | 3720 |
| ctgactttgc atgtgcaaac gccttcaaca acagcattat tccagaagac accttcttcc | 3780 |
| ccagcccagg taagggcagc tttggtgcct tcgcaggctg tttccttgct tcaggaatgg | 3840 |
| ccaggttctg cccagagctc tggtcaatga tgtctaaaac cctctgatt ggtggtctcg | 3900 |
| gccttatcca ttgccaccaa aaccctcttt ttactaagaa acagtgagcc ttgttctggc | 3960 |
| agtccagaga atgacacggg aaaaaagcag atgaagagaa ggtggcagga gagggcacgt | 4020 |
| ggcccagcct cagtctctcc aactgagttc ctgcctgcct gcctttgctc agactgtttg | 4080 |
| cccccttactg ctcttctagg cctcattcta agccccttct ccaagttgcc tctccttatt | 4140 |
| tctccctgtc tgccaaaaaa tcttcccag ctcactaagt cagtctcacg cagtcactca | 4200 |
| ttaacccacc aatcactgat tgtgccggca catgaatgca ccaggtgttg aagtggagga | 4260 |
| attaaaagt cagatgaggg gtgtgcccag aggaagcacc attctagttg ggggagccca | 4320 |
| tctgtcagct gggaaaagtc caaataactt cagattggaa tgtgttttaa ctcagggttg | 4380 |
| agaaaacagc taccttcagg acaaaagtca gggaagggct ctctgaagaa atgctacttg | 4440 |
| aagataccag ccctaccaag ggcagggaga ggaccctata gaggcctggg acaggagctc | 4500 |
| aatgagaaag gtaaccacgt gcggaccgag gctgcagcgt cgtcctccct aggaacccct | 4560 |
| agtgatggag ttggccactc cctctctgcg cgctcgctcg ctcactgagg ccgggcgacc | 4620 |
| aaaggtcgcc cgacgcccgg gctttgcccg ggcggcctca gtgagcgagc gagcgcgcag | 4680 |
| ctgcctgcag g | 4691 |

<210> SEQ ID NO 88
<211> LENGTH: 22
<212> TYPE: PRT
<213> ORGANISM: Artificial Sequence
<220> FEATURE:
<223> OTHER INFORMATION: Synthetic: signal peptide

<400> SEQUENCE: 88

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 89
<211> LENGTH: 21
<212> TYPE: PRT
<213> ORGANISM: Artificial Sequence

```
<220> FEATURE:
<223> OTHER INFORMATION: Synthetic: signal peptide

<400> SEQUENCE: 89

Met Ala Leu Pro Val Thr Ala Leu Leu Leu Pro Leu Ala Leu Leu Leu
1               5                   10                  15

His Ala Ala Arg Pro
            20

<210> SEQ ID NO 90
<211> LENGTH: 84
<212> TYPE: PRT
<213> ORGANISM: Artificial Sequence
<220> FEATURE:
<223> OTHER INFORMATION: Synthetic: CD8a transmembrane domain

<400> SEQUENCE: 90

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 91
<211> LENGTH: 20
<212> TYPE: RNA
<213> ORGANISM: Artificial Sequence
<220> FEATURE:
<223> OTHER INFORMATION: Synthetic: CD70 sgRNA (E1_T1) spacer

<400> SEQUENCE: 91
ucaccaagcc cgcgaccaau                                             20

<210> SEQ ID NO 92
<211> LENGTH: 20
<212> TYPE: RNA
<213> ORGANISM: Artificial Sequence
<220> FEATURE:
<223> OTHER INFORMATION: Synthetic: CD70 sgRNA (E1_T3) spacer

<400> SEQUENCE: 92
aucaccaagc ccgcgaccaa                                             20

<210> SEQ ID NO 93
<211> LENGTH: 20
<212> TYPE: RNA
<213> ORGANISM: Artificial Sequence
<220> FEATURE:
<223> OTHER INFORMATION: Synthetic: CD70 sgRNA (E1_T4) spacer

<400> SEQUENCE: 93
cggugcggcg caggcccuau                                             20

<210> SEQ ID NO 94
<211> LENGTH: 20
<212> TYPE: RNA
<213> ORGANISM: Artificial Sequence
```

```
<220> FEATURE:
<223> OTHER INFORMATION: Synthetic: CD70 sgRNA (E1_T7) spacer

<400> SEQUENCE: 94
gcuuuggucc cauuggucgc                                               20

<210> SEQ ID NO 95
<211> LENGTH: 20
<212> TYPE: RNA
<213> ORGANISM: Artificial Sequence
<220> FEATURE:
<223> OTHER INFORMATION: Synthetic: CD70 sgRNA (E1_T8) spacer

<400> SEQUENCE: 95
gcccgcagga cgcacccaua                                               20

<210> SEQ ID NO 96
<211> LENGTH: 20
<212> TYPE: RNA
<213> ORGANISM: Artificial Sequence
<220> FEATURE:
<223> OTHER INFORMATION: Synthetic: CD70 sgRNA (E1_T10) spacer

<400> SEQUENCE: 96
gugcauccag cgcuucgcac                                               20

<210> SEQ ID NO 97
<211> LENGTH: 20
<212> TYPE: RNA
<213> ORGANISM: Artificial Sequence
<220> FEATURE:
<223> OTHER INFORMATION: Synthetic: CD70 sgRNA (E3_T1) spacer

<400> SEQUENCE: 97
cagcuacgua uccaucguga                                               20

<210> SEQ ID NO 98
<211> LENGTH: 20
<212> TYPE: RNA
<213> ORGANISM: Artificial Sequence
<220> FEATURE:
<223> OTHER INFORMATION: Synthetic: TRAC spacer

<400> SEQUENCE: 98
agagcaacag ugcuguggcc                                               20

<210> SEQ ID NO 99
<211> LENGTH: 20
<212> TYPE: RNA
<213> ORGANISM: Artificial Sequence
<220> FEATURE:
<223> OTHER INFORMATION: Synthetic: b2M sgRNA spacer

<400> SEQUENCE: 99
gcuacucucu cuuucuggcc                                               20

<210> SEQ ID NO 100
<211> LENGTH: 20
<212> TYPE: RNA
<213> ORGANISM: Artificial Sequence
<220> FEATURE:
<223> OTHER INFORMATION: Synthetic: PD-1 sgRNA spacer

<400> SEQUENCE: 100
cugcagcuuc uccaacacau                                               20
```

```
<210> SEQ ID NO 101
<211> LENGTH: 20
<212> TYPE: RNA
<213> ORGANISM: Artificial Sequence
<220> FEATURE:
<223> OTHER INFORMATION: Synthetic: CD70 sgRNA (E1_T3) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 101
ucaccaagcc cgcgaccaau                                              20

<210> SEQ ID NO 102
<211> LENGTH: 20
<212> TYPE: RNA
<213> ORGANISM: Artificial Sequence
<220> FEATURE:
<223> OTHER INFORMATION: Synthetic: CD70 sgRNA (E1_T4) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 102
aucaccaagc ccgcgaccaa                                              20

<210> SEQ ID NO 103
<211> LENGTH: 20
<212> TYPE: RNA
<213> ORGANISM: Artificial Sequence
<220> FEATURE:
<223> OTHER INFORMATION: Synthetic: CD70 sgRNA (E1_T7) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 103
cggugcggcg caggcccuau                                              20

<210> SEQ ID NO 104
<211> LENGTH: 20
<212> TYPE: RNA
<213> ORGANISM: Artificial Sequence
<220> FEATURE:
<223> OTHER INFORMATION: Synthetic: CD70 sgRNA (E1_T8) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 104
gcuuuggucc cauuggucgc                                              20

<210> SEQ ID NO 105
<211> LENGTH: 20
<212> TYPE: RNA
<213> ORGANISM: Artificial Sequence
<220> FEATURE:
<223> OTHER INFORMATION: Synthetic: CD70 sgRNA (E1_T10) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 105
gcccgcagga cgcacccaua                                              20
```

```
<210> SEQ ID NO 106
<211> LENGTH: 20
<212> TYPE: RNA
<213> ORGANISM: Artificial Sequence
<220> FEATURE:
<223> OTHER INFORMATION: Synthetic: CD70 sgRNA (E3_T10) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 106
gugcauccag cgcuucgcac                                                  20

<210> SEQ ID NO 107
<211> LENGTH: 20
<212> TYPE: RNA
<213> ORGANISM: Artificial Sequence
<220> FEATURE:
<223> OTHER INFORMATION: Synthetic: CD70 sgRNA (E1_T3) spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 107
cagcuacgua uccaucguga                                                  20

<210> SEQ ID NO 108
<211> LENGTH: 20
<212> TYPE: RNA
<213> ORGANISM: Artificial Sequence
<220> FEATURE:
<223> OTHER INFORMATION: Synthetic: TRAC spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 108
agagcaacag ugcuguggcc                                                  20

<210> SEQ ID NO 109
<211> LENGTH: 20
<212> TYPE: RNA
<213> ORGANISM: Artificial Sequence
<220> FEATURE:
<223> OTHER INFORMATION: Synthetic: b2M sgRNA spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 109
gcuacucucu cuuucuggcc                                                  20

<210> SEQ ID NO 110
<211> LENGTH: 20
<212> TYPE: RNA
<213> ORGANISM: Artificial Sequence
<220> FEATURE:
<223> OTHER INFORMATION: Synthetic: PD-1 sgRNA spacer
<220> FEATURE:
<221> NAME/KEY: modified_base
<222> LOCATION: (1)..(3)
<223> OTHER INFORMATION: 2'-O-methyl phosphorothioate

<400> SEQUENCE: 110
```
cugcagcuuc uccaacacau        20

<210> SEQ ID NO 111
<211> LENGTH: 23
<212> TYPE: DNA
<213> ORGANISM: Artificial Sequence
<220> FEATURE:
<223> OTHER INFORMATION: Synthetic: CD70 sgRNA (E1_T1) with PAM

<400> SEQUENCE: 111
tcaccaagcc cgcgaccaat ggg        23

<210> SEQ ID NO 112
<211> LENGTH: 23
<212> TYPE: DNA
<213> ORGANISM: Artificial Sequence
<220> FEATURE:
<223> OTHER INFORMATION: Synthetic: CD70 sgRNA (E1_T3) with PAM

<400> SEQUENCE: 112
atcaccaagc ccgcgaccaa tgg        23

<210> SEQ ID NO 113
<211> LENGTH: 23
<212> TYPE: DNA
<213> ORGANISM: Artificial Sequence
<220> FEATURE:
<223> OTHER INFORMATION: Synthetic: CD70 sgRNA (E1_T4) with PAM

<400> SEQUENCE: 113
cggtgcggcg caggccctat ggg        23

<210> SEQ ID NO 114
<211> LENGTH: 23
<212> TYPE: DNA
<213> ORGANISM: Artificial Sequence
<220> FEATURE:
<223> OTHER INFORMATION: Synthetic: CD70 sgRNA (E1_T7) with PAM

<400> SEQUENCE: 114
gctttggtcc cattggtcgc ggg        23

<210> SEQ ID NO 115
<211> LENGTH: 23
<212> TYPE: DNA
<213> ORGANISM: Artificial Sequence
<220> FEATURE:
<223> OTHER INFORMATION: Synthetic: CD70 sgRNA (E1_T8) with PAM

<400> SEQUENCE: 115
gcccgcagga cgcacccata ggg        23

<210> SEQ ID NO 116
<211> LENGTH: 23
<212> TYPE: DNA
<213> ORGANISM: Artificial Sequence
<220> FEATURE:
<223> OTHER INFORMATION: Synthetic: CD70 sgRNA (E1_T10) with PAM

<400> SEQUENCE: 116
gtgcatccag cgcttcgcac agg        23

<210> SEQ ID NO 117
<211> LENGTH: 23
<212> TYPE: DNA
<213> ORGANISM: Artificial Sequence -continued

```
<220> FEATURE:
<223> OTHER INFORMATION: Synthetic: CD70 sgRNA (E3_T1) with PAM

<400> SEQUENCE: 117
cagctacgta tccatcgtga tgg                                             23

<210> SEQ ID NO 118
<211> LENGTH: 23
<212> TYPE: DNA
<213> ORGANISM: Artificial Sequence
<220> FEATURE:
<223> OTHER INFORMATION: Synthetic: TRAC sgRNA with PAM

<400> SEQUENCE: 118
agagcaacag tgctgtggcc tgg                                             23

<210> SEQ ID NO 119
<211> LENGTH: 23
<212> TYPE: DNA
<213> ORGANISM: Artificial Sequence
<220> FEATURE:
<223> OTHER INFORMATION: Synthetic: b2M sgRNA with PAM

<400> SEQUENCE: 119
gctactctct ctttctggcc tgg                                             23

<210> SEQ ID NO 120
<211> LENGTH: 23
<212> TYPE: DNA
<213> ORGANISM: Artificial Sequence
<220> FEATURE:
<223> OTHER INFORMATION: Synthetic: PD-1 sgRNA with PAM

<400> SEQUENCE: 120
ctgcagcttc tccaacacat cgg                                             23

<210> SEQ ID NO 121
<211> LENGTH: 120
<212> TYPE: DNA
<213> ORGANISM: Artificial Sequence
<220> FEATURE:
<223> OTHER INFORMATION: Synthetic: CD28 nucleotide sequence

<400> SEQUENCE: 121
tcaaagcgga gtaggttgtt gcattccgat tacatgaata tgactcctcg ccggcctggg     60
ccgacaagaa aacattacca accctatgcc cccccacgag acttcgctgc gtacaggtcc    120

<210> SEQ ID NO 122
<211> LENGTH: 800
<212> TYPE: DNA
<213> ORGANISM: Artificial Sequence
<220> FEATURE:
<223> OTHER INFORMATION: Synthetic: TRAC-LHA

<400> SEQUENCE: 122
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300 gaagatccta ttaaataaaa gaataagcag tattattaag tagccctgca tttcaggttt    360
```

```
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttgggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca                                                 800

<210> SEQ ID NO 123
<211> LENGTH: 1178
<212> TYPE: DNA
<213> ORGANISM: Artificial Sequence
<220> FEATURE:
<223> OTHER INFORMATION: Synthetic: EF1-alpha promoter

<400> SEQUENCE: 123
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg ccttttttcc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccactg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaatttt gatgacctgc tgcgacgctt tttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg cctttccgt    900 cctcagccgt cgcttcatgt gactccacgg agtaccgggc gccgtccagg cacctcgatt    960
agttctcgag cttttggagt acgtcgtctt taggttgggg ggagggggttt tatgcgatgg   1020 agtttcccca cactgagtgg gtggagactg aagttaggcc agcttggcac ttgatgtaat   1080
tctccttgga atttgccctt tttgagtttg gatcttggtt cattctcaag cctcagacag   1140
tggttcaaag ttttttctt ccatttcagg tgtcgtga                             1178

<210> SEQ ID NO 124
<211> LENGTH: 49
<212> TYPE: DNA
<213> ORGANISM: Artificial Sequence
<220> FEATURE:
<223> OTHER INFORMATION: Synthetic: Synthetic poly(A) signal

<400> SEQUENCE: 124
aataaaatcg ctatccatcg aagatggatg tgtgttggtt ttttgtgtg                 49
```

<210> SEQ ID NO 125
<211> LENGTH: 804
<212> TYPE: DNA
<213> ORGANISM: Artificial Sequence
<220> FEATURE:
<223> OTHER INFORMATION: Synthetic: TRACRHA

<400> SEQUENCE: 125

```
tggagcaaca aatctgactt tgcatgtgca acgccttca acaacagcat tattccagaa      60
gacaccttct tccccagccc aggtaagggc agctttggtg ccttcgcagg ctgtttcctt     120
gcttcaggaa tggccaggtt ctgcccagag ctctggtcaa tgatgtctaa aactcctctg    180
attggtggtc tcggccttat ccattgccac caaaaccctc tttttactaa gaaacagtga    240
gccttgttct ggcagtccag agaatgacac gggaaaaaag cagatgaaga aaggtggca     300
ggagagggca cgtggcccag cctcagtctc tccaactgag ttcctgcctg cctgcctttg    360
ctcagactgt tgccccctta ctgctcttct aggcctcatt ctaagcccct ctccaagtt     420
gcctctcctt atttctccct gtctgccaaa aaatctttcc cagctcacta agtcagtctc    480
acgcagtcac tcattaaccc accaatcact gattgtgccg gcacatgaat gcaccaggtg    540
ttgaagtgga ggaattaaaa agtcagatga ggggtgtgcc cagaggaagc accattctag    600
ttgggggagc ccatctgtca gctgggaaaa gtccaaataa cttcagattg gaatgtgttt    660
taactcaggg ttgagaaaac agctaccttc aggacaaaag tcaggaagg gctctctgaa     720
gaaatgctac ttgaagatac cagccctacc aagggcaggg agaggaccct atagaggcct    780
gggacaggag ctcaatgaga aagg                                           804
```

<210> SEQ ID NO 126
<211> LENGTH: 23
<212> TYPE: PRT
<213> ORGANISM: Artificial Sequence
<220> FEATURE:
<223> OTHER INFORMATION: Synthetic: CD8a transmembrane

<400> SEQUENCE: 126

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 127
<211> LENGTH: 65
<212> TYPE: DNA
<213> ORGANISM: Artificial Sequence
<220> FEATURE:
<223> OTHER INFORMATION: Synthetic: CD70 forward primer

<400> SEQUENCE: 127

```
tcgtcggcag cgtcagatgt gtataagaga cagcccaact tttccatctc aactcacccc     60
aagtg                                                                 65
```

<210> SEQ ID NO 128
<211> LENGTH: 53
<212> TYPE: DNA
<213> ORGANISM: Artificial Sequence
<220> FEATURE:
<223> OTHER INFORMATION: Synthetic: CD70 reverse primer

<400> SEQUENCE: 128

```
gtctcgtggg ctcggagatg tgtataagag acagcccctc ctgcgctagc gga           53
```

<210> SEQ ID NO 129
<211> LENGTH: 58
<212> TYPE: DNA
<213> ORGANISM: Artificial Sequence
<220> FEATURE:
<223> OTHER INFORMATION: Synthetic: CD70 Indel

<400> SEQUENCE: 129
cacaccacga ggcagatcac caagcccgcg caatgggacc aaagcagccc gcaggacg      58

<210> SEQ ID NO 130
<211> LENGTH: 61
<212> TYPE: DNA
<213> ORGANISM: Artificial Sequence
<220> FEATURE:
<223> OTHER INFORMATION: Synthetic: CD70 Indel

<400> SEQUENCE: 130
cacaccacga ggcagatcac caagcccgcg aaccaatggg accaaagcag cccgcaggac      60
g      61

<210> SEQ ID NO 131
<211> LENGTH: 48
<212> TYPE: DNA
<213> ORGANISM: Artificial Sequence
<220> FEATURE:
<223> OTHER INFORMATION: Synthetic: CD70 Indel

<400> SEQUENCE: 131
cacaccacga ggcagatcac caatgggacc aaagcagccc gcaggacg      48

<210> SEQ ID NO 132
<211> LENGTH: 59
<212> TYPE: DNA
<213> ORGANISM: Artificial Sequence
<220> FEATURE:
<223> OTHER INFORMATION: Synthetic: CD70 Indel

<400> SEQUENCE: 132
cacaccacga ggcagatcac caagcccgcg ccaatgggac caaagcagcc cgcaggacg      59

<210> SEQ ID NO 133
<211> LENGTH: 59
<212> TYPE: DNA
<213> ORGANISM: Artificial Sequence
<220> FEATURE:
<223> OTHER INFORMATION: Synthetic: CD70 Indel

<400> SEQUENCE: 133
cacaccacga ggcagatcac caagcccgca ccaatgggac caaagcagcc cgcaggacg      59

<210> SEQ ID NO 134
<211> LENGTH: 35
<212> TYPE: DNA
<213> ORGANISM: Artificial Sequence
<220> FEATURE:
<223> OTHER INFORMATION: Synthetic: CD70 Indel

<400> SEQUENCE: 134
cacaccacga ggcagatcac caagcccgca ggacg      35

<210> SEQ ID NO 135
<211> LENGTH: 4367
<212> TYPE: DNA
<213> ORGANISM: Artificial Sequence
<220> FEATURE:
<223> OTHER INFORMATION: Synthetic: Anti-CD33 CAR Donor LHA to RHA 41BB
      costim.

<400> SEQUENCE: 135

| | | | | | |
|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | ggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggtttctaag | 480 |
| atgctatttc | ccgtataaag | catgagaccg | tgacttgcca | gccccacaga | gccccgccct | 540 |
| tgtccatcac | tggcatctgg | actccagcct | gggttggggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | ggctccggtg | cccgtcagtg | ggcagagcgc | acatcgccca | 840 |
| cagtccccga | gaagttgggg | ggaggggtcg | gcaattgaac | cggtgcctag | agaaggtggc | 900 |
| gcggggtaaa | ctgggaaagt | gatgtcgtgt | actggctccg | ccttttctccc | gagggtgggg | 960 |
| gagaaccgta | tataagtgca | gtagtcgccg | tgaacgttct | ttttcgcaac | gggtttgccg | 1020 |
| ccagaacaca | ggtaagtgcc | gtgtgtggtt | cccgcgggcc | tggcctctt | acgggttatg | 1080 |
| gcccttgcgt | gccttgaatt | acttccactg | gctgcagtac | gtgattcttg | atcccgagct | 1140 |
| tcgggttgga | agtgggtggg | agagttcgag | gccttgcgct | taaggagccc | cttcgcctcg | 1200 |
| tgcttgagtt | gaggcctggc | ctgggcgctg | gggccgccgc | gtgcgaatct | ggtggcacct | 1260 |
| tcgcgcctgt | ctcgctgctt | tcgataagtc | tctagccatt | taaaattttt | gatgacctgc | 1320 |
| tgcgacgctt | tttttctggc | aagatagtct | tgtaaatgcg | ggccaagatc | tgcacactgg | 1380 |
| tatttcggtt | tttggggccg | cggcggcga | cggggcccgt | gcgtcccagc | gcacatgttc | 1440 |
| ggcgaggcgg | ggcctgcgag | cgcggccacc | gagaatcgga | cggggggtagt | ctcaagctgg | 1500 |
| ccggcctgct | ctggtgcctg | gcctcgcgcc | gccgtgtatc | gccccgccct | gggcggcaag | 1560 |
| gctggcccgg | tcggcaccag | ttgcgtgagc | ggaaagatgg | ccgcttcccg | gccctgctgc | 1620 |
| agggagctca | aaatggagga | cgcggcgctc | gggagagcgg | gcgggtgagt | cacccacaca | 1680 |
| aaggaaaagg | gcctttccgt | cctcagccgt | cgcttcatgt | gactccacgg | agtaccgggc | 1740 |
| gccgtccagg | cacctcgatt | agttctcgag | cttttggagt | acgtcgtctt | taggttgggg | 1800 |
| ggaggggttt | tatgcgatgg | agtttcccca | cactgagtgg | gtggagactg | aagttaggcc | 1860 |
| agcttggcac | ttgatgtaat | tctccttgga | atttgccctt | tttgagtttg | atcttggtt | 1920 |
| cattctcaag | cctcagacag | tggttcaaag | ttttttttctt | ccatttcagg | tgtcgtgacc | 1980 |
| accatggcgc | ttccggtgac | agcactgctc | ctcccttgg | cgctgttgct | ccacgcagca | 2040 |
| aggccggaaa | tcgtcctcac | acaatccccg | gggagcctcg | cagtcagtcc | tggggaacga | 2100 |
| gtcactatga | gctgcaaatc | cagtcagagt | gttttttttct | caagtagcca | gaagaactac | 2160 |
| ctcgcatggt | accaacaaat | accggggcaa | tctccccgct | tgcttatata | ctgggcaagt | 2220 |

```
acccgcgaat ccggcgtacc ggatcgattc acgggatctg ggtcaggtac tgatttcact    2280
ttgactatca gctctgttca gcctgaagat ttggcaattt actactgtca ccaatacttg    2340
agtagccgaa ctttcggcca gggcacgaag ctcgaaatca agggcggagg gggaggttct    2400 ggtggggcg gttctggcgg tggaggaagc caagtacagt tgcaacagcc aggggcggag     2460
gtcgtaaaac ctggggcgtc tgtcaagatg agctgtaaag caagtggata ccccttcacc    2520
tcctactata tacattggat taagcaaact ccgggtcagg ggctggaatg ggttggcgtt    2580
atataccccg ggaacgatga tatatcatac aaccaaaaat ttcaaggcaa ggcgactctg    2640
actgccgata agagtagcac aacagcttac atgcagcttt cttccctgac cagcgaagat    2700
tcagcagttt actactgcgc tcgggaagtg cgcctgcgat actttgatgt ctggggtcaa    2760
ggaactacag ttactgtatc aagcagtgct gctgcctttg tcccggtatt tctcccagcc    2820
aaaccgacca cgactcccgc cccgcgccct ccgacacccg ctcccaccat cgcctctcaa    2880
cctcttagtc ttcgcccga ggcatgccga cccgccgccg ggggtgctgt tcatacgagg     2940
ggcttggact tcgcttgtga tatttacatt tgggctccgt tggcgggtac gtgcggcgtc    3000
cttttgttgt cactcgttat tacttttgtat tgtaatcaca ggaatcgcaa acggggcaga   3060
aagaaactcc tgtatatatt caaacaacca tttatgagac cagtacaaac tactcaagag    3120
gaagatggct gtagctgccg atttccagaa gaagaagaag gaggatgtga actgcgagtg    3180
aagttttccc gaagcgcaga cgctccggca tatcagcaag gacagaatca gctgtataac    3240
gaactgaatt tgggacgccg cgaggagtat gacgtgcttg ataaacgccg gggagagac    3300 ccggaaatgg ggggtaaacc ccgaagaaag aatccccaag aaggactcta caatgaactc    3360
cagaaggata gatggcggaa ggcctactca gaaataggta tgaagggcga acgacgacgg    3420
ggaaaaggtc acgatggcct ctaccaaggg ttgagtacgg caaccaaaga tacgtacgat    3480
gcactgcata tgcaggccct gcctcccaga taataataaa atcgctatcc atcgaagatg    3540
gatgtgtgtt ggttttttgt gtgtggagca acaaatctga ctttgcatgt gcaaacgcct    3600
tcaacaacag cattattcca gaagacacct tcttccccag cccaggtaag ggcagctttg    3660
gtgccttcgc aggctgtttc cttgcttcag gaatggccag gttctgccca gagctctggt    3720
caatgatgtc taaaactcct ctgattggtg gtctcggcct tatccattgc caccaaaacc    3780 ctcttttttac taagaaacag tgagccttgt tctggcagtc cagagaatga cacggaaaaa    3840
aagcagatga agagaaggtg gcaggagagg gcacgtggcc cagcctcagt ctctccaact    3900
gagttcctgc ctgcctgcct ttgctcagac tgtttgcccc ttactgctct tctaggcctc    3960
attctaagcc ccttctccaa gttgcctctc cttatttctc cctgtctgcc aaaaaatctt    4020
tcccagctca ctaagtcagt ctcacgcagt cactcattaa cccaccaatc actgattgtg    4080
ccggcacatg aatgcaccag gtgttgaagt ggaggaatta aaaagtcaga tgagggtgt     4140 gcccagagga agcaccattc tagttggggg agcccatctg tcagctggga aaagtccaaa    4200
taacttcaga ttggaatgtg ttttaactca gggttgagaa aacagctacc ttcaggacaa    4260
aagtcaggga agggctctct gaagaaatgc tacttgaaga taccagccct accaagggca    4320
gggagaggac cctatagagg cctgggacag gagctcaatg agaaagg                  4367
```

<210> SEQ ID NO 136
<211> LENGTH: 1585
<212> TYPE: DNA
<213> ORGANISM: Artificial Sequence
<220> FEATURE:

<223> OTHER INFORMATION: Synthetic: Anti-CD33 CAR 41BB costim

<400> SEQUENCE: 136

```
ccaccatggc gcttccggtg acagcactgc tcctcccctt ggcgctgttg ctccacgcag      60
caaggccgga atcgtcctc acacaatccc cggggagcct cgcagtcagt cctggggaac     120
gagtcactat gagctgcaaa tccagtcaga gtgttttttt ctcaagtagc cagaagaact     180
acctcgcatg gtaccaacaa ataccggggc aatctccccg cttgcttata tactgggcaa     240
gtacccgcga atccggcgta ccggatcgat tcacgggatc tgggtcaggt actgatttca     300
ctttgactat cagctctgtt cagcctgaag atttggcaat ttactactgt caccaatact     360
tgagtagccg aactttcggc cagggcacga agctcgaaat caagggcgga ggggaggtt     420
ctggtggggg cggttctggc ggtggaggaa gccaagtaca gttgcaacag ccaggggcgg     480
aggtcgtaaa acctggggcg tctgtcaaga tgagctgtaa agcaagtgga tacaccttca     540
cctcctacta tatacattgg attaagcaaa ctccgggtca ggggctggaa tgggttggcg     600
ttatatacccc cggaacgat gatatatcat acaaccaaaa atttcaaggc aaggcgactc     660
tgactgccga taagagtagc acaacagctt acatgcagct tcttccctg accagcgaag     720
attcagcagt ttactactgc gctcgggaag tgcgcctgcg atactttgat gtctggggtc     780
aaggaactac agttactgta tcaagcagtg ctgctgcctt tgtcccggta tttctcccag     840
ccaaaccgac cacgactccc gccccgcgcc ctccgacacc cgctcccacc atcgcctctc     900
aacctcttag tcttcgcccc gaggcatgcc gacccgccgc cggggggtgct gttcatacga     960
ggggcttgga cttcgcttgt gatatttaca tttgggctcc gttggcgggt acgtgcggcg    1020
tccttttgtt gtcactcgtt attactttgt attgtaatca caggaatcgc aaacggggca    1080
gaaagaaact cctgtatata ttcaaacaac catttatgag accagtacaa actactcaag    1140
aggaagatgg ctgtagctgc cgatttccag aagaagaaga aggaggatgt gaactgcgag    1200
tgaagttttc ccgaagcgca gacgctccgg catatcagca aggacagaat cagctgtata    1260
acgaactgaa tttgggacgc cgcgaggagt atgacgtgct tgataaacgc ggggggagag    1320
acccggaaat gggggtaaa ccccgaagaa agaatcccca agaaggactc tacaatgaac    1380
tccagaagga taagatggcg gaggcctact cagaaatagg tatgaagggc gaacgacgac    1440
ggggaaaagg tcacgatggc ctctaccaag ggttgagtac ggcaaccaaa gatacgtacg    1500
atgcactgca tatgcaggcc ctgcctccca gataataata aaatcgctat ccatcgaaga    1560
tggatgtgtg ttggttttt gtgtg                                           1585
```

<210> SEQ ID NO 137
<211> LENGTH: 246
<212> TYPE: PRT
<213> ORGANISM: Artificial Sequence
<220> FEATURE:
<223> OTHER INFORMATION: Synthetic: Anti-CD33  scFv Linker

<400> SEQUENCE: 137

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Gln Pro Glu Asp Leu Ala Ile Tyr Tyr Cys His Gln
                 85                  90                  95

Tyr Leu Ser Ser Arg Thr Phe Gly Gln Gly Thr Lys Leu Glu Ile Lys
                100                 105                 110

Gly Gly Gly Gly Gly Ser Gly Gly Gly Ser Gly Gly Gly Gly Ser
            115                 120                 125

Gln Val Gln Leu Gln Gln Pro Gly Ala Glu Val Val Lys Pro Gly Ala
130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
                180                 185                 190

Gln Gly Lys Ala Thr Leu Thr Ala Asp Lys Ser Ser Thr Thr Ala Tyr
                195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Gln Gly Thr
225                 230                 235                 240

Thr Val Thr Val Ser Ser
                245
```

<210> SEQ ID NO 138
<211> LENGTH: 738
<212> TYPE: DNA
<213> ORGANISM: Artificial Sequence
<220> FEATURE:
<223> OTHER INFORMATION: Synthetic: Anti-CD33 scFv

<400> SEQUENCE: 138

```
gaaatcgtcc tcacacaatc cccggggagc ctcgcagtca gtcctgggga acgagtcact      60
atgagctgca atccagtca gagtgttttt ttctcaagta gccagaagaa ctacctcgca     120
tggtaccaac aaataccggg gcaatctccc cgcttgctta tatactgggc aagtacccgc     180
gaatccggcg taccggatcg attcacggga tctgggtcag gtactgattt cactttgact     240
atcagctctg ttcagcctga gatttggca atttactact gtcaccaata cttgagtagc     300
cgaactttcg gccagggcac gaagctcgaa atcaagggcg gagggggagg ttctggtggg     360
ggcggttctg gcggtggagg aagccaagta cagttgcaac agccaggggc ggaggtcgta     420
aaacctgggg cgtctgtcaa gatgagctgt aaagcaagtg gatacacctt cacctcctac     480
tatatacatt ggattaagca aactccgggt caggggctgg aatgggttgg cgttatatac     540
cccgggaacg atgatatatc atacaaccaa aaatttcaag gcaaggcgac tctgactgcc     600
gataagagta gcacaacagc ttacatgcag ctttcttccc tgaccagcga agattcagca     660
gtttactact gcgctcggga agtgcgcctg cgatactttg atgtctgggg tcaaggaact     720
acagttactg tatcaagc                                                   738
```

<210> SEQ ID NO 139
<211> LENGTH: 509
<212> TYPE: PRT
<213> ORGANISM: Artificial Sequence
<220> FEATURE:

<223> OTHER INFORMATION: Synthetic: Anti-CD33 CAR 41BB costim.

<400> SEQUENCE: 139

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Ser Leu
            20                  25                  30

Ala Val Ser Pro Gly Glu Arg Val Thr Met Ser Cys Lys Ser Ser Gln
        35                  40                  45

Ser Val Phe Phe Ser Ser Gln Lys Asn Tyr Leu Ala Trp Tyr Gln
    50                  55                  60

Gln Ile Pro Gly Gln Ser Pro Arg Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Pro Glu Asp Leu Ala Ile
            100                 105                 110

Tyr Tyr Cys His Gln Tyr Leu Ser Ser Arg Thr Phe Gly Gln Gly Thr
        115                 120                 125

Lys Leu Glu Ile Lys Gly Gly Gly Gly Ser Gly Gly Gly Gly Ser
130                 135                 140

Gly Gly Gly Gly Ser Gln Val Gln Leu Gln Gln Pro Gly Ala Glu Val
145                 150                 155                 160

Val Lys Pro Gly Ala Ser Val Lys Met Ser Cys Lys Ala Ser Gly Tyr
                165                 170                 175

Thr Phe Thr Ser Tyr Tyr Ile His Trp Ile Lys Gln Thr Pro Gly Gln
            180                 185                 190

Gly Leu Glu Trp Val Gly Val Ile Tyr Pro Gly Asn Asp Asp Ile Ser
        195                 200                 205

Tyr Asn Gln Lys Phe Gln Gly Lys Ala Thr Leu Thr Ala Asp Lys Ser
    210                 215                 220

Ser Thr Thr Ala Tyr Met Gln Leu Ser Ser Leu Thr Ser Glu Asp Ser
225                 230                 235                 240

Ala Val Tyr Tyr Cys Ala Arg Glu Val Arg Leu Arg Tyr Phe Asp Val
                245                 250                 255

Trp Gly Gln Gly Thr Thr Val Thr Val Ser Ser Ala Ala Ala Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
            340                 345                 350

Arg Asn Arg Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400
```

```
Phe Ser Arg Ser Ala Asp Ala Pro Ala Tyr Gln Gln Gly Gln Asn Gln
            405                 410                 415

Leu Tyr Asn Glu Leu Asn Leu Gly Arg Arg Glu Glu Tyr Asp Val Leu
        420                 425                 430

Asp Lys Arg Arg Gly Arg Asp Pro Glu Met Gly Gly Lys Pro Arg Arg
    435                 440                 445

Lys Asn Pro Gln Glu Gly Leu Tyr Asn Glu Leu Gln Lys Asp Lys Met
450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 140
<211> LENGTH: 118
<212> TYPE: PRT
<213> ORGANISM: Artificial Sequence
<220> FEATURE:
<223> OTHER INFORMATION: Synthetic: anti-CD33 antibody VH CDRs

<400> SEQUENCE: 140

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
            100                 105                 110

Thr Val Thr Val Ser Ser
        115

<210> SEQ ID NO 141
<211> LENGTH: 112
<212> TYPE: PRT
<213> ORGANISM: Artificial Sequence
<220> FEATURE:
<223> OTHER INFORMATION: Synthetic: antiCD33 antibody VL CDRs

<400> SEQUENCE: 141

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

Ile Ser Ser Val Gln Pro Glu Asp Leu Ala Ile Tyr Tyr Cys His Gln
            85                  90                  95

Tyr Leu Ser Ser Arg Thr Phe Gly Gln Gly Thr Lys Leu Glu Ile Lys
        100                 105                 110

<210> SEQ ID NO 142
<211> LENGTH: 5
<212> TYPE: PRT
<213> ORGANISM: Artificial Sequence
<220> FEATURE:
<223> OTHER INFORMATION: Synthetic: anti-CD33 antibody VH CDR1 (Kabat)

<400> SEQUENCE: 142

Ser Tyr Tyr Ile His
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic: anti-CD33 antibody VH CDR2 (Kabat)

<400> SEQUENCE: 143

Val Ile Tyr Pro Gly Asn Asp Asp Ile Ser Tyr Asn Gln Lys Phe Gln
1               5                   10                  15
Gly

<210> SEQ ID NO 144
<211> LENGTH: 9
<212> TYPE: PRT
<213> ORGANISM: Artificial Sequence
<220> FEATURE:
<223> OTHER INFORMATION: Synthetic: anti-CD33 antibody VH CDR3 (Kabat)

<400> SEQUENCE: 144

Glu Val Arg Leu Arg Tyr Phe Asp Val
1               5

<210> SEQ ID NO 145
<211> LENGTH: 17
<212> TYPE: PRT
<213> ORGANISM: Artificial Sequence
<220> FEATURE:
<223> OTHER INFORMATION: Synthetic: anti-CD33 antibody VL CDR1 (Kabat &
      Chothia)

<400> SEQUENCE: 145

Lys Ser Ser Gln Ser Val Phe Phe Ser Ser Gln Lys Asn Tyr Leu
1               5                   10                  15
Ala

<210> SEQ ID NO 146
<211> LENGTH: 7
<212> TYPE: PRT
<213> ORGANISM: Artificial Sequence
<220> FEATURE:
<223> OTHER INFORMATION: Synthetic: anti-CD33 antibody VL CDR2 (Kabat &
      Chothia

<400> SEQUENCE: 146

Trp Ala Ser Thr Arg Glu Ser
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic: anti-CD33 antibody VL CDR3 (Kabat & Chothia)

<400> SEQUENCE: 147

His Gln Tyr Leu Ser Ser Arg Thr
1               5

<210> SEQ ID NO 148
<211> LENGTH: 1518
<212> TYPE: DNA
<213> ORGANISM: Artificial Sequence
<220> FEATURE:
<223> OTHER INFORMATION: Synthetic: Anti-CD19 CAR CD8[tm]-CD28[co-stimulatory domain]-CD3z)

<400> SEQUENCE: 148

```
atgcttcttt tggttacgtc tctgttgctt tgcgaacttc ctcatccagc gttcttgctg      60
atccccgata ttcagatgac tcagaccacc agtagcttgt ctgcctcact gggagaccga     120
gtaacaatct cctgcagggc aagtcaagac attagcaaat acctcaattg gtaccagcag     180
aagcccgacg gaacggtaaa actcctcatc tatcatacgt caaggttgca ttccggagta     240
ccgtcacgat tttcaggttc tgggagcgga actgactatt ccttgactat ttcaaacctc     300
gagcaggagg acattgcgac atatttttgt caacaaggta ataccctccc ttacactttc     360
ggaggaggaa ccaaactcga aattaccggg tccaccagtg gctctgggaa gcctggcagt     420
ggagaaggtt ccactaaagg cgaggtgaag ctccaggaga gcggcccgg tctcgttgcc     480
cccagtcaaa gcctctctgt aacgtgcaca gtgagtggtg tatcattgcc tgattatggc     540
gtctcctgga taaggcagcc cccgcgaaag ggtcttgaat ggcttggggt aatatggggc     600
tcagagacaa cgtattataa ctccgctctc aaaagtcgct tgacgataat aaaagataac     660
tccaagagtc aagttttcct taaaatgaac agtttgcaga ctgacgatac cgctatatat     720
tattgtgcta acattatta ctacggcggt agttacgcga tggattattg ggggcagggg     780
acttctgtca cagtcagtag tgctgctgcc tttgtcccgg tatttctccc agccaaaccg     840
accacgactc ccgccccgcg ccctccgaca cccgctccca ccatcgcctc tcaacctctt     900
agtcttcgcc ccgaggcatg ccgacccgcc gccggggtg ctgttcatac gaggggcttg     960
gacttcgctt gtgatattta catttgggct ccgttggcgg gtacgtgcgg cgtccttttg    1020
ttgtcactcg ttattacttt gtattgtaat cacaggaatc gctcaaagcg gagtaggttg    1080
ttgcattccg attacatgaa tatgactcct cgcggcctg gccgacaag aaaacattac    1140
caaccctatg cccccccacg agacttcgct gcgtacaggt cccgagtgaa gttttcccga    1200
agcgcagacg ctccggcata tcagcaagga cagaatcagc tgtataacga actgaatttg    1260
ggacgccgcg aggagtatga cgtgcttgat aaacgccggg ggagagaccc ggaaatgggg    1320
ggtaaacccc gaagaaagaa tccccaagaa ggactctaca tgaactcca gaaggataag    1380
atggcggagg cctactcaga aataggtatg aaggcgaac gacgacgggg aaaaggtcac    1440
gatggcctct accaagggtt gagtacggca accaaagata cgtacgatgc actgcatatg    1500
caggccctgc ctcccaga                                                  1518
```

<210> SEQ ID NO 149
<211> LENGTH: 506

```
<212> TYPE: PRT
<213> ORGANISM: Artificial Sequence
<220> FEATURE:
<223> OTHER INFORMATION: Synthetic: Anti-CD19 CAR  CD8[tm]-CD28[co-
      stimulatory domain]-CD3z) Amino Acid

<400> SEQUENCE: 149
```

| | | | | | | | | | | | | | | | |
|---|---|---|---|---|---|---|---|---|---|---|---|---|---|---|---|

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

```
Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
            405                 410                 415

Glu Leu Asn Leu Gly Arg Arg Glu Glu Tyr Asp Val Leu Asp Lys Arg
        420                 425                 430

Arg Gly Arg Asp Pro Glu Met Gly Gly Lys Pro Arg Arg Lys Asn Pro
    435                 440                 445

Gln Glu Gly Leu Tyr Asn Glu Leu Gln Lys Asp Lys Met Ala Glu Ala
450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505
```

<210> SEQ ID NO 150
<211> LENGTH: 735
<212> TYPE: DNA
<213> ORGANISM: Artificial Sequence
<220> FEATURE:
<223> OTHER INFORMATION: Synthetic: Anti-CD19 scFv

<400> SEQUENCE: 150

```
gatattcaga tgactcagac caccagtagc ttgtctgcct cactgggaga ccgagtaaca    60
atctcctgca gggcaagtca agacattagc aaatacctca attggtacca gcagaagccc   120
gacggaacgg taaaactcct catctatcat acgtcaaggt tgcattccgg agtaccgtca   180
cgattttcag ttctgggagc ggaactgac tattccttga ctatttcaaa cctcgagcag   240
gaggacattg cgacatattt tgtcaacaa ggtaatacccc tcccttacac tttcggagga   300
ggaaccaaac tcgaaattac cgggtccacc agtggctctg ggaagcctgg cagtggagaa   360
ggttccacta aggcgaggt gaagctccag gagagcggcc ccggtctcgt tgccccagt    420
caaagcctct ctgtaacgtg cacagtgagt ggtgtatcat tgcctgatta tggcgtctcc   480
tggataaggc agccccgcg aaagggtctt gaatggcttg gggtaatatg gggctcagag   540
acaacgtatt ataactccgc tctcaaaagt cgcttgacga taataaaaga taactccaag   600
agtcaagttt tccttaaaat gaacagtttg cagactgacg ataccgctat atattattgt   660
gctaaacatt attactacgg cggtagttac gcgatggatt attgggggca ggggacttct   720
gtcacagtca gtagt                                                   735
```

<210> SEQ ID NO 151
<211> LENGTH: 245
<212> TYPE: PRT
<213> ORGANISM: Artificial Sequence
<220> FEATURE:
<223> OTHER INFORMATION: Synthetic: CD19 scFv amino acid sequence Linker

<400> SEQUENCE: 151

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45
```

```
Tyr His Thr Ser Arg Leu His Ser Gly Val Pro Ser Arg Phe Ser Gly
                50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                    85                  90                  95

Thr Phe Gly Gly Gly Thr Lys Leu Glu Ile Thr Gly Ser Thr Ser Gly
                100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
                180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 152
<211> LENGTH: 120
<212> TYPE: PRT
<213> ORGANISM: Artificial Sequence
<220> FEATURE:
<223> OTHER INFORMATION: Synthetic: Anti-CD19 VH

<400> SEQUENCE: 152

Glu Val Lys Leu Gln Glu Ser Gly Pro Gly Leu Val Ala Pro Ser Gln
 1               5                  10                  15

Ser Leu Ser Val Thr Cys Thr Val Ser Gly Val Ser Leu Pro Asp Tyr
             20                  25                  30

Gly Val Ser Trp Ile Arg Gln Pro Pro Arg Lys Gly Leu Glu Trp Leu
         35                  40                  45

Gly Val Ile Trp Gly Ser Glu Thr Thr Tyr Tyr Asn Ser Ala Leu Lys
 50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 153
<211> LENGTH: 107
<212> TYPE: PRT
<213> ORGANISM: Artificial Sequence
```

```
<220> FEATURE:
<223> OTHER INFORMATION: Synthetic: Anti-CD19 VL

<400> SEQUENCE: 153

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 154
<211> LENGTH: 18
<212> TYPE: PRT
<213> ORGANISM: Artificial Sequence
<220> FEATURE:
<223> OTHER INFORMATION: Synthetic: Anti-CD19 scFv linker

<400> SEQUENCE: 154

Gly Ser Thr Ser Gly Ser Gly Lys Pro Gly Ser Gly Glu Gly Ser Thr
1               5                   10                  15

Lys Gly

<210> SEQ ID NO 155
<211> LENGTH: 4682
<212> TYPE: DNA
<213> ORGANISM: Artificial Sequence
<220> FEATURE:
<223> OTHER INFORMATION: Synthetic: anti-CD19 CAR rAAV

<400> SEQUENCE: 155
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
agggggttcct gcggccgcac gcgtgagatg taaggagctg ctgtgacttg ctcaaggcct    180
tatatcgagt aaacggtagt gctggggctt agacgcaggt gttctgattt atagttcaaa    240
acctctatca atgagagagc aatctcctgg taatgtgata gatttcccaa cttaatgcca    300
acataccata aacctcccat tctgctaatg cccagcctaa gttggggaga ccactccaga    360
ttccaagatg tacagtttgc tttgctgggc cttttcccca tgcctgcctt tactctgcca    420
gagttatatt gctggggttt tgaagaagat cctattaaat aaaagaataa gcagtattat    480
taagtagccc tgcatttcag gtttccttga gtggcaggcc aggcctggcc gtgaacgttc    540
actgaaatca tggcctcttg gccaagattg atagcttgtg cctgtccctg agtcccagtc    600
catcacgagc agctggtttc taagatgcta tttcccgtat aaagcatgag accgtgactt    660
gccagcccca cagagccccg cccttgtcca tcactggcat ctggactcca gcctgggttg    720
gggcaaagag ggaaatgaga tcatgtccta accctgatcc tcttgtccca cagatatcca    780
gaaccctgac cctgccgtgt accagctgag agactctaaa tccagtgaca gtctgtctg    840
```

```
cctattcacc gattttgatt ctcaaacaaa tgtgtcacaa agtaaggatt ctgatgtgta      900
tatcacagac aaaactgtgc tagacatgag gtctatggac ttcaggctcc ggtgcccgtc      960
agtgggcaga gcgcacatcg cccacagtcc ccgagaagtt ggggggaggg gtcggcaatt     1020
gaaccggtgc ctagagaagg tggcgcgggg taaactggga aagtgatgtc gtgtactggc     1080
tccgcctttt tcccgagggt gggggagaac cgtatataag tgcagtagtc gccgtgaacg     1140 ttcttttttcg caacgggttt gccgccagaa cacaggtaag tgccgtgtgt ggttcccgcg     1200
ggcctggcct ctttacgggt tatggccctt gcgtgccttg aattacttcc actggctgca     1260
gtacgtgatt cttgatcccg agcttcgggt tggaagtggg tgggagagtt cgaggccttg     1320
cgcttaagga gccccttcgc ctcgtgcttg agttgaggcc tggcctgggc gctggggccg     1380
ccgcgtgcga atctggtggc accttcgcgc ctgtctcgct gctttcgata agtctctagc     1440
catttaaaat ttttgatgac ctgctgcgac gctttttttc tggcaagata gtcttgtaaa     1500
tgcgggccaa gatctgcaca ctggtatttc ggttttttggg gccgcgggcg gcgacggggc     1560
ccgtgcgtcc cagcgcacat gttcggcgag gcggggcctg cgagcgcggc caccgagaat     1620
cggacggggg tagtctcaag ctggccggcc tgctctggtg cctggcctcg cgccgccgtg     1680
tatcgccccg ccctgggcgg caaggctggc ccggtcggca ccagttgcgt gagcggaaag     1740
atggccgctt cccggccctg ctgcaggag ctcaaaatgg aggacgcggc gctcgggaga     1800
gcgggcgggt gagtcaccca cacaaaggaa aagggccttt ccgtcctcag ccgtcgcttc     1860
atgtgactcc acggagtacc gggcgccgtc caggcacctc gattagttct cgagcttttg     1920
gagtacgtcg tctttaggtt ggggggaggg gttttatgcg atggagtttc cccacactga     1980
gtgggtggag actgaagtta ggccagcttg gcacttgatg taattctcct tggaatttgc     2040
ccttttggag tttggatctt ggttcattct caagcctcag acagtggttc aaagttttt      2100 tcttccattt caggtgtcgt gaccaccatg cttcttttgg ttacgtctct gttgctttgc     2160
gaacttcctc atccagcgtt cttgctgatc ccgatattc agatgactca gaccaccagt     2220
agcttgtctg cctcactggg agaccgagta acaatctcct gcagggcaag tcaagacatt     2280
agcaaatacc tcaattggta ccagcagaag cccgacggaa cggtaaaact cctcatctat     2340
catacgtcaa ggttgcattc cggagtaccg tcacgatttt caggttctgg gagcggaact     2400
gactattcct tgactatttc aaacctcgag caggaggaca ttgcgacata ttttgtcaa      2460 caaggtaata ccctccctta cactttcgga ggaggaacca aactcgaaat taccgggtcc     2520
accagtggct ctgggaagcc tggcagtgga gaaggttcca ctaaaggcga ggtgaagctc     2580
caggagagcg gccccggtct cgttgccccc agtcaaagcc tctctgtaac gtgcacagtg     2640
agtggtgtat cattgcctga ttatggcgtc tcctggataa ggcagccccc gcgaaagggt     2700
cttgaatggc ttgggtaat atggggctca gagacaacgt attataactc cgctctcaaa     2760
agtcgcttga cgataataaa agataactcc aagagtcaag ttttccttaa aatgaacagt     2820
ttgcagactg acgataccgc tatatattat tgtgctaaac attattacta cggcggtagt     2880
tacgcgatgg attattgggg gcaggggact tctgtcacag tcagtagtgc tgctgccttt     2940
gtcccggtat ttctcccagc caaaccgacc acgactcccg ccccgcgccc tccgacaccc     3000
gctcccacca tcgcctctca acctcttagt cttcgccccg aggcatgccg acccgccgcc     3060
gggggtgctg ttcatacgag gggcttggac ttcgcttgtg atatttacat ttgggctccg     3120
ttggcgggta cgtgcggcgt ccttttgttg tcactcgtta ttacttttgta ttgtaatcac     3180 aggaatcgct caaagcggag taggttgttg cattccgatt acatgaatat gactcctcgc     3240
```

```
cggcctgggc cgacaagaaa acattaccaa ccctatgccc ccccacgaga cttcgctgcg    3300
tacaggtccc gagtgaagtt ttcccgaagc gcagacgctc cggcatatca gcaaggacag    3360
aatcagctgt ataacgaact gaatttggga cgccgcgagg agtatgacgt gcttgataaa    3420
cgccggggga gagacccgga aatgggggt aaacccgaa gaaagaatcc caagaagga      3480 ctctacaatg aactccagaa ggataagatg gcggaggcct actcagaaat aggtatgaag    3540
ggcgaacgac gacggggaaa aggtcacgat ggcctctacc aagggttgag tacggcaacc    3600
aaagatacgt acgatgcact gcatatgcag gccctgcctc ccagataata ataaaatcgc    3660
tatccatcga agatggatgt gtgttggttt tttgtgtgtg gagcaacaaa tctgactttg    3720
catgtgcaaa cgccttcaac aacagcatta ttccagaaga caccttcttc cccagcccag    3780
gtaagggcag ctttggtgcc ttcgcaggct gtttccttgc ttcaggaatg ccaggttct    3840 gcccagagct ctggtcaatg atgtctaaaa ctcctctgat tggtggtctc ggccttatcc    3900
attgccacca aaaccctctt tttactaaga aacagtgagc cttgttctgg cagtccagag    3960
aatgacacgg gaaaaagca gatgaagaga aggtggcagg agagggcacg tggcccagcc    4020
tcagtctctc caactgagtt cctgcctgcc tgcctttgct cagactgttt gccccttact    4080
gctcttctag gcctcattct aagccccttc tccaagttgc ctctccttat ttctccctgt    4140
ctgccaaaaa atctttccca gctcactaag tcagtctcac gcagtcactc attacccac    4200 caatcactga ttgtgccggc acatgaatgc accaggtgtt gaagtggagg aattaaaaag    4260
tcagatgagg ggtgtgccca gaggaagcac cattctagtt gggggagccc atctgtcagc    4320
tgggaaaagt ccaaataact tcagattgga atgtgtttta actcagggtt gagaaaacag    4380
ctaccttcag gacaaaagtc agggaagggc tctctgaaga aatgctactt gaagatacca    4440
gccctaccaa gggcagggag aggaccctat agaggcctgg gacaggagct caatgagaaa    4500
ggtaaccacg tgcggaccga ggctgcagcg tcgtcctccc taggaacccc tagtgatgga    4560
gttggccact ccctctctgc gcgctcgctc gctcactgag gccgggcgac caaaggtcgc    4620
ccgacgcccg ggctttgccc gggcggcctc agtgagcgag cgagcgcgca gctgcctgca    4680
gg                                                                   4682
```

<210> SEQ ID NO 156
<211> LENGTH: 4358
<212> TYPE: DNA
<213> ORGANISM: Artificial Sequence
<220> FEATURE:
<223> OTHER INFORMATION: Synthetic: Anti-CD19 CAR LHA to RHA

<400> SEQUENCE: 156

```
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300 gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
```

```
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga aagttgggg ggaggggtcg gcaattgaac cggtgcctag agaaggtggc    900
gcggggtaaa ctgggaaagt gatgtcgtgt actggctccg ccttttccc gagggtgggg    960
gagaaccgta taagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaatttt gatgacctgc   1320
tgcgacgctt ttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cggggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatgcttc ttttggttac gtctctgttg cttttgcgaac ttcctcatcc agcgttcttg   2040
ctgatccccg atattcagat gactcagacc accagtagct tgtctgcctc actgggagac   2100
cgagtaacaa tctcctgcag ggcaagtcaa gacattagca aataccctcaa ttggtaccag   2160
cagaagcccg acggaacggt aaaactcctc atctatcata cgtcaaggtt gcattccgga   2220
gtaccgtcac gattttcagg ttctgggagc ggaactgact attccttgac tatttcaaac   2280
ctcgagcagg aggacattgc gacatatttt tgtcaacaag gtaataccct cccttacact   2340
ttcggaggag gaaccaaact cgaaattacc gggtccacca gtggctctgg gaagcctggc   2400
agtggagaag gttccactaa aggcgaggtg aagctccagg agagcggccc cggtctcgtt   2460
gcccccagtc aaagcctctc tgtaacgtgc acagtgagtg gtgtatcatt gcctgattat   2520
ggcgtctcct ggataaggca gccccgcgca aagggtcttg aatggcttgg ggtaaatatgg   2580
ggctcagaga caacgtatta taactccgct ctcaaaagtc gcttgacgat aataaaagat   2640
aactccaaga gtcaagtttt ccttaaaatg aacagtttgc agactgacga taccgctata   2700
tattattgtg ctaaacatta ttactacggc ggtagttacg cgatggatta ttgggggcag   2760
gggacttctg tcacagtcag tagtgctgct gcctttgtcc cggtatttct cccagccaaa   2820
ccgaccacga ctcccgcccc cgcgccctcg acacccgctc ccaccatcgc ctctcaacct   2880
cttagtcttc gccccgaggc atgccgaccc gccgccgggg gtgctgttca tacgagggc    2940
```

```
ttggacttcg cttgtgatat ttacatttgg gctccgttgg cgggtacgtg cggcgtcctt    3000
ttgttgtcac tcgttattac tttgtattgt aatcacagga atcgctcaaa gcggagtagg    3060
ttgttgcatt ccgattacat gaatatgact cctcgccggc ctgggccgac aagaaaacat    3120
taccaaccct atgcccccccc acgagacttc gctgcgtaca ggtcccgagt gaagttttcc    3180
cgaagcgcag acgctccggc atatcagcaa ggacagaatc agctgtataa cgaactgaat    3240
ttgggacgcc gcgaggagta tgacgtgctt gataaacgcc gggggagaga cccggaaatg    3300
gggggtaaac cccgaagaaa gaatccccaa gaaggactct acaatgaact ccagaaggat    3360
aagatggcgg aggcctactc agaaataggt atgaagggcg aacgacgacg gggaaaaggt    3420
cacgatggcc tctaccaagg gttgagtacg gcaaccaaag atacgtacga tgcactgcat    3480
atgcaggccc tgcctcccag ataataataa aatcgctatc catcgaagat ggatgtgtgt    3540 tggtttttg tgtgtggagc aacaaatctg actttgcatg tgcaaacgcc ttcaacaaca    3600
gcattattcc agaagacacc ttcttcccca gcccaggtaa gggcagcttt ggtgccttcg    3660
caggctgttt ccttgcttca ggaatggcca ggttctgccc agagctctgg tcaatgatgt    3720
ctaaaactcc tctgattggt ggtctcggcc ttatccattg ccaccaaaac cctctttta    3780 ctaagaaaca gtgagccttg ttctggcagt ccagagaatg acacgggaaa aaagcagatg    3840
aagagaaggt ggcaggagag ggcacgtggc ccagcctcag tctctccaac tgagttcctg    3900
cctgcctgcc tttgctcaga ctgtttgccc cttactgctc ttctaggcct cattctaagc    3960
cccttctcca agttgcctct ccttatttct ccctgtctgc caaaaatct ttcccagctc    4020 actaagtcag tctcacgcag tcactcatta acccaccaat cactgattgt gccggcacat    4080
gaatgcacca ggtgttgaag tggaggaatt aaaaagtcag atgaggggtg tgcccagagg    4140
aagcaccatt ctagttgggg gagcccatct gtcagctggg aaaagtccaa ataacttcag    4200
attggaatgt gttttaactc agggttgaga aaacagctac cttcaggaca aaagtcaggg    4260
aagggctctc tgaagaaatg ctacttgaag ataccagccc taccaagggc agggagagga    4320
ccctatagag gcctgggaca ggagctcaat gagaaagg                             4358
```

<210> SEQ ID NO 157
<211> LENGTH: 20
<212> TYPE: DNA
<213> ORGANISM: Artificial Sequence
<220> FEATURE:
<223> OTHER INFORMATION: Synthetic: CD70 sgRNA (E1_T1)

<400> SEQUENCE: 157
tcaccaagcc cgcgaccaat                                                  20

<210> SEQ ID NO 158
<211> LENGTH: 20
<212> TYPE: DNA
<213> ORGANISM: Artificial Sequence
<220> FEATURE:
<223> OTHER INFORMATION: Synthetic: CD70 sgRNA (E1_T3)

<400> SEQUENCE: 158
atcaccaagc ccgcgaccaa                                                  20

<210> SEQ ID NO 159
<211> LENGTH: 20
<212> TYPE: DNA
<213> ORGANISM: Artificial Sequence
<220> FEATURE:

<223> OTHER INFORMATION: Synthetic: CD70 sgRNA (E1_T4)

<400> SEQUENCE: 159
cggtgcggcg caggccctat                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic: CD70 sgRNA (E1_T7)

<400> SEQUENCE: 160
gctttggtcc cattggtcgc                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic: CD70 sgRNA (E1_T8)

<400> SEQUENCE: 161
gcccgcagga cgcacccata                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic: CD70 sgRNA (E1_T10)

<400> SEQUENCE: 162
gtgcatccag cgcttcgcac                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic: CD70 sgRNA (E3_T1)

<400> SEQUENCE: 163
cagctacgta tccatcgtga                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic: b2M sgRNA

<400> SEQUENCE: 164
gctactctct ctttctggcc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic: PD-1 sgRNA

<400> SEQUENCE: 165
ctgcagcttc tccaacacat                                               20

-continued

```
<210> SEQ ID NO 166
<211> LENGTH: 11
<212> TYPE: PRT
<213> ORGANISM: Artificial Sequence
<220> FEATURE:
<223> OTHER INFORMATION: Synthetic: anti-CD19 VL CDR1 (Kabat)

<400> SEQUENCE: 166

Arg Ala Ser Gln Asp Ile Ser Lys Tyr Leu Asn
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Synthetic: anti-CD19 VL CDR2 (Kabat)

<400> SEQUENCE: 167

His Thr Ser Arg Leu His Ser
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic: anti-CD19 VL CDR3 (Kabat)

<400> SEQUENCE: 168

Gln Gln Gly Asn Thr Leu Pro Tyr Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic: anti-CD19 VH CDR1 (Kabat)

<400> SEQUENCE: 169

Asp Tyr Gly Val Ser
1               5

<210> SEQ ID NO 170
<211> LENGTH: 16
<212> TYPE: PRT
<213> ORGANISM: Artificial Sequence
<220> FEATURE:
<223> OTHER INFORMATION: Synthetic: anti-CD19 VH CDR2 (Kabat)

<400> SEQUENCE: 170

Val Ile Trp Gly Ser Glu Thr Thr Tyr Tyr Asn Ser Ala Leu Lys Ser
1               5                   10                  15

<210> SEQ ID NO 171
<211> LENGTH: 12
<212> TYPE: PRT
<213> ORGANISM: Artificial Sequence
<220> FEATURE:
<223> OTHER INFORMATION: Synthetic: anti-CD19 VH CDR3 (Kabat)

<400> SEQUENCE: 171

His Tyr Tyr Tyr Gly Gly Ser Tyr Ala Met Asp Tyr
1               5                   10

<210> SEQ ID NO 172
```

```
<211> LENGTH: 11
<212> TYPE: PRT
<213> ORGANISM: Artificial Sequence
<220> FEATURE:
<223> OTHER INFORMATION: Synthetic: anti-CD19 VL CDR1 (Chothia)

<400> SEQUENCE: 172

Arg Ala Ser Gln Asp Ile Ser Lys Tyr Leu Asn
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Synthetic: anti-CD19 VL CDR2 (Chothia)

<400> SEQUENCE: 173

His Thr Ser Arg Leu His Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic: anti-CD19 VL CDR3 (Chothia)

<400> SEQUENCE: 174

Gln Gln Gly Asn Thr Leu Pro Tyr Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic: anti-CD19 VH CDR1 (Chothia)

<400> SEQUENCE: 175

Gly Val Ser Leu Pro Asp Tyr
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic: anti-CD19 VH CDR2 (Chothia)

<400> SEQUENCE: 176

Trp Gly Ser Glu Thr
1               5

<210> SEQ ID NO 177
<211> LENGTH: 12
<212> TYPE: PRT
<213> ORGANISM: Artificial Sequence
<220> FEATURE:
<223> OTHER INFORMATION: Synthetic: anti-CD19 VH CDR3 (Chothia)

<400> SEQUENCE: 177

His Tyr Tyr Tyr Gly Gly Ser Tyr Ala Met Asp Tyr
1               5                   10

<210> SEQ ID NO 178
<211> LENGTH: 7
```

```
<212> TYPE: PRT
<213> ORGANISM: Artificial Sequence
<220> FEATURE:
<223> OTHER INFORMATION: Synthetic: anti-CD33 VH CDR1 (Chothia)

<400> SEQUENCE: 178

Gly Tyr Thr Phe Thr Ser Tyr
1               5

<210> SEQ ID NO 179
<211> LENGTH: 6
<212> TYPE: PRT
<213> ORGANISM: Artificial Sequence
<220> FEATURE:
<223> OTHER INFORMATION: Synthetic: anti-CD33 VH CDR2 (Chothia)

<400> SEQUENCE: 179

Tyr Pro Gly Asn Asp Asp
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic: anti-CD33 VH CDR3 (Chothia)

<400> SEQUENCE: 180

Glu Val Arg Leu Arg Tyr Phe Asp Val
1               5
```

UNITED STATES PATENT AND TRADEMARK OFFICE
CERTIFICATE OF CORRECTION

PATENT NO. : 11,254,912 B2
APPLICATION NO. : 17/238729
DATED : February 22, 2022
INVENTOR(S) : Terrett et al.

It is certified that error appears in the above-identified patent and that said Letters Patent is hereby corrected as shown below:

In the Claims

In Claim 1, Column 279, Line 37, delete "(ii) a disrupted f12M gene;" and replace with --(ii) a disrupted B2M gene;--

In Claim 1, Column 279, Line 41, delete "SEO ID NO: 46." and replace with --SEQ ID NO: 46.--

Signed and Sealed this
Twenty-fifth Day of October, 2022

Katherine Kelly Vidal
*Director of the United States Patent and Trademark Office*